US012110319B2

(12) United States Patent
Wec et al.

(10) Patent No.: US 12,110,319 B2
(45) **Date of Patent: *Oct. 8, 2024**

(54) ANTI-YELLOW FEVER VIRUS ANTIBODIES, AND METHODS OF THEIR GENERATION AND USE

(71) Applicant: Mabloc, LLC, Washington, DC (US)

(72) Inventors: Anna Wec, Lebanon, NH (US); Laura Walker, Norwich, VT (US)

(73) Assignee: Mabloc, LLC, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/485,163

(22) Filed: Oct. 11, 2023

(65) Prior Publication Data

US 2024/0218054 A1 Jul. 4, 2024

Related U.S. Application Data

(63) Continuation of application No. 18/045,802, filed on Oct. 11, 2022, now abandoned, which is a continuation of application No. 17/103,844, filed on Nov. 24, 2020, now Pat. No. 11,479,598.

(60) Provisional application No. 62/940,049, filed on Nov. 25, 2019.

(51) Int. Cl.

| | |
|---|---|
| *C07K 16/10* | (2006.01) |
| *A61K 39/42* | (2006.01) |
| *A61P 31/14* | (2006.01) |

(52) U.S. Cl.
CPC .............. *C07K 16/10* (2013.01); *A61K 39/42* (2013.01); *A61P 31/14* (2018.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,596,541 | B2 | 7/2003 | Murphy et al. |
| 11,479,598 | B2 | 10/2022 | Wec et al. |
| 2004/0101920 | A1 | 5/2004 | Radziejewski et al. |
| 2011/0311515 | A1 | 12/2011 | Bouche et al. |
| 2012/0128669 | A1 | 5/2012 | Depla et al. |
| 2021/0253675 | A1 | 8/2021 | Wec et al. |
| 2023/0203135 | A1 | 6/2023 | Wec et al. |

FOREIGN PATENT DOCUMENTS

| | | | |
|---|---|---|---|
| CN | 106589116 | A | 4/2017 |
| CN | 110343172 | A | 10/2019 |
| CN | 110343173 | A | 10/2019 |
| CN | 110343174 | A | 10/2019 |
| WO | 2005103081 | A2 | 11/2005 |
| WO | 2019200160 | A1 | 10/2019 |
| WO | 2021108448 | A1 | 6/2021 |

OTHER PUBLICATIONS

International Search Report and Written Opinion received for PCT Application No. PCT/US2020/062084, mailed on Apr. 19, 2021, 20 pages.

Altschul et al. (Oct. 5, 1990) “Basic Local Alignment Search Tool”, Journal of Molecular Biology , 215(3):403-410.

Altschul et al. (Sep. 1, 1997) “Gapped BLAST and PSI-BLAST: A New Generation of Protein Database Search Programs”, Nucleic Acids Research, 25(17):3389-3402.

Bitonti et al. (2006) “Pulmonary Administration of Therapeutic Proteins Using an Immunoglobulin Transport Pathway”, Advanced Drug Delivery Reviews, 58(9-10):1106-1118.

Bornholdt et al. (Mar. 2016) “Isolation of Potent Neutralizing Antibodies from a Survivor of the 2014 Ebola Virus Outbreak”, Science, 351(6277):1078-1083.

Calvert et al. (Jul. 2016) “A Humanized Monoclonal Antibody Neutralizes Yellow Fever Virus Strain 17D-204 in Vitro but Does Not Protect a Mouse Model From Disease”, Antiviral Research, 131:92-99(21 pages).

Casset et al. (2003) “A Peptide Mimetic of an Anti-CD4 Monoclonal Antibody by Rational Design”, Biochemical and Biophysical Research Communications, 307(1):198-205.

Chen et al. (Nov. 5, 1999) “Selection and Analysis of an Optimized Anti-VEGF Antibody: Crystal Structure of an Affinity-Matured Fab in Complex with Antigen”, Journal of Molecular Biology, 293(4):865-881.

Daffis et al. (2005) “Antibody Responses Against Wild-type Yellow Fever Virus and the 17D Vaccine Strain: Characterization with Human Monoclonal Antibody Fragments and Neutralization Escape Variants”, Virology, 337:262-272.

Dondelinger et al., “Understanding the Significance and Implications of Antibody Numbering and Antigen-binding Surface/Residue Definition”, Frontiers in Immunology, Oct. 16, 2018, 9:2278 (15 pages).

Ehring, Hanno (1999) “Hydrogen Exchange/Electrospray Ionization Mass Spectrometry Studies of Structural Features of Proteins and Protein/Protein Interactions”, Analytical Biochemistry, 267(2):252-259.

Engen et al. (May 1, 2001) “A Powerful New Approach That Goes Beyond Deciphering Protein Structures”, Analytical Chemistry, 73(9):256A-265A.

Gietz et al. (2007) “High-efficiency Yeast Transformation Using the LiAc/SS Carrier DNA/PEG Method”, Nature Protocols, 2(1):31-34.

Gietz et al. (2007) “Large-scale High-efficiency Yeast Transformation Using the LiAc/SS Carrier DNA/PEG Method”, Nature Protocols, 2(1):38-41.

Gonnet et al. (Jun. 5, 1992) “Exhaustive Matching of the Entire Protein Sequence Database”, Science, 256(5062):1443-1445.

Hochleitner et al. (2000) “Characterization of a Discontinuous Epitope of the Human Immunodeficiency Virus (HIV) Core Protein p24 by Epitope Excision and Differential Chemical Modification Followed by Mass Spectrometric Peptide Mapping Analysis”, Protein Science, 9(3):487-496.

(Continued)

*Primary Examiner* — Amy E Juedes

*Assistant Examiner* — Peter Johansen

(74) *Attorney, Agent, or Firm* — MINTZ, LEVIN, COHN, FERRIS, GLOVSKY AND POPEO, P.C.

(57) ABSTRACT

Antibodies and antigen-binding fragments thereof specific to the YFV E protein and with neutralizing potency against YFV are provided. These antibodies and antigen-binding fragments are useful in treating YFV.

17 Claims, 24 Drawing Sheets

Specification includes a Sequence Listing.

(56) References Cited

OTHER PUBLICATIONS

Junghans et al. (Mar. 1, 1990) "Anti-Tac-H, a Humanized Antibody to the Interleukin 2 Receptor with New Features for Immunotherapy in Malignant and Immune Disorders", Cancer Research, 50(5):1495-1502.
Kufer et al. (May 1, 2004) "A Revival of Bispecific Antibodies", Trends in Biotechnology, 22(5):238-244.
Lamminmaki et al. (2001) "Crystal Structure of a Recombinant Anti-estradiol Fab Fragment In Complex with 17beta-estradiol", The Journal of Biological Chemistry, 276(39):36687-94.
Langer, Robert (Sep. 28, 1990) "New Methods of Drug Delivery", Science, 249:1527-1533.
Lu et al. (Jan. 8, 2019) "Double Lock of a Human Neutralizing and Protective Monoclonal Antibody Targeting the Yellow Fever Virus Envelope", Cell Reports, 26(2):438-446.
MacCallum et al. (1996) "Antibody-Antigen Interactions: Contact Analysis And Binding Site Topography", Journal of Molecular Biology, 262(5):732-745.
Maillet et al. (Jun. 2008) "Aerodynamical, Immunological and Pharmacological Properties of the Anticancer Antibody Cetuximab Following Nebulization", Pharmaceutical Research, 25(6):1318-1326.
McGuinness et al. (2017) "An Overview of Yellow Fever Virus Disease", The Neurohospitalist, 7(4):157-158.
Padlan et al. (1989) "Structure Of An Antibody-antigen Complex: Crystal Structure Of The Hyhel-10 Fab-lysozyme Complex", Proceedings of the National Academy of Science of United States of America, 86(15):5938-42.
Pascalis et al. (Sep. 15, 2002) "Grafting of "Abbreviated" Complementarity-Determining Regions Containing Specificity-Determining Residues Essential for Ligand Contact to Engineer a Less Immunogenic Humanized Monoclonal Antibody", The Journal of Immunology, 169(6):3076-3084.
Zhang et al. (2017) "Structures and Functions of the Envelope Glycoprotein in Flavivirus Infections", Viruses, 9(11):338(14 pages).
Wu et al. (Apr. 5, 1987) "Receptor-Mediated in Vitro Gene Transformation by a Soluble DNA Carrier System", The Journal of Biological Chemistry, 262(10):4429-4432.
Pugachev et al. (Jan. 2004) "High Fidelity of Yellow Fever Virus RNA Polymerase", Journal of Virology, 78(2):1032-1038.
Reineke, Ulrich (2004) "Antibody Epitope Mapping Using Arrays of Synthetic Peptides", Methods in Molecular Biology, 248:443-463.
Rudikoff et al. (1982) "Single Amino Acid Substitition Altering Antigen-Binding Specificity", Proceedings of the National Academy of Sciences, 79(6):1979-1983.
Taylor et al. (1992) "A Transgenic Mouse that Expresses A Diversity of Human Sequence Heavy and Light Chain Immunoglobulin", Nucleic Acids Research, 20(23):6287-6295.
Tiller et al. (Jan. 1, 2008) "Efficient Generation of Monoclonal Antibodies from Single Human B Cells by Single Cell RT-PCR and Expression Vector Cloning", Journal of Immunological Methods, 329(1-2):112-124.
Tutt et al. (Jul. 1, 1991) "Trispecific F(ab')3 Derivatives that use Cooperative Signaling via the TCR/CD3 Complex and CD2 to Activate and Redirect Resting Cytotoxic T Cells", Journal of Immunology, 147(1):60-69.
UNIPROT (Jul. 21, 1986) "Genome Polyprotein", Accession No. P03314, 30 pages.
UNIPROT (Nov. 28, 2006) "Genome Polyprotein", Accession No. Q6DV88, 25 pages.
Vajdos et al. (Jul. 5, 2002) "Comprehensive Functional Maps of the Antigen-Binding Site of an Anti-ErbB2 Antibody Obtained with Shotgun Scanning Mutagenesis", Journal of Molecular Biology, 320(2):415-428.
Volk et al. (Nov. 10, 2009) "Structure of Yellow Fever Virus Envelope Protein Domain III", Virology, 394(1):12-18.
Vratskikh (Jun. 20, 2013) "Dissection of Antibody Specificities Induced by Yellow Fever Vaccination", PLOS Pathogens, e1003458, 9(6):1-12.
Wu et al. (Nov. 19, 1999) "Humanization of a Murine Monoclonal Antibody by Simultaneous Optimization of Framework and CDR Residues", Journal of Molecular Biology, 294(1):151-162.
Wec et al. (Mar. 24, 2020) "Longitudinal Dynamics of the Human B Cell Response to the Yellow Fever 17D Vaccine", Proceedings of the National Academy of Science, 117(12):6675-6685.

FIG. 2B

FIG. 7D

ANTI-YELLOW FEVER VIRUS ANTIBODIES, AND METHODS OF THEIR GENERATION AND USE

CROSS-REFERENCE TO RELATED APPLICATIONS

This application claims priority to U.S. patent application Ser. No. 18/045,802, filed Oct. 11, 2022, which is a continuation of U.S. patent application Ser. No. 17/103,844, filed Nov. 24, 2022, which issued as U.S. Pat. No. 11,479,598 on Oct. 25, 2022, and U.S. Provisional Application No. 62/940,049, filed Nov. 25, 2019, each of which is hereby incorporated by reference in their entirety.

REFERENCE TO A "SEQUENCE LISTING," A TABLE, OR A COMPUTER PROGRAM LISTING APPENDIX

The Sequence Listing written in file "059359-501C02US_SL_ST26.xml", created Oct. 11, 2023, 1,323,730 bytes, machine format IBM-PC, MS Windows operating system, is hereby incorporated by reference.

FIELD OF THE DISCLOSURE

The disclosure relates to anti-Yellow Fever Virus (YFV) antibodies and antigen-binding fragments thereof, and compositions containing such antibodies and antigen-binding fragments thereof, and therapeutic and diagnostic uses for the antibodies, antigen-binding fragments, and compositions.

BACKGROUND OF THE DISCLOSURE

Yellow Fever Virus (YFV) is a mosquito-borne flavivirus found in tropical and subtropical areas of Africa and South America. It is transmitted to humans primarily through the bite of infected *Aedes* or *Haemagogus* mosquito species and has three distinct transmission cycles: 1) jungle or sylvatic cycle; 2) African savannah (intermediate) cycle; and 3) urban cycle. (www.cdc.gov/yellowfever/transmission/index.html). While many people infected with YFV are asymptomatic, others develop symptoms such as fever, chills, headache, low back pain, myalgia, loss of appetite, nausea, vomiting, and/or fatigue following an incubation period of 3-6 days. (www.who.int/news-room/fact-sheets/detail/yellow-fever). Roughly 15% of people infected develop a severe form of YFV that includes high fever, bleeding diatheses, adominal pain, renal failure, cardiovascular instability, and liver failure; up to 50% of patients with the severe form of YFV will die. (McGuinness et al, Neurohospitalist 2017, 7(4); 157-158).

YFV has a RNA genome of 10,862 nucleotides that encode three structural and seven non-structural proteins. From the 5' terminus, the order of the encoded proteins is: C; prM/M; E; NS1; NS2A; NS2B; NS3; NS4A; NS4B and NS5. The three structural proteins include the C (capsid) protein, the membrane protein, M, and the envelope protein, E. The envelope protein plays an important role in cell tropism, virulence, and immunity.

Live attenuated 17D vaccine is considered one of the safest and most efficacious vaccines developed to date. However, despite the availability of the vaccine, Yellow Fever remains a serious public health issue. There are some data suggesting immunity, though protective, may wane over time in certain populations. Additionally, YFV outbreaks in non-endemic countries (such as the 11 imported cases in China in 2016) and concurrent outbreaks exhausting stockpiles of 17D have underscored the importance of developing a treatment.

Indeed, to date there are currently no approved YFV treatments (the only course being supportive therapy) and, despite decades of research, the development of safe and effective therapeutic antibodies against YFV has remained elusive. The YFV E-specific serum antibody response has been shown to be overwhelmingly mediated by antibodies targeting domain I (DI) and/or domain II (DII) of the E protein, whereas antibodies targeting domain III (DIII) are absent or present at very low titers (DVratskikh et al. PLOS pathogens 9, e1003458 (2013)). Correspondingly, the six YFV E-specific human monoclonal antibodies described to date all target overlapping epitopes within DII of the E protein (Lu et al. Cell Reports 26, 438-446 e435 (2019); Daffis et al. Virology 337, 262-272 (2005)). Recently, the crystal structure of one of these mAbs (5A) in complex with a soluble YFV E dimer was determined, which showed that this mAb binds to a conserved neutralizing epitope within DII of one E monomer (Lu et al. Cell Reports 26, 438-446 e435 (2019)). Therefore, there remains a need for highly specific, high affinity, and highly potent neutralizing anti-YFV antibodies and antigen-binding fragments thereof.

SUMMARY OF THE DISCLOSURE

The disclosure pertains to the discovery of antibodies and antigen-binding fragments thereof that bind to YFV protein and exhibit neutralizing potency, in particular antibodies binding to the domain III (DIII) of the E protein that exhibit high neutralization potency. The antibodies of the present disclosure may also cross-react with other flaviviruses, e.g., display binding reactivity to DENV-2, DENV-4, WNV, and/or ZIKV E proteins. An extensive panel of YFV-specific monoclonal antibodies is described. Binding studies demonstrated that the neutralizing antibody response to YFV-17D is primarily mediated by antibodies that recognize FL proximal epitopes within DII of the YFV E protein. A small set of DIII-targeting antibodies having potent neutralizing activity was also identified. Additionally, binding assays revealed that YFV-17D vaccination appears to induce a subset of antibodies that display broad flavivirus binding activity, the majority of which target the highly conserved FL and show little to no cross-neutralizing activity. Neutralization studies showed a proportion of antibodies display highly potent neutralizing activity. Altogether, the panel of antibodies described herein provides promising therapeutic candidates and a framework for the rational design of YFV vaccines.

Such antibodies may be useful when administered prophylactically (prior to exposure to the virus and infection with the virus) to lessen the severity, or duration of a primary infection with YFV, or ameliorate at least one symptom associated with the infection. The antibodies may be used alone or in conjunction with a second agent useful for treating an YFV infection. In certain embodiments, the antibodies may be given therapeutically (after exposure to and infection with the virus) either alone, or in conjunction with a second agent to lessen the severity or duration of the primary infection, or to ameliorate at least one symptom associated with the infection. In certain embodiments, the antibodies may be used prophylactically as stand-alone therapy to protect patients who are at risk for acquiring an infection with YFV, such as those described above. Any of these patient populations may benefit from treatment with the antibodies of the disclosure, when given alone or in conjunction with a second agent, including for example, an anti-viral therapy, or other anti-viral vaccines.

In certain embodiments are provided isolated antibodies or antigen-binding fragments thereof that specifically bind to YFV, wherein at least one of a CDRH1, a CDRH2, a CDRH3, a CDRL1, a CDRL2, and a CDRL3 amino acid sequence of such antibodies or the antigen-binding fragments thereof is at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to at least one of the CDRH1, CDRH2, CDRH3, CDRL1, CDRL2, and/or CDRL3 amino acid sequences as disclosed in Table 3 of an antibody selected from Antibody Number 1 through Antibody Number 152 as disclosed in Table 3.

The antibody or the antigen-binding fragment thereof may also have one or more of the following characteristics: a) the antibodies or antigen-binding fragments thereof display a clean or low polyreactivity profile; b) the antibodies or antigen-binding fragments thereof display an in vitro neutralization potency ($IC_{50}$) of between about 0.5 microgram/milliliter (µg/ml) to about 5 µg/ml; between about 0.05 µg/ml to about 0.5 µg/ml; or less than about 0.05 mg/ml; c) the antibodies or antigen-binding fragments thereof bind YFV-17D particles; or d) the antibody or antigen-binding fragment thereof binds to an envelope protein of YFV. In certain embodiments, the isolated antibodies or antigen-binding fragments thereof comprise at least two; at least three; or 4 of characteristics a) through d) above.

In certain other embodiments, the isolated antibodies or antigen-binding fragments thereof comprise: a) the CDRH1 amino acid sequence of any one of the antibodies designated Antibody Number 1 through Antibody Number 152 as disclosed in Table 3; b) the CDRH2 amino acid sequence of any one of the antibodies designated Antibody Number 1 through Antibody Number 152 as disclosed in Table 3; c) the CDRH3 amino acid sequence of any one of the antibodies designated Antibody Number 1 through Antibody Number 152 as disclosed in Table 3; d) the CDRL1 amino acid sequence of any one of the antibodies designated Antibody Number 1 through Antibody Number 152 as disclosed in Table 3; e) the CDRL2 amino acid sequence of any one of the antibodies designated Antibody Number 1 through Antibody Number 152 as disclosed in Table 3; f) the CDRL3 amino acid sequence of any one of the antibodies designated Antibody Number 1 through Antibody Number 152 as disclosed in Table 3; and/or g) any combination of two or more of a), b), c), d), e), and f).

In certain other embodiments, the isolated antibodies or antigen-binding fragments thereof are selected from the group consisting of antibodies that are at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to any one of the antibodies designated as Antibody Number 1 through Antibody Number 152 as disclosed in Table 3.

In certain other embodiments, the isolated antibodies or antigen-binding fragments thereof comprise: a) a heavy chain (HC) amino acid sequence of any one of the antibodies designated Antibody Number 1 through Antibody Number 152 as disclosed in Table 3; and/or b) a light chain (LC) amino acid sequence of any one of the antibodies designated Antibody Number 1 through Antibody Number 152 as disclosed in Table 3.

The disclosure also contemplates nucleic acids encoding the described anti-YFV antibodies and expression vectors comprising said nucleic acids, as well as host cells that express such antibodies via the nucleic acids and/or expression vectors.

In one embodiment is provided isolated nucleic acid sequences encoding antibodies or antigen-binding fragments thereof disclosed herein.

In other embodiments are provided expression vectors comprising isolated nucleic acid sequences encoding antibodies or antigen-binding fragments disclosed herein.

In other embodiments are provided host cells transfected, transformed, or transduced with nucleic acid sequences encoding antibodies or antigen-binding fragments disclosed herein or expression vectors comprising isolated nucleic acid sequences encoding antibodies or antigen-binding fragments disclosed herein.

In other embodiments are provided pharmaceutical compositions comprising one or more of the isolated antibodies or antigen-binding fragments thereof disclosed herein; and a pharmaceutically acceptable carrier and/or excipient.

In other embodiments are provided pharmaceutical compositions comprising one or more nucleic acid sequences encoding antibodies or antigen-binding fragments disclosed herein, or one or more expression vectors comprising nucleic acid sequences encoding antibodies or antigen-binding fragments disclosed herein; and a pharmaceutically acceptable carrier and/or excipient.

In other embodiments are provided expression vectors comprising nucleic acid sequences encoding antibodies or antigen-binding fragments disclosed herein; or a host cell comprising nucleic acid sequences encoding antibodies or antigen-binding fragments disclosed herein.

The disclosure further contemplates methods of prevention and/or treatment using the described anti-YFV antibodies (or nucleic acids encoding or expression vectors comprising such nucleic acids).

In one embodiment is provided methods of treating or preventing a Yellow Fever Virus (YFV) infection, or at least one symptom associated with YFV infection, comprising administering to a patient in need thereof or suspected of being in need thereof: a) one or more antibodies or antigen-binding fragments thereof according to other embodiments disclosed herein; b) one or more nucleic acid sequences encoding antibodies or antigen-binding fragments disclosed herein; an expression vector comprising nucleic acid sequences encoding antibodies or antigen-binding fragments disclosed herein; or a host cell comprising an expression vector comprising nucleic acid sequences encoding antibodies or antigen-binding fragments disclosed herein; or c) a pharmaceutical composition according to other embodiments disclosed herein; such that the YFV infection is treated or prevented, or the at least one symptom associated with YFV infection is treated, alleviated, or reduced in severity.

In other embodiments the methods further comprise administering to the patient a second therapeutic agent.

In embodiments the second therapeutic agent is selected from: an antiviral agent; a vaccine specific for YFV; a vaccine specific for a flavivirus; an siRNA specific for a YFV antigen; and a second antibody specific for a YFV antigen.

In certain embodiments are provided pharmaceutical compositions for use in preventing a YFV infection in a patient in need thereof or suspected of being in need thereof, or for treating a patient suffering from an YFV infection, or for ameliorating at least one symptom or complication associated with the infection, wherein the infection is either prevented, or at least one symptom or complication associated with the infection is prevented, ameliorated, or lessened in severity and/or duration as a result of such use. In certain embodiments are provided pharmaceutical compositions for use in preventing a YFV infection in a patient in need thereof or suspected of being in need thereof. In certain embodiments are provided pharmaceutical compositions for use in treating a patient suffering from an YFV infection. In certain embodiments are provided pharmaceutical compositions for use in ameliorating at least one symptom or complication associated with the infection. In certain embodiments the infection is prevented. In certain embodiments at least one symptom or complication associated with the infection is prevented, ameliorated, or lessened in severity and/or duration as a result of such use.

In certain embodiments are provided pharmaceutical compositions for use in treating or preventing a YFV infection, or at least one symptom associated with said YFV infection, in a patient in need thereof or suspected of being in need thereof, wherein the infection is either prevented, or at least one symptom or complication associated with the infection is prevented, ameliorated, or lessened in severity and/or duration as a result of such use.

In certain other embodiments are provided uses of the pharmaceutical compositions in the manufacture of a medicament for preventing a YFV infection in a patient in need thereof, or for treating a patient suffering from a YFV infection, or for ameliorating at least one symptom or complication associated with the infection, wherein the infection is either prevented, or at least one symptom or complication associated with the infection is prevented, ameliorated, or lessened in severity and/or duration.

In certain other embodiments are provided uses of the pharmaceutical compositions in the manufacture of a medicament for preventing a YFV infection, or at least one symptom associated with said YFV infection, in a patient in need thereof or suspected of being in need thereof, wherein the infection is either prevented, or at least one symptom or complication associated with the infection is prevented, ameliorated, or lessened in severity and/or duration as a result of such use.

In certain other embodiments, an antibody that binds to the YFV E-Protein is provided. This antibody can bind to at least one of an epitope within FL of Domain II of the YFV E protein, proximal to the FL of Domain II of the YFV E protein, and to a protein in Domain III of YFV. This antibody can also have one or more of the following characteristics: a) the antibodies or antigen-binding fragments thereof display a clean or low polyreactivity profile; b) the antibodies or antigen-binding fragments thereof display an in vitro neutralization potency ($IC_{50}$) of between about 0.5 microgram/milliliter (μg/ml) to about 5 μg/ml; between about 0.05 μg/ml to about 0.5 μg/ml; or less than about 0.05 mg/ml; c) the antibodies or antigen-binding fragments thereof bind YFV-17D particles; and d) the antibody or antigen-binding fragment thereof binds to an envelope protein of YFV.

BRIEF DESCRIPTION OF THE FIGURES

FIG. 1A: Serum neutralizing activity against YFV-17D at day −5 (pre-vaccination), 10, 14, 28, 90, 180, 270, and 360 post-vaccination. Averages±SD (n=6) from two independent experiments are shown. FIG. 1B: Neutralization $IC_{50}$s of serum samples at each time point post-vaccination, expressed as reciprocal serum dilution.

FIG. 2A through FIG. 2D show characterization of the YFV-17D vaccination-induced plasmablast responses at days 10 and 14. FIG. 2A: Frequency of plasmablasts among $CD19^+CD20^{-/lo}$ B cells in peripheral blood at days 0, 10, and 14 post-vaccination. Plasmablasts are defined herein as $CD19^+CD3^-CD8^-CD14^-CD16^-CD20^{-/lo}CD38^{hi}CD27^{hi}$ cells. FIG. 2B: Percentage of PB-derived mAbs that showed ELISA binding reactivity to whole YFV-17D particles at 100 nM. FIG. 2C: Neutralizing activity of PB-derived mAbs against YFV-17D at 100 nM and 10 nM concentrations. Green dots indicate the number of nucleotide substitutions in $V_H+V_L$. FIG. 2D: Proportion of YFV-17D reactive PB-derived mAbs with the indicated neutralization potencies ($IC_{50}$s).

FIG. 5A: YFV E reactivity of $swIg^+$ B cells at each sampling time point. Fluorescence activated cell sorting (FACS) plots shown are gated on $CD19^+CD20IgD^-IgM^-$ B cells. YFV E was labeled with two different colors to reduce background binding. FIG. 5B: Percentage of $swIg^+$ B cells at each sampling time point that display YFV E reactivity.

FIG. 6A: VH germline gene usage of YFV E-specific mAbs isolated from each sampling time point. VH germline gene frequencies of unselected human MBC repertoires ("Unselected") are also included for comparison. Sequencing data for unselected human MBCs was obtained from multiple high-throughput sequencing studies. FIG. 6B: VL germline gene usage of mAbs utilizing the VH3-72 germline gene. MAbs from all sampling time points were pooled for this analysis. The numbers in the center of the pies denote the total number of VH3-72 mAbs. FIG. 6C: Length distribution of CDR H3 in YFV E-specific mAbs utilizing the VH3-72 germline gene, mAbs utilizing all other VH germline genes, or unselected Abs from MBCs. FIG. 6D: SHM loads (expressed as number of nucleotide substitutions in VH) of YFV E-specific mAbs utilizing the VH3-72 germline gene or all other VH germline genes. FIG. 6E: Apparent binding affinities of mAbs utilizing the VH3-72 germline gene or all other VH germline genes to the YFV E protein, as determined by BLI. Black bars indicate medians. Avid $KD^{App}$s are plotted for the mAbs isolated from day 14 MBCs because only a small subset of these mAb showed detectable binding to YFV E in a monovalent orientation. Statistical comparisons were made using the Mann-Whitney test (*** $P<0.001$, $P<0.01$, *$P<0.05$).

FIG. 7A through 7D illustrate antibodies targeting epitopes within or proximal to the FL dominate the memory B cell response to YFV-17D vaccination. FIG. 7A: Proportion of mAbs in each of the major competition groups at each sampling time point. FIG. 7B: VH3-72 utilizing mAbs are shaded according to the competition group; natively paired light chain germline genes are indicated. FIG. 7C: Proportion of mAbs that compete with 4G2 and use the VH3-72 germline gene. FIG. 7D: Apparent affinities of 4G2-competing mAbs that either use the VH3-72 germline gene or all other germline genes. Statistical comparisons were made using the Mann-Whitney test (** P<0.01).

FIG. 8A: Proportion of mAbs with neutralization $IC_{50}$s (less than 1, 1-10, greater than 10-100, and greater than 100 nM) against YFV-17D in each epitope bin. n.n—non-binder. FIG. 8B: Neutralization $IC_{50}$s of individual mAbs against YFV-17D across the indicated epitope bins. Black bars indicate medians. FIG. 8C: Proportion of highly potent neutralizing antibodies ($IC_{50}$<1 nM) targeting the indicated antigenic sites on YFV E. The number in the center of the pie indicates the number of highly potent neutralizing antibodies. FIG. 8D: VH and VL germline gene usage of 5A-only or 5A/ADI-45107 competitor neutralizing antibodies. MAbs from both donors were combined for all analyses shown.

FIG. 9A: Proportion of mAbs that react with one or more of the flavivirus E proteins tested (YFV, DENV-1, DENV-2, ZIKV, and WNV). Recombinant E protein binding was measured in an avid orientation by BLI. Numbers in the center of the pies indicate the number of mAbs analyzed. FIG. 9B: Proportion of cross-reactive mAbs that recognize the indicated antigenic sites. Cross-reactive mAbs from both donors were combined for this analysis. FIG. 9C: Heatmap showing the cross-reactivity profiles of 50 mAbs that showed binding to at least one flavivirus E protein aside from YFV E. Apparent affinities ($KD^{App}$s) were determined in avid orientation using BLI. A heat map showing virus neutralizing activity against YFV-17D and ZIKV is shown below the binding heat map. Competition group assignments for the individual mAbs are indicated at the top of the heatmap. N.B., non-binding; n.n., non-neutralizing; neut., neutralization.

DETAILED DESCRIPTION OF THE DISCLOSURE

Figure 1A:
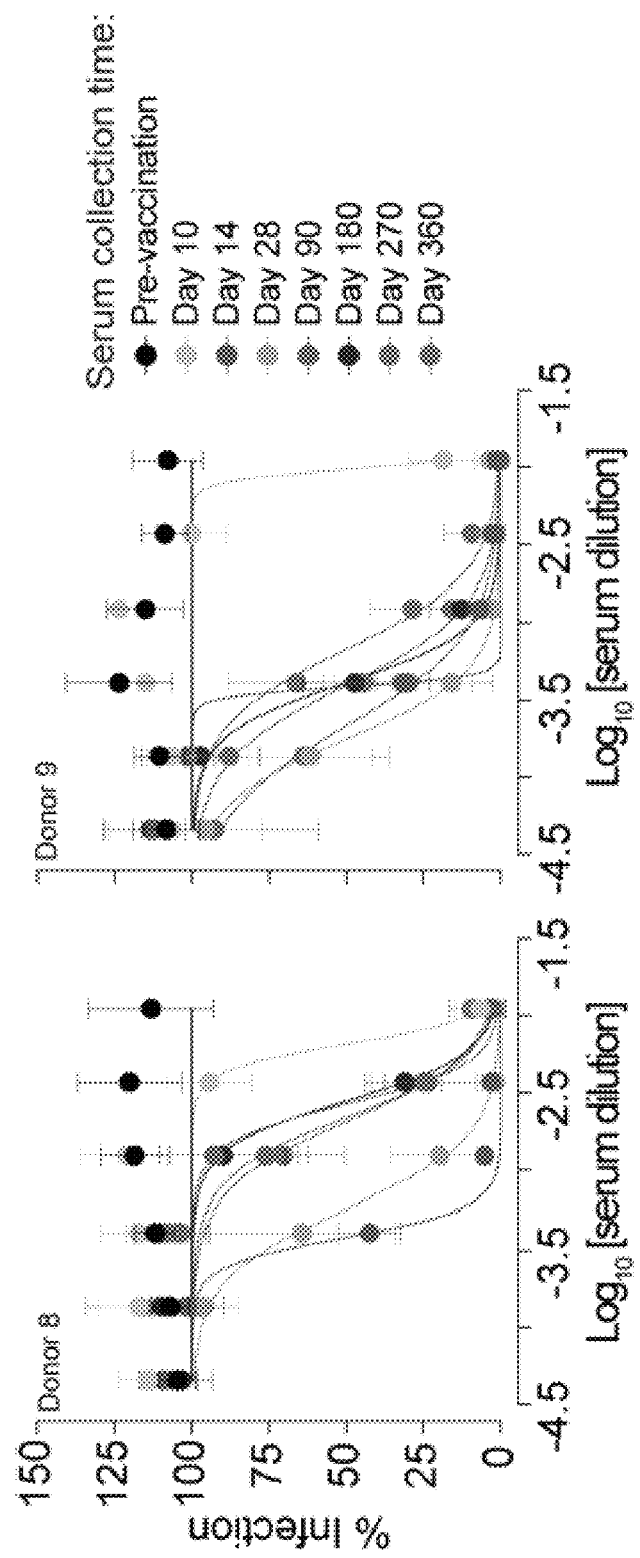
FIG. 1A and FIG. 1B illustrate donor serum analysis following YVF-14D vaccination.

An in-depth understanding of the human antibody response to YFV infection will aid the development and evaluation of YFV vaccine and therapeutic and/or prophylactic antibodies for the treatment and/or prevention of YFV infection. A high-throughput antibody isolation platform was used to dissect the human memory B cell response to YFV in two vaccinated adult donors and highly potent and selective YFV-neutralizing antibodies were isolated and characterized.

High-throughput epitope mapping studies revealed that epitopes within or proximal to the FL on DII of the YFV E protein are immunodominant. While many of the mAbs that bound to FL-specific epitopes were non-neutralizing, most of the mAbs that targeted FL-proximal epitopes overlapping the 5A epitope showed neutralizing activity. Furthermore, the vast majority of potent nAbs recognized this antigenic site suggesting that the nAb response induced by YFV-17D vaccination is primarily mediated by this class of Abs. A subset of these mAbs displayed exceptionally potent neutralizing activity, with $IC_{50}$s that were about 10 times lower than previously described YFV mAbs. Given the recent YFV outbreaks in Brazil and the Democratic Republic of Congo, coupled with YFV-17D vaccine supply shortages and the lack of effective treatments for YFV disease, these mAbs represent promising candidates for prophylaxis and/or therapy Accordingly, disclosed herein are highly selective and potent anti-YFV antibodies, as well as possible vaccine candidates, for the treatment and/or prophylaxis of YFV infection. Additionally, the reagents disclosed here provide a useful set of tools for the evaluation of clinical trials, which will be critical for selecting the optimal YFV vaccination or antibody-based therapeutic strategy from those currently under investigation.

Unless defined otherwise, all technical and scientific terms used herein have the same meaning as commonly understood by one of ordinary skill in the art to which this disclosure belongs. In this specification and in the claims that follow, reference will be made to a number of terms that shall be defined to have the following meanings:

The terminology used herein is for the purpose of describing particular embodiments only and is not intended to be limiting. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to an amount means that the amount may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this disclosure.

"Yellow Fever Virus", also referred to as "YFV", is an RNA virus typically spread by the bite of infected *Aedes* or *Haemagogus* species mosquito bites.

The term "YFV-17D" refers to the attenuated YFV vaccine strain developed by passaging a wild-type Asibi strain in chicken and mouse tissue. There are three 17D substrains in current production: 17DD manufactured in Brazil, 17D-213 manufactured in Russia, and 17D-204 manufactured in China, France, Senegal, and the USA. While the mechanism of attenuation is poorly understood, it is hypothesized that the limited genetic diversity of the 17D vaccine virus attributes to vaccine attenuation and safety. There is evidence that replication of 17D is not as error-prone as wild-type RNA viruses. See Pugachev et al., J Virol. 78(2): 1032-8 (2004).

The term "envelope protein" or "E protein" refers to the structural YFV protein that is a primary immunogen that plays a central role in receptor binding and membrane fusion. The structure of the E protein ectodomain (the soluble N-terminal portion consisting of 395 residues) includes three distinct structural domains, referred to as domains I, II, and III. (Volk et al., Virology 2009, 394(1): 12-18). Domain II contains a S-S bridge stabilized loop at its distal end that functions as a highly conserved fusion loop (FL). When a virus enters a target host cell, the FL of Domain II is exposed and inserts into the host cellular membrane. (Zhang et al., Viruses 2017, 9(11): 338). In some embodiments, the antibodies and antigen-binding fragments thereof bind to the FL of Domain II YFV E protein. In other embodiments, the antibodies and antigen-binding fragments thereof bind to Domain III of the YFV E protein.

The development of an effective YFV therapeutic has presented a number of unique challenges. The in-depth analysis of the human antibody response to the YFV vaccine performed here provides insights for the development of such a therapeutic treatment. The antibody repertoire analysis disclosed herein reveals that the majority of neutralizing YFV-specific antibodies target FL-proximal epitopes overlapping the 5A epitope, whereas a small number of potent neutralizing antibodies targeted the DIII domain—a region of the E protein that, until now, was not the epitope for any effective anti-YFV antibodies.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. The term "antibody" (or "Ab"), as used herein, is intended to refer to immunoglobulin molecules comprised of four polypeptide chains, two heavy (H) chains and two light (L) chains interconnected by disulfide bonds (i.e., "full antibody molecules"), as well as multimers thereof (e.g. IgM) or antigen-binding fragments thereof.

The terms "antigen-binding portion", "antigen-binding fragment", and the like, as used herein, include any naturally occurring, enzymatically obtainable, synthetic, or genetically engineered polypeptide or glycoprotein that specifically binds an antigen to form a complex. In certain embodiments, the terms "antigen-binding portion" or "antibody fragment", as used herein, refer to one or more fragments of an antibody that retains the ability to bind to YFV.

An antibody fragment may include a Fab fragment, a F(ab')2 fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H$1; (ii) $V_H$-$C_H$2; (iii) $V_H$-$C_H$3; (iv) $V_H$-$C_H$1-$C_H$2; (V) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

Each heavy chain is comprised of a heavy chain variable region ("HCVR" or "$V_H$") and a heavy chain constant region (comprised of domains $C_H1$, $C_H2$, and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining region (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the disclosure, the FRs of the antibody (or antigen binding fragment thereof) may be identical to the human germline sequences, or may be naturally or artificially modified. An amino acid consensus sequence may be defined based on a side-by-side analysis of two or more CDRs. Accordingly, the CDRs in a heavy chain are designated "CDRH1", "CDRH2", and "CDRH3", respectively, and the CDRs in a light chain are designated "CDRL1", "CDRL2", and "CDRL3".

In some embodiments, the antibody or antigen-binding fragment thereof contains a CDRL3 binding domain comprising a consensus motif having the sequence $QQX_1X_2X_3X_4X_5X_6T$. $X_1$ is Y, F, or A, $X_2$ is N, H, or Y, $X_3$ is R, S, T, or D, $X_4$ is D, F, Y, W, or P, $X_5$ is P or S, $X_6$ is Y, F, K, or W. The following clones include this consensus motif: ADI-50211; ADI-48899; ADI-45136; ADI-45078; ADI-49162; ADI-49141; ADI-42844; ADI-48910; ADI-45074; ADI-49041; ADI-50220; ADI-42172; ADI-42178; ADI-50218; and ADI-49194.

In some embodiments, the present disclosure provides an antibody comprising a YFV binding domain, CDRL3, wherein the CDRL3 binding domain comprises a consensus motif, the consensus motif comprising the sequence $QX_1X_2X_3X_4TX_5X_6T$, wherein $X_1$ is Q or H, $X_2$ is A or S, $X_3$ is S or Y, $X_4$ is T or S, $X_5$ is R or P, and $X_6$ is Y, L, W, or R. The following clones include this consensus motif: ADI-42201; ADI-45164; ADI-46729; ADI-42223; ADI-46718; ADI-45076; ADI-48968; ADI-45156; ADI-50536; and ADI-50537.

In some embodiments, the present disclosure provides an antibody comprising a YFV binding domain, CDRL3, wherein the CDRL3 binding domain comprises a consensus motif, the consensus motif comprising the sequence $GTWDXISX_2X_3SAGX_4V$, wherein $X_1$ is S or T, $X_2$ is S or no amino acid, $X_3$ is L or P, and $X_4$ is K, G, or R. The following clones include this consensus motif: ADI-45083; ADI-42225; ADI-42210; ADI-42198; ADI-42809; ADI-42830; ADI-42818; ADI-42151; and ADI-50533.

In some embodiments, the present disclosure provides an antibody comprising a YFV binding domain, CDRH3, wherein the CDRH3 binding domain comprises a consensus motif, the consensus motif comprising the sequence $AX_1X_2YDSX_3X_4YYX_5X_6X_7X_8$, wherein $X_1$ is K or R, $X_2$ is Y, F, T, A, G, Y, or H, $X_3$ is S, N, or R, $X_4$ is A or G, $X_5$ is W or Y, $X_6$ is F, L, I, A, or E, $X_7$ is D, E, or H, and Xx is Y, H, or S. The following clones include this consensus motif: ADI-45085; ADI-50211; ADI-45078; ADI-49162; ADI-45136; ADI-42172; ADI-49194; ADI-50203; ADI-42178; ADI-48908; ADI-42844; ADI-48910; and ADI-49168.

In some embodiments, the present disclosure provides an antibody comprising a YFV binding domain, CDRL2, wherein the CDRL2 binding domain comprises a consensus motif, the consensus motif comprising the sequence $X_1X_2X_3X_4RPS$, wherein $X_1$ is D or E, $X_2$ is N, V, or D, $X_3$ is K, N, D, or S, and $X_4$ is K, E, or R. The following clones include this consensus motif: ADI-49039; ADI-42229; ADI-45097; ADI-45083; ADI-42225; ADI-49139; ADI-48969; ADI-48900; ADI-42786; ADI-42210; ADI-42198; ADI-49154; ADI-49188; ADI-42188; ADI-42809; ADI-46596; ADI-42830; ADI-46591; ADI-48955; ADI-42818; ADI-46586; ADI-42151; ADI-45140; ADI-46722; ADI-45128; ADI-45127; ADI-46739; ADI-46724; ADI-50539; ADI-42114; ADI-50533; and ADI-49205.

In some embodiments, present disclosure provides an antibody comprising a YFV binding domain, CDRL2, wherein the CDRL2 binding domain comprises a consensus motif, the consensus motif comprising the sequence $X_1X_2X_3X_4LX_5X_6$, wherein $X_1$ is A, G, or R, $X_2$ is A or T, $X_3$ is S or T, $X_4$ is T, G, S, or I, $X_5$ is Q or R, and $X_6$ is S or R. The following clones include this consensus motif: ADI-49133; ADI-49033; ADI-48895; ADI-42201; ADI-42230; ADI-48916; ADI-42211; ADI-5164; ADI-42191; ADI-49145; ADI-46729; ADI-42189; ADI-46718; ADI-45076; ADI-48968; ADI-50203; ADI-42227; ADI-48894; ADI-50218; ADI-45156; ADI-50536; ADI-50537; ADI-46737; ADI-45123; and ADI-50200.

In some embodiments, present disclosure provides an antibody comprising a YFV binding domain, CDRL2, wherein the CDRL2 binding domain comprises a consensus motif, the consensus motif comprising the sequence $X_1X_2SX_3RAX_4$, wherein $X_1$ is G, D, R, or A, $X_2$ is A or S, $X_3$ is S, T, or N, and $X_4$ is T or A. The following clones include this consensus motif: ADI-49147; ADI-50201; ADI-45113; ADI-50219; ADI-48897; ADI-42194; ADI-42847; ADI-48908; ADI-42231; ADI-42233; ADI-45148; ADI-42187; ADI-42787; ADI-49141; ADI-42213; ADI-42192; ADI-49590; ADI-48462; ADI-42200; ADI-42181; ADI-49037; ADI-49137; and ADI-42817.

In some embodiments, present disclosure provides an antibody comprising a YFV binding domain, CDRL2, wherein the CDRL2 binding domain comprises a consensus motif, the consensus motif comprising the sequence $X_1VX_2X_3RPS$, wherein $X_1$ is D, E, or R, $X_2$ is S, T, N, or A, and $X_3$ is N, K, or Q. The following clones include this consensus motif: ADI-42228; ADI-42190; ADI-49183; ADI-49189; ADI-50205; ADI-50531; ADI-49138; ADI-45154; ADI-49161; ADI-49561; ADI-42219; ADI-48435; ADI-45161; ADI-42193; ADI-42149; ADI-42216; ADI-42810; ADI-48890; ADI-42206; ADI-48950; and ADI-42124.

In some embodiments, the present disclosure provides an antibody comprising a YFV binding domain, CDRL2, wherein the CDRL2 binding domain comprises a consensus motif, the consensus motif comprising the sequence $XIASX_2LEX_3$, wherein $X_1$ is R, Q, or K, $X_2$ is T, S, G, R, or I, and $X_3$ is T or S. The following clones include this consensus motif: ADI-42831; ADI-42821; ADI-45085; ADI-50211; ADI-48899; ADI-49168; ADI-45136; ADI-45078; ADI-42844; ADI-48910; ADI-49041; ADI-42172; ADI-42178; ADI-49032; and ADI-49194.

In some embodiments, the present disclosure provides an antibody comprising a YFV binding domain, CDRH2, wherein the CDRH2 binding domain comprises a consensus motif, the consensus motif comprising the sequence $X_1X_2X_3HX_4X_5X_6X_7X_8YX_9PX_{10}X_{11}X_{12}S$, wherein $X_1$ is D, E, or S, $X_2$ is I or V, $X_3$ is F or Y, $X_4$ is X or T, $X_5$ is G or E, $X_6$ is S, G, or T, $X_7$ is T or A, $X_8$ is N, S, H, K, or T, $X_9$ is N or S, $X_{10}$ is S or F, Xu is L or V, and $X_{12}$ of K or E. The following clones include this consensus motif: ADI-45083; ADI-42225; ADI-49139; ADI-48900; ADI-42232; ADI-42786; ADI-42210; ADI-42198; ADI-49154; ADI-42188;

ADI-42809; ADI-42818; ADI-42151; ADI-46722; ADI-46742; ADI-49141; ADI-46739; ADI-46724; ADI-50539; ADI-48951; ADI-50538; and ADI-50533.

In some embodiments, the present disclosure provides an antibody comprising a YFV binding domain, CDRH2, wherein the CDRH2 binding domain comprises a consensus motif, the consensus motif comprising the sequence $X_1X_2X_3X_4DX_5X_6X_7KX_8X_9ADSX_{10}X_{11}G$, wherein $X_1$ is V or L, $X_2$ is I or M, $X_3$ is S, W, or L, $X_4$ is F or Y, $X_5$ is E or G, $X_6$ is S or T, $X_7$ is K, N, or Y, $X_8$ is F, W, or Y, $X_9$ is Y or F, $X_{10}$ is V or L, and $X_{11}$ is K or R. The following clones include this consensus motif: ADI-45097; ADI-42144; ADI-49138; ADI-45154; ADI-49561; ADI-42189; ADI-42844; ADI-45161; ADI-48462; ADI-42172; ADI-42178; ADI-42217; ADI-46737; ADI-49205; ADI-45151; and ADI-46728.

In some embodiments, the present disclosure provides an antibody comprising a YFV binding domain, CDRL1, wherein the CDRL1 binding domain comprises a consensus motif, the consensus motif comprising the sequence $RX_1SX_2X_3X_4X_5X_6X_7X_8X_9$, wherein $X_1$ is A or T, $X_2$ is Q or R, $X_3$ is S or T, $X_4$ is I or V, $X_5$ is S or T, $X_6$ is S, N, T, F, D, or G, $X_7$ is N, Y, W, F, or K, $X_8$ is L or V, and $X_9$ is A or N. The following clones include this consensus motif: ADI-49147; ADI-50201; ADI-45113; ADI-42201; ADI-42194; ADI-42847; ADI-45085; ADI-48908; ADI-50211; ADI-42231; ADI-45164; ADI-48899; ADI-46729; ADI-49168; ADI-49040; ADI-45136; ADI-45078; ADI-46718; ADI-49141; ADI-42844; ADI-42192; ADI-48910; ADI-42200; ADI-50203; ADI-42181; ADI-49041; ADI-50220; ADI-42172; ADI-42178; ADI-49032; ADI-49137; ADI-42817; ADI-45156; ADI-50536; ADI-50537; and ADI-49194.

In some embodiments, the present disclosure provides an antibody comprising a YFV binding domain, CDRL1, wherein the CDRL1 binding domain comprises a consensus motif, the consensus motif comprising the sequence $SGSX_1SNX_2GX_3X_4X_5VX_6$, wherein $X_1$ is N or S, $X_2$ is I or F, $X_3$ is S or N, $X_4$ is N, Y, S, or D, $X_5$ is Y, F, or D, and $X_6$ is S or A. The following clones include this consensus motif: ADI-49039; ADI-42229; ADI-45097; ADI-45083; ADI-42225; ADI-48900; ADI-42786; ADI-42210; ADI-42198; ADI-49154; ADI-42188; ADI-42809; ADI-46596; ADI-42830; ADI-46591; ADI-48955; ADI-42818; ADI-46586; ADI-42151; ADI-45140; ADI-46722; ADI-45128; ADI-46739; ADI-46724; ADI-50539; ADI-42114; and ADI-50533.

In some embodiments, the present disclosure provides an antibody comprising a YFV binding domain, CDRL1, wherein the CDRL1 binding domain comprises a consensus motif, the consensus motif comprising the sequence $X_1GTX_2X_3DX_4GX_5X_6X_7X_8$ VS, wherein $X_1$ is A or T, $X_2$ is S, G, or R, $X_3$ is S or T, $X_4$ is V, F, or I, $X_5$ is G or A, $X_6$ is Y, D, or F, $X_7$ K or N, and $X_8$ is Y or F. The following clones include this consensus motif: ADI-48969; ADI-42228; ADI-42190; ADI-49183; ADI-49189; ADI-50205; ADI-50531; ADI-49138; ADI-45154; ADI-49161; ADI-49561; ADI-42219; ADI-48435; ADI-45161; ADI-45127; ADI-42149; ADI-42216; ADI-42810; ADI-48890; ADI-42206; ADI-48950; ADI-42124; and ADI-49205.

In some embodiments, the present disclosure provides an antibody comprising a YFV binding domain, CDRH1, wherein the CDRH1 binding domain comprises a consensus motif, the consensus motif comprising the sequence: X1X2FX3X4X5X6X7X8, wherein X1 is F, Y, or L, X2 is T, A, S, or N, X3 is S or T, X4 is S, T, or R, X5 is Y or L, X6 is G, A, T, W, S, or D, X7 is M, I, or L, and X8 is H, S, N, or T. The following clones include this consensus motif: ADI-45090; ADI-49044; ADI-45113; ADI-42144; ADI-50026; ADI-45075; ADI-42230; ADI-42154; ADI-45085; ADI-42211; ADI-50211; ADI-42231; ADI-42233; ADI-49168; ADI-42187; ADI-49561; ADI-42219; ADI-50535; ADI-45136; ADI-42189; ADI-48435; ADI-46718; ADI-42844; ADI-45161; ADI-48910; ADI-48462; ADI-42200; ADI-50203; ADI-42149; ADI-42172; ADI-42178; ADI-50197; ADI-42810; ADI-50218; ADI-45156; ADI-50536; ADI-50537; ADI-46737; ADI-42114; ADI-49194; ADI-42124; and ADI-46728.

In some embodiments, the present disclosure provides an antibody comprising a YFV binding domain, CDRH1, wherein the CDRH1 binding domain comprises a consensus motif, the consensus motif comprising the sequence: $X_1SIX_2X_3X_4X_5X_6$ $WX_7$, wherein $X_1$ is G or I, $X_2$ is S or T, $X_3$ is S, T, G, or no amino acid, $X_4$ is D, S, T, or G, $X_5$ is Y, N, or D, $X_6$ is W or Y, and $X_7$ is S or T. The following clones include this consensus motif: ADI-45083; ADI-42225; ADI-48900; ADI-42786; ADI-42210; ADI-49188; ADI-42188; ADI-42818; ADI-42151; ADI-48913; ADI-46722; ADI-49141; ADI-46741; ADI-46739; ADI-50539; ADI-50538; and ADI-50533.

In some embodiments, the present disclosure provides an antibody comprising a YFV binding domain, CDRH1, wherein the CDRH1 binding domain comprises a consensus motif, the consensus motif comprising the sequence: FX1FSDX2YMX3, wherein X1 is I or T, X2 is H or Y, and X3 is A or D. The following clones include this consensus motif: ADI-42191; ADI-49040; ADI-42223; ADI-42193; ADI-48968; ADI-42212; ADI-45126; ADI-42141; ADI-49140; ADI-48894; ADI-42226; ADI-49137; ADI-48890; ADI-42206; and ADI-49030.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically.

The fully human monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes fully monoclonal antibodies comprising variants of any of the CDR amino acid sequences disclosed herein having one or more conservative substitutions. For example, the present disclosure includes antibodies having CDR amino acid sequences with, e.g., 10 or fewer, 8 or fewer, 6 or fewer, 4 or fewer, etc. conservative amino acid substitutions relative to any of the CDR amino acid sequences disclosed herein. In some embodiments, the anti-YFV antibodies and antigen-binding fragments disclosed are human antibodies. The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3.

In some embodiments, the anti-YFV antibodies and antigen-binding fragments disclosed are recombinant antibodies. The term "recombinant" generally refers to any protein, polypeptide, or cell expressing a gene of interest that is produced by genetic engineering methods. The term "recombinant" as used with respect to a protein or polypeptide, means a polypeptide produced by expression of a recombinant polynucleotide. The proteins used in the immunogenic compositions of the disclosure may be isolated from a natural source or produced by genetic engineering methods.

The antibodies of the disclosure may, in some embodiments, be recombinant human antibodies. The term "recombinant human antibody", as used herein, is intended to include all antibodies, including human or humanized antibodies, that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

In some embodiments, the anti-YFV antibodies and antigen-binding fragments thereof are isolated antibodies. An "isolated antibody", as used herein, refers to an antibody that is substantially free of other antibodies having different antigenic specificities (e.g., an isolated antibody that specifically binds YFV, or a fragment thereof, is substantially free of Abs that specifically bind antigens other than YFV). In some embodiments, the anti-YFV antibodies and antigen-binding fragments specifically bind to the YFV E protein, e.g., the FL of DII domain or DIII. The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, biolayer interferometry measurements using, e.g., a ForteBio Octet HTX instrument (Pall Life Sciences), which bind specifically to YFV. Moreover, multi-specific antibodies that bind to YFV protein and one or more additional antigens, or a bi-specific that binds to two different regions of YFV are nonetheless considered antibodies that "specifically bind", as used herein. In certain embodiments, the antibodies disclosed herein display equilibrium dissociation constants (and hence specificities) of about $1\times10^{-6}$ M; about $1\times10^{-7}$ M; about $1\times10^{-8}$ M; about $1\times10^{-9}$ M; about $1\times10^{-10}$ M; between about $1\times10^{-6}$ M and about $1\times10^{-7}$ M; between about $1\times10^{-7}$ M and about $1\times10^{-8}$ M; between about $1\times10^{-8}$ M and about $1\times10^{-9}$ M; between about $1\times10^{-9}$ M and about $1\times10^{-10}$ M; or between about $1\times10^{-9}$ M and about $1\times10^{-10}$ M.

In some embodiments, the anti-YFV antibodies and antigen-binding fragments are high affinity binders. The term "high affinity" refers to those mAbs having a binding affinity to YFV, expressed as KD, of at least $10^{-9}$ M; more preferably $10^{-10}$ M, more preferably $10^{-11}$ M, more preferably $10^{-12}$ M as measured by surface plasmon resonance, e.g., BIACORE™, biolayer interferometry measurements using, e.g., a ForteBio Octet HTX instrument (Pall Life Sciences), or solution-affinity ELISA.

By the term "slow off rate", "Koff" or "kd" is meant an antibody that dissociates from YFV, with a rate constant of $1\times10^{-3}$ $s^{-1}$ or less, preferably $1\times10^{-4}$ $s^{-1}$ or less, as determined by surface plasmon resonance, e.g., BIACORE™ or a ForteBio Octet HTX instrument (Pall Life Sciences).

The specific embodiments, antibody or antibody fragments of the disclosure may be conjugated to a therapeutic moiety ("immunoconjugate"), such as an antibiotic, a second anti-YFV antibody, a vaccine, or a toxoid, or any other therapeutic moiety useful for treating a YFV infection.

Also contemplated are antibodies and antigen-binding fragments substantially identical to the antibodies provided herein. The term "substantial identity", or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. Accordingly, nucleic acid sequences that display a certain percentage "identity" share that percentage identity, and/or are that percentage "identical" to one another. A nucleic acid molecule having substantial identity to a reference nucleic acid molecule may, in certain instances, encode a polypeptide having the same or substantially similar amino acid sequence as the polypeptide encoded by the reference nucleic acid molecule.

In some embodiments, the antibody or antibody binding fragment thereof comprises at least one of a CDRH1, a CDRH2, a CDRH3, a CDRL1, a CDRL2, and a CDRL3 amino acid sequence of such antibodies or the antigen-binding fragments thereof are at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to at least one the CDRH1, a CDRH2, a CDRH3, a CDRL1, a CDRL2, and/or a CDRL3 amino acid sequences as disclosed in Table 3 of an antibody selected from Antibody Number 1 through Antibody Number 152 as disclosed in Table 3.

In certain embodiments, the antibodies and antigen-binding fragments thereof comprise the CDRH3 amino acid sequence of any one of the antibodies designated Antibody Number 1 through Antibody Number 152 as disclosed in Table 3.

In certain embodiments, the antibodies and antigen-binding fragments thereof comprise the CDRH2 amino acid sequence of any one of the antibodies designated Antibody Number 1 through Antibody Number 152 as disclosed in Table 3.

In certain embodiments, the antibodies and antigen-binding fragments thereof comprise the CDRH1 amino acid sequence of any one of the antibodies designated Antibody Number 1 through Antibody Number 152 as disclosed in Table 3.

In certain embodiments, the antibodies and antigen-binding fragments thereof comprise the CDRL3 amino acid sequence of any one of the antibodies designated Antibody Number 1 through Antibody Number 152 as disclosed in Table 3.

In certain embodiments, the antibodies and antigen-binding fragments thereof comprise the CDRL2 amino acid sequence of any one of the antibodies designated Antibody Number 1 through Antibody Number 152 as disclosed in Table 3.

In certain embodiments, the antibodies and antigen-binding fragments thereof comprise the CDRL1 amino acid sequence of any one of the antibodies designated Antibody Number 1 through Antibody Number 152 as disclosed in Table 3.

In some embodiments, an anti-YFV antibody and antigen-binding fragment thereof is at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to any one of the antibodies designated as Antibody Number 1 through Antibody Number 152 as disclosed in Table 3.

In certain embodiments, the antibodies and antigen-binding fragments thereof comprise a heavy chain (HC) amino acid sequence of any one of the antibodies designated Antibody Number 1 through Antibody Number 152 as disclosed in Table 3.

In certain embodiments, the inventive antibodies and antigen-binding fragments thereof comprise a light chain (LC) amino acid sequence of any one of the antibodies designated Antibody Number 1 through Antibody Number 152 as disclosed in Table 3. In certain embodiments, the inventive antibodies and antigen-binding fragments thereof comprise a heavy chain (HC) amino acid sequence and a light chain (LC) amino acid sequence of any one of the antibodies designated Antibody Number 1 through Antibody Number 152 as disclosed in Table 3.

In certain embodiments, the antibodies and antigen-binding fragments thereof are each selected from the group consisting of the antibodies designated as Antibody Number 1 through Antibody Number 152 as disclosed in Table 3.

Also provided are nucleic acids encoding the antibodies described herein. In certain embodiments, isolated nucleic acid sequences are provided that encode antibodies that specifically bind to YFV and antigen-binding fragments thereof, wherein at least one of the CDRH1, CDRH2, CDRH3, CDRL1, CDRL2, and/or CDRL3 amino acid sequences of the antibody or the antigen-binding fragment thereof is at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to at least one the CDRH1, CDRH2, CDRH3, CDRL1, CDRL2, and/or CDRL3 amino acid sequences as disclosed in Table 3 of an antibody selected from Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRH3 amino acid sequence of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRH2 amino acid sequences of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRH1 amino acid sequences of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRL3 amino acid sequences of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRL2 amino acid sequences of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRL1 amino acid sequences of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the heavy chain (HC) amino acid sequences of any one of the antibodies designated Antibody Number 1 through Antibody Number 152 as disclosed in Table 3

In certain embodiments, isolated nucleic acid sequences are provided that encode the antibodies and antigen-binding fragments thereof, wherein such nucleic acid sequences comprise sequences that encode the heavy chain (LC) amino acid sequences of any one of the antibodies designated Antibody Number 1 through Antibody Number 152 as disclosed in Table 3. As applied to polypeptides, the term "substantial identity" or "substantially identical" means that two peptide sequences, when optimally aligned, such as by the programs GAP or BESTFIT using default gap weights, share at least 90% sequence identity, even more preferably at least 95%, 98% or 99% sequence identity. Accordingly, amino acid sequences that display a certain percentage "identity" share that percentage identity, and/or are that percentage "identical" to one another. Accordingly, amino acid sequences that display a certain percentage "identity" share that percentage identity, and/or are that percentage "identical" to one another.

In certain embodiments, the disclosed antibody amino acid sequences are, e.g.,: at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to other sequences and/or share such percentage identities with one another (or with certain subsets of the herein-disclosed antibody sequences).

Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. (See, e.g., Pearson (1994) Methods Mol. Biol. 24: 307-331). Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. (See, e.g., Altschul et al. (1990) J. Mol. Biol. 215: 403 410 and (1997) Nucleic Acids Res. 25:3389 402).

In certain embodiments, the antibody or antibody fragment for use in the method of the disclosure may be mono-specific, bi-specific, or multi-specific. Multi-specific antibodies may be specific for different epitopes of one target polypeptide or may contain antigen-binding domains specific for epitopes of more than one target polypeptide.

As disclosed herein, anti-YFV antibodies may be obtained from human B cells using techniques available to the artisan, and, for example, as described in the EXAMPLES below. Methods for generating human antibodies in transgenic animals, such as mice, are also known in the art and may be employed in order to derive antibodies in accordance with the present disclosure. Any such known methods can be used in the context of the present disclosure to make human antibodies that specifically bind to YFV (see, for example, U.S. Pat. No. 6,596,541).

In certain embodiments, the antibodies of the instant disclosure possess affinities ($K_D$) ranging from about $1.0 \times 10^{-7}$ M to about $1.0 \times 10^{-12}$ M, when measured by binding to antigen either immobilized on solid phase or in solution phase. In certain embodiments, the antibodies of the disclosure possess affinities ($K_D$) ranging from about $1 \times 10^{-7}$ M to about $6 \times 10^{-10}$ M, when measured by binding to antigen either immobilized on solid phase or in solution phase. In certain embodiments, the antibodies of the disclosure possess affinities ($K_D$) ranging from about $1 \times 10^{-7}$ M to about $9 \times 10^{-10}$ M, when measured by binding to antigen either immobilized on solid phase or in solution phase.

In addition to the specific anti-YFV antibodies and antibody fragments disclosed herein, the present disclosure also contemplates variants of those antibodies and antibody fragments that maintain bioequivalency. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Biological and Biophysical Characteristics of the Antibodies

In certain embodiments, the inventive antibodies and antigen-binding fragments thereof specifically bind to YFV, wherein at least one of the CDRH1, CDRH2, CDRH3, CDRL1, CDRL2, and/or CDRL3 amino acid sequences is at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to the corresponding CDRH1, CDRH2, CDRH3, CDRL1, CDRL2, and/or CDRL3 amino acid sequence as disclosed in Table 3 of an antibody selected from Antibody Number 1 through Antibody Number 152 as disclosed in Table 3.

In some embodiments, the anti-YFV antibodies and antigen-binding fragments thereof are neutralizing antibodies, i.e., exhibit neutralizing potency. A "neutralizing antibody", as used herein (or an "antibody that neutralizes YFV activity" or "an antibody with neutralizing activity"), refers to an antibody whose binding to an antigen, e.g., the YFV E protein as the case may be as disclosed herein, results in inhibition of at least one biological activity. For example, an antibody of the disclosure may aid in blocking the fusion of YFV to a host cell, or prevent syncytia formation, or prevent the primary disease caused by YFV. Alternatively, an antibody of the disclosure may demonstrate the ability to ameliorate at least one symptom of the YFV infection. This inhibition of the biological activity of YFV can be assessed by measuring one or more indicators of YFV biological activity by one or more of several standard in vitro assays (such as a neutralization assay, as described herein) or in vivo assays known in the art (for example, animal models to look at protection from challenge with YFV following administration of one or more of the antibodies described herein).

In certain embodiments, the antibodies and antigen-binding fragments thereof display an in vitro neutralization potency ($IC_{50}$) of between about 0.5 microgram/milliliter (μg/ml) to about 5 μg/ml; between about 0.05 μg/ml to about 0.5 μg/ml; or less than about 0.05 mg/ml.

The term "$IC_{50}$" refers to the "half maximal inhibitory concentration", which value measures the effectiveness of compound (e.g. anti-YFV antibody) inhibition towards a biological or biochemical utility. This quantitative measure indicates the quantity required for a particular inhibitor to inhibit a given biological process by half. In certain embodiments, YFV neutralization potencies for anti-YFV neutralizing antibodies disclosed herein are expressed as neutralization $IC_{50}$ values. Of the antibodies described herein, generally the antibodies binding to DIII of the YFV E protein possess the highest neutralization potency.

In some embodiments, the antibodies and antigen-binding fragments thereof cross-react with DENV-2, DENV-4, WNV, or ZIKV E proteins, i.e., bind to YFV E protein and an E protein from one or more of the other flaviviruses. In certain embodiments, such antibodies and antigen-binding fragments thereof bind to DENV-2, DENV-4, WNV, YFV, and ZIKV E proteins with high apparent avid affinities ($K_D^{Apps}$<10 nM). In certain embodiments, the cross-reactive antibodies or antigen-binding fragments thereof have neutralizing activity against YFV-17D and another flavivirus. In certain embodiments, the cross-reactive antibodies and antigen-binding fragments thereof bind to the FL epitope. In certain embodiments, the cross-reactive antibodies and antigen-binding fragments thereof bind to DIII. In a certain embodiment, the cross-reactive antibody is ADI-48905.

Epitope Binning and Related Technologies

As described above and as demonstrated in the EXAMPLES, Applicant has characterized the epitopic binning of the inventive antibodies and antigen-binding fragments thereof. In addition to the methods for conducting such characterization, various other techniques are available to the artisan that can be used to carry out such characterization or to otherwise ascertain whether an antibody "interacts with one or more amino acids" within a polypeptide or protein. Exemplary techniques include, for example, a routine cross-blocking assay such as that described Antibodies, Harlow and Lane (Cold Spring Harbor Press, Cold Spring Harb., NY) can be performed. Other methods include alanine scanning mutational analysis, peptide blot analysis (Reineke (2004) Methods Mol Biol 248:443-63), peptide cleavage analysis crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) Analytical Biochemistry 267 (2):252-259; Engen and Smith (2001) Anal. Chem. 73:256A-265A.

As the artisan will understand, an epitope can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920). Each category may reflect a unique epitope either distinctly different from or partially overlapping with an epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

As the artisan understands, one can easily determine whether an antibody binds to the same epitope as, or competes for binding with, a reference anti-YFV antibody by using routine methods available in the art. For example, to determine if a test antibody binds to the same epitope as a reference YFV antibody of the disclosure, the reference antibody is allowed to bind to a YFV protein or peptide under saturating conditions. Next, the ability of a test antibody to bind to the YFV molecule is assessed. If the test antibody is able to bind to YFV following saturation binding with the reference anti-YFV antibody, it can be concluded that the test antibody binds to a different epitope than the reference anti-YFV antibody. On the other hand, if the test antibody is not able to bind to the YFV molecule following saturation binding with the reference anti-YFV antibody, then the test antibody may bind to the same epitope as the epitope bound by the reference anti-YFV antibody of the disclosure.

To determine if an antibody competes for binding with a reference anti-YFV antibody, the above-described binding methodology is performed in two orientations: In a first orientation, the reference antibody is allowed to bind to a YFV molecule under saturating conditions followed by assessment of binding of the test antibody to the YFV molecule. In a second orientation, the test antibody is allowed to bind to a YFV molecule under saturating conditions followed by assessment of binding of the reference antibody to the YFV molecule. If, in both orientations, only the first (saturating) antibody is capable of binding to the YFV molecule, then it is concluded that the test antibody and the reference antibody compete for binding to YFV. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. (1990) 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The disclosure encompasses a human YFV monoclonal antibody conjugated to a therapeutic moiety ("immunoconjugate"), such as an agent that is capable of reducing the severity of primary infection with YFV, or to ameliorate at least one symptom associated with YFV infection, including fever, muscle pains, headache, vomiting, diarrhea, bleeding, or the severity thereof. Such an agent may be a second different antibody to YFV, or a vaccine. The type of therapeutic moiety that may be conjugated to the anti-YFV antibody will take into account the condition to be treated and the desired therapeutic effect to be achieved. Alternatively, if the desired therapeutic effect is to treat the sequelae or symptoms associated with YFV infection, or any other condition resulting from such infection, such as, but not limited to, disseminated intravascular coagulation, acute kidney failure, and acute respiratory distress syndrome, it may be advantageous to conjugate an agent appropriate to treat the sequelae or symptoms of the condition, or to alleviate any side effects of the antibodies of the disclosure. Examples of suitable agents for forming immunoconjugates are known in the art, see for example, WO 05/103081.

Multi-Specific Antibodies

The antibodies of the present disclosure may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity.

Therapeutic Administration and Formulations

The disclosure provides therapeutic compositions comprising the inventive anti-YFV antibodies or antigen-binding fragments thereof. The administration of therapeutic compositions in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of each of the antibodies of the disclosure may vary depending upon the age and the size of a subject to be administered, target disease, conditions, route of administration, and the like. When the antibodies of the present disclosure are used for treating a YFV infection, or for treating one or more symptoms associated with a YFV infection, such as the fever, nausea, or muscle aches associated with a YFV infection in a patient, or for lessening the severity of the disease, it is advantageous to administer each of the antibodies of the present disclosure intravenously or subcutaneously. Normally, each of the antibodies would be administered at a single dose of about 0.01 to about 30 mg/kg body weight, more preferably about 0.1 to about 20 mg/kg body weight, or about 0.1 to about 15 mg/kg body weight, or about 0.02 to about 7 mg/kg body weight, about 0.03 to about 5 mg/kg body weight, or about 0.05 to about 3 mg/kg body weight, or about 1 mg/kg body weight, or about 3.0 mg/kg body weight, or about 10 mg/kg body weight, or about 20 mg/kg body weight. Multiple doses may be administered as necessary. Depending on the severity of the condition, the frequency and the duration of the treatment can be adjusted. In certain embodiments, the antibodies or antigen-binding fragments thereof of the disclosure can be administered as an initial dose of at least about 0.1 mg to about 800 mg, about 1 to about 600 mg, about 5 to about 300 mg, or about 10 to about 150 mg, to about 100 mg, or to about 50 mg. In certain embodiments, the initial dose may be followed by administration of a second or a plurality of subsequent doses of the antibodies or antigen-binding fragments thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings {e.g., oral mucosa, nasal mucosa, rectal and intestinal mucosa, etc.) and may be administered together with other biologically active agents. Administration can be systemic or local. It may be delivered as an aerosolized formulation (See US2011/0311515 and US2012/0128669). The delivery of agents useful for treating respiratory diseases by inhalation is becoming more widely accepted (See A. J. Bitonti and J. A. Dumont, (2006), Adv. Drug Deliv. Rev, 58:1 106-1 1 18). In addition to being effective at treating local pulmonary disease, such a delivery mechanism may also be useful for systemic delivery of antibodies (See Maillet et al. (2008), Pharmaceutical Research, Vol. 25, No. 6, 2008).

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present disclosure include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Administration Regimens

In some embodiments, a therapeutically effective amount of an anti-YFV antibody or antigen-binding fragment thereof is provided to a subject in feed thereof, e.g., infected with YFV or at risk for infection with YFV. By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

According to certain embodiments, multiple doses of an antibody to YFV may be administered to a subject over a defined time course. The methods according to this aspect of the disclosure comprise sequentially administering to a subject multiple doses of an antibody to YFV. As used herein, "sequentially administering" means that each dose of antibody to YFV is administered to the subject at a different point in time, e.g., on different days separated by a predetermined interval (e.g., hours, days, weeks or months). The present disclosure includes methods which comprise sequentially administering to the patient a single initial dose of an antibody to YFV, followed by one or more secondary doses of the antibody to YFV and optionally followed by one or more tertiary doses of the antibody to YFV.

The terms "initial dose," "secondary doses," and "tertiary doses," refer to the temporal sequence of administration of the antibody to YFV. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of antibody to YFV, but generally may differ from one another in terms of frequency of administration. In certain embodiments, however, the amount of antibody to YFV contained in the initial, secondary and/or tertiary doses vary from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antibody to YFV which is administered to a patient prior to the administration of the very next dose in the sequence with no intervening doses.

The methods according to this aspect of the disclosure may comprise administering to a patient any number of secondary and/or tertiary doses of an antibody to YFV. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Accordingly, in certain embodiments are provided pharmaceutical compositions comprising: one or more of the inventive antibodies or antigen-binding fragments thereof disclosed herein and throughout and a pharmaceutically acceptable carrier and/or one or more excipients. In certain other embodiments are provided pharmaceutical compositions comprising: one or more nucleic acid sequences encoding one or more inventive antibodies or antigen-binding fragments thereof; or one or more the expression vectors harboring such nucleic acid sequences; and a pharmaceutically acceptable carrier and/or one or more excipients.

Therapeutic Uses of the Antibodies

The anti-YFV antibodies disclosed herein may be used to treat a subject with YFV and/or prevent YFV infection.

As used herein, the terms "treat," "treatment" and "treating" refer to the reduction or amelioration of the progression, severity, and/or duration of a YFV infection, or a symptom or condition related thereto (such as fever, chills, headache, low back pain, myalgia, loss of appetite, nausea, vomiting, fatigue, or a combination thereof) resulting from the administration of one or more therapies (including, but not limited to, the administration of one or more prophylactic or therapeutic agents). In certain embodiments, such terms refer to the reduction or inhibition of the replication of YFV, the inhibition or reduction in the spread of YFV to other subjects, the inhibition or reduction of infection of a cell with YFV, or the amelioration of one or more symptoms associated with a YFV infection.

As used herein, the terms "prevent," "preventing," and "prevention" refer to the prevention or inhibition of the development or onset of a YFV infection or condition related thereto in a subject, the prevention or inhibition of the progression of a YFV infection or a condition related thereto resulting from the administration of a therapy (e.g., a prophylactic or therapeutic agent), the prevention of a symptom of a YFV infection or condition related thereto, or the administration of a combination of therapies (e.g., a combination of prophylactic or therapeutic agents). As used herein, the terms "ameliorate" and "alleviate" refer to a reduction or diminishment in the severity a condition or any symptoms thereof.

Due to their binding to and interaction with YFV, it is believed that the inventive antibodies and antigen-binding fragments thereof are useful—without wishing to be bound to any theory—for preventing fusion of the virus with the host cell membrane, for preventing cell to cell virus spread, and for inhibition of syncytia formation. Alternatively, the antibodies of the present disclosure may be useful for ameliorating at least one symptom associated with the infection, such as fever, diarrhea, and bleeding, or for lessening the severity, duration, and/or frequency of the infection. The antibodies of the disclosure are also contemplated for prophylactic use in patients at risk for developing or acquiring a YFV infection. It is contemplated that the antibodies of the disclosure may be used alone, or in conjunction with a second agent, or third agent for treating YFV infection, or for alleviating at least one symptom or complication associated with the YFV infection, such as fever, nausea, or muscle aches associated with, or resulting from such an infection. The second or third agents may be delivered concurrently with the antibodies of the disclosure, or they may be administered separately, either before or after the antibodies of the disclosure. The second or third agent may be an anti-viral, an NSAID or other agents to reduce fever or pain, another second but different antibody that specifically binds YFV, an agent (e.g. an antibody) that binds to another YFV antigen, a vaccine against YFV, and an siRNA specific for a YFV antigen.

In yet a further embodiment of the disclosure the present antibodies are used for the preparation of a pharmaceutical composition for treating patients suffering from a YFV infection. In yet another embodiment of the disclosure the present antibodies are used for the preparation of a pharmaceutical composition for reducing the severity of a primary infection with YFV, or for reducing the duration of the infection, or for reducing at least one symptom associated with the YFV infection. In a further embodiment of the disclosure the present antibodies are used as adjunct therapy with any other agent useful for treating an YFV infection, including an antiviral, a toxoid, a vaccine, a second YFV antibody, or any other antibody specific for a YFV antigen, or any other palliative therapy known to those skilled in the art.

Accordingly, in certain embodiments are provided methods of treating or preventing a YFV infection, or at least one symptom associated with YFV infection, comprising administering to a patient in need thereof or suspected of being in need thereof one or more of the inventive antibodies or antigen-binding fragments thereof disclosed herein and throughout, such as, e.g., one or more of the anti-YFV antibodies disclosed in Table 3, such that the YFV infection is treated or prevented, or the at least one symptom associated with YFV infection is treated, alleviated, or reduced in severity.

In certain other embodiments are provided methods of treating or preventing a YFV infection, or at least one symptom associated with YFV infection, comprising administering to a patient in need thereof or suspected of being in need thereof a nucleic acid sequence encoding one or more of the inventive antibodies or antigen-binding fragments thereof, such nucleic acid sequence encoding an amino acid sequence disclosed in Table 3 and compliments thereof, such that the YFV infection is treated or prevented, or the at least one symptom associated with YFV infection is treated, alleviated, or reduced in severity.

In additional embodiments are provided methods of treating or preventing a YFV infection, or at least one symptom associated with YFV infection, comprising administering to a patient in need thereof or suspected of being in need thereof a host cell harboring a nucleic acid sequence or an expression vector comprising such a nucleic acid sequence, wherein such nucleic acid sequences encode an amino acid sequence selected from sequences disclosed in Table 3 and compliments thereof, such that the YFV infection is treated or prevented, or the at least one symptom associated with YFV infection is treated, alleviated, or reduced in severity.

In additional embodiments are provided methods of treating or preventing a YFV infection, or at least one symptom associated with YFV infection, comprising administering to a patient in need thereof or suspected of being in need thereof a pharmaceutical composition comprising either: one or more of the inventive antibodies or antigen-binding fragments thereof as disclosed in Table 3; one or more nucleic acid sequences or an expression vectors comprising such a nucleic acid sequence, wherein such nucleic acid sequences encode amino acid sequences selected from sequences disclosed in Table 3 and compliments thereof; one or more host cells harboring one or more nucleic acid sequences or expression vectors comprising such one or more nucleic acid sequences, wherein such nucleic acid sequences encode amino acid sequences selected from sequences disclosed in Table 3 and compliments thereof; and a pharmaceutically acceptable carrier and/or one or more excipients, such that the YFV infection is treated or prevented, or the at least one symptom associated with YFV infection is treated, alleviated, or reduced in severity.

In certain embodiments are provided methods of treating or preventing a YFV infection, or at least one symptom associated with said YFV infection, comprising administering to a patient in need thereof or suspected of being in need thereof one or more of the inventive antibodies or antigen-binding fragments thereof disclosed herein and throughout, such as, e.g., one or more of the anti-YFV antibodies disclosed in Table 3, such that the YFV infection is treated or prevented, or the at least one symptom associated with YFV infection is treated, alleviated, or reduced in severity.

In certain other embodiments are provided methods of treating or preventing a YFV infection, or at least one symptom associated with said YFV infection, comprising administering to a patient in need thereof or suspected of being in need thereof a nucleic acid sequence encoding one or more of the inventive antibodies or antigen-binding fragments thereof, such nucleic acid sequences encoding amino acid sequences disclosed in Table 3 and compliments thereof, such that the YFV infection is treated or prevented, or the at least one symptom associated with YFV infection is treated, alleviated, or reduced in severity.

In additional embodiments are provided methods of treating or preventing a YFV infection, or at least one symptom associated with said YFV infection, comprising administering to a patient in need thereof or suspected of being in need thereof a host cell harboring a nucleic acid sequence or an expression vector comprising such a nucleic acid sequence, wherein such nucleic acid sequences encode amino acid sequences selected from sequences disclosed in Table 3 and compliments thereof, such that the YFV infection is treated or prevented, or the at least one symptom associated with YFV infection is treated, alleviated, or reduced in severity.

In additional embodiments are provided methods of treating or preventing a YFV infection, or at least one symptom associated with said YFV infection, comprising administering to a patient in need thereof or suspected of being in need thereof a pharmaceutical composition comprising either: one or more of the inventive antibodies or antigen-binding fragments thereof as disclosed in Table 3; one or more nucleic acid sequences or an expression vectors comprising such a nucleic acid sequence, wherein such nucleic acid sequences encode amino acid sequences selected from sequences disclosed in Table 3 and compliments thereof; one or more host cells harboring one or more nucleic acid sequences or an expression vectors comprising such one or more nucleic acid sequences, wherein such nucleic acid sequences encode amino acid sequences selected from sequences disclosed in Table 3 and compliments thereof; and a pharmaceutically acceptable carrier and/or one or more excipients, such that the YFV infection is treated or prevented, or the at least one symptom associated with YFV infection is treated, alleviated, or reduced in severity.

Combination Therapies

As noted above, according to certain embodiments, the disclosed methods comprise administering to the subject one or more additional therapeutic agents in combination with an antibody to YFV. As used herein, the expression "in combination with" means that the additional therapeutic agents are administered before, after, or concurrent with the pharmaceutical composition comprising the anti-YFV antibody. The term "in combination with" also includes sequential or concomitant administration of the anti-YFV antibody and a second therapeutic agent.

For example, when administered "before" the pharmaceutical composition comprising the anti-YFV antibody, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the anti-YFV antibody. When administered "after" the pharmaceutical composition comprising the anti-YFV antibody, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the anti-YFV antibodies. Administration "concurrent" or with the pharmaceutical composition comprising the anti-YFV antibody means that the additional therapeutic agent is administered to the subject in a separate dosage form within less than 5 minutes (before, after, or at the same time) of administration of the pharmaceutical composition comprising the anti-YFV antibody, or administered to the subject as a single combined dosage formulation comprising both the additional therapeutic agent and the anti-YFV antibody.

Combination therapies may include an anti-YFV antibody of the disclosure and any additional therapeutic agent that may be advantageously combined with an antibody of the disclosure, or with a biologically active fragment of an antibody of the disclosure.

For example, a second or third therapeutic agent may be employed to aid in reducing the viral load in the liver, such as an antiviral. The antibodies may also be used in conjunction with other therapies, as noted above, including a toxoid, a vaccine specific for YFV, a second antibody specific for YFV, or an antibody specific for another YFV antigen.

Diagnostic Uses of the Antibodies

The inventive anti-YFV antibodies and antigen-binding fragments thereof may also be used to detect and/or measure YFV in a sample, e.g., for diagnostic purposes. It is envisioned that confirmation of an infection thought to be caused by YFV may be made by measuring the presence of the virus through use of any one or more of the antibodies of the disclosure. Exemplary diagnostic assays for YFV may comprise, e.g., contacting a sample, obtained from a patient, with an anti-YFV antibody of the disclosure, wherein the YFV antibody is labeled with a detectable label or reporter molecule or used as a capture ligand to selectively isolate the virus containing the protein from patient samples. Alternatively, an unlabeled YFV antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, ß-galactosidase, horseradish peroxidase, or luciferase. Specific exemplary assays that can be used to detect or measure YFV in a sample include enzyme-linked immunosorbent assay (ELISA), radioimmunoassay (RIA), and fluorescence-activated cell sorting (FACS).

Samples that can be used in YFV diagnostic assays according to the present disclosure include any tissue or fluid sample obtainable from a patient, which contains detectable quantities of YFV protein, or fragments thereof, under normal or pathological conditions. Generally, levels of YFV in a particular sample obtained from a healthy patient (e.g., a patient not afflicted with a disease or condition associated with the presence of YFV) will be measured to initially establish a baseline, or standard, level of YFV protein. This baseline level of YFV can then be compared against the levels of YFV measured in samples obtained from individuals suspected of having an YFV infection, or symptoms associated with such infection.

EXAMPLES

The human antibody response to YFV was comprehensively profiled by isolating and characterizing 152 YFV-specific monoclonal antibodies from the memory B cells of two flavivirus-naive donors following immunization with YFV-17D, and these antibodies were then used to map the antigenic topology of YFV. The anti-YFV antibodies obtained were found to bind several antigenic sites, most commonly targeting an epitope within or proximal to the FL of Domain II of the YFV E protein and, thus, providing support for the development of YFV antibodies that target Domain II. However, a second less common class of antibodies with highly potent neutralizing activity were found to target DIII of the virus. Such DIII-directed antibodies may be particularly valuable in the context of therapeutic application of monoclonal antibodies or cocktails as this epitope is subdominant in the natural immune response. Taken together, these results have implications for the design and evaluation of YFV vaccine and antibody-based therapeutic candidates and offer new options for passive prophylaxis.

Study design: Two flavivirus-naïve healthy adult donors ("Donor 8" and "Donor 9") were immunized with the YFV-17D vaccine (Stamaril; Sanofi) and blood samples were collected at 10, 14, 28, 90, 180, 270, and 360 days post-vaccination. Serum neutralizing activity against YFV-17D appeared in both donors by day 14 post-vaccination and persisted through the course of the study (FIG. 1A). Pre-vaccination sera from both donors lacked reactivity with YFV-17D and showed no detectable neutralizing activity against YFV-17D (data not shown) and also lacked reactivity with E and NS1 proteins from other commonly circulating flaviviruses, i.e., dengue virus serotypes 1-4 (DENV1-4), JEV, TBEV, West Nile virus (WNV) and Zika virus (ZIKV), confirming that both donors were likely flavivirus-naïve at the time of vaccination (data not shown).

Figure 2A:
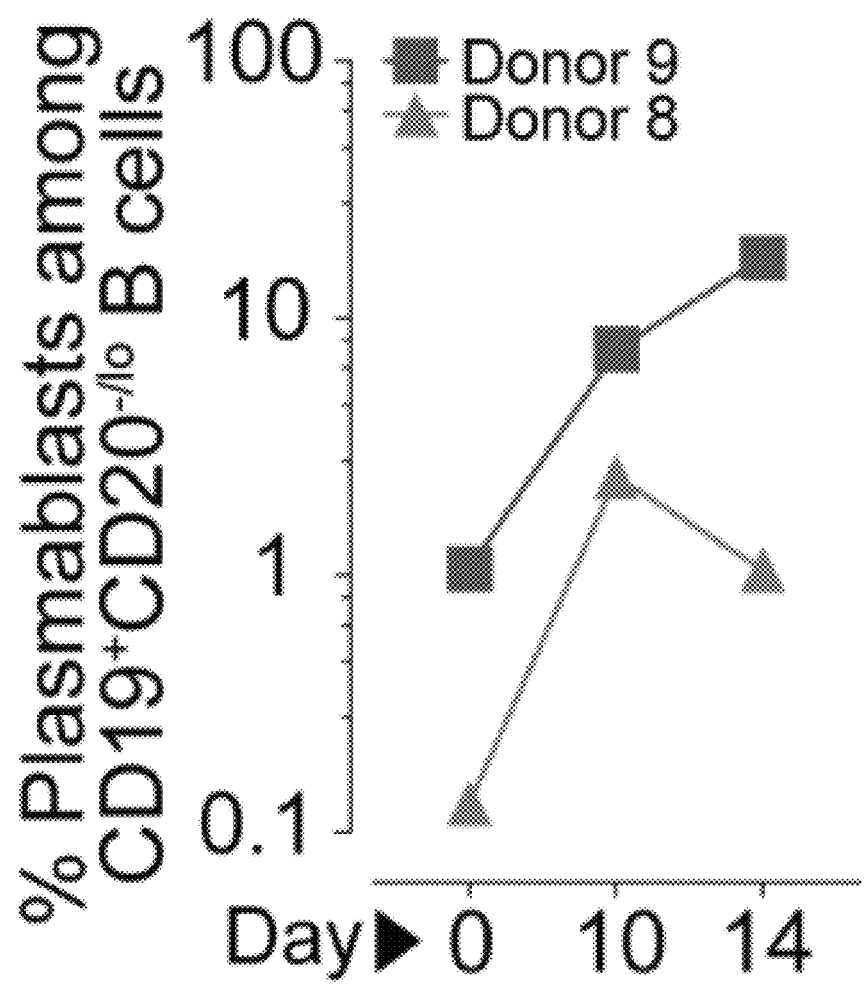

Molecular and Functional Characterization of YFV-17D Induced Plasmablast Response Plasmablast responses in both donors were monitored at 10 and 14 days post-vaccination. In both donors, expanded plasmablast populations were observed at both 10 and 14-day time points that were approximately 10-fold greater than pre-vaccination levels (FIG. 2A). Approximately 300 plasmablasts from each donor were sorted and amplified the corresponding VH and VL regions by single-cell PCR. 161 and 210 natively-paired antibodies were cloned from Donor 8 and Donor 9, respectively, and expressed as full-length IgGs in an engineered strain of Saccharomyces cerevisiae. Sequence analysis showed the plasmablast responses were highly diverse in both donors, with only about 15% of clones belonging to expanded clonal lineages (data not shown). A large fraction of plasmablast-derived antibodies from both donors contained high levels of somatic hypermutation (SHM), suggesting efficient recruitment of MBCs into the PB response (data not shown). The median level of SHM in the PB-derived mAbs was significantly higher on Day 10 than Day 14. Correspondingly, a larger proportion of mAbs cloned from day 14 PBs lacked SHM, suggesting an increased recruitment of cells from the naïve B cell compartment at this time point (data not shown).

Figure 3:
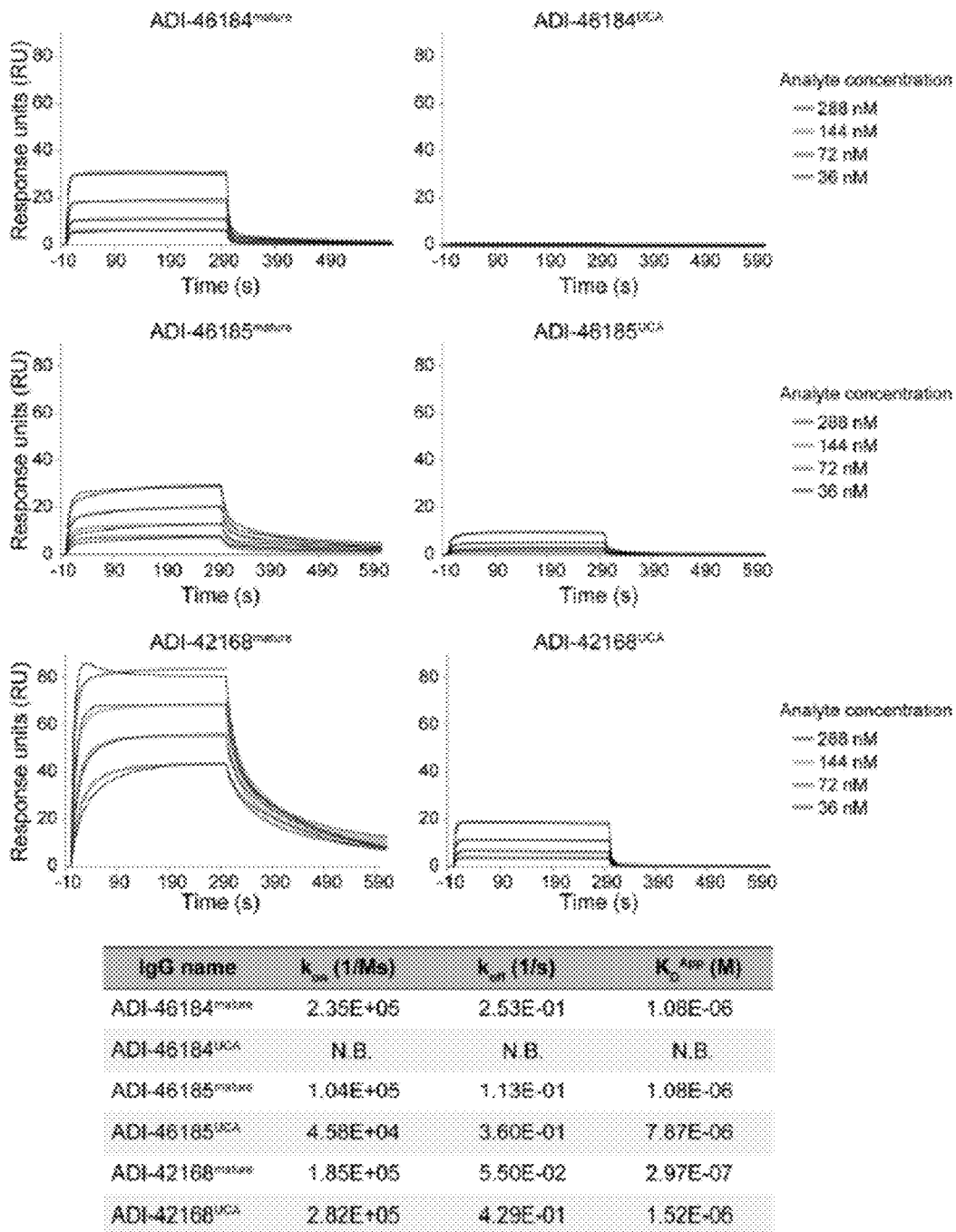
FIG. 3 illustrates the binding activity of germline-reverted plasmablast monoclonal antibodies. Binding traces and affinities of three somatically mutated PB-derived mAbs (ADI-46184, ADI-46185, and ADI-42168) and their corresponding UCAs, as determined by Biacore. UCA, unmutated common ancestor.

To analyze whether the somatic mutations in the PB-derived mAbs contribute to binding activity, inferred unmutated common ancestor (UCA) mAbs were generated from three somatically mutated PB clones and their binding affinities to a recombinant YFV E protein were measured. In all three cases, the UCA mAbs showed substantially reduced binding affinities compared to the mature mAbs, suggesting that somatic mutations in the PB mAbs are important for recognition of YFV E (FIG. 3).

Figure 2B:
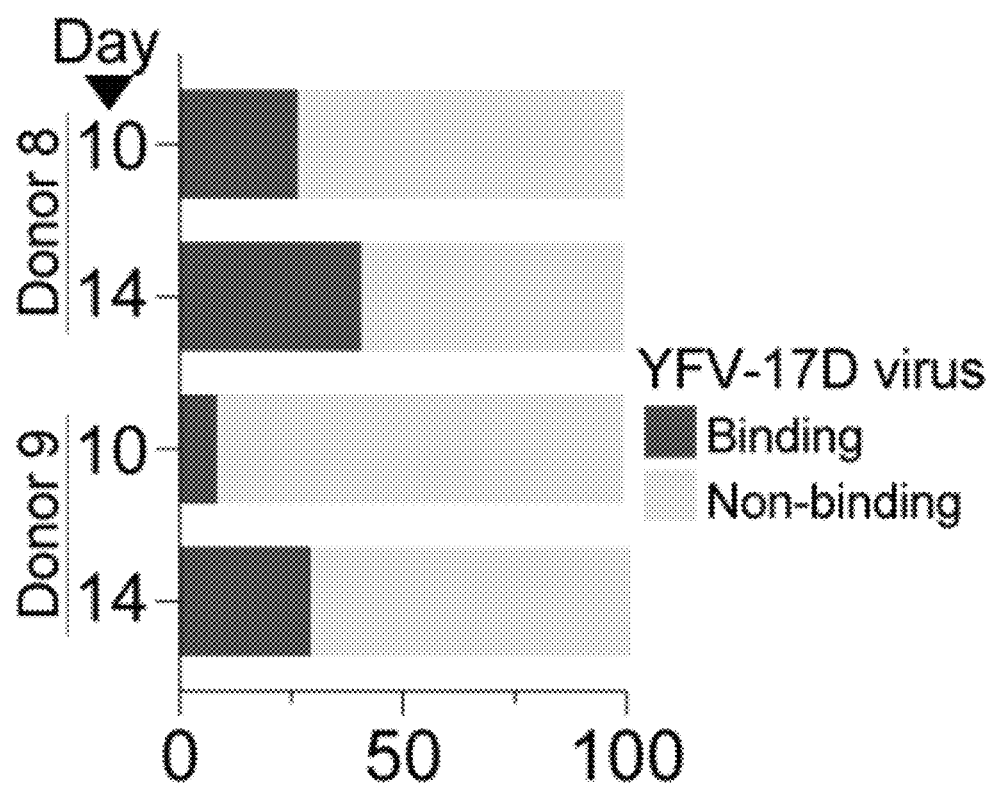
Figure 2C:
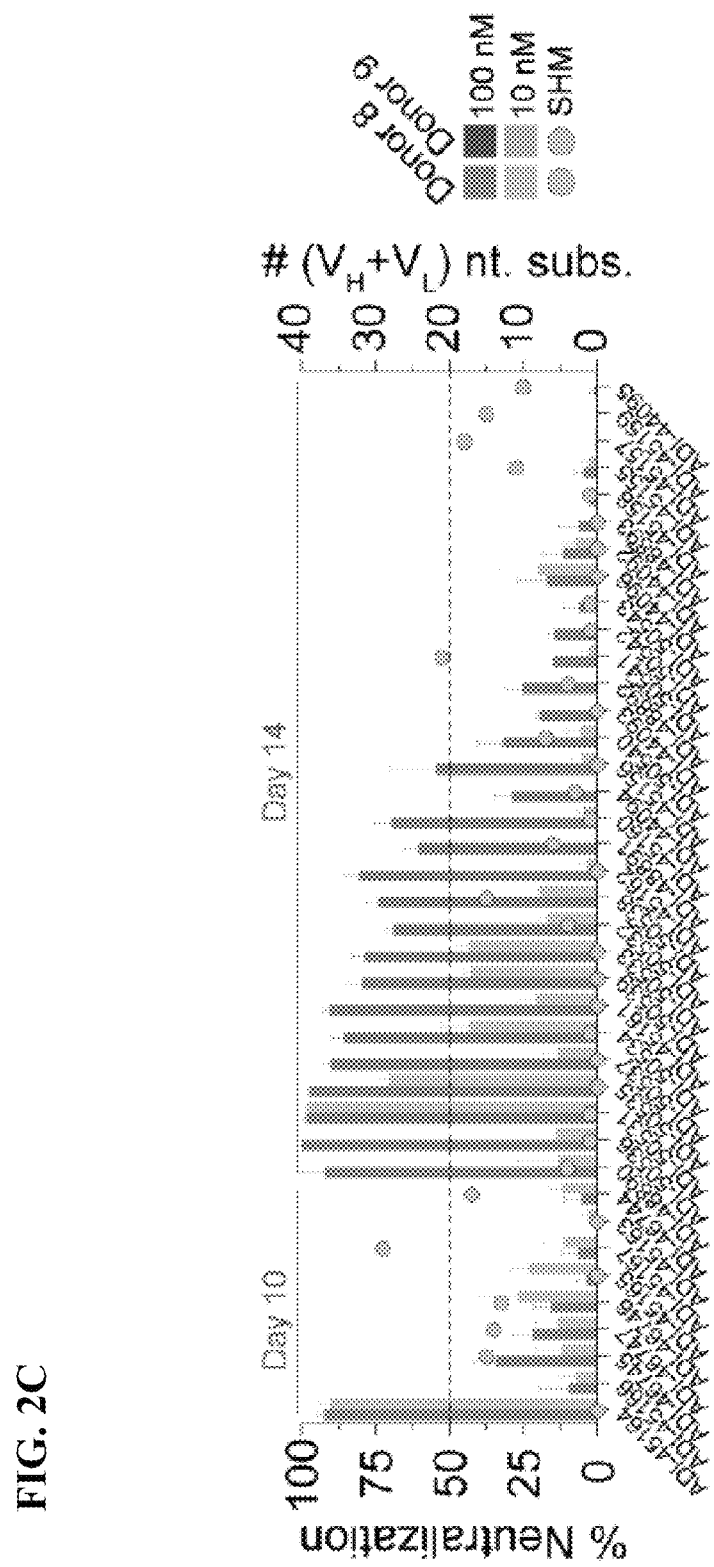
Figure 2D:
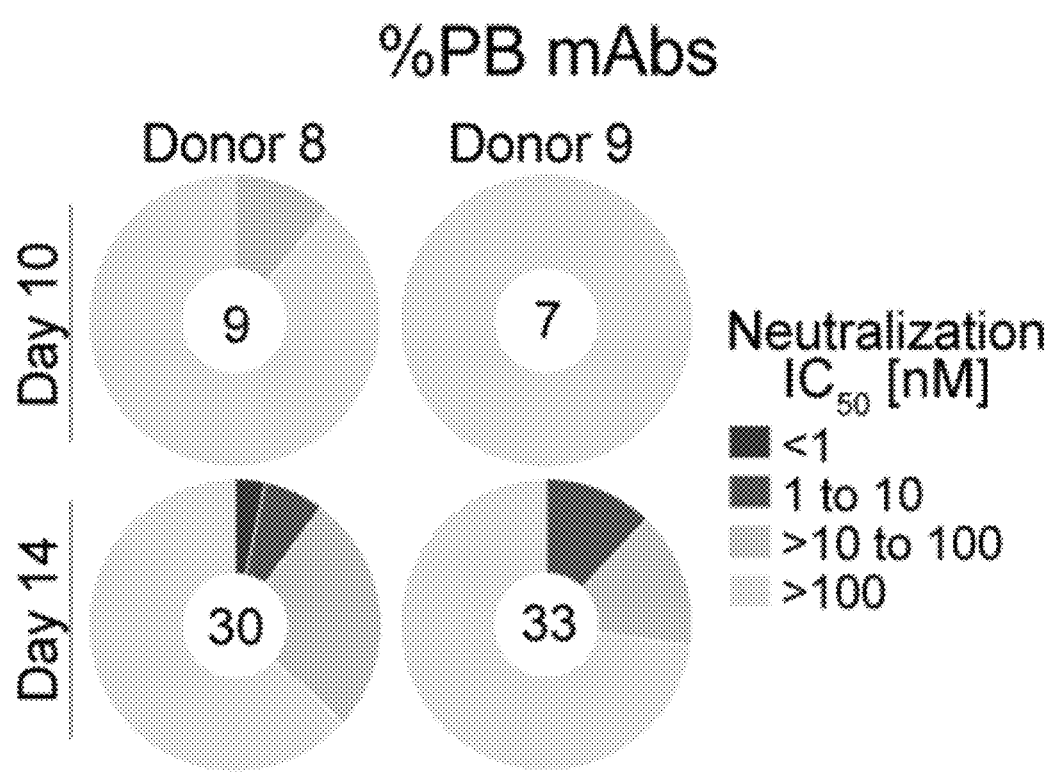
Figure 4:
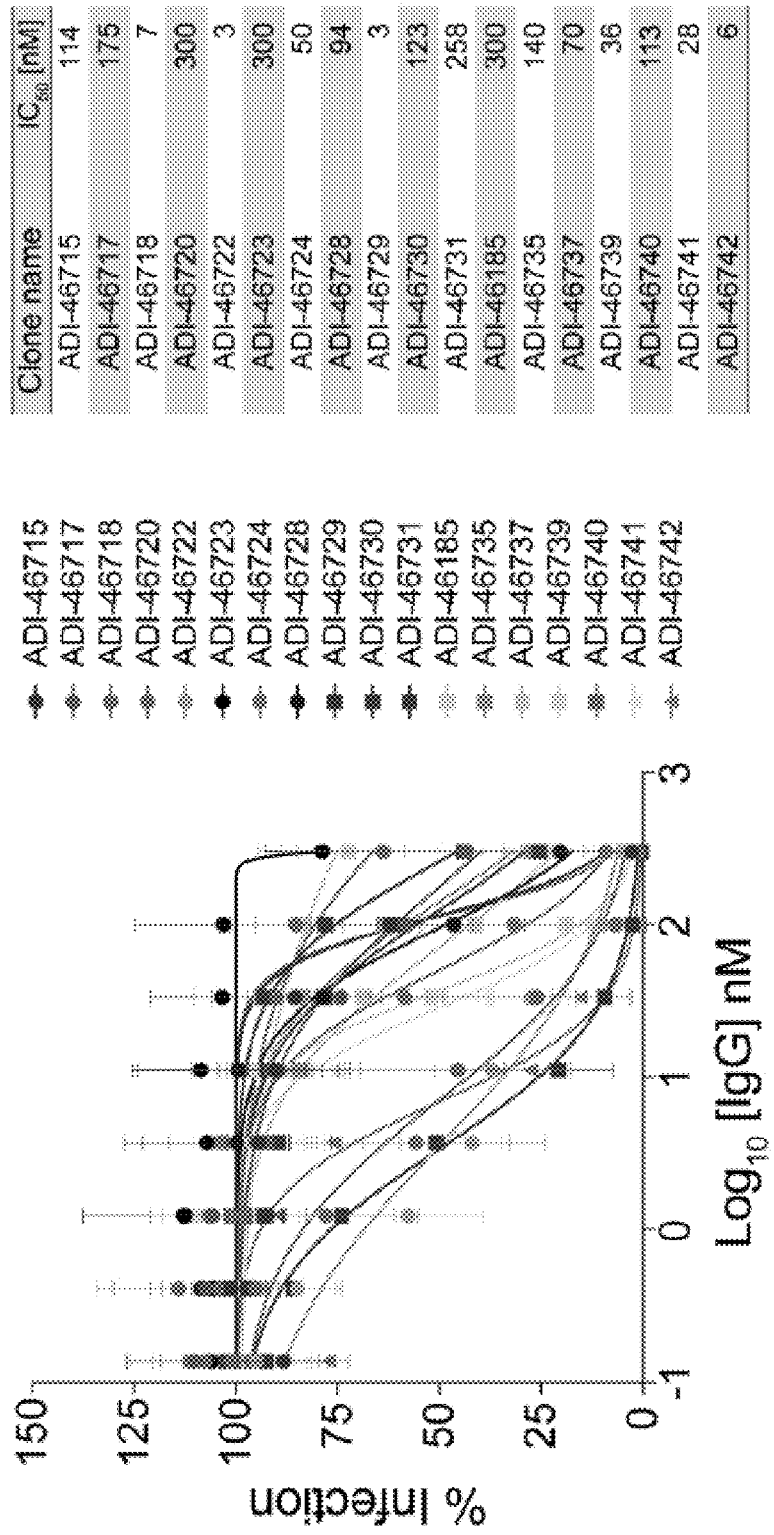
FIG. 4 shows neutralization screening of PB-derived mAbs. Representative YFV-17D neutralization titration curves for PB mAbs screened by micro-titer neutralization assay. Averages±SD (n=6) from two independent experiments are shown.

PB-derived mAbs were then tested for binding reactivity to YFV-17D particles using a sandwich ELISA assay (FIG. 2B). The frequency of YFV-17D binding mAbs isolated from day 10 and 14 PBs ranged from 8-41%. 45 and 46 YFV-17D binding mAbs were recovered from the expanded PB populations in Donor 8 and 9, respectively, and then analyzed the neutralizing activities of the mAbs in a microtiter neutralization assay at 100 and 10 nM concentrations. Neutralizing activities ranged from complete neutralization at 10 nM to no detectable neutralization at 100 nM (FIG. 2C). A higher fraction of mAbs isolated from day 14 PBs displayed neutralizing activity compared to those isolated from day 10 PBs, which is consistent with the increased serum neutralizing activity on day 14 versus day 10 in both donors (data not shown). Neutralization titration experiments on the mAbs displaying at least 50% infection inhibition at 100 nM revealed that 9-12% of YFV-17D binding mAbs isolated from day 14 PBs displayed medium to high neutralizing activity ($IC_{50}s \leq 10$ nM) (FIG. 2D and FIG. 4). Sequence analysis showed that 12.5-33% of the PB-derived nAbs utilized VH4-4/VL1-51 germline gene pairing, suggesting recognition of a common antigenic site (data not shown).

Figure 1B:
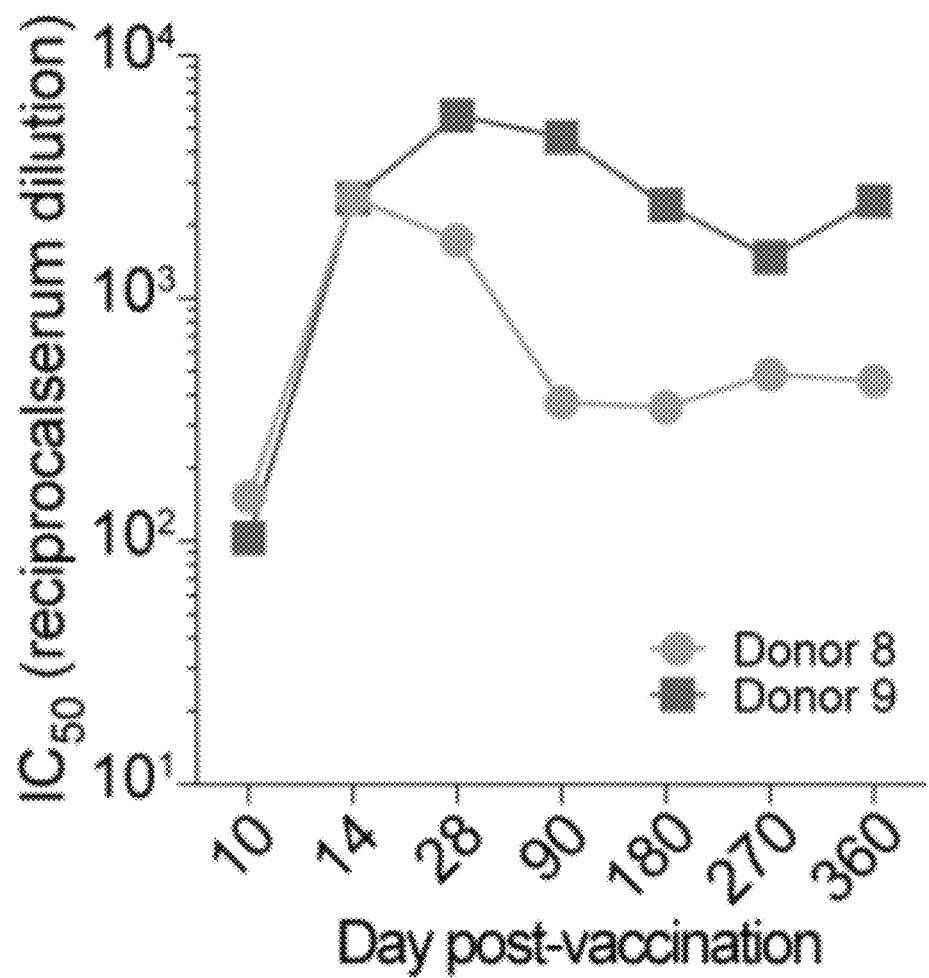

About 50% and 22% of the neutralizing antibodies isolated from donor 8 and 9, respectively, lacked somatic mutations, indicating that YFV-17D neutralizing antibodies are present in the naïve B cell repertoire and suggesting that YFV-17D vaccination induces PB responses that originate from both naïve and MBCs, and only a minority of these B cells encode Abs that display neutralizing activity. See FIGS. 1A and 1B.

Molecular and Functional Characterization of YFV-17D Induced MBC Response

Figure 5A:
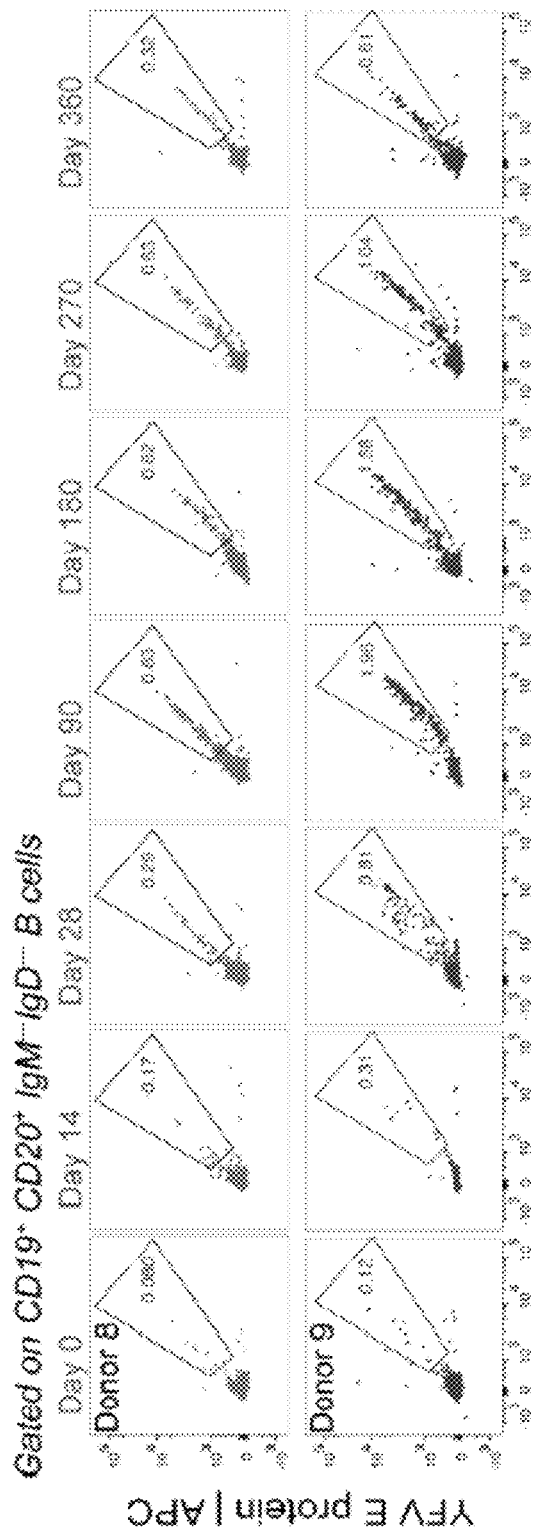
FIGS. 5A and 5B show the presence of $swIg^+$ B cells that display reactivity to YFV-17D.
Figure 5B:
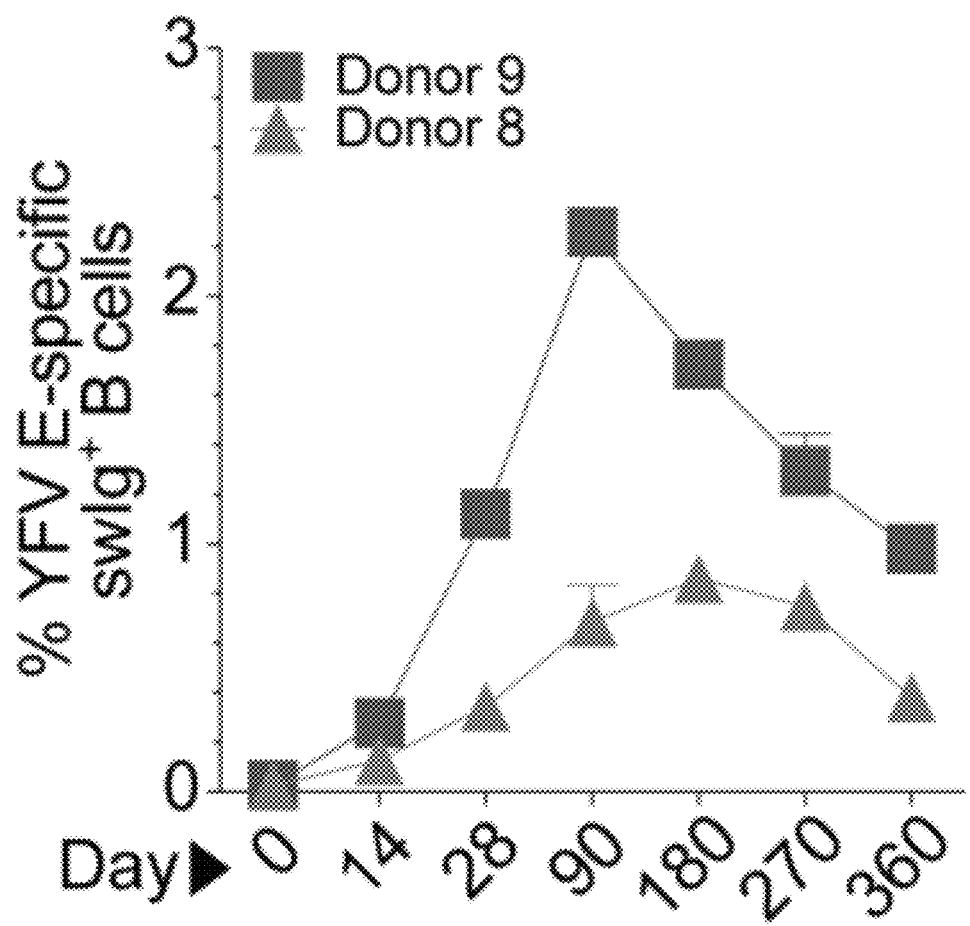

MBC responses in both donors were monitored by collecting PBMCs at days 14, 28, 90, 180, 270, and 360 post-vaccination and purified B cells were stained with a panel of previously described B cell surface markers (CD19, CD20, CD27, IgM, IgD, CD21, and CD71) and a fluorescently-labeled recombinant YFV E protein (FIG. 5A). YFV E-specific swIg+ MBCs emerged in both donors by Days 14-28, peaked between Days 90 and 180, and slowly declined between Days 180 and 360 (FIG. 5B).

Figure 8A:
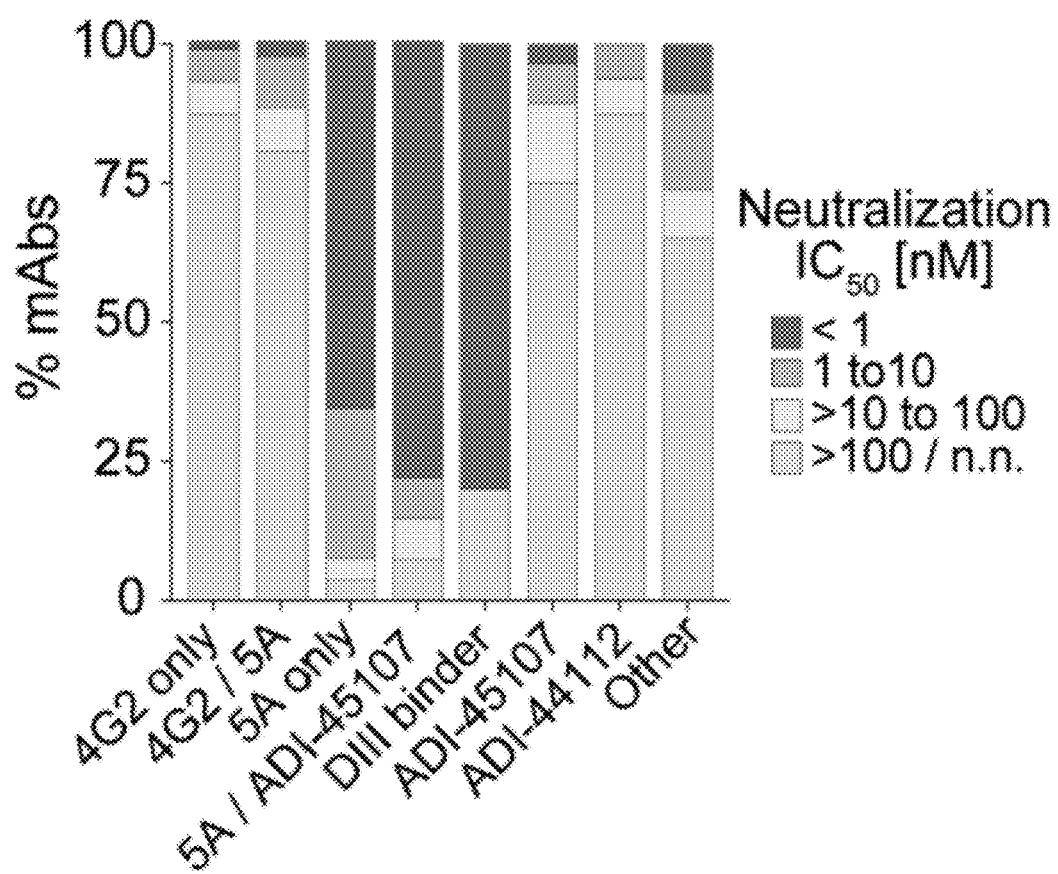
FIG. 8A through 8D illustrate a majority of highly potent neutralizing antibodies recognize FL-proximal epitopes.
Figure 8B:
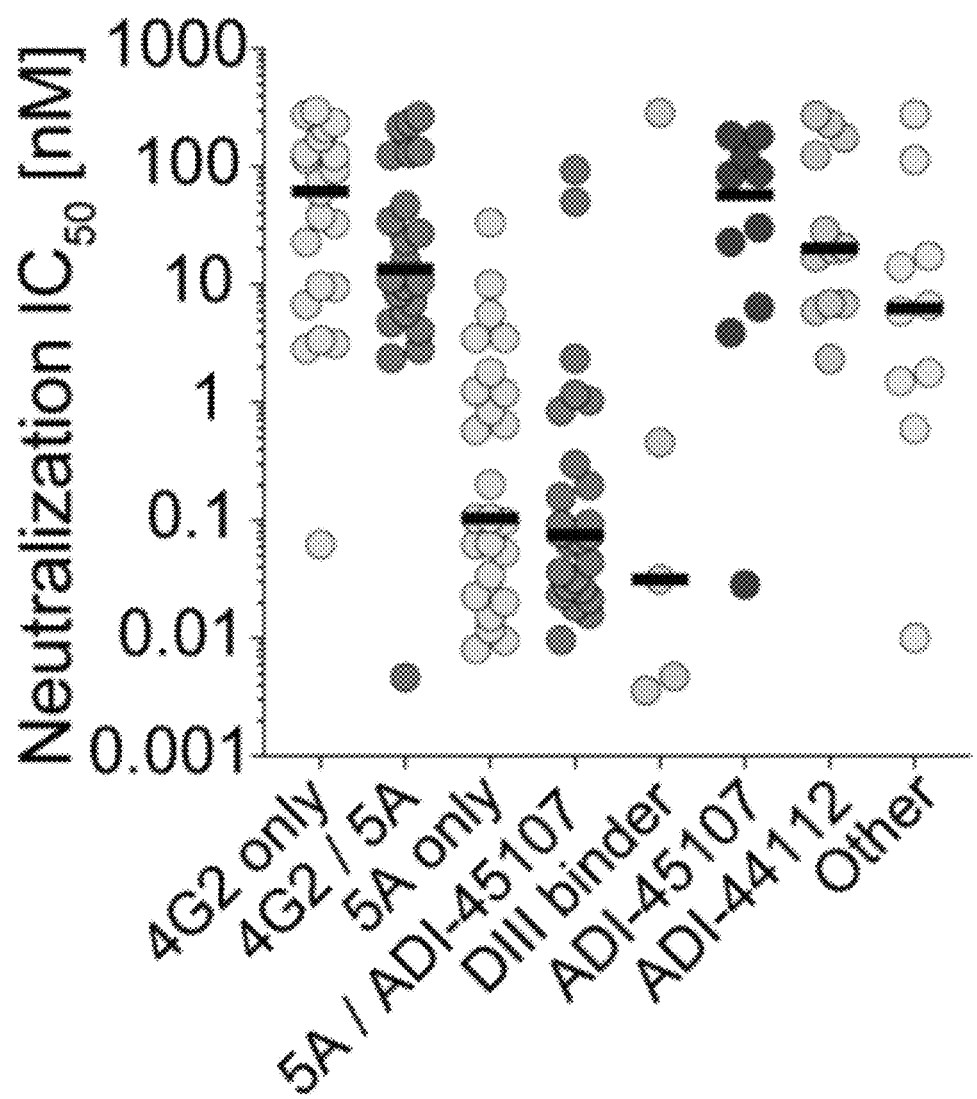

Between 100-400 YFV E-reactive B cells were sorted from both donors at each sampling time point. Naïve B cell-derived non-binding mAbs were captured via the sorting strategy employed but excluded from subsequent analyses. Analysis of the B cell surface markers expressed on the single-cell sorted, YFV E-reactive B cells revealed that the MBC response to YFV E was highly heterogenous at all time points (data not shown). At the earliest sampling time point (day 14), activated naïve B cells and IgM+CD27+MBCs dominated the response in both donors, but these B cell populations waned rapidly over time. By day 90, less than 15% of the YFV E-specific response was comprised of IgM+CD27+MBCs, and by day 360, only about 5% of YFV E-specific B cells belonged to this MBC population (FIG. 8B). In contrast, the swIg+MBC population—which was comprised of both CD27+ and CD27− B cells-expanded between day 14 and day 90 and then remained stable throughout the course of the study. The MBC response observed following YFV-17D vaccination was also observed following natural infection with PUUV (data not shown).

SHM loads, apparent binding affinities ($K_D^{Apps}$), and neutralization potencies of the YFV E-specific mAbs were tracked at each sampling time point. In both donors, the median level of SHM was low at day 14—with over 50% of Abs lacking somatic mutations—and increased gradually over a 6-9-month time period, plateauing in both donors by 9 months post-vaccination, with a median of 9 and 7 nucleotide substitutions in VH for donor 8 and 9, respectively (data not shown). Binding studies with a recombinant YFV E protein showed that the $K_D^{Apps}$ of the MBC-derived mAbs were very weak at early time points and progressively improved for 6-9 months following vaccination (data not shown). On days 14 and 28 post-vaccination, the majority of YFV E-specific mAbs displayed $K_D^{Apps}$ >50 nM, whereas by day 180, about 50% of the YFV E-specific mAbs displayed $K_D^{Apps}$ <5 nM. In parallel with the increase in affinity, the emergence of highly potent neutralizing antibodies ($IC_{50}$<1 nM) were observed beginning at day 90 (data not shown). These neutralizing antibodies were derived from multiple MBC subsets, including atypical IgM+ and/or IgD+ MBCs (data not shown). Table 2 summarizes affinity and neutralization data for the isolated and characterized neutralizing mAbs.

Ongoing B cell activation was assessed by analyzing expression of CD71 and CD21 on YFV E-specific MBCs. CD71 was expressed on 75-85% YFV E-specific B cells at day 14 and remained elevated for about 6 months in both donors (data not shown). In both donors, YFV E-specific CD21$^{lo}$ cells were present at high frequencies on days 14 and 28 post-vaccination, comprising about 40-80% of the YFV E-specific response, and then declined rapidly by day 90. While there was a high degree of overlap between the CD71+ and CD21$^{lo}$ populations, with 50-80% of YFV E-specific activated B cells (defined as CD71+ and/or CD21$^{lo}$) displaying a CD71+CD21$^{lo}$ phenotype at day 14, by day 28-90, the CD71+CD21$^{lo}$ population waned to <50% of the activated B cell response in both donors and the majority of YFV E-specific activated B cells displayed either a CD71+CD21+ or CD71−CD21$^{lo}$ phenotype and were heterogenous with regard to isotype and CD27 expression(data not shown).

Isolation and Characterization of Anti-YFV Antibodies

Approximately 152 neutralizing monoclonal antibodies were isolated and characterized. Antibody variable heavy (VH) and variable light (VL) chain genes were rescued by single-cell PCR. Tiller et al. (2008) J Immunol Methods 329, 112-124. Cognate heavy and light chain pairs were subsequently cloned and expressed as full-length IgGs in an engineered strain of *Saccharomyces cerevisiae* for further characterization. Bornholdt et al., (2016) Science 351, 1078-1083.

Figure 6A:
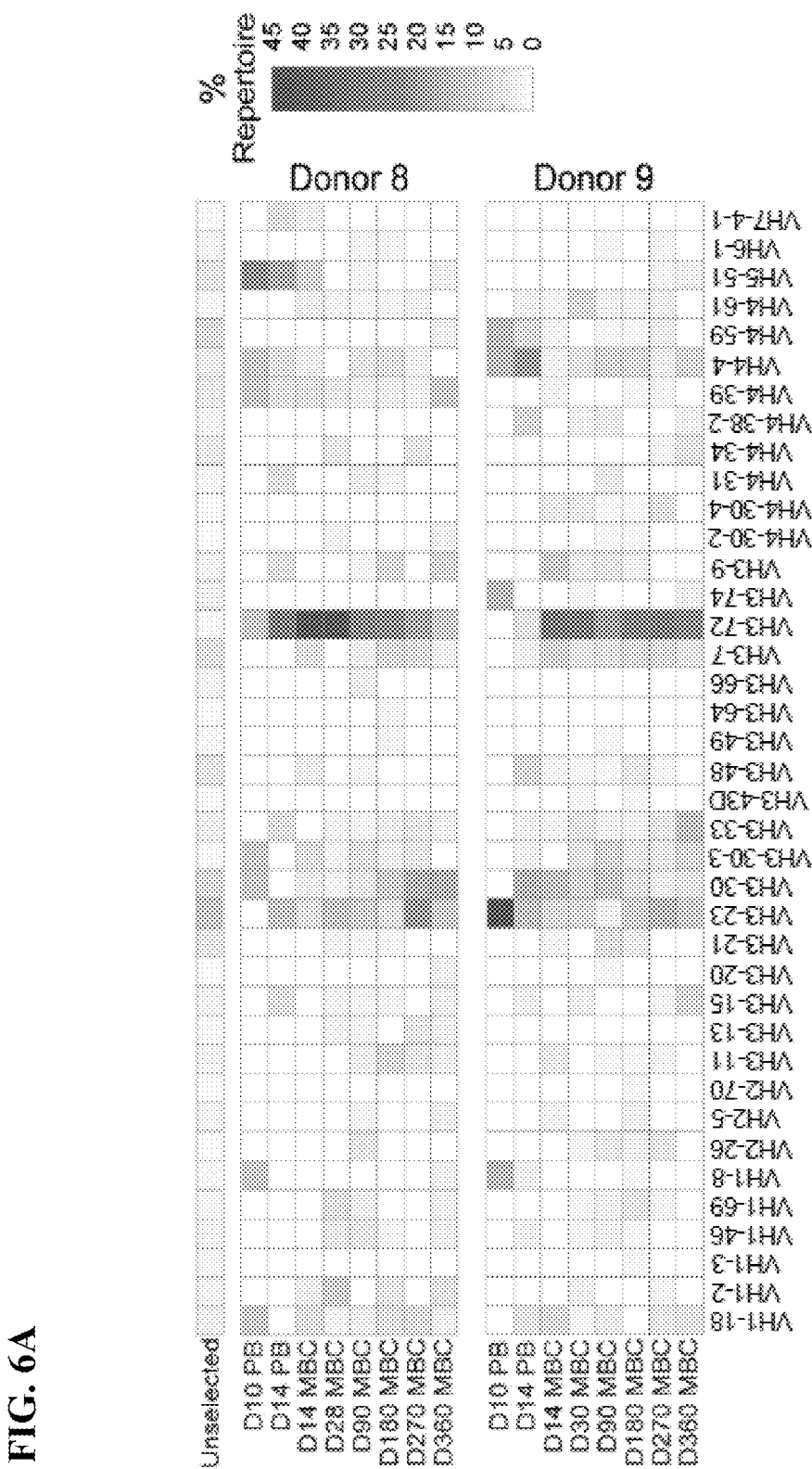
FIG. 6A through 6E illustrate that YFV E-specific antibodies show preferential usage of the VH3-72 germline gene.
Figure 6B:
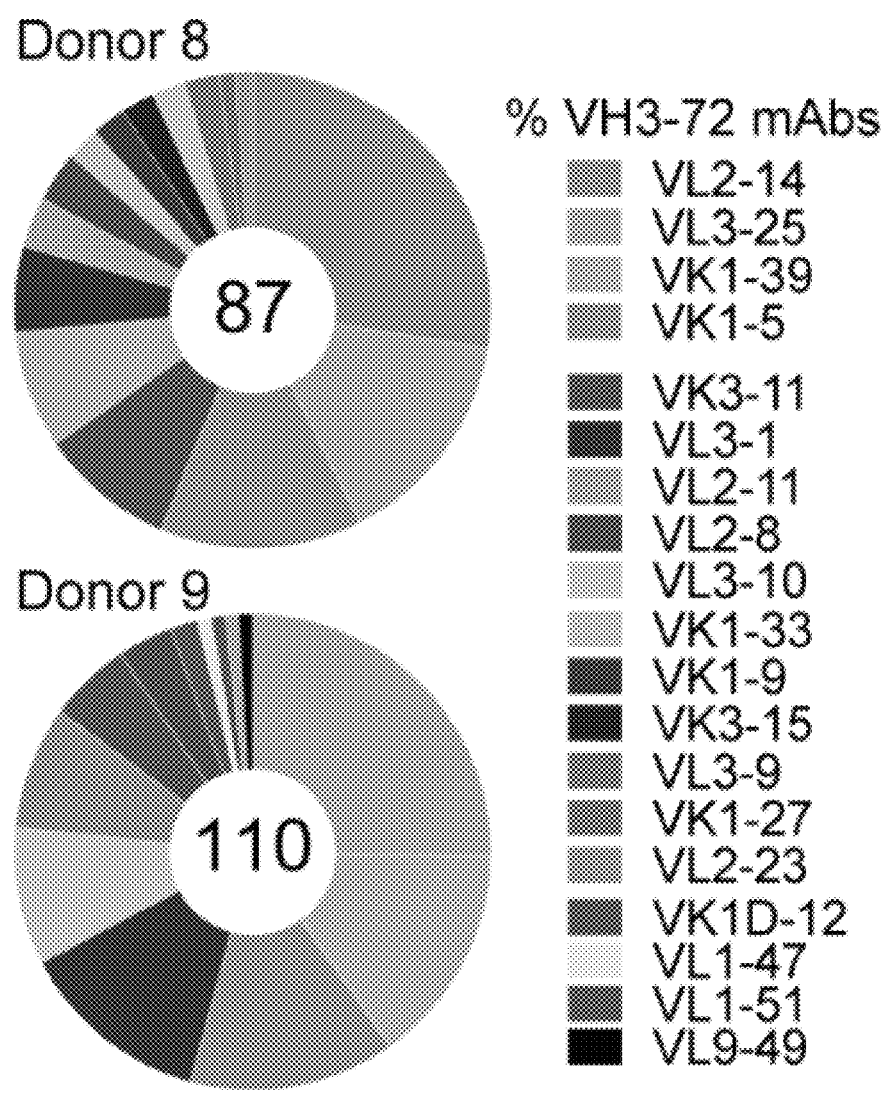
Figure 6C:
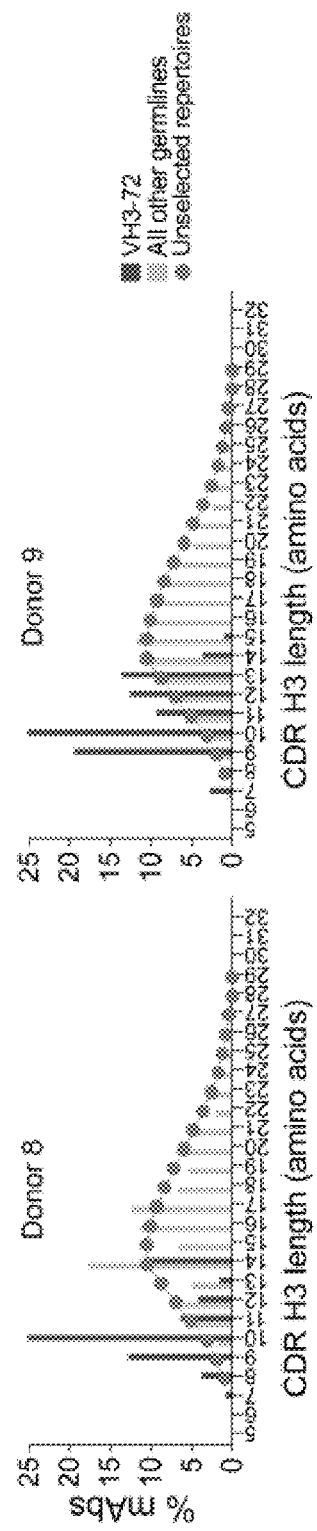
Figure 6D:
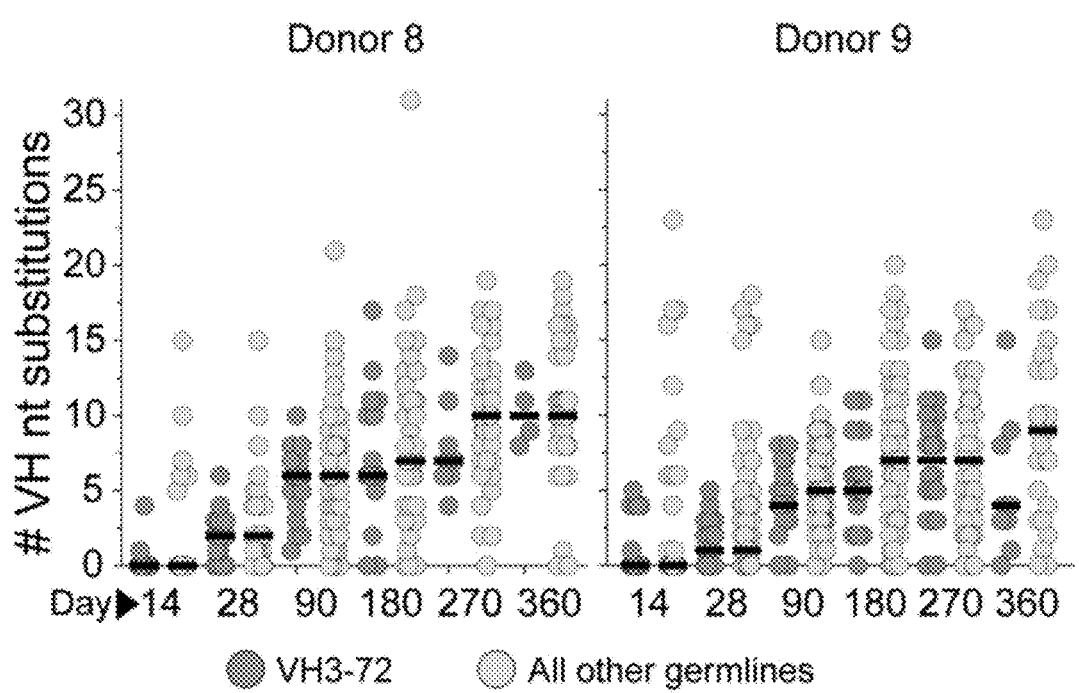
Figure 6E:
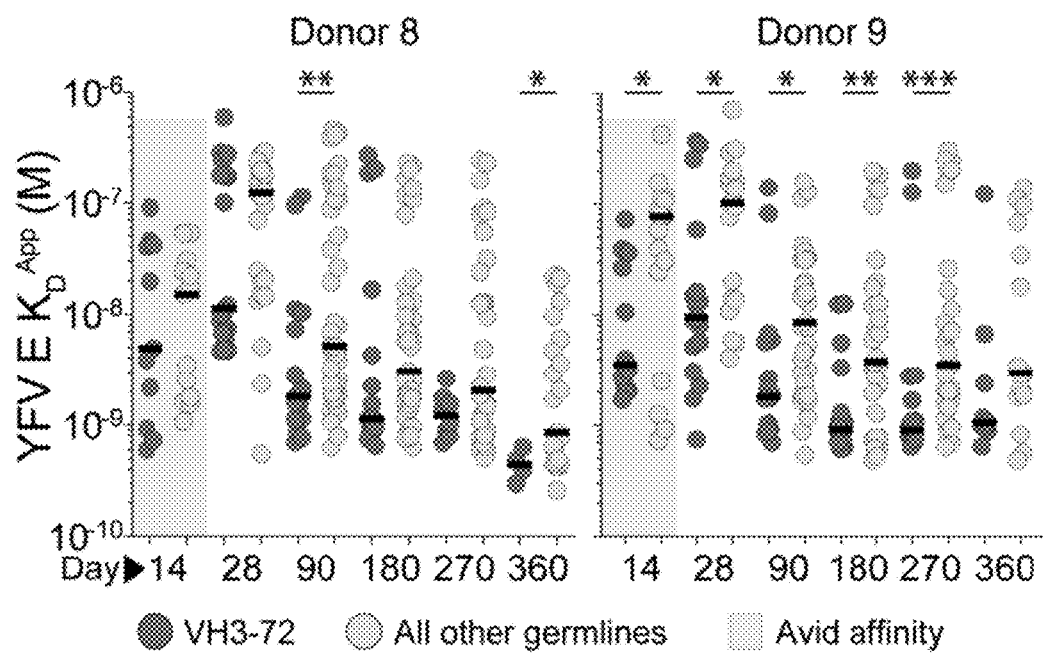

Germline gene usage of the isolated mAbs was analyzed. In both donors, mAbs utilizing the VH3-72 germline gene dominated the response at all time points (FIG. 6A). A large fraction of these mAbs also utilized one of five dominant light chain (LC) germline genes and displayed shorter-than-average heavy chain (HC) complementary determining region 3 (CDRH3) lengths, suggesting a shared mode of antigen recognition (FIG. 6B-C). The binding affinities of the mAbs utilizing VH3-72 were significantly higher than those observed for mAbs utilizing other VH germlines, despite containing similar levels of SHM (FIG. 6D-E). Table 1 summarizes germline usage and number of nucleotide substitutions for isolated mAbs.

Figure 7A:
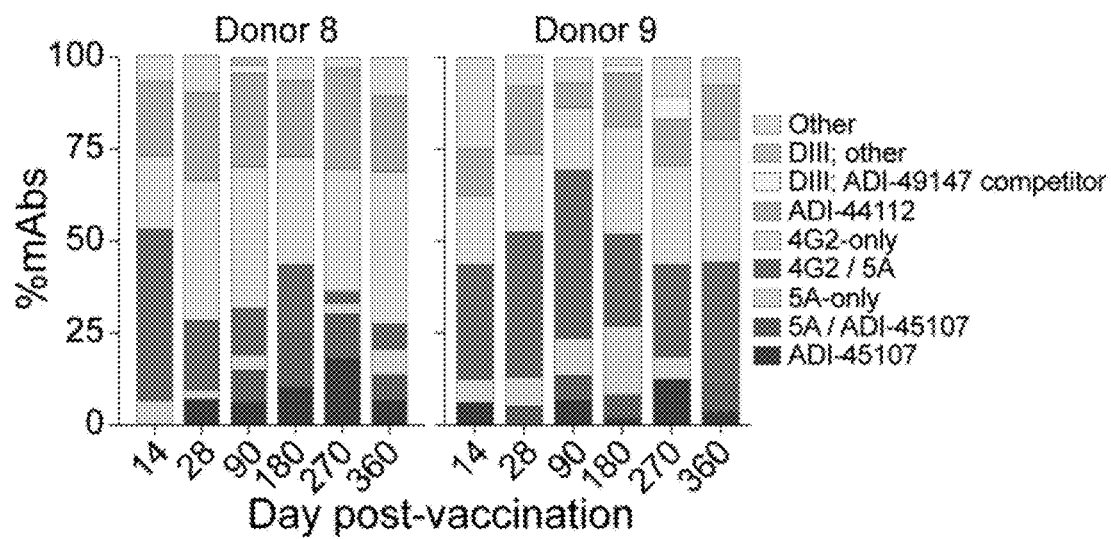
Figure 7B:
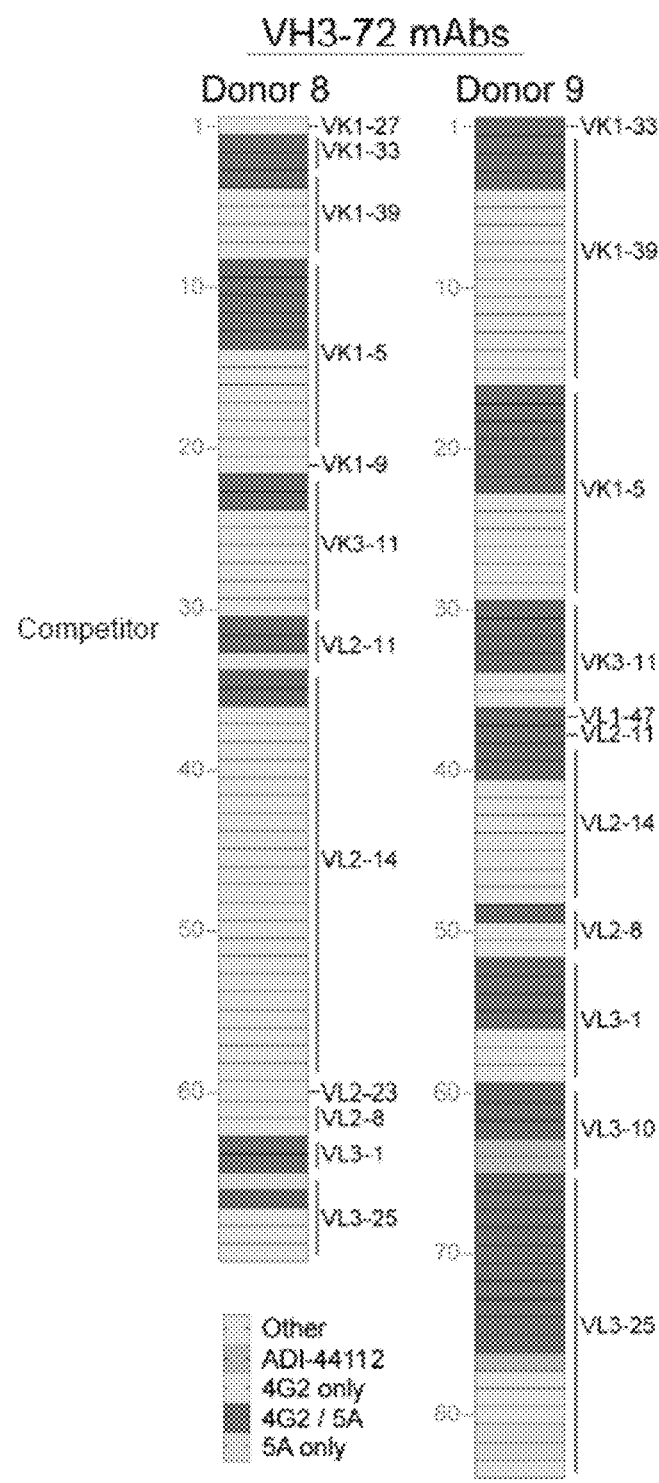
Figure 7C:
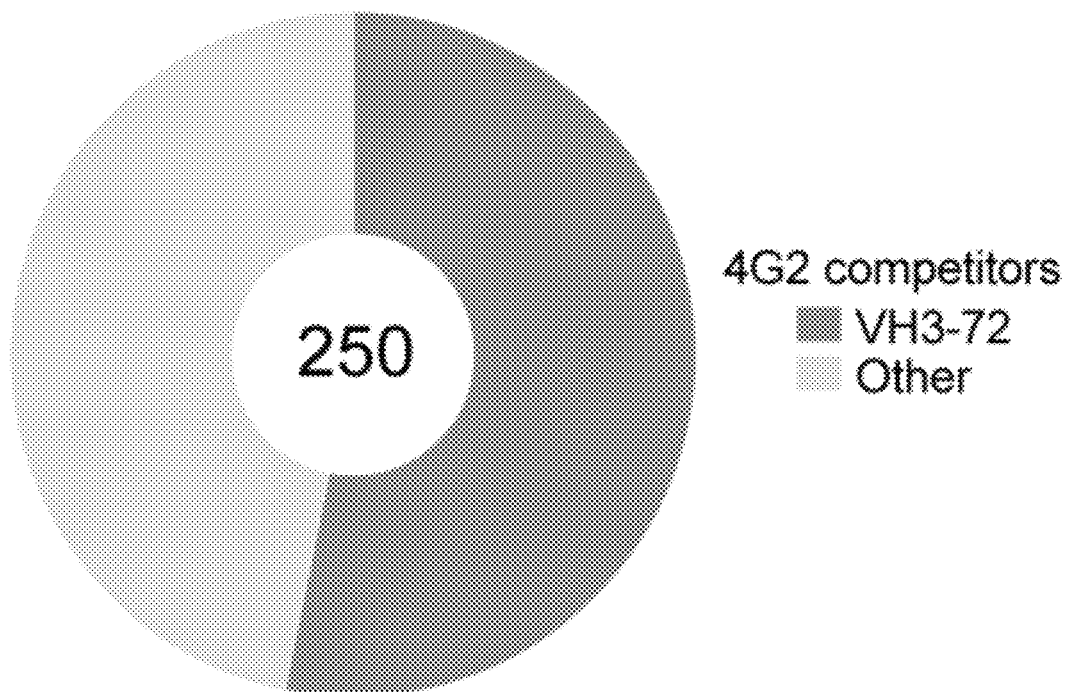
Figure 7D:
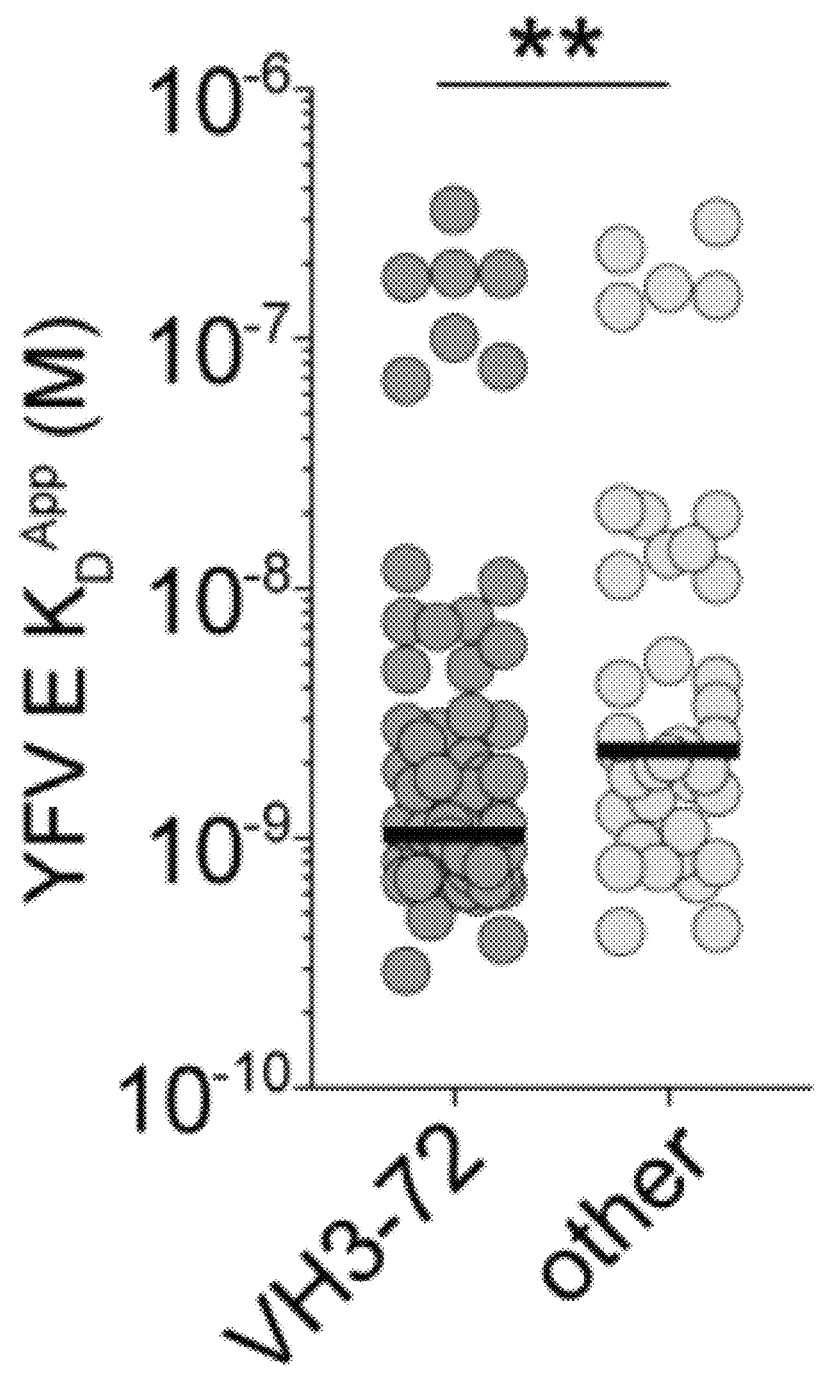

To explore the epitope coverage of the isolated mAbs, pairwise competition experiments were performed using the newly isolated mAbs and two well-characterized control mAbs, 4G2 and 5A, which recognize proximal but non-overlapping epitopes within DII of the YFV E monomer. 4G2 is a pan-flavivirus mAb that targets the FL, whereas 5A is a YFV E-specific mAb that binds to a FL-proximal epitope overlapping the proposed prM association region. Competition experiments were performed using high-throughput surface plasmon resonance (SPR) on a Carterra LSA instrument. Reactivity of the mAbs with a recombinant YFV-17D DIII protein by BLI was also evaluated. The majority of mAbs recognized one of eight distinct antigenic sites, which were defined based on reactivity with DIII and competition with 4G2, 5A, and three of the newly isolated mAbs (ADI-49147, ADI-44112, and ADI-45107) (FIG. 7A). A subset of mAbs competed with both 5A and ADI-45107, suggesting that these two antigenic sites are in close proximity. A small subset of mAbs (6 of 772) recognized epitopes within DIII. Five of the DIII-directed mAbs cross-competed, whereas the sixth, ADI-48945, may recognize a unique epitope. Over half of the mAbs from both donors competed with 4G2 and/or 5A, suggesting that the majority of the YFV E-specific response is mediated by Abs that target epitopes within or proximal to the FL on DII (FIG. 7A). Nearly all the mAbs that utilized the VH3-72 germline gene competed with 4G2 (FIG. 7B). Accordingly, analysis of the sequence features of the mAbs clustered by competition group revealed that over half of the mAbs that competed with 4G2 utilized the VH3-72 germline gene (FIG. 7C). The 4G2 competitor mAbs utilizing VH3-72 showed significantly higher affinities compared to those utilizing other VH germline genes (FIG. 7D). Although the proportion of mAbs targeting each antigenic site did not change dramatically over time, suppression of 4G2/5A competitor mAbs was observed at later timepoints in donor 8 (days 270 and 360). Furthermore, in both donors, mAbs that competed with both 5A and ADI-45107 did not emerge until day 28-90. Results suggest that the vast majority of the YFV E-specific response is directed against epitopes within or proximal to the FL on domain II, and there are only minor shifts in Ab immunodominance hierarchy during the maturation of the B cell response to YFV-17D.

Highly Potent Neutralizing Antibodies Recognize FL Proximal Epitopes

Figure 8C:
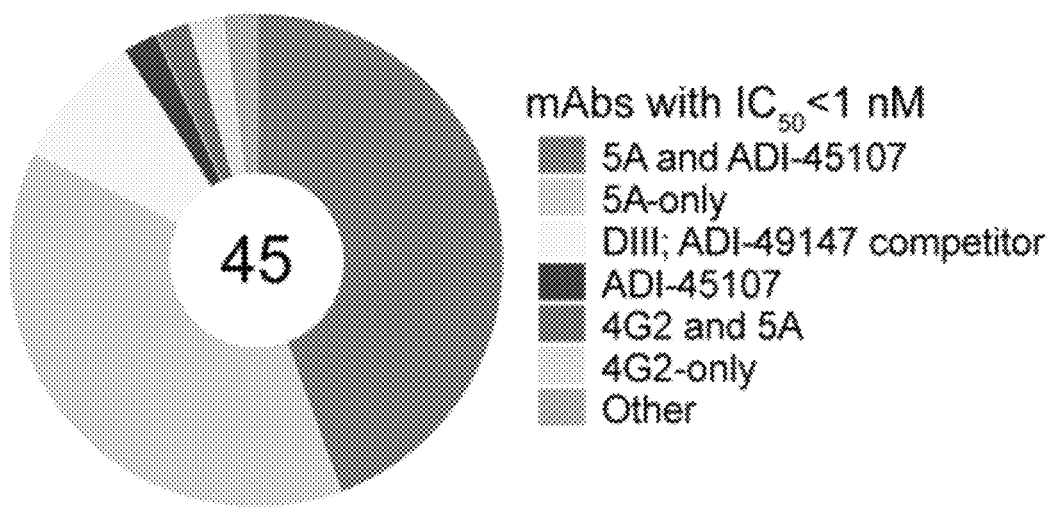
Figure 8D:
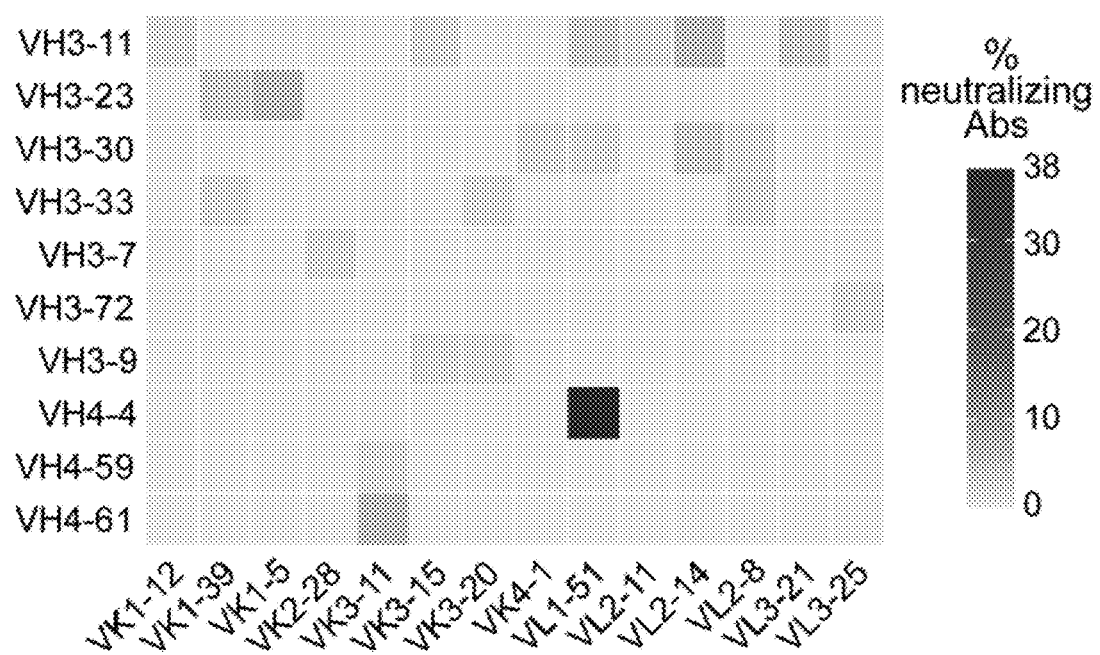

The relationship between antigenic site and neutralization potency was investigated. Over 90% of the mAbs that competed either with 5A only or both 5A and ADI-45107 showed neutralizing activity (FIG. 8A). The majority (78%) of highly potent neutralizing antibodies ($IC_{50}$<1 nM) in the panel belonged to these two competition groups (FIG. 8B-8C). Table 2 provides bin data for these antibodies. Analysis of the sequence features of these 5A-only or 5A/ADI-45107 competitor neutralizing antibodies revealed that nearly 40% utilized VH4-4/VL1-51 germline gene pairing and did not show evidence of a convergent CDRH3 sequence, suggesting a common mode of germline-encoded antigen recognition (FIG. 8D). In line with prior studies, most of the DIII-directed mAbs also showed highly potent neutralizing activity. In contrast to the 5A competitors and DIII-directed mAbs, only a minority of the mAbs belonging to other competition groups showed neutralizing activity. For example, only 12% and 20% of mAbs that competed with 4G2 only or both 4G2 and 5A, respectively, displayed neutralization $IC_{50}$s <100 nM. The results demonstrate that the nAb response to YFV-17D is primarily mediated by Abs that recognize FL proximal epitopes within DII of the YFV E protein.

Figure 9A:
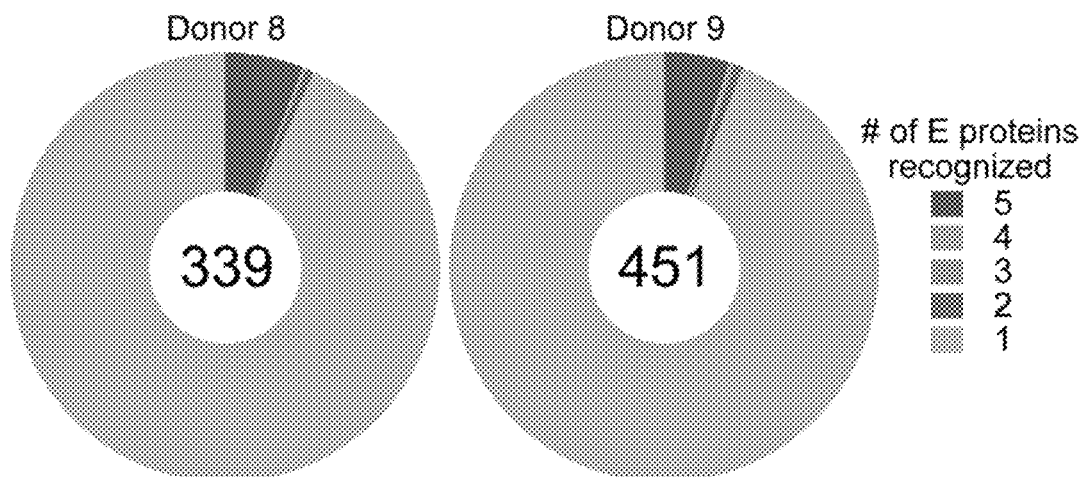
FIG. 9A through 9C shows a subset of monoclonal antibodies show broad flavivirus cross-reactivity.
Figure 9B:
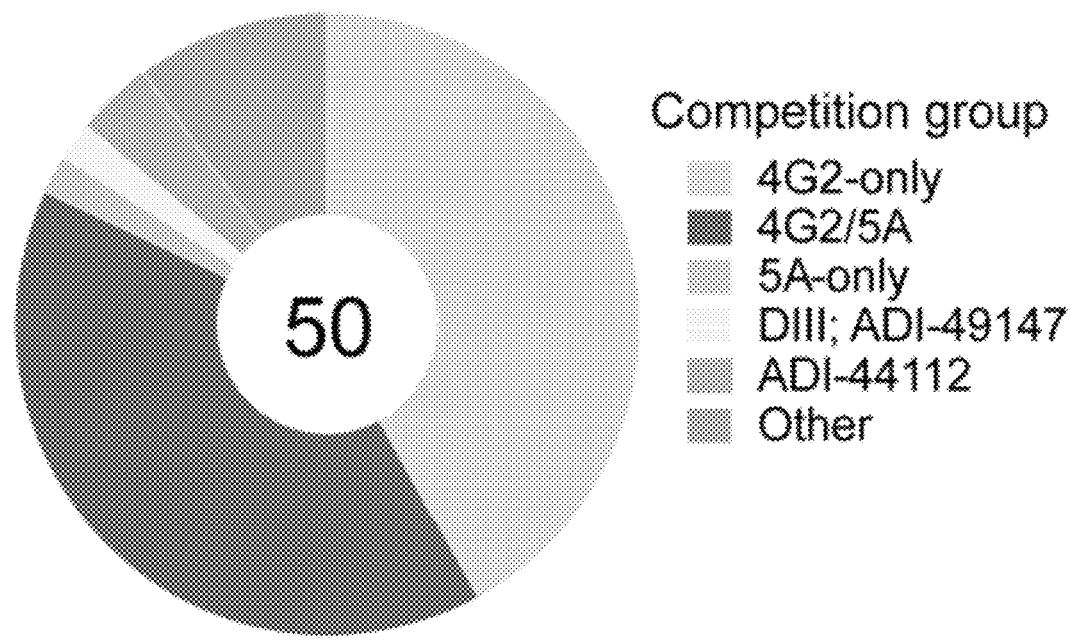
Figure 9C:
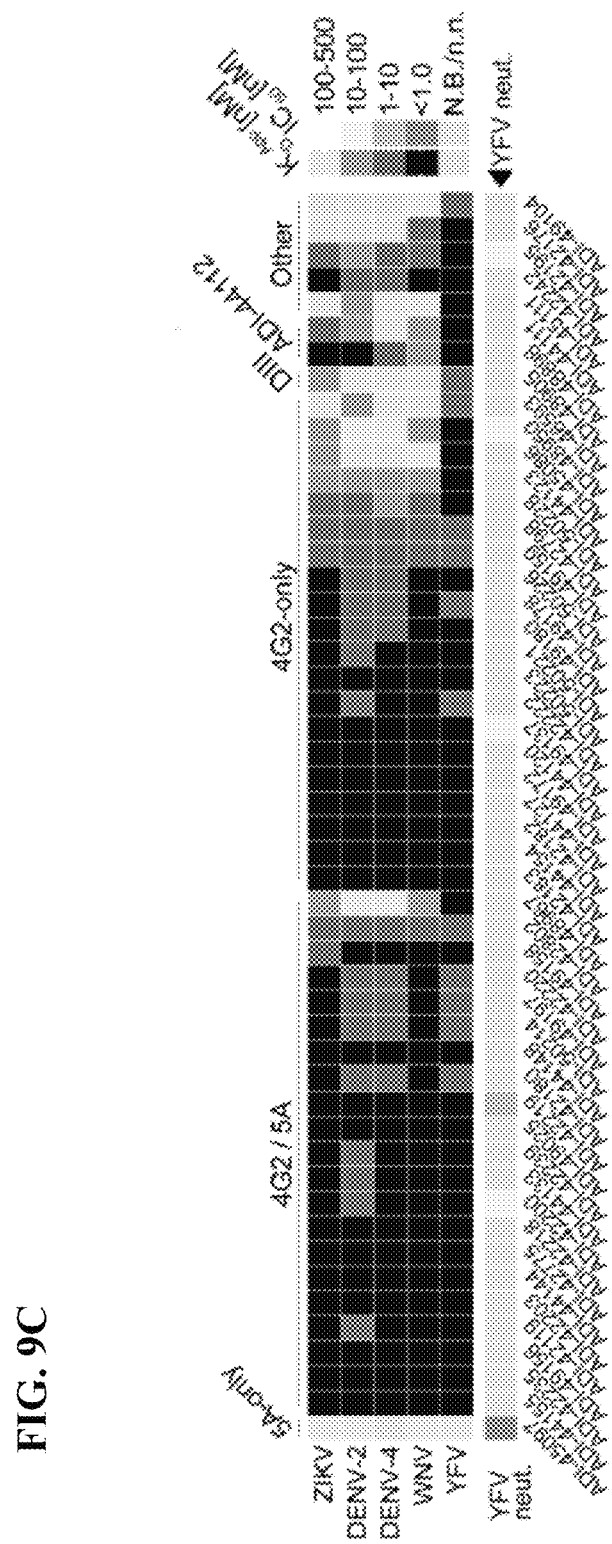

A Subset of mAbs Display Cross-Reactivity with E Proteins from Other Flaviviruses The isolated mAbs were evaluated for binding reactivity to recombinant DENV-2, DENV-4, WNV, or ZIKV E proteins. In both donors, about 6% of YFV E-reactive mAbs showed cross-reactivity to at least one heterologous flavivirus E protein (FIG. 9A). The majority of these cross-reactive mAbs targeted the highly conserved FL epitope and bound to all five flavivirus E proteins with high apparent avid affinities ($K_D^{Apps}$<10 nM) (FIG. 9B-9C). Correspondingly, the small subset of mAbs that bound to epitopes outside of the FL generally displayed more limited cross-reactivity profiles and lower $K_D^{Apps}$ (FIG. 9C). Only 6 out of 50 cross-reactive mAbs showed neutralizing activity against YFV-17D, and only a single mAb, the DIII binder ADI-48905, showed detectable albeit weak neutralizing activity against ZIKV ($IC_{50}$~100 nM). None of the mAbs had measurable neutralization activity against the West Nile virus or Japanese encephalitis virus reporter viral particles. YFV-17D vaccination thus appears to induce a subset of Abs that display broad flavivirus binding activity, the majority of which target the highly conserved FL and show little to no cross-neutralizing activity.

Table 1 below provides the germline usage and amino acid sequence information of 152 anti-YFV antibodies as described herein. The sequences provided in Table 1 include the CDRH3 sequence (SEQ ID NOs. 1, 3, 5, 7, 9, 11, 13, 15, 17, 19, 21, 23, 27, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, and 302) and the CDRL3 sequence (SEQ ID NOs. 2, 4, 6, 8, 10, 12, 14, 16, 18, 20, 22, 24, 26, 29, 31 33 35 37 39 41 43 45 47 49 51 53 55 57 59 61 63 65 67 69 71 73 75 77 79 81 83 85 87 89 91 93 95 97 99 101 103 105 107 109 111 113 115 117 119 121 123 125 127 129 131 133 135 137 139 141 143 145 147 149 151 153 155 157 159 161 163 165 167 169 171 173 175 177 179 181 183 185 187 189 191 193 195 197 199 201 203 205 207 209 211 213 215 217 219 221 223 225 227 229 231 233 235 237 239 241 243 245 247 249 251 253 255 257 259 261 263 265 267 269 271 273 275 277 279 281 283 285 287 289 291 293 295 297 299 301, and 303) for each listed antibody.

Table 2 below provides affinity and neutralization data for the 152 anti-YFV antibodies set forth in Table 1.

Table 3 below provides partial amino acid sequences for the CDRs of the heavy and light chains of each of the 152 anti-YFV antibodies set forth in Table 1. CDRs are indicated in bold/underlined. Each CDR amino acid sequence is also listed separately in the sequence listing (CDRH1 and CDRH2 correspond to SEQ ID NOs.: 607-840; CDRL1 and CDRL2 correspond to SEQ ID NOs.: 841-1005).

TABLE 1

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 1 | ADI-49039 | VH4-38-2 | VL1-51 | ARNAPENYYGSGRESFDI (SEQ ID NO: 1) | GTWDSSLSAWV (SEQ ID NO: 2) | 7 | 5 |
| 2 | ADI-49147 | VH3-23 | VK3-15 | AKDHGGKYGWWYFDL (SEQ ID NO: 3) | QQYDNWPLT (SEQ ID NO: 4) | 8 | 4 |
| 3 | ADI-42229 | VH4-38-2 | VL1-51 | ARNAPENYYGSGRESFDI (SEQ ID NO: 5) | GTWDSSLSAWV (SEQ ID NO: 6) | 5 | 5 |
| 4 | ADI-45090 | VH3-33 | VL1-44 | ARDLEVGAEYLYYHYGMDV (SEQ ID NO: 7) | AAWDDSLNGWV (SEQ ID NO: 8) | 11 | 10 |
| 5 | ADI-45097 | VH3-30 | VL1-51 | AKDSSTSWYQVVYHIDY (SEQ ID NO: 9) | ETWDSSLNAVV (SEQ ID NO: 10) | 7 | 6 |
| 6 | ADI-49133 | VH3-23 | VK1-39 | AKDLAVSTPRYWFDS (SEQ ID NO: 11) | QQSYSIPRIT (SEQ ID NO: 12) | 10 | 9 |
| 7 | ADI-49033 | VH3-23 | VK1-39 | AKDMAVSVHR GWFDD (SEQ ID NO: 13) | QQSYSPPMYT (SEQ ID NO: 14) | 14 | 9 |
| 8 | ADI-49044 | VH3-33 | VL 1-44 | ARDLEVGAEYIYYYYGMDV (SEQ ID NO: 15) | AAWDDSRNGWV (SEQ ID NO: 16) | 10 | 9 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 9 | ADI-45083 | VH4-4 | VL1-51 | ARSHWRSPQSVTFDL (SEQ ID NO: 17) | GTWDTSSLSAGRV (SEQ ID NO: 18) | 16 | 5 |
| 10 | ADI-42225 | VH4-4 | VL1-51 | ARIAAGYSTSWYYFDY (SEQ ID NO: 19) | GTWDTSLSAGRV (SEQ ID NO: 20) | 5 | 3 |
| 11 | ADI-49139 | VH4-4 | VL1-51 | AKDMWAGTTTNWFGP (SEQ ID NO: 21) | GTWDTSLGVV (SEQ ID NO: 22) | 9 | 5 |
| 12 | ADI-48969 | VH3-11 | VL2-11 | AREFSSRPFDL (SEQ ID NO: 23) | CSYAGTYTSNYV (SEQ ID NO: 24) | 10 | 6 |
| 13 | ADI-48900 | VH4-4 | VL1-51 | ARVNPPQYSSGWYSVY (SEQ ID NO: 25) | GTWDNSLGAVV (SEQ ID NO: 26) | 7 | 3 |
| 14 | ADI-42232 | VH4-4 | N/A | ARVAWTSSSSCYYDY (SEQ ID NO: 27) | N/A | 5 | 0 |
| 15 | ADI-42786 | VH4-4 | VL1-51 | ARDGEGHYYRSGDNWFDR (SEQ ID NO: 28) | GTWDSSLSAVV (SEQ ID NO: 29) | 6 | 4 |
| 16 | ADI-42210 | VH4-4 | VL1-51 | ARAELSAWYYFDH (SEQ ID NO: 30) | GTWDTSLSAGRV (SEQ ID NO: 31) | 6 | 0 |
| 17 | ADI-50201 | VH3-11 | VK3-15 | ARVSPLDDGYGYTYYGMDV (SEQ ID NO: 32) | QQYNNWPPRT (SEQ ID NO: 33) | 10 | 2 |
| 18 | ADI-48895 | VH3-11 | VK1-12 | ARDWAELTTITNYFYP (SEQ ID NO: 34) | QQAKSFPPT (SEQ ID NO: 35) | 8 | 1 |
| 19 | ADI-42228 | VH3-9 | VL2-14 | AKAENRIGYCSAGSCYLTYFDY (SEQ ID NO: 36) | NSYTSSSTLV (SEQ ID NO: 37) | 4 | 4 |
| 20 | ADI-45113 | VH3-23 | VK3-15 | AKDPKYSSGWWAFDY (SEQ ID NO: 38) | QQYDDWPL (SEQ ID NO: 39) | 2 | 1 |
| 21 | ADI-42198 | VH4-4 | VL1-51 | ARVEWAYSSSWWLDY (SEQ ID NO: 40) | GTWDTSLSAGGV (SEQ ID NO: 41) | 4 | 3 |
| 22 | ADI-42190 | VH3-11 | VL2-14 | AKHTGDKPLVWAPSVYGLDV (SEQ ID NO: 42) | SSYTRRSTLV (SEQ ID NO: 43) | 9 | 7 |
| 23 | ADI-49154 | VH4-4 | VL1-51 | ARVSVSTSAWYADY (SEQ ID NO: 44) | GTWDTSLSTV (SEQ ID NO: 45) | 8 | 1 |
| 24 | ADI-49183 | VH3-11 | VL2-14 | ARELSSRIDY (SEQ ID NO: 46) | SSYPGTSALVI (SEQ ID NO: 47) | 16 | 5 |
| 25 | ADI-42201 | VH3-33 | VK1-39 | ARAQDGQQLVNYYGMDV (SEQ ID NO: 48) | QQSYSTPYT (SEQ ID NO: 49) | 8 | 4 |
| 26 | ADI-42144 | VH3-30 | VL1-40 | ARGGDYGDYESNNPAEYFQH (SEQ ID NO: 50) | QSYDSSLSGHVV (SEQ ID NO: 51) | 1 | 0 |
| 27 | ADI-50219 | VH4-59 | VK3-11 | AGHREDPYGAYGAS (SEQ ID NO: 52) | QQRTNWPFT (SEQ ID NO: 53) | 15 | 4 |
| 28 | ADI-48897 | VH4-61 | VK3-11 | ASRKEVRGTEDYFDY (SEQ ID NO: 54) | HQRTNWPWT (SEQ ID NO: 55) | 12 | 2 |
| 29 | ADI-42194 | VH4-61 | VK3-11 | AKVEEDGYTNVVRDY (SEQ ID NO: 56) | LQRTNWPFT (SEQ ID NO: 57) | 6 | 4 |
| 30 | ADI-49189 | VH3-11 | VL2-14 | AREGTRGRMD (SEQ ID NO: 58) | SSYTSGTTLGV (SEQ ID NO: 59) | 9 | 4 |
| 31 | ADI-49188 | VH4-4 | VL1-51 | ARDSWSGPTRNWFDP (SEQ ID NO: 60) | GTWDSSLGGVI (SEQ ID NO: 61) | 14 | 8 |
| 32 | ADI-42188 | VH4-4 | VL1-51 | ARVVWEYSNAWCVDF (SEQ ID NO: 62) | ETWDSSLGVVV (SEQ ID NO: 63) | 3 | 0 |
| 33 | ADI-50026 | VH3-30 | VK1-33 | ARNTYYDRSGLIAY (SEQ ID NO: 64) | QQYDNLSRLT (SEQ ID NO: 65) | 7 | 3 |
| 34 | ADI-42809 | VH4-4 | VL1-51 | ARGPLKSYWYFDL (SEQ ID NO: 66) | GTWDTSLSAGRV (SEQ ID NO: 67) | 7 | 0 |
| 35 | ADI-46596 | VH4-4 | VL1-51 | ARYCSGATCYGSNGMDV (SEQ ID NO: 68) | GTWDFRLSAL (SEQ ID NO: 69) | 8 | 5 |
| 36 | ADI-50205 | VH3-30 | VL2-14 | AKDQCGGDCTADY (SEQ ID NO: 70) | SSYTSSGTPVV (SEQ ID NO: 71) | 6 | 3 |
| 37 | ADI-42830 | VH4-4 | VL1-51 | ASTLWGGPLSVASDY (SEQ ID NO: 72) | GTWDSSPSAGRV (SEQ ID NO: 73) | 8 | 4 |
| 38 | ADI-49186 | VH3-30 | VK4-1 | ARDYYASGDGYFDY (SEQ ID NO: 74) | QQYYSTPRT (SEQ ID NO: 75) | 17 | 8 |
| 39 | ADI-46591 | VH4-4 | VL1-51 | VRYCSSTSCYGLNGMDV (SEQ ID NO: 76) | GTWDTRLSAL (SEQ ID NO: 77) | 11 | 3 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 40 | ADI-48955 | VH3-11 | VL1-51 | ARDGSLVNAIDY (SEQ ID NO: 78) | GTWDTSLSAAWV (SEQ ID NO: 79) | 8 | 3 |
| 41 | ADI-42818 | VH4-4 | VL1-51 | ARVRWSGSTSWDLDY (SEQ ID NO: 80) | GTWDTSPSAGGV (SEQ ID NO: 81) | 9 | 2 |
| 42 | ADI-50531 | VH2-5 | VL2-14 | AHSPRRITMVRGVIITWGDGMDV (SEQ ID NO: 82) | SSYTSSSTLAV (SEQ ID NO: 83) | 0 | 1 |
| 43 | ADI-46586 | VH3-11 | VL1-51 | ARDGSMVNAIDY (SEQ ID NO: 84) | GTWDSSLSAAWV (SEQ ID NO: 85) | 6 | 2 |
| 44 | ADI-49138 | VH3-33 | VL2-14 | ARDAYASGDGGIDY (SEQ ID NO: 86) | SSYRSSGTPYV (SEQ ID NO: 87) | 6 | 3 |
| 45 | ADI-45075 | VH3-23 | VK1-33 | AKDLRGVGGWYYFDY (SEQ ID NO: 88) | QQYDNLPLT (SEQ ID NO: 89) | 2 | 2 |
| 46 | ADI-42831 | VH3-23 | VK1-5 | AKDQGVTTDWPSDY (SEQ ID NO: 90) | QHYETYSVR (SEQ ID NO: 91) | 20 | 13 |
| 47 | ADI-42230 | VH3-30-3 | VK1-27 | PRDGLPGANQYFFYYGMDV (SEQ ID NO: 92) | QKYNSAPLT (SEQ ID NO: 93) | 2 | 4 |
| 48 | ADI-42847 | VH4-61 | VK3-11 | VRVEEYVNNEEVRDY (SEQ ID NO: 94) | LQRTNWPFT (SEQ ID NO: 95) | 11 | 1 |
| 49 | ADI-42821 | VH3-23 | VK1-5 | ARDQGFTTDWPCDY (SEQ ID NO: 96) | QHYNSFSVK (SEQ ID NO: 97) | 15 | 10 |
| 50 | ADI-42849 | VH3-11 | VL3-21 | ARDSNFNSNLDY (SEQ ID NO: 98) | QVWDSSSDHPWV (SEQ ID NO: 99) | 3 | 2 |
| 51 | ADI-42151 | VH4-4 | VL1-51 | ARGPLKTYWYFDL (SEQ ID NO: 100) | GTWDTSLSAGRV (SEQ ID NO: 101) | 1 | 0 |
| 52 | ADI-46001 | VH3-11 | VL3-21 | ARDSNYFYGLDV (SEQ ID NO: 102) | QVWDTSIDHHWV (SEQ ID NO: 103) | 3 | 7 |
| 53 | ADI-45154 | VH3-30 | VL2-8 | AKDICSGDCGGGDY (SEQ ID NO: 104) | SSYAGSNNWVV (SEQ ID NO: 105) | 3 | 1 |
| 54 | ADI-49161 | VH1-18 | VL2-14 | AREDDDYYSMDV (SEQ ID NO: 106) | SSYTTTSLVI (SEQ ID NO: 107) | 15 | 6 |
| 55 | ADI-42154 | VH3-7 | VK2-28 | ARDISCISTSCYGGYYYYGMDV (SEQ ID NO: 108) | MQALQTPPRT (SEQ ID NO: 109) | 1 | 0 |
| 56 | ADI-48916 | VH3-33 | VK1-17 | ARDYYASGDGSIDY (SEQ ID NO: 110) | LOHNSYPLT (SEQ ID NO: 111) | 8 | 2 |
| 57 | ADI-45085 | VH3-23 | VK1-5 | AKYYDSSGYYYFDY (SEQ ID NO: 112) | KQYNRNPYT (SEQ ID NO: 113) | 4 | 4 |
| 58 | ADI-42211 | VH3-30 | VK1-27 | AKGSVSVAGAEDY (SEQ ID NO: 114) | QKYNSAPQT (SEQ ID NO: 115) | | |
| 59 | ADI-48908 | VH3-9 | VK3-15 | AKGYDSSGYYWADY (SEQ ID NO: 116) | QQYNNWPPLT (SEQ ID NO: 117) | 10 | 6 |
| 60 | ADI-48913 | VH4-4 | VK4-1 | ARERGGYFTEPFDI (SEQ ID NO: 118) | QQYYRTPWT (SEQ ID NO: 119) | 9 | 3 |
| 61 | ADI-45140 | VH3-48 | VL1-51 | AATIFGVVSFDY (SEQ ID NO: 120) | GTWDSALGAAV (SEQ ID NO: 121) | 7 | 1 |
| 62 | ADI-50211 | VH3-23 | VK1-5 | AKYYDSSGYYYLDY (SEQ ID NO: 122) | QQYNRDPYT (SEQ ID NO: 123) | 9 | 4 |
| 63 | ADI-42199 | VH3-72 | VL3-25 | CRESGEGFDP (SEQ ID NO: 124) | QSADRSGSVI (SEQ ID NO: 125) | 5 | 11 |
| 64 | ADI-42231 | VH1-18 | VK3-11 | ARDQSHGTFGGVIDSTTLFYYYGMDV (SEQ ID NO: 126) | QQRSNWPS (SEQ ID NO: 127) | 6 | 0 |
| 65 | ADI-45164 | VH4-39 | VK1-39 | ARGYCSSTSCFYYYYGMDV (SEQ ID NO: 128) | QQSYSTPLT (SEQ ID NO: 129) | 0 | 0 |
| 66 | ADI-42233 | VH3-21 | VK3-20 | ARDHYFDSSGDYLSYYYNGMDV (SEQ ID NO: 130) | QQYGSSPRA (SEQ ID NO: 131) | 8 | 6 |
| 67 | ADI-42191 | VH3-72 | VK1-39 | ARVYGGPDDY (SEQ ID NO: 132) | QQSSITPPT (SEQ ID NO: 133) | 3 | 2 |
| 68 | ADI-48899 | VH3-23 | VK1-5 | AKDGVTTINGWFHFEY (SEQ ID NO: 134) | QQYNSFPFT (SEQ ID NO: 135) | 9 | 2 |
| 69 | ADI-49145 | VH3-72 | VK1-39 | TRITGDRYWYLDL (SEQ ID NO: 136) | QQTYSASGS (SEQ ID NO: 137) | 11 | 13 |
| 70 | ADI-46729 | VH4-61 | VK1-39 | ARGWFGYSNYGLYYYYGMDV (SEQ ID NO: 138) | QQSYSTPWT (SEQ ID NO: 139) | 1 | 0 |
| 71 | ADI-46722 | VH4-4 | VL1-51 | ARDFWSGSNWFDP (SEQ ID NO: 140) | GTWDNSLGVV (SEQ ID NO: 141) | 1 | 0 |
| 72 | ADI-45148 | VH3-9 | VK3-20 | AKDIGDSYGSGSYYLPYGAYYGMDV (SEQ ID NO: 142) | QQYGSSPG (SEQ ID NO: 143) | 0 | 2 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 73 | ADI-49168 | VH3-23 | VK1-5 | AKHYDSSGYYYEDY (SEQ ID NO: 144) | HQYKDFPWT (SEQ ID NO: 145) | 11 | 6 |
| 74 | ADI-49040 | VH3-72 | VK1-5 | ARVRDGEYDY (SEQ ID NO: 146) | QQYNSYSP (SEQ ID NO: 147) | 9 | 4 |
| 75 | ADI-42187 | VH3-21 | VK3-20 | ARDNSEVEDYGDYVLYHYYGMDV (SEQ ID NO: 148) | QQYGSSPF (SEQ ID NO: 149) | 4 | 3 |
| 76 | ADI-49561 | VH3-30 | VL2-14 | AKDQCGGDCTADY (SEQ ID NO: 150) | SSYTSSSTPVV (SEQ ID NO: 151) | 2 | 3 |
| 77 | ADI-42219 | VH3-30-3 | VL2-11 | ARGYTGYDGFDY (SEQ ID NO: 152) | CSYATNYGVV (SEQ ID NO: 153) | 8 | 2 |
| 78 | ADI-50535 | VH1-18 | VL6-57 | ARRPYYYGSRRPAGHMDV (SEQ ID NO: 154) | QSYDSSNVV (SEQ ID NO: 155) | 0 | 0 |
| 79 | ADI-45128 | VH4-30-4 | VL1-51 | GRDSDKNYFDY (SEQ ID NO: 156) | GAWDSSLSAHVV (SEQ ID NO: 157) | 8 | 2 |
| 80 | ADI-45136 | VH3-33 | VK1-5 | AKTYDSNAYYYLDY (SEQ ID NO: 158) | QQYNRYPYT (SEQ ID NO: 159) | 7 | 7 |
| 81 | ADI-42189 | VH3-30 | VK1-17 | ASLWFIVMTMSKNPETDY (SEQ ID NO: 160) | LQHHSYPWT (SEQ ID NO: 161) | 6 | 2 |
| 82 | ADI-45078 | VH3-23 | VK1-5 | AKYYDSSGYYYFDH (SEQ ID NO: 162) | QQYNRDPYT (SEQ ID NO: 163) | 15 | 11 |
| 83 | ADI-49162 | VH3-23 | VK1-5 | AKFYDSSGYYYFDY (SEQ ID NO: 164) | QQYNTYPYT (SEQ ID NO: 165) | 17 | 13 |
| 84 | ADI-42223 | VH3-72 | VK1-39 | VRLYGDYVAYFDY (SEQ ID NO: 166) | QQSYSTPWT (SEQ ID NO: 167) | 5 | 7 |
| 85 | ADI-48435 | VH1-18 | VL2-14 | ARRGTTVTRFGVIQYYYGMDV (SEQ ID NO: 168) | SSYTSSSTLV (SEQ ID NO: 169) | 0 | 1 |
| 86 | ADI-46742 | VH4-59 | VL3-21 | ARETANNWFDP (SEQ ID NO: 170) | QVWDNSSDRRV (SEQ ID NO: 171) | 16 | 8 |
| 87 | ADI-42787 | VH3-30-3 | VK3-15 | ARASMMPRPPVHDY (SEQ ID NO: 172) | QQYNTWWT (SEQ ID NO: 173) | 9 | 3 |
| 88 | ADI-46718 | VH3-23 | VK1-39 | AKDRSQGDYGDYVADY (SEQ ID NO: 174) | QQSYSTPLT (SEQ ID NO: 175) | 0 | 0 |
| 89 | ADI-49141 | VH4-4 | VK3-15 | ARVQTSHSELWFGEFGAD (SEQ ID NO: 176) | QQYNTWPKT (SEQ ID NO: 177) | 3 | 1 |
| 90 | ADI-42213 | VH3-23 | VK3-20 | AKDGGYSTDWYFDL (SEQ ID NO: 178) | QQYGSSRRT (SEQ ID NO: 179) | 7 | 2 |
| 91 | ADI-42844 | VH3-30 | VK1-5 | AKGYDSNGYYYIDY (SEQ ID NO: 180) | QQYNRYPYT (SEQ ID NO: 181) | 5 | 1 |
| 92 | ADI-45161 | VH3-33 | VL2-14 | ARDVGYQLLQVYGMDV (SEQ ID NO: 182) | SSYTSSSTLDVV (SEQ ID NO: 183) | 0 | 0 |
| 93 | ADI-42192 | VH4-31 | VK3-15 | ARAEYDTSGYYQQRLPEYFQH (SEQ ID NO: 184) | QQYNSWPPIT (SEQ ID NO: 185) | 5 | 1 |
| 94 | ADI-48910 | VH3-23 | VK1-5 | AKYYDSSGYYYFHS (SEQ ID NO: 186) | QQYNRYPYT (SEQ ID NO: 187) | 13 | 7 |
| 95 | ADI-42193 | VH3-72 | VL1-47 | AREHGDYGLDY (SEQ ID NO: 188) | ATWDVSLSNDVL (SEQ ID NO: 189) | 8 | 4 |
| 96 | ADI-49590 | VH1-2 | VK3-20 | YVDYYYDSSGYYSPFDY (SEQ ID NO: 190) | QQYGSSPPIT (SEQ ID NO: 191) | 1 | 2 |
| 97 | ADI-45076 | VH3-72 | VK1-39 | ARVDGEEVALIY (SEQ ID NO: 192) | QQSSTTRWT (SEQ ID NO: 193) | 8 | 11 |
| 98 | ADI-48968 | VH3-72 | VK1-39 | VRVWGGEAARYDY (SEQ ID NO: 194) | QHASTTPWT (SEQ ID NO: 195) | 13 | 12 |
| 99 | ADI-42212 | VH3-72 | VL3-1 | SRHMGFGLDL (SEQ ID NO: 196) | QAWDTTTAGGV (SEQ ID NO: 197) | 3 | 6 |
| 100 | ADI-48462 | VH3-33 | VK3-20 | ARDYYGSGDGYFDY (SEQ ID NO: 198) | QQYGSSPRA (SEQ ID NO: 199) | 0 | 0 |
| 101 | ADI-45127 | VH2-26 | VL2-8 | ARIPVEYGTPRGSFDT (SEQ ID NO: 200) | SSYGGNNDLV (SEQ ID NO: 201) | 11 | 8 |
| 102 | ADI-42200 | VH3-30-3 | VK3-11 | AGGSPDY (SEQ ID NO: 202) | QQRSNWPYT (SEQ ID NO: 203) | 9 | 4 |
| 103 | ADI-50203 | VH3-30 | VK1-5 | ARAYDSRGYYYIEH (SEQ ID NO: 204) | QQYKTYWT (SEQ ID NO: 205) | 14 | 8 |
| 104 | ADI-42149 | VH1-18 | VL2-14 | AREIDSNYVFDY (SEQ ID NO: 206) | SSYTSSGTNI (SEQ ID NO: 207) | 2 | 0 |
| 105 | ADI-42181 | VH3-7 | VK3-15 | ARKLSYSSGWYYFDY (SEQ ID NO: 208) | QQYNNWPPLT (SEQ ID NO: 209) | 2 | 3 |
| 106 | ADI-45126 | VH3-72 | VL3-10 | VTTTVILFDY (SEQ ID NO: 210) | YSTDSSGLLGV (SEQ ID NO: 211) | 9 | 8 |
| 107 | ADI-45074 | VH4-34 | VK4-1 | ARGRLAWGLRGQKSPNFFAY (SEQ ID NO: 212) | QQFHSPPWT (SEQ ID NO: 213) | 7 | 5 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 108 | ADI-49041 | VH3-15 | VK1-5 | ATAGIFGVVIMKGFDH (SEQ ID NO: 214) | QQYNDYPWT (SEQ ID NO: 215) | 9 | 9 |
| 109 | ADI-42227 | VH1-69 | VK1-17 | ARETYYYGSGSVPVHD (SEQ ID NO: 216) | LQHNTYPWT (SEQ ID NO: 217) | 9 | 1 |
| 110 | ADI-50220 | VH3-30 | VK1-5 | ARGYDSSGYWGFGDN (SEQ ID NO: 218) | QQYYSYPYT (SEQ ID NO: 219) | 16 | 6 |
| 111 | ADI-42141 | VH3-72 | VL3-25 | ARVEGGAWGAFDI (SEQ ID NO: 220) | QSADRSGTVV (SEQ ID NO: 221) | 1 | 1 |
| 112 | ADI-42216 | VH2-26 | VL2-8 | ARLWFTEYPGAFDI (SEQ ID NO: 222) | SSYAGSNALV (SEQ ID NO: 223) | 5 | 4 |
| 113 | ADI-50534 | VH4-39 | VL6-57 | ARHSSGSYYLAGYYFDY (SEQ ID NO: 224) | QSYDSSNWV (SEQ ID NO: 225) | 0 | 1 |
| 114 | ADI-49140 | VH3-72 | VL3-25 | ARLTDSGYDD (SEQ ID NO: 226) | HSPDSHVV (SEQ ID NO: 227) | 6 | 3 |
| 115 | ADI-46741 | VH4-59 | VL3-21 | ARETCSGGSCYYRVGSAFDI (SEQ ID NO: 228) | QVWDSSSDHEV (SEQ ID NO: 229) | 0 | 1 |
| 116 | ADI-42195 | VH3-9 | VK1-33 | VKDYCSGGRCYSFDY (SEQ ID NO: 230) | QQWGT (SEQ ID NO: 231) | 6 | 4 |
| 117 | ADI-42172 | VH3-30 | VK1-5 | AKAYDSSAYYYLDY (SEQ ID NO: 232) | QQYNRYPYT (SEQ ID NO: 233) | 3 | 4 |
| 118 | ADI-42178 | VH3-30 | VK1-5 | AKAYDSRGYYYLDY (SEQ ID NO: 234) | QQYNRYSYT (SEQ ID NO: 235) | 3 | 6 |
| 119 | ADI-49032 | VH3-23 | VK1-5 | AKDLTHRLGSIFGKLTFDAFDI (SEQ ID NO: 236) | QQYNNFWT (SEQ ID NO: 237) | 23 | 4 |
| 120 | ADI-50197 | VH3-30 | VL1-40 | AKDLTPYFYDSGAFDH (SEQ ID NO: 238) | HSYDSNMSGSV (SEQ ID NO: 239) | 17 | 7 |
| 121 | ADI-48894 | VH3-72 | VK1-27 | ARVFGGPTDY (SEQ ID NO: 240) | QKYYSAPLIT (SEQ ID NO: 241) | 7 | 2 |
| 122 | ADI-42226 | VH3-72 | VL3-25 | ARVVNGLDV (SEQ ID NO: 242) | QSADSSVADSSVV (SEQ ID NO: 243) | 7 | 1 |
| 123 | ADI-49037 | VH3-30-3 | VK3-11 | ARGQPDY (SEQ ID NO: 244) | QQRSNWPYT (SEQ ID NO: 245) | 7 | 4 |
| 124 | ADI-46739 | VH4-4 | VL1-51 | AGKKWELLGFRFDP (SEQ ID NO: 246) | GTWDNSLGMVV (SEQ ID NO: 247) | 9 | 4 |
| 125 | ADI-42810 | VH1-3 | VL2-14 | ARQWLGHFDY (SEQ ID NO: 248) | SSYTSSSTYV (SEQ ID NO: 249) | 1 | 0 |
| 126 | ADI-49137 | VH3-72 | VK3-11 | ARVFSYYLDY (SEQ ID NO: 250) | QQPGNWPPAFT (SEQ ID NO: 251) | 11 | 3 |
| 127 | ADI-42817 | VH2-5 | VK3-15 | AHRHIAARLYRDDDVFDV (SEQ ID NO: 252) | QQYNNWIT (SEQ ID NO: 253) | 2 | 2 |
| 128 | ADI-50218 | VH1-8 | VK1D-12 | ARGLNTVTNSDY (SEQ ID NO: 254) | QQANSFPWT (SEQ ID NO: 255) | 0 | 0 |
| 129 | ADI-42126 | VH1-2 | VK2-28 | ASGLSPDFSVLDV (SEQ ID NO: 256) | MQALQTPYT (SEQ ID NO: 257) | 0 | 1 |
| 130 | ADI-42186 | VH6-1 | VL1-44 | AREGAGYYDSSGYYPLSYDAFDI (SEQ ID NO: 258) | AAWDDNLIGVV (SEQ ID NO: 259) | 3 | 4 |
| 131 | ADI-48890 | VH3-72 | VL2-8 | ARVRGSYWDY (SEQ ID NO: 260) | SSFAGSNNLYV (SEQ ID NO: 261) | 6 | 0 |
| 132 | ADI-42206 | VH3-72 | VL2-14 | GRDRGWLDI (SEQ ID NO: 262) | SSYTRSSTRV (SEQ ID NO: 263) | 2 | 3 |
| 133 | ADI-46724 | VH4-4 | VL1-51 | ARVIRDLRDYYDGSGYGPDAFDI (SEQ ID NO: 264) | ETWDSRLSVV (SEQ ID NO: 265) | 16 | 4 |
| 134 | ADI-50539 | VH4-4 | VL1-51 | ARARWEDGNYYYGMDV (SEQ ID NO: 266) | GTWDSSLSAVV (SEQ ID NO: 267) | 0 | 0 |
| 135 | ADI-45156 | VH3-23 | VK1-39 | AKDQSSGWPNYYYGMDV (SEQ ID NO: 268) | QQSYSTPWT (SEQ ID NO: 269) | 0 | 0 |
| 136 | ADI-50536 | VH7-4-1 | VK1-39 | VRGYCSSTSCYGGLYWFDP (SEQ ID NO: 270) | QQSYSTPRT (SEQ ID NO: 271) | 0 | 1 |
| 137 | ADI-42217 | VH3-30-3 | VL1-40 | ARHSGGYSSKDKPTEYFQH (SEQ ID NO: 272) | QSYDSSLSGVV (SEQ ID NO: 273) | 6 | 2 |
| 138 | ADI-48951 | VH4-4 | VK4-1 | ARDVGVAAVITGSVR (SEQ ID NO: 274) | QQFYTTPST (SEQ ID NO: 275) | 6 | 4 |
| 139 | ADI-50537 | VH7-4-1 | VK1-39 | ARGYCSSTSCYGGLYWFDP (SEQ ID NO: 276) | QQSYSTPRT (SEQ ID NO: 277) | 0 | 0 |
| 140 | ADI-46737 | VH3-30 | VK1-17 | ARDGAGDYIWGSYRHKGLHYYYGMDV (SEQ ID NO: 278) | LQHNSYPLT (SEQ ID NO: 279) | 0 | 0 |
| 141 | ADI-50538 | VH4-4 | VL6-57 | AKDPRTFYGVVMLLDDP (SEQ ID NO: 280) | QSYDSTTVV (SEQ ID NO: 281) | 9 | 7 |
| 142 | ADI-48950 | VH3-30 | VL2-8 | ARGFGELPGFDI (SEQ ID NO: 282) | SSYAGSNNFVV (SEQ ID NO: 283) | 15 | 4 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 143 | ADI-42114 | VH3-21 | VL1-51 | ARDSWGPFDY (SEQ ID NO: 284) | GTWDSSLSAKV (SEQ ID NO: 285) | 0 | 0 |
| 144 | ADI-49194 | VH3-33 | VK1-5 | AKTYDSRAYYYLDY (SEQ ID NO: 286) | QQYNRYPYT (SEQ ID NO: 287) | 8 | 7 |
| 145 | ADI-42124 | VH3-23 | VL2-11 | AKDLFYDFWTGITIDY (SEQ ID NO: 288) | CSYAGSYTFVL (SEQ ID NO: 289) | 4 | 0 |
| 146 | ADI-45123 | VH3-7 | VK1-39 | ARDGGTVSDGLDV (SEQ ID NO: 290) | QQTFSIWT (SEQ ID NO: 291) | 8 | 7 |
| 147 | ADI-50533 | VH4-4 | VL1-51 | ARVVWYSSSSHLFDY (SEQ ID NO: 292) | GTWDSSLSAGKV (SEQ ID NO: 293) | 0 | 0 |
| 148 | ADI-49205 | VH3-33 | VL2-8 | ARIKSDAFDL (SEQ ID NO: 294) | FSYAGSNNYV (SEQ ID NO: 295) | 10 | 6 |
| 149 | ADI-45151 | VH3-30 | VK2-24 | AKFPLRDGGSGEGFDY (SEQ ID NO: 296) | MQASQFPLT (SEQ ID NO: 297) | 17 | 3 |
| 150 | ADI-46728 | VH3-30-3 | VK1-33 | ARNTYYDRRRTFDY (SEQ ID NO: 298) | QQYDNLPPVT (SEQ ID NO: 299) | 0 | 0 |
| 151 | ADI-49030 | VH3-72 | VL3-1 | AGVGITGTTGIDY (SEQ ID NO: 300) | QAWDSSTDVV (SEQ ID NO: 301) | 0 | 0 |
| 152 | ADI-50200 | VH3-9 | VK1-27 | AKGAAAGPFPYFYYAMDV (SEQ ID NO: 302) | QKYQSAPPT (SEQ ID NO: 303) | 14 | 5 |

TABLE 2

Affinity and Neutralization data for anti-YFV antibodies

| Antibody Number | Name | Monovalent Binding (KD) | Neut (100 nM) Avg. % Neutralization | Neut (10 nM) Avg. % Neutralization | Epitope Binning Data | B Cell Classification |
|---|---|---|---|---|---|---|
| 1 | ADI-49039 | 4.15E-07 | 99.07 | 99.41 | 4G2 and 5A | Atypical IgM memory (IgM+IgD-CD27-SHM+) |
| 2 | ADI-49147 | 3.73E-09 | 97.78 | 99.65 | DIII; ADI-49147 competitor | IgD memory (IgM-IgD+SHM+) |
| 3 | ADI-42229 | 7.87E-09 | 99.64 | 99.76 | 4G2 and 5A | IgM-only (IgM+IgD-CD27+) |
| 4 | ADI-45090 | 2.11E-09 | 99.56 | 98.83 | DIII; ADI-49147 competitor | swIg+CD27+ |
| 5 | ADI-45097 | 1.62E-09 | 99.32 | 99.38 | Blocks 5A only | swIg+CD27- |
| 6 | ADI-49133 | 6.91E-09 | 99.90 | 98.57 | Blocks 5A only | IgM+IgD+CD27+ |
| 7 | ADI-49033 | 1.80E-08 | 99.86 | 99.95 | 5A and ADI-45107 | Atypical IgM memory (IgM+IgD+CD27-SHM+) |
| 8 | ADI-49044 | 1.88E-09 | 99.93 | 99.68 | Other | swIg+CD27- |
| 9 | ADI-45083 | 3.45E-09 | 99.69 | 99.59 | Blocks 5A only | swIg+CD27- |
| 10 | ADI-42225 | 3.15E-08 | 99.69 | 99.76 | Blocks 5A only | swIg+CD27+ |
| 11 | ADI-49139 | 3.45E-09 | 99.53 | 100.00 | 5A and ADI-45107 | swIg+CD27+ |
| 12 | ADI-48969 | 5.86E-09 | 99.88 | 98.12 | 5A and ADI-45107 | IgG+CD27- |
| 13 | ADI-48900 | 2.62E-08 | 99.70 | 99.94 | Blocks 5A only | Atypical IgM memory (IgM+IgD+CD27-SHM+) |
| 14 | ADI-42232 | 1.46E-08 | 99.77 | 99.85 | 5A and ADI-45107 | swIg+CD27+ |
| 15 | ADI-42786 | 1.27E-08 | 92.79 | 89.16 | Blocks 5A only | swIg+CD27+ |
| 16 | ADI-42210 | 1.87E-08 | 99.64 | 99.76 | 5A and ADI-45107 | swIg+CD27+ |
| 17 | ADI-50201 | 1.31E-08 | 99.28 | 97.94 | 5A and ADI-45107 | Atypical IgM memory (IgM+IgD+CD27-SHM+) |
| 18 | ADI-48895 | 4.49E-09 | 99.71 | 99.78 | 5A and ADI-45107 | IgG+CD27+ |
| 19 | ADI-42228 | 8.64E-09 | 97.69 | 69.43 | ADI-45107 | swIg+CD27- |
| 20 | ADI-45113 | 2.53E-07 | 98.92 | 98.77 | DIII; ADI-49147 competitor | IgD memory (IgM-IgD+SHM+) |

TABLE 2-continued

Affinity and Neutralization data for anti-YFV antibodies

| Antibody Number | Name | Monovalent Binding (KD) | Neut (100 nM) Avg. % Neutralization | Neut (10 nM) Avg. % Neutralization | Epitope Binning Data | B Cell Classification |
|---|---|---|---|---|---|---|
| 21 | ADI-42198 | 3.32E−08 | 99.71 | 99.77 | 5A and ADI-45107 | Atypical IgM memory (IgM+IgD+CD27-SHM+) |
| 22 | ADI-42190 | 1.31E−08 | 99.80 | 99.18 | Blocks 5A only | swIg+CD27+ |
| 23 | ADI-49154 | 1.41E−07 | 98.78 | 98.26 | 5A and ADI-45107 | Atypical IgM memory (IgM+IgD-CD27-SHM+) |
| 24 | ADI-49183 | 2.21E−09 | 99.90 | 99.86 | 5A and ADI-45107 | IgG+CD27+ |
| 25 | ADI-42201 | 1.13E−07 | 99.33 | 98.70 | Blocks 5A only | IgM+IgD+CD27+ |
| 26 | ADI-42144 | 1.09E−08 | 5.24 | 16.76 | blocks 4G2 only | swIg+CD27- |
| 27 | ADI-50219 | 8.59E−10 | 99.54 | 99.48 | Blocks 5A only | IgG+CD27+ |
| 28 | ADI-48897 | 3.22E−09 | 96.74 | 98.45 | 5A and ADI-45107 | IgG+CD27- |
| 29 | ADI-42194 | 5.44E−09 | 99.59 | 99.58 | Blocks 5A only | swIg+CD27+ |
| 30 | ADI-49189 | 1.27E−08 | 99.84 | 98.09 | 5A and ADI-45107 | Atypical IgM memory (IgM+IgD+CD27-SHM+) |
| 31 | ADI-49188 | 9.54E−09 | 99.96 | 99.47 | 5A and ADI-45107 | IgG+CD27+ |
| 32 | ADI-42188 | 3.71E−08 | 99.80 | 99.77 | 5A and ADI-45107 | IgM-only (IgM+IgD-CD27+) |
| 33 | ADI-50026 | >1.0E−07 | 99.93 | 99.91 | Other | swIg+CD27+ |
| 34 | ADI-42809 | 3.78E−09 | 94.44 | 95.50 | 5A and ADI-45107 | swIg+CD27+ |
| 35 | ADI-46596 | 5.11E−09 | 96.03 | 99.34 | 5A and ADI-45107 | Atypical IgM memory (IgM+IgD+CD27-SHM+) |
| 36 | ADI-50205 | 1.88E−08 | 99.70 | 99.64 | Blocks 5A only | IgM+IgD+CD27+ |
| 37 | ADI-42830 | 3.48E−09 | 95.10 | 93.86 | Blocks 5A only | swIg+CD27- |
| 38 | ADI-49186 | 1.23E−08 | 99.46 | 99.81 | Blocks 5A only | IgG+CD27+ |
| 39 | ADI-46591 | 9.60E−09 | 98.23 | 97.22 | 5A and ADI-45107 | Atypical IgM memory (IgM+IgD+CD27-SHM+) |
| 40 | ADI-48955 | 2.05E−09 | 99.87 | 96.91 | 5A and ADI-45107 | IgG+CD27+ |
| 41 | ADI-42818 | 2.41E−09 | 95.52 | 94.94 | Blocks 5A only | swIg+CD27+ |
| 42 | ADI-50531 | >1.0E−07 | 98.70 | 98.22 | Other | n.d. |
| 43 | ADI-46586 | 2.16E−09 | 97.63 | 97.56 | 5A and ADI-45107 | IgG+CD27+ |
| 44 | ADI-49138 | 1.75E−08 | 99.75 | 94.66 | Other | IgD memory (IgM-IgD+SHM+) |
| 45 | ADI-45075 | 2.61E−08 | 99.36 | 98.41 | DIII; ADI-49147 competitor | Atypical IgM memory (IgM+IgD+CD27-SHM+) |
| 46 | ADI-42831 | 1.96E−08 | 90.78 | 93.35 | Blocks 5A only | IgD memory (IgM-IgD+SHM+) |
| 47 | ADI-42230 | 1.99E−09 | 94.25 | 32.22 | Other | swIg+CD27- |
| 48 | ADI-42847 | 3.21E−09 | 83.08 | 91.27 | Blocks 5A only | swIg+CD27+ |
| 49 | ADI-42821 | 1.21E−08 | 93.76 | 90.48 | Blocks 5A only | swIg+CD27+ |
| 50 | ADI-42849 | 1.98E−09 | 95.03 | 94.68 | 5A and ADI-45107 | swIg+CD27- |
| 51 | ADI-42151 | 2.97E−07 | 94.29 | 71.97 | 5A and ADI-45107 | IgM+IgD+CD27+ |
| 52 | ADI-46001 | 6.17E−09 | 98.61 | 99.26 | 5A and ADI-45107 | IgG+CD27- |
| 53 | ADI-45154 | >1.0E−07 | 97.85 | 96.42 | Blocks 5A only | IgM-only (IgM+IgD-CD27+) |
| 54 | ADI-49161 | 1.81E−09 | 92.08 | 91.30 | Other | swIg+CD27- |
| 55 | ADI-42154 | 1.64E−07 | 98.99 | 96.53 | Blocks 5A only | Atypical IgM memory (IgM+IgD+CD27-SHM+) |
| 56 | ADI-48916 | 3.93E−07 | 99.79 | 88.13 | Other | Atypical IgM memory (IgM+IgD+CD27-SHM+) |
| 57 | ADI-45085 | 1.52E−07 | 99.32 | 96.95 | Other | swIg+CD27+ |
| 58 | ADI-42211 | 1.64E−09 | 99.73 | 92.83 | Other | IgM+IgD+CD27+ |
| 59 | ADI-48908 | 1.76E−09 | 99.80 | 74.90 | Blocks 5A only | IgG+CD27+ |
| 60 | ADI-48913 | 1.86E−07 | 98.86 | 81.30 | Other | Atypical IgM memory (IgM+IgD+CD27-SHM+) |

TABLE 2-continued

Affinity and Neutralization data for anti-YFV antibodies

| Antibody Number | Name | Monovalent Binding (KD) | Neut (100 nM) Avg. % Neutralization | Neut (10 nM) Avg. % Neutralization | Epitope Binning Data | B Cell Classification |
|---|---|---|---|---|---|---|
| 61 | ADI-45140 | 4.60E−09 | 82.51 | 41

TABLE 2-continued

Affinity and Neutralization data for anti-YFV antibodies

| Antibody Number | Name | Monovalent Binding (KD) | Neut (100 nM) Avg. % Neutralization | Neut (10 nM) Avg. % Neutralization | Epitope Binning Data | B Cell Classification |
|---|---|---|---|---|---|---|
| 120 | ADI-50197 | >1.0E−07 | 70.54 | 12.24 | Other | IgG+CD27− |
| 121 | ADI-48894 | 9.56E−08 | 97.88 | 59.39 | blocks 4G2 only | Atypical IgM memory (IgM+IgD+CD27-SHM+) |
| 122 | ADI-42226 | 8.43E−10 | 94.21 | 33.76 | Blocks 5A only | swIg+CD27− |
| 123 | ADI-49037 | 3.53E−09 | 79.59 | 7.14 | 4G2 and 5A | swIg+CD27+ |
| 124 | ADI-46739 | >1.0E−07 | 95.66 | 55.09 | Other | n.d. |
| 125 | ADI-42810 | >1.0E−07 | 0 | 0 | Other | Atypical IgM memory (IgM+IgD+CD27-SHM+) |
| 126 | ADI-49137 | 8.54E−10 | 46.64 | 50.93 | blocks 4G2 only | IgD memory (IgM-IgD+SHM+) |
| 127 | ADI-42817 | 4.15E−09 | 72.58 | 34.36 | Other | swIg+CD27+ |
| 128 | ADI-50218 | >1.0E−07 | 66.77 | 14.49 | Other | Naïve (IgM+IgD+CD71-CD21+SHM−) |
| 129 | ADI-42126 | 3.31E−07 | 20.23 | 1.07 | Other | swIg+CD27+ |
| 130 | ADI-42186 | 1.21E−09 | 84.73 | 43.51 | Other | swIg+CD27− |
| 131 | ADI-48890 | >1.0E−07 | 84.12 | 0 | Other | n.d. |
| 132 | ADI-42206 | 1.73E−09 | 71.04 | 23.09 | 4G2 and 5A | swIg+CD27+ |
| 133 | ADI-46724 | >1.0E−07 | 93.22 | 62.53 | 5A and ADI-45107 | n.d. |
| 134 | ADI-50539 | >1.0E−07 | 79.84 | 42.88 | Other | n.d. |
| 135 | ADI-45156 | >1.0E−07 | 54.57 | 2.90 | Other | n.d |
| 136 | ADI-50536 | >1.0E−07 | 99.76 | 13.96 | Other | n.d |
| 137 | ADI-42217 | 4.00E−09 | 50.24 | 3.33 | blocks 4G2 only | swIg+CD27+ |
| 138 | ADI-48951 | 2.67E−09 | 78.84 | 41.95 | Other | Atypical IgM memory (IgM+IgD+CD27-SHM+) |
| 139 | ADI-50537 | >1.0E−07 | 90.56 | 13.47 | Other | n.d. |
| 140 | ADI-46737 | >1.0E−07 | 66.49 | 49.68 | Other | n.d. |
| 141 | ADI-50538 | >1.0E−07 | 74.32 | 19.58 | Other | n.d. |
| 142 | ADI-48950 | 1.53E−09 | 69.81 | 14.45 | blocks 4G2 only | IgD memory (IgD+IgM-CD27-SHM+) |
| 143 | ADI-42114 | >1.0E−07 | 70.93 | 23.01 | ADI-45107 | n.d |
| 144 | ADI-49194 | 2.34E−07 | 80.83 | 46.50 | Other | IgG+CD27+ |
| 145 | ADI-42124 | 5.88E−09 | 63.14 | 62.65 | Other | IgM-only (IgM+IgD-CD27+) |
| 146 | ADI-45123 | 2.10E−09 | 59.03 | 27.03 | ADI-45107 | swIg+CD27+ |
| 147 | ADI-50533 | >1.0E−07 | 78.78 | 43.72 | Other | n.d. |
| 148 | ADI-49205 | 1.29E−08 | 90.74 | 44.01 | 5A and ADI-45107 | IgG+CD27− |
| 149 | ADI-45151 | >1.0E−07 | 0 | 0 | blocks 4G2 only | swIg+CD27+ |
| 150 | ADI-46728 | >1.0E−07 | 89.49 | 48.99 | Other | n.d. |
| 151 | ADI-49030 | 1.25E−07 | 63.26 | 4.97 | Other | Naïve |
| 152 | ADI-50200 | >1.0E−07 | 97.30 | 0 | 4G2 and 5A | IgM+IgD+CD27+ |

*NN-non-neutralizing;
n.d.-not determined;
Other-did not block any of the listed competition assay controls

TABLE 3

Informal Sequence Listing

| Antibody Number | SEQ ID NO: | Sequence | Clone # (ADI) | Descriptors |
|---|---|---|---|---|
| 1 | 304 | QVQLQESGPGLVKPSETLSLTCAVSGYSISSG FYWGWIRQPPGKGLEWIGSMYQSGITYYNP SLKSRVTISVDTSKSQFSLKLTSVTAADTAM YYCARNAPENYYGSGRESFDIWGQGTMVT VSS | ADI-49039 | Heavy chain variable region ("HC") amino acid sequence |
| 2 | 305 | QVQLQESGGDLVQPGGSLRLSCAASGFTFSN YAMNWVRQAPGKGLEWVSAINRGGDSTY YADSVKGRFTISRDNSKNTLYLQMNSLRAE DTAVYYCAKDHGGKYGWWYFDLWGRGT LVTVSS | ADI-49147 | Heavy chain variable region ("HC") amino acid sequence |
| 3 | 306 | QVQLQESGPGLVKPSETLSLTCAVSGYSISSG FYWGWIRQPPGKGLEWIGSMYHSGITYYNP SLKSRVTISVDTSKNQFSLKLTSVTAADTAM YYCARNAPENYYGSGRESFDIWGQGTTVT VSS | ADI-42229 | Heavy chain variable region ("HC") amino acid sequence |

TABLE 3-continued

Informal Sequence Listing

| Antibody Number | SEQ ID NO: | Sequence | Clone # (ADI) | Descriptors |
|---|---|---|---|---|
| 4 | 307 | EVQLVESGGGLVQPGRPLRLSCAASGFAFSS YGMHWVRQAPGKGLEWVALIRFDGTIKY YADSVKGRFTISRDNAKNTLYLQMSSLRAE DTAVYYCARDLEVGAEYLYYHYGMDVWG QGTTVTVSS | ADI-45090 | Heavy chain variable region ("HC") amino acid sequence |
| 5 | 308 | EVQLVESGGGVVQPGRSLRLSCAASGFTFNS HGMHWVRQAPGKGLEWVAVISYDGTKKY FADSVKGRFTISRDNSKNTLYLQMSSLRADD TAVYYCAKDSSTSWYQVVYHIDYWGQGTL VTVSS | ADI-45097 | Heavy chain variable region ("HC") amino acid sequence |
| 6 | 309 | EVQLLESGGGLVQPGGSLRLSCAASGFTFRN YAMNWVRQTPGKGLEWVSGISGGGDSTNY ADSVKGRFTISRDNSRNTLYLQLNSLRAEDT AVYYCAKDLAVSTPRYWFDSWGQGTLVTV SS | ADI-49133 | Heavy chain variable region ("HC") amino acid sequence |
| 7 | 310 | EVQLVESGGGLVQPGGSLRLSCAASGLIFRN YAMSWVRQAPGKGLEWVSSFSGSGGSAYY ADSVKGRFTISRDNSKSTVYLQMNRLRVED TAVYYCAKDMAVSVHRGWFDDWGQGTLV TVSS | ADI-49033 | Heavy chain variable region ("HC") amino acid sequence |
| 8 | 311 | QVQLVESGGGVVQPGRSLRLSCAASGFAFSS YGMHWVRQAPGKGLEWVAGMRFDGTKIY YADSVKGRFTISRDNSKNTLYLQMNSLRAE DTAVYFCARDLEVGAEYIYYYYGMDVWG QGTTVTVSS | ADI-49044 | Heavy chain variable region ("HC") amino acid sequence |
| 9 | 312 | QVQLVESGPGLVKPSGTLSLTCAVSGGSISS DYWWSWVRQPPGKGLEYIGEIYHTGSTNY NPSLKSRVTVSLDRSKNVFSLTLRSVTAADT AVYYCARSHWRSPQSVTFDLWGQGTTVTV SS | ADI-45083 | Heavy chain variable region ("HC") amino acid sequence |
| 10 | 313 | QVQLQESGPGLVKPSGTLSLTCAVSGGSITSS NWWSWVRQPPGKGLEWIGDIYHSGSTSYN PSLKSRVTISVDKSKNHFSLKLTSVTADTA VYYCARIAAGYSTSWYYFDYWGQGTLVTV SS | ADI-42225 | Heavy chain variable region ("HC") amino acid sequence |
| 11 | 314 | EVQLVETGSGLVRPSGTLSLTCAVSGDSISSN NWWSWVRQPPGKGLEWIGEIYHSGSTSYN PSLKSRVTISIDKSNNHFSLKLTSVTAADTAV YYCAKDMWAGTTTNWFGPWGQGTLVTVS S | ADI-49139 | Heavy chain variable region ("HC") amino acid sequence |
| 12 | 315 | QVTLKESGGALVKPAGSLTLSCAASGFTFG DYYMSWIRQAPGKGLEWISYISSSGSSIYYT DSVRGRFTISRDNARNSLYLQMNSLRVEDT AVYYCAREFSSRPFDLWGQGTLVTVSS | ADI-48969 | Heavy chain variable region ("HC") amino acid sequence |
| 13 | 316 | EVQLQESGPGLVKPSGTLSLTCAVSGGSISSS DWWSWVRQPPGKGLEWIGEIYHSGSTSYN PSVKSRVSISVDKSKNQFSLQLSSVTAADTAI YYCARVNPPQYSSGWYSVYWGQGTLVTVS S | ADI-48900 | Heavy chain variable region ("HC") amino acid sequence |
| 14 | 317 | QVQLQQSGPGLVKPSGTLSLTCAVSGDSISSS HWWCWVRQPPGKGLEWIGEIYHSGSTSYN PSLKSRVTISVDKSKNQFSLKLSSVTAADTA VYFCARVAWTSSSSCYYDYWGQGTLVTVS S | ADI-42232 | Heavy chain variable region ("HC") amino acid sequence |
| 15 | 318 | EVQLVESGPGLVKPSGTLSLTCAVSGGSISSS YWWSWVRQSPGKGLEWIGEVYHSGSTHY NPSLKSRVTISVDKSKNQFSLKLTSVTAADT AVYYCARDGEGHYYRSGDNWFDRWGQGT LVTVSS | ADI-42786 | Heavy chain variable region ("HC") amino acid sequence |
| 16 | 319 | EVQLLESGPGLVQPSGTLSLTCTASGGSISSS NWWSWVRQPPGKGLEWIGDIYHTGSTSYN PSLKSRVTISVDKSKNQFSLKLSSVTAADTA VYYCARAELSAWYYFDHWGQGTLVTVSS | ADI-42210 | Heavy chain variable region ("HC") amino acid sequence |
| 17 | 320 | QVQLVESGGGLVKPGGSLRLSCAASGFIFSD YYMNWIRQAPGKGLDWVSTISGSGKSIYYA DSVKGRFTISRDNAKNSLYLQMNSLSAEDT AVYYCARVSPLDDGYGYTYYGMDVWGQG TTVTVSS | ADI-50201 | Heavy chain variable region ("HC") amino acid sequence |
| 18 | 321 | EVQLLESGGGLVKPGGSLRLSCAASGFTFSD YYMSWIRQAPGKGLEWVSYITSSGNTKYY ADSVKGRFTISRDNAKNSLYLQISSLRAEDT AVYYCARDWAELTTITNYFYPWGQGTTVT VSS | ADI-48895 | Heavy chain variable region ("HC") amino acid sequence |
| 19 | 322 | EVQLLESGGGLVQPGRSLRLSCAASGFTFDD YAMHWVRQPPGKGLEWVSGISWNGGGIG | ADI-42228 | Heavy chain variable region |

TABLE 3-continued

Informal Sequence Listing

| Antibody Number | SEQ ID NO: | Sequence | Clone # (ADI) | Descriptors |
|---|---|---|---|---|
| | | YADSVKGRFTISRDNAKNSLYLQMNSLRAD DTALYYCAKAENRIGYCSAGSCYLTYFDY WGQGTLVTVSS | | ("HC") amino acid sequence |
| 20 | 323 | QVQLVQSGGGLVQPGGSLRLSCAASGFTFSS YAMSWVRQAPGKGLEWVSAISGSGGSTYY ADSVKGRFTISRDNSKNTLHLQMSSLRAEDT AVYYCAKDPKYSSGWWAFDYWGQGTLVT VSS | ADI-45113 | Heavy chain variable region ("HC") amino acid sequence |
| 21 | 324 | EVQLVESGPGLVKPSGTLSLTCAVSGGSISSN KWWSWVRQPPGKGLEWIGEIYHSGSTSYN PSLKSRVSISVDKSKNQFSLKLSSVTAADTA VYYCARVEWAYSSSWWLDYWGQGTLVTV SS | ADI-42198 | Heavy chain variable region ("HC") amino acid sequence |
| 22 | 325 | QVQLVESGGGLVKPGGSLRLSCAASGFTFSD DYMSWIRQAPGKGLEWVSYISGSGRAMYY ADSVQGRFTVSRDNAKNSLFLQMNNLRAED TAVYYCAKHTGDKPLVWAPSVYGLDVWG QGTTVTVSS | ADI-42190 | Heavy chain variable region ("HC") amino acid sequence |
| 23 | 326 | QVQLQESGPGLVKPSGTLSLTCAVSGSSITSS HWWSWVRQPPGKGLAWIGDIYHSGGTTY NPSLKSRVTISVDKSKNQFSLKLSSVTAADT AVYYCARVSVSTSAWYADYWGQGTLVTVS S | ADI-49154 | Heavy chain variable region ("HC") amino acid sequence |
| 24 | 327 | QVQLVESGGGLVKPGGSLRLSCVASGFTFN NYYMRWMRQAPGKGLEWVSQISSSGSIKD YADSVKGRFTVSRDNAKNSLYLQLNSLRAD DTAVYFCARELSSRIDYWGQGTLVTVSS | ADI-49183 | Heavy chain variable region ("HC") amino acid sequence |
| 25 | 328 | EVQLVESGGGVVQPGRSLRLSCVASGFTLRS YGMHWVRQVPGKGLEWVAVSWYDGSNK HYADSVKGRFSISRDNSKNTLYLQMNSLRA EDTAVYYCARAQDGQQLVNYYGMDVWG QGTTVTVSS | ADI-42201 | Heavy chain variable region ("HC") amino acid sequence |
| 26 | 329 | QVQLVESGGGVVQPGRSLRLSCAASGFTFSS YTMHWVRQAPGKGLEWVAVISYDGSNKY YADSVKGRFTISRDNSKNTLYLQMNSLRAE DTAVYYCARGGDYGDYESNNPAEYFQHW GQGTLVTVSS | ADI-42144 | Heavy chain variable region ("HC") amino acid sequence |
| 27 | 330 | QVQLQESGPGLVKPSETLSLTCTVSGDSISVS YWSWIRQFPGKGLEWIGYIYNSGNANYNPS LESRVTISIDTSKNRFSLRLSSVTAADTAVYY CAGHREDPYGAYGASWGQGTLVTVSS | ADI-50219 | Heavy chain variable region ("HC") amino acid sequence |
| 28 | 331 | EVQLLESGPGLVKPSETLSLTCTVSGGSLSSD SHFWGWIRQPPGKGLEWIGYIYYSGNANYN PSLQSRVTISLDKSKNQFSLRLTSVTAADTA VYYCASRKEVRGTEDYFDYWGQGTLVTVS S | ADI-48897 | Heavy chain variable region ("HC") amino acid sequence |
| 29 | 332 | EVQLQESGPGLVKPSETLSLTCTVSGGSVSS GSYYWSWIRQPPGKGLEWIGYIYDSGNTNY NPSLKSRVSIVDTSKRQFSLRLTSVTAADT AVYYCAKVEEDGYTNVVRDYWGQGTLVT VSS | ADI-42194 | Heavy chain variable region ("HC") amino acid sequence |
| 30 | 333 | EVQLVESGGGLVKPGGSLRLSCAASGFTFSD YYMSWIRQAPGKGLECIACISSSGSMIYYAD SVKGRFTISRDNAKNSLYLQLNSLRVEDTAV YYCAREGTRGRMDWGQGTLVTVSS | ADI-49189 | Heavy chain variable region ("HC") amino acid sequence |
| 31 | 334 | EVQLLESGPGLVRPSGTLSLTCAVSGGSISTT DWWSWVRQPPGKGLEWIGEINQSGSTSYSP SFKSRVSISVDKSKRQFSLKLTSVTAADTAV YYCARDSWSGPTRNWFDPWGRGTLVTVSS | ADI-49188 | Heavy chain variable region ("HC") amino acid sequence |
| 32 | 335 | EVQLLESGPGLVKPSGTLSLTCAVSGGSISSG NWWSWVRQPPGKGLEWIGEIYHSGSANYN PSLKSRVTISVDKSKNQFSLKLTSVTAADTA VYYCARVVWEYSNAWCVDFWGQGTTVTV SS | ADI-42188 | Heavy chain variable region ("HC") amino acid sequence |
| 33 | 336 | EVQLLESGGGVVQPGRSLRLSCAASGFTFTT YAMHWVRQAPGKGLEWVAAVSYDGNNKY YADSVKGRFTISRDNSRNTLYLQMNSLRAE DTAVYFCARNTYYDRSGLIAYWGQGALVT VSS | ADI-50026 | Heavy chain variable region ("HC") amino acid sequence |
| 34 | 337 | QVQLVESGPGLVKPSGTLSLTCAVSGDSISST NWWSWVRQPPGKGLEYIGEIFHSGSTNYNP FLKSRVTISVDKSKNHFSLKLSSVTAADTAV YYCARGPLKSYWYFDLWGRGTLVTVSS | ADI-42809 | Heavy chain variable region ("HC") amino acid sequence |
| 35 | 338 | QVQLQESGPGLVKPSGTLSLTCAVSGGSISS NNWWSWVRQPPGKGLEWIGDTYHSGSPSY | ADI-46596 | Heavy chain variable region |

TABLE 3-continued

Informal Sequence Listing

| Antibody Number | SEQ ID NO: | Sequence | Clone # (ADI) | Descriptors |
|---|---|---|---|---|
| | | NPSLKSRVTISVDKSKNEFSLKLSSVTAADT AVYFCARYCSGATCYGSNGMDVWGQGTT VTVSS | | ("HC") amino acid sequence |
| 36 | 339 | QVQLQESGGGVVQPGRSLRLSCAASGFTFS NFGMHWVRQAPGKGLEWVAIISYDRSNKD YADSVKGRFTISRDNSKNTLYLQMNSLRAE DTAVYYCAKDQCGGDCTADYWGQGTLVT VSS | ADI-50205 | Heavy chain variable region ("HC") amino acid sequence |
| 37 | 340 | EVQLLESGPGLVRPSGTLSLTCAVSGASISSN HWWTWVRQPPGKGLEWIGEIYHSGSPTYN PSLKSRVTISVDKSKNQFSLKLNSVTAADTA VYYCASTLWGGPLSVASDYWGQGTLVTVS S | ADI-42830 | Heavy chain variable region ("HC") amino acid sequence |
| 38 | 341 | QVQLVESGGGVVQPGRSLRLSCAASGFTFS NSGMHWVRQAPGQGLEWVALISYTGETK YYSDSLKARFTISRDNSKNTLYLQMSSLSNE DTAVYYCARDYYASGDGYFDYWGQGTLV TVSS | ADI-49186 | Heavy chain variable region ("HC") amino acid sequence |
| 39 | 342 | QVQLQQWGPELVKPSGTLSLTCTVSGGSISSI SWWSWVRQSPGKGLEWIGEINHSGSTVYN PSLKSRVTISVDKSKKQFSLKLRSVTAADTA VYYCVRYCSSTSCYGLNGMDVWGQGTTV TVSS | ADI-46591 | Heavy chain variable region ("HC") amino acid sequence |
| 40 | 343 | QVQLVQSGGGLVNPGGSLRLSCAASGFTFT DYYMSWIRQAPGKGLEWVSYISSSGNTRYY ADSVKGRFTISRDNAKNSLSLQMNSLRPEDT AIYYCARDGSLVNAIDYWGQGTLVTVSS | ADI-48955 | Heavy chain variable region ("HC") amino acid sequence |
| 41 | 344 | EVQLVESGPGLVKPSGTLSLTCAVSGGSITG SNWWSWVRQPPGKGLEWIGEIYHTGSTSY NPSLKSRVTISVDNSKNHFSLRLTSVTAADT AVYYCARVRWSGSTSWDLDYWGQGTLVT VSS | ADI-42818 | Heavy chain variable region ("HC") amino acid sequence |
| 42 | 345 | EVTLKESGPTLVKPTQTLTLTCTFSGFSLSTS GVGVGWIRQPPGKALEWLALIYWDDDKRY SPSLKSRLTITKDTSKNQVVLTMTNMDPVDT ATYYCAHSPRRITMVRGVIITWGDGMDV WGQGTTVTVSS | ADI-50531 | Heavy chain variable region ("HC") amino acid sequence |
| 43 | 346 | EVQLVESGGGLVKPGGSLRLSCAASGFTFTD YYMSWIRQAPGKGLEWVSYITSSGNTKYY ADSVKGRFTISRDNAKNSLFLQMNSLRAEDT AVYFCARDGSMVNAIDYWGQGTLVTVSS | ADI-46586 | Heavy chain variable region ("HC") amino acid sequence |
| 44 | 347 | QVQLVESGGGVVQPGRSLRLSCAASGFTFS NSGMHWVRQAPGKGLEWVSVIWYDESNK YYADSVKGRFTISRDNSKNTVYLQMNTLRA EDTAVYYCARDAYASGDGGIDYWGQGALV TVSS | ADI-49138 | Heavy chain variable region ("HC") amino acid sequence |
| 45 | 348 | EVQLLESGGGLVQPGGSLRLSCAASGFTFSS YAMSWVRQAPGKGLEWVSVISDSGGSTYY ADSVKGRFTISRDNSKNTLYLQMNSLRAED TAVYYCAKDLRGVGGWYYFDYWGQGTLV TVSS | ADI-45075 | Heavy chain variable region ("HC") amino acid sequence |
| 46 | 349 | EVQLVESGGGLVQPGGSLRLSCAASGFTFIN YAMTWVRQAPGKGLEWVSAISGNGDGTY YADSVKGRFTLSRDNAKNTIYLHMSALRDE DTALYYCAKDQGVTTDWPSDYWGQGTLV TVSS | ADI-42831 | Heavy chain variable region ("HC") amino acid sequence |
| 47 | 350 | QVQLVESGGGVVQPGRSLRLSCAASGFTFSS YAMHWVRQAPGKGLEWVAVISHDGSNKY YADSVKGRFTISRDNSKNTLYLQINSLRAED TAVYYCPRDGLPGANQYFFYYGMDVWGQ GTTVTVSS | ADI-42230 | Heavy chain variable region ("HC") amino acid sequence |
| 48 | 351 | EVQLLESGPRLVKPSETLSLTCTVSGGSVRG GSHYWSWIRQPPGKGLEWIGYVYDSGSTNY NPSLKSRVSISVDMSKKQFSLKLRSVTAADT AVYHCVRVEEYVNNEEVRDYWGQGTMVT VSS | ADI-42847 | Heavy chain variable region ("HC") amino acid sequence |
| 49 | 352 | EVQLLESGGGLVPPGGSLRLSCAASGFTFSN YAMSWVRQAPGKGLEWVSAISGSGDSTYY ADSVKGRFTLSRDTSKKMVYLHMSNLRDD DTAVYYCARDQGFTTDWPCDYWGQGTLV TVSS | ADI-42821 | Heavy chain variable region ("HC") amino acid sequence |
| 50 | 353 | QVQLVESGGGLVKPGGSLRLSCAASGFTFSD YYMSWIRQAPGKGLEWVSYITSSGNTMYY ADSVKGRFTISRDNAKNSLYLQMNSLRAED TAVYYCARDSNFNSNLDYWGQGTLVTVSS | ADI-42849 | Heavy chain variable region ("HC") amino acid sequence |

TABLE 3-continued

Informal Sequence Listing

| Antibody Number | SEQ ID NQ: | Sequence | Clone # (ADI) | Descriptors |
|---|---|---|---|---|
| 51 | 354 | QVQLQESGPGLVKPSGTLSLTCAVSGGSISSS NWWSWVRQPPGKGLEWIGEIYHSGSTTYN PSLKSRVTISVDKSKNQFSLKLSSVTAADTA VYYCARGPLKTYWYFDLWGRGTLVTVSS | ADI-42151 | Heavy chain variable region ("HC") amino acid sequence |
| 52 | 355 | EVQLVESGGGLVKPGGSLRLSCAASGFTFSD YYMSWIRQAPGKGLEWVSYISSSGNTIYYA DSVKGRFTISRDNAKNSLYLQLNSLRAGDTA VYYCARDSNYFYGLDVWGQGTTVTVSS | ADI-46001 | Heavy chain variable region ("HC") amino acid sequence |
| 53 | 356 | EVQLVESGGGVVQPGRSLRLSCAASGFTFSN YGMHWVRQAPGKGLEWVAVISYDGSNKY YADSVKGRFTISRDDSKNTLYLQVNSLRAED TAVYYCAKDICSGDCGGGDYWGQGTLVTV SS | ADI-45154 | Heavy chain variable region ("HC") amino acid sequence |
| 54 | 357 | QVQLVQSGAEVKKPGASVKVSCKASGYTFN TYAMTWVRQAPGQGLEWMGWISTYNGNT VFGQKFQGRVTLSTDTSTSTAYMELRSLTS DDTAVYYCAREDDDYYSMDVWGQGTTVT VSS | ADI-49161 | Heavy chain variable region ("HC") amino acid sequence |
| 55 | 358 | EVQLVQSGGGLVQPGGSLRLSCAASGFTFST YWMSWVRQAPGKGLEWVANIKQDGSEKY YVDSVKGRFTISRDNAKNSLYLQMNSLRAE DTAVYYCARDISCISTSCYGGYYYYGMDV WGQGTTVTVSS | ADI-42154 | Heavy chain variable region ("HC") amino acid sequence |
| 56 | 359 | EVQLVESGGGVVQPGRSLRLSCAASGFTFSN SGMHWVRQAPGKGLEWVAVIWYDSRNQN YADSVKGRFTISRDNSKNTLFLQMNSLRAED TAVYYCARDYYASGDGSIDYWGQGTLVTV SS | ADI-48916 | Heavy chain variable region ("HC") amino acid sequence |
| 57 | 360 | EVQLVESGGGLVQPGGSLRLSCAASGFTFSS YAMSWVRQAPGKGLEWVSTFSGRGGSTYY ADFVKGRFTISRDNSKNTLYLQMNSLRAED TAVYYCAKYYDSSGYYYFDYWGQGTLVTV SS | ADI-45085 | Heavy chain variable region ("HC") amino acid sequence |
| 58 | 361 | QVQLVESGGGVVQPGRSLRLSCGGSGFTFSS YGMHWVRQAPGKGLEWVAVISYDGSKKY SADSVKGRFTISRDNSKNTLYLQMNSLRAED TAVYYCAKGSVSVAGAEDYWGQGTLVTVS S | ADI-42211 | Heavy chain variable region ("HC") amino acid sequence |
| 59 | 362 | EVQLLESGGGLVQPGRSLRLSCAVSGFTFAE YAMHWVRQAPGKGLEWVSSSISWNSGRIGY VDSVRGRFTISRDNAKNSLYLQMNSLRVED TAFYYCAKGYDSSGYYWADYWGQGTLVT VSS | ADI-48908 | Heavy chain variable region ("HC") amino acid sequence |
| 60 | 363 | EVQLLESGPGLVKPSETLSLTCTVSGGSISSY YWSWIRQPAGKGLELIGRIYTSGSGNYNPSL KRRVTMSVDTSKNQISLRLNSVTAADTAVY YCARERGGYFTEPFDIWGQGTMVTVSS | ADI-48913 | Heavy chain variable region ("HC") amino acid sequence |
| 61 | 364 | EVQLLESGGGLVHPGGSLRLSCAASGFTFSD YEMNWVRQAPGKGLEWVSHISSSGNTIYYA DSVKGRFTISRDNAKDSLYLQMNSLRAEDT AVYYCAATIFGVVSFDYWGQGTLVTVSS | ADI-45140 | Heavy chain variable region ("HC") amino acid sequence |
| 62 | 365 | EVQLVESGGGLVQPGGSLRLSCAASGFTFSA YAMSWVRQAPGRGLEWVSAISGSDRRIYY ADSVKGRFSISRDNSKNTLYLQMSSLRAEDT AVYYCAKYYDSSGYYYLDYWGQGTLVTVS S | ADI-50211 | Heavy chain variable region ("HC") amino acid sequence |
| 63 | 366 | EVQLVESGGGLVQPGGSLRLSCAASGFTFSD HYMAWVRQAPGKGLEWVGRIRNKPNSYT TEYAASVKGRFTISRHDSENSLYLQMNSLKT EDTAVYYCCRESGEGFDPWGQGTLVTVSS | ADI-42199 | Heavy chain variable region ("HC") amino acid sequence |
| 64 | 367 | QVQLVQSGAEVKKPGASVKVSCKASGYSFT TYGISWVRQAPGQGLEWMGWISGYSGDTN YAQKVQGRVTMTTDTSTSTAYMELRSLRSD DTAVYYCARDQSHGTFGGVIDSTTLFYYY GMDVWGQGTTVTVSS | ADI-42231 | Heavy chain variable region ("HC") amino acid sequence |
| 65 | 368 | EVQLQESGPGLVKPSETLSLTCTVSGGSISSS SYYWGWIRQPPGKGLEWIGSIYYSGSTYYN PSLKSRVTISVDTSKNQFSLKLSSVTAADTA VYYCARGYCSSTSCFYYYYGMDVWGQGT TVTVSS | ADI-45164 | Heavy chain variable region ("HC") amino acid sequence |
| 66 | 369 | EVQLVESGGGLVKPGGSLRLSCVASGFTFSR YSMNWVRQAPGKGLEWVSSISHSGRYIYY ADSEKGRFTISRDNAKNSLYLQMNSLRAED TAVYYCARDHYFDSSGDYLSYYYNGMDV WGQGTTVTVSS | ADI-42233 | Heavy chain variable region ("HC") amino acid sequence |

TABLE 3-continued

Informal Sequence Listing

| Antibody Number | SEQ ID NO: | Sequence | Clone # (ADI) | Descriptors |
|---|---|---|---|---|
| 67 | 370 | EVQLVESGGGLVQPGGSLRLSCAASGFTFSD HYMDWVRQAPGKGLEWVGRTRNKPNSHT TEYAASVKGRFTISRDDSKNSLYLQMNSLQ TEDTAVYYCARVYGGPDDYWGQGTLVTVS S | ADI-42191 | Heavy chain variable region ("HC") amino acid sequence |
| 68 | 371 | EVQLVESGGGLVQPGGSLRLSCAASGFIYTN YAMYWVRQAPGKGLEWVSAISGSGGITYY ADSVKGRFTISRDNSKNTLYLQMNSLRAED KAVYYCAKDGVTTINGWFHFEYWGQGTL VTVSS | ADI-48899 | Heavy chain variable region ("HC") amino acid sequence |
| 69 | 372 | EVQLLESGGGLVQPGGSLRLSCAASGFIFSD YYMDWVRQTPGKGPEWVGRITNRPNSYTT EYAASVKGRFTISRDDSTNSLFLHMNSLKTE DTAVYYCTRITGDRYWYLDLWGRGTLVTV SS | ADI-49145 | Heavy chain variable region ("HC") amino acid sequence |
| 70 | 373 | EVQLVESGPGLVKPSQTLSLTCTVSGGSISSG SYYWSWIRQPAGKGLEWIGRIYTSGSTNYN PSLKSRVTMSVDTSKNQFSLKLSSVTAADTA VYYCARGWFGYSNYGLYYYYGMDVWGQ GTTVTVSS | ADI-46729 | Heavy chain variable region ("HC") amino acid sequence |
| 71 | 374 | EVQLVESGPGLVKPSGTLSLTCAVSGGSISSS NWWSWVRQPPGKGLEWIGEIYHSESTNYN PSLKSRVTISVDKSKNQFSLKLSSVTAADTA VYYCARDFWSGSNWFDPWGQGTLVTVSS | ADI-46722 | Heavy chain variable region ("HC") amino acid sequence |
| 72 | 375 | EVQLLESGGGLVQPGRSLRLSCAASGFTFDD YAMHWVRQAPGKGLEWVSGISWNSGSIGY ADSVKGRFTISRDNAKNSLYLQMNSLRAED TALYYCAKDIGDSYGSGSYYLPYGAYYGM DVWGQGTTVTVSS | ADI-45148 | Heavy chain variable region ("HC") amino acid sequence |
| 73 | 376 | EVQLLESGGGLVQPGGSLRLSCAASGFTFSS YAMSWVRQATGRGLEWVSSIRSSGGRTEY ADSVKGRFTISRDNSKNTLYLQMDSLRAED TALYYCAKHYDSSGYYYEDYWGQGTLVTV SS | ADI-49168 | Heavy chain variable region ("HC") amino acid sequence |
| 74 | 377 | EVQLVESGGALVHPGGSLGLSCAASGFTFSD HYMDWVRQAPGKGLEWVGRIRNKPNSYA TQYAASVKGRFTISRDDSKKSLYLQMNSLN TEDTAVYYCARVRDGEYDYWGQGTLVTVS S | ADI-49040 | Heavy chain variable region ("HC") amino acid sequence |
| 75 | 378 | EVQLLESGGGLVKPGGSLRLSCAASGFTFSS YSMNWVRQAPGKGLEWVSSISSRSSFMYY ADSVKGRFTISRDNAKNSLYLQMNSLRVED TAVYYCARDNSEVEDYGDYVLYHYYGMD VWGQGTTVTVSS | ADI-42187 | Heavy chain variable region ("HC") amino acid sequence |
| 76 | 379 | EVQLLESGGGVVQPGRSLRLSCVASGFTFSS YGMHWVRQAPGKGLEWVALISYDGSNKY YADSVKGRFTISRDNSKNTLYLQMNSLRAE DTAVYYCAKDQCGGDCTADYWGQGTLVT VSS | ADI-49561 | Heavy chain variable region ("HC") amino acid sequence |
| 77 | 380 | QVQLVESGGGVVQPGRSLRLSCAASGFTFSS LAMHWVRQAPGKGLEWVATISYDVSNKY YADSVKGRFTISRDNSKNTLFLQMNSLRPED TAVYYCARGYTGYDGFDYWGQGTLVTVSS | ADI-42219 | Heavy chain variable region ("HC") amino acid sequence |
| 78 | 381 | QVQLVQSGAEVKKPGASVKVSCKASGYTFT SYGISWVRQAPGQGLEWMGWISAYNGNTN YAQKLQGRVTMTTDTSTSTAYMELRSLRSD DTAVYYCARRPYYYGSRRPAGHMDVWGQ GTTVTVSS | ADI-50535 | Heavy chain variable region ("HC") amino acid sequence |
| 79 | 382 | QVQLQESGPGLVRPSQTLSLTCTVSGGAISS GDYYWSWVRQPPGKGLEWIGYIHYSGTTY NNPSLKSRVTIAVDTSKNQFSLKLSSVTAAD TAVYFCGRDSDKNYFDYWGQGTLVTVSS | ADI-45128 | Heavy chain variable region ("HC") amino acid sequence |
| 80 | 383 | EVQLVESGGGVVRPGRSLRLSCAASGFTFSS YGMHWVRQAPGKGLEWVAVIRFDGSNTV YADSVKGRFTISRDNSKNTLYLQMNSLRAE DTAVYYCAKTYDSNAYYYLDYWGQGTLVT VSS | ADI-45136 | Heavy chain variable region ("HC") amino acid sequence |
| 81 | 384 | EVQLVESGGGVVQPGWSLRLSCAVSGFTFS SYAMHWVRQAPGKGLEWVAVISYDGSYK WYADSVKGRFTISRDNSKNTVYLQMNSLRA EDTAVYYCASLWFIVMTMSKNPETDYWG QGTLVTVSS | ADI-42189 | Heavy chain variable region ("HC") amino acid sequence |
| 82 | 385 | EVQLVESGGGLIQPGGSLRLSCAASGFSFSSH AMTWVRQAPGKGLQWVSSIRGSDRTTNYA DSVKGRFTVSRDNSKNTLYLQMNSLRAEDT | ADI-45078 | Heavy chain variable region ("HC") amino acid |

TABLE 3-continued

Informal Sequence Listing

| Antibody Number | SEQ ID NO: | Sequence | Clone # (ADI) | Descriptors |
|---|---|---|---|---|
| | | AIYYCAKYYDSSGYYYFDHWGQGTLVTVSS | | sequence |
| 83 | 386 | EVQLVESGGTFLQPGGSLRLSCVASGFTFGTHAMSWVRQAPGKGLEWVSTFSGSGGRTYYADSVKGRFTISRDNSKSTLYLEMSALRAEDTAVYYCAKFYDSSGYYYFDYWGQGTLVTVSS | ADI-49162 | Heavy chain variable region ("HC") amino acid sequence |
| 84 | 387 | EVQLVESGGGLVQPGGSLRLSCAASGFTFSDYYMDWVRQAPGKGLEWVGGIRNKPNSYTTEYAASVKGRFTISRDDSKNSLFLQMNSLKTEDTAVYYCVRLYGDYVAYFDYWGQGTLVTVSS | ADI-42223 | Heavy chain variable region ("HC") amino acid sequence |
| 85 | 388 | QVQLVQSGAEVKKPGASVKVSCKASGYTFTSYGISWVRQAPGQGLEWMGWISAYNGNTNYAQKLQGRVTMTTDTSTAYMELRSLRSDDTAVYYCARRGTTVTRFGVIQYYYGMDVWGQGTTVTVSS | ADI-48435 | Heavy chain variable region ("HC") amino acid sequence |
| 86 | 389 | QVQLQESGPGLVKPSETLSLTCTVSGASIRSYLWSWIRQPPGKELEWLGSIYHSGSTKYNPSLKSRVTISADTSKNQFSLKLNSVTAADTAVFYCARETANNWFDPWGQGTLVTVSS | ADI-46742 | Heavy chain variable region ("HC") amino acid sequence |
| 87 | 390 | EVQLVESGGGVVQSGRSLRLSCAASGFTFSGNAMHWVRQAPGKGLEWVAVILYDGSNQYYADSVKGRFTISRDNSKNTLYLQMNSLRPADTAVYYCARASMMPRPPVHDYWGQGTLVTVSS | ADI-42787 | Heavy chain variable region ("HC") amino acid sequence |
| 88 | 391 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKDRSQGDYGDYVADYWSQGTLVTVSS | ADI-46718 | Heavy chain variable region ("HC") amino acid sequence |
| 89 | 392 | EVQLQESGPGLVKPSGTLSLTCAVSGGSISSSNWWTWVRQPPGKGLEWIGEIYHSGSTNYNPSLESRVTMSVDKSKNQFSLKLSSVTAADTAVYYCARVQTSHSELWFGEFGADWGQGTLVTVSS | ADI-49141 | Heavy chain variable region ("HC") amino acid sequence |
| 90 | 393 | EVQLLESGGGLVQPGGSLRLSCAASGFTFTYYAMSWVRQAPGKGLEWVSGISGSGDSTYNADSVKGRVTISRDNSKNTLYLQMNSLRAEDTAVYYCAKDGGYSTDWYFDLWGRGTLVTVSS | ADI-42213 | Heavy chain variable region ("HC") amino acid sequence |
| 91 | 394 | QVQLVESGGGVVQPGRSLRLSCTASGFTFSSYGMHWVRQAPGKGPEWVAVISYDGSKKYFADSVKGRFTISRDNSKNTLYLQMNSLRAEDTAVYSCAKGYDSNGYYYIDYWGQGTPVTVSS | ADI-42844 | Heavy chain variable region ("HC") amino acid sequence |
| 92 | 395 | QVQLQESGGGVVQPGRSLRLSCAASGFTFSSYGMHWVRQAPGKGLEWVAVIWYDGSNKYYADSVKGRFTISRDNSKNTLYLQMNSLRAEDTAVYYCARDVGYQLLQVYGMDVWGQGTTVTVSS | ADI-45161 | Heavy chain variable region ("HC") amino acid sequence |
| 93 | 396 | EVQLLESGPGLVKPSQTLSLTCSVSGGSISSGGYYWTWIRQPPGKGLEWIGYIYYTGSTYYNPSLKSRVTISVDTSKNQFSLKLSSVTAADTAVYFCARAEYDTSGYYQQRLPEYFQHWGQGTLVTVSS | ADI-42192 | Heavy chain variable region ("HC") amino acid sequence |
| 94 | 397 | EVQLVQSGGGLVQRGGSLRLSCAASGFTFSSYAMTWVRQAPGKGLEWVSDMNHSGDRTNYADSVRGRFTISRDNSKNTLYLQMNSLRAEDTAVYYCAKYYDSSGYYYFHSWGQGTLVTVSS | ADI-48910 | Heavy chain variable region ("HC") amino acid sequence |
| 95 | 398 | EVQLLESGGGLVQPGGSLRLSCAASGFIFSDHYMAWVRQAPGKGLEWVGRSRNRPNSYTTEYAASAKGRFTISRDDSKTSLYLQMNSLKTEDTAVYYCAREHGDYGLDYWGQGTLVTVSS | ADI-42193 | Heavy chain variable region ("HC") amino acid sequence |
| 96 | 399 | QVQLVQSGAEVKKPGASVKVSCKASGYTFTGYYMHWVRQAPGQGLEWMGRINPNSGGTNYAQKFQGRVTMTRDTSISTAYMELSRLRSDDTAVYYCVDYYYDSSGYYSPFDYWGQGTLVTVSS | ADI-49590 | Heavy chain variable region ("HC") amino acid sequence |
| 97 | 400 | EVQLVESGGGFVQPGGSLRLSCAASGFIFSDYYMDWVRQAPGKGLEWVGRIRNKPNSYT | ADI-45076 | Heavy chain variable region |

TABLE 3-continued

Informal Sequence Listing

| Antibody Number | SEQ ID NO: | Sequence | Clone # (ADI) | Descriptors |
|---|---|---|---|---|
| | | TEYAASVKGRFSISRDDLKNSLYLQMNSLKTEDTAEYYCARVDGEEVALIYWGQGALVTVSS | | ("HC") amino acid sequence |
| 98 | 401 | EVQLLESGGGLGQPGGSLRLSCVASKFTFSDHYMDWVRQAPGKGLEWVGRIRNKPNGYTTEYAASVKGRFIISRDDSKNSLYLQMKSLKIEDTAIYYCVRVWGGEAARYDYWGQGALVTVSS | ADI-48968 | Heavy chain variable region ("HC") amino acid sequence |
| 99 | 402 | EVQLVESGGGLVQPGGSLRLSCAASGFTFSDHYMDWVRQAPGKGLEWVGRSRNKPNSYITEYAASVKGRFTISRDDSKNSLYLQMNSLKTEDTAVYYCSRHMGFGLDLWGQGTLVTVSS | ADI-42212 | Heavy chain variable region ("HC") amino acid sequence |
| 100 | 403 | QVQLVQSGGGVVQPGRSLRLSCAASGFTFSSYGMHWVRQAPGKGLEWVAVIWYDGSNKYYADSVKGRFTISRDNSKNTLYLQMNSLRAEDTAVYYCARDYYGSGDGYFDYWGQGTTVTVSS | ADI-48462 | Heavy chain variable region ("HC") amino acid sequence |
| 101 | 404 | EVQLVESGPVLVKPTETLRLTCTVSGFSLSNTKLGVSWIRQPPGKALEWLAHIFSNAEKSSSKSLKSRLSISQDTSKSLVVLTMTNMDPVDTATYFCARIPVEYGTPRGSFDTWGQGTTVTVSS | ADI-45127 | Heavy chain variable region ("HC") amino acid sequence |
| 102 | 405 | EVQLVESGGGVVQPGRSLRLSCAASGLTFSTYTLHWVRQAPGKGLEWVAVISSDGGNKYYADSVKGRFTISRDSSKNTLYLQMNSLRTEDTAVYYCAGGSPDYWGQGALVTVSS | ADI-42200 | Heavy chain variable region ("HC") amino acid sequence |
| 103 | 406 | EVQLVESGGGVVQPGRSLRLSCVPSGFTFSSYAMHWVRQAPGKGLEWVAMMSYDGGDKNYADSVKGRFTISRDNSKNTLYLQMRSLRAEDTAIYYCARAYDSRGYYYIEHWGQGTLVTVSS | ADI-50203 | Heavy chain variable region ("HC") amino acid sequence |
| 104 | 407 | QVQLVQSGAEVRKPGASVKVSCKASGYTFTSYGISWVRQAPGQGLEWMGWISTYNGNTNYAQKLQGRVTMTTDTSTSTAYMELRSLRSDDTAVYYCAREIDSNYVFDYWGQGTLVTVSS | ADI-42149 | Heavy chain variable region ("HC") amino acid sequence |
| 105 | 408 | EVQLVESGGGLVQPGGSLRLSCAASGFTFSNYWMNWVRQAPGKGLEWVANIKQDGSEKYYVDSVKGRFTISRDNAKNSLYLQMNSLRAEDTAVYYCARKLSYSSGWYYFDYWGQGTLVTVSS | ADI-42181 | Heavy chain variable region ("HC") amino acid sequence |
| 106 | 409 | EVQLVESGGGLVQPGGSLRLSCAASGFTFSDHYMDWVRQAPGKGLEWVGRSTNKPNSYTTTYAASVRGRFTISRDESKNSLYLQMNSLKSDDTAVYYCVTTTVILFDYWGQGTLVTVSS | ADI-45126 | Heavy chain variable region ("HC") amino acid sequence |
| 107 | 410 | QVQLQQWGAGLLKPSETLSLTCAVYGGSFSGYYWSWIRQPPGKGLEWIGEINHRGSTDYNPSLKSRVTMSVDTSKNQFSLRLSSVTAADTALYYCARGRLAWGLRGQKSPNFFAYWGQGATVTVSS | ADI-45074 | Heavy chain variable region ("HC") amino acid sequence |
| 108 | 411 | EVQLVESGGGLVKPGGSLRLSCAASGFTFSHAWMTWVRQAPGKGLEWVGRIKSETDGGTANYAAPVKGRFTISRDDSKNTVYLQMVSLKTEDTAVYYCATAGIFGVVIMKGFDHWGQGTTVTVSS | ADI-49041 | Heavy chain variable region ("HC") amino acid sequence |
| 109 | 412 | EVQLLESGAEVKEPGSSVKVSCKPSGGTFSSYVISWVRQAPGQGLEWMGGIIPIFGTPNYAQKFQGRVTITADDSTSTAHMELSSLTSDDTAVYYCARETYYYGSGSVPVHDWGQGTLVTVSS | ADI-42227 | Heavy chain variable region ("HC") amino acid sequence |
| 110 | 413 | EVQLVESGGGVVQPGRSLRLSCAASGFIFSSNSMHWVRQAPGKGLKWVAIISNDGRNKFYADAVKGRFTVSRDNSKNTLYLQMNSLRPEDTAVYYCARGYDSSGYWGFGDNWGQGTLVTVSS | ADI-50220 | Heavy chain variable region ("HC") amino acid sequence |
| 111 | 414 | QVQLVQSGGGLVQPGGSLRLSCAASGFTFSDHYMDWVRQAPGKGLEWVGRTRNKANSYTTKYAASVKGRFTISRDDSKNSLYLQMNSLKTEDTAVYYCARVEGGAWGAFDIWGQGTTVTVSS | ADI-42141 | Heavy chain variable region ("HC") amino acid sequence |
| 112 | 415 | QVTLKESGPVLVKPTETLTLTCTVSGFSLSNTKMGVTWIRQPPGKALEWLAHIFSNDEKSCNTSLKSRLTISKDTSKSQVVLTMTNMDPVDTATYYCARLWFTEYPGAFDIWGQGTMVTVSS | ADI-42216 | Heavy chain variable region ("HC") amino acid sequence |

TABLE 3-continued

Informal Sequence Listing

| Antibody Number | SEQ ID NO: | Sequence | Clone # (ADI) | Descriptors |
|---|---|---|---|---|
| 113 | 416 | EVQLQESGPGLVKPSETLSLTCTVSGGSISSS SYYWGWIRQPPGKGLEWIGSIYYSGSTYYN PSLKSRVTISVDTSKNQFSLKLSSVTAADTA VYYCARHSSGSYYLAGYYFDYWGQGTLVT VSS | ADI-50534 | Heavy chain variable region ("HC") amino acid sequence |
| 114 | 417 | EVQLVESGGGLVQPGGSLRLSCAASGFTFSD HYMDWVRQAPGRGLEWVGRSRNKVNSYT TDYAASVKGRFTISRDDSKNSLFLRMNSLKT EDTAVYYCARLTDSGYDDWGLGTLVTVSS | ADI-49140 | Heavy chain variable region ("HC") amino acid sequence |
| 115 | 418 | EVQLVESGPGLVKPSETLSLTCTVSGGSISSY YWSWIRQPPGKGLEWIGYIYYSGSTNYNPS LKSRVTISVDTSKNQFSLKLSSVTAADTAVY YCARETCSGGSCYYRVGSAFDIWGQGTTV TVSS | ADI-46741 | Heavy chain variable region ("HC") amino acid sequence |
| 116 | 419 | EVQLLESGGGMVQPGRSLRLSCAASGFTFD DYDMHWVRQGPGKGLEWVSGISWNSGGR GYADSVKGRFTISRDNAKNSLYLQMNSLRV EDTALYYCVKDYCSGGRCYSFDYWGQGTL VTVSS | ADI-42195 | Heavy chain variable region ("HC") amino acid sequence |
| 117 | 420 | QVQLVESGGGVVQPGRSLRLSCAASGFTFSS YGMHWVRQAPGKGLEWVAVMSYDGSNK YYADSLKGRFTISRDNSKNTLYLQMNSLRA EDTAVYFCAKAYDSSAYYYLDYWGQGTLV TVSS | ADI-42172 | Heavy chain variable region ("HC") amino acid sequence |
| 118 | 421 | EVQLVESGGGVIQPGRSLRLSCAASGFNFSS YGMHWVRQAPGKGLEWVAVISYDGSNKY YADSVKGRFTISRDNSKNTLYLQMNSLRAE DTAVHYCAKAYDSRGYYYLDYWGQGTLV TVSS | ADI-42178 | Heavy chain variable region ("HC") amino acid sequence |
| 119 | 422 | EVQLVQSGGGLVQPGGSLRLSCVGSGLTLSS SAMSWVRQAPGKGLECVSGITGSGSDSSYA ASVKGRFTISRDNSKNTVYLQMNSLRAEDT AVYYCAKDLTHRLGSIFGKLTFDAFDIWG PGTMVTVSS | ADI-49032 | Heavy chain variable region ("HC") amino acid sequence |
| 120 | 423 | EVQLVESGGGVVQPGRSLRLSCAASGFTFSS YGMHWVRQAPGKGPEWVAVISEDGNKDH YVDSVKGRFSIYRDNSKSTVFLRMTSLRAED TAVYYCAKDLTPYFYDSGAFDHWGQGTLV TVSS | ADI-50197 | Heavy chain variable region ("HC") amino acid sequence |
| 121 | 424 | EVQLVESGGGLVQPGGSLRLSCAVSGFTFSD HYMDWVRQAPGKGLEWVGRSRNKVNSYI TEYAASVKGRFSISRDDSKNSLYLQMNSLKI EDTAVYYCARVFGGPTDYWGQGTLVTVSS | ADI-48894 | Heavy chain variable region ("HC") amino acid sequence |
| 122 | 425 | EVQLLESGGGLVQPGGSLRLSCAASGFIFSD HYMDWVRQAPGKGLEWVGRIRNKPNSYT TDYAAYVKGRFSISRDDSKNSLFLQMNSLK TEDTAVYYCARVVNGLDVWGQGTTVTVSS | ADI-42226 | Heavy chain variable region ("HC") amino acid sequence |
| 123 | 426 | EVQLVESGGGVVQPGRSLRLSCAASGFTLSS YVMHWVRQAPGKGLEWVAVISSDGTNKY YADSVKGRFTISRDSSKNTLYLQMNSLRPED SAVYYCARGQPDYWGQGTLVTVSS | ADI-49037 | Heavy chain variable region ("HC") amino acid sequence |
| 124 | 427 | EVQLVESGPGLVKPSGTLSLTCAVSGGSISSD NWWSWVRQAPGKGLEWIGEIYHTGSTSYN PSLKSRVTISLDKSKNHFSLKLNSLTAADTA VYYCAGKKWELLGFRFDPWGQGTLVTVSS | ADI-46739 | Heavy chain variable region ("HC") amino acid sequence |
| 125 | 428 | QVQLVESGAEEKKPGASVKVSCKASGYTFT SYAMHWVRQAPGQRLEWMGWINAGNGNT KYSQKFQGRVTITRDTSASTAYMELSSLRSE DTAVYYCARQWLGHFDYWGQGTLVTVSS | ADI-42810 | Heavy chain variable region ("HC") amino acid sequence |
| 126 | 429 | EVQLVESGGGLVQPGGSLRLSCAASGFIFSD HYMAWVRQAPGKGLEWVGHVGNKANTY TTEYAASVKGRFTISRDDSKKSLYLQMNRL KSEDTAVYYCARVFSYYLDYWGQGTPVTV SS | ADI-49137 | Heavy chain variable region ("HC") amino acid sequence |
| 127 | 430 | QVTLKESGPTLVKPTQTLTLTCTFSGFSLSTS GVGVGWTRQPPGKALEWLALIYWDDDKR YSPSLKSRLTITKDTSKNQVVLTMTKMDPV DTATYYCAHRHIAARLYRDDDVFDVWGQ GTMVTVSS | ADI-42817 | Heavy chain variable region ("HC") amino acid sequence |
| 128 | 431 | QVQLVQSGAEVKKPGASVKVSCKASGYTFT SYDINWVRQATGQGLEWMGWMNPNSGNT GYAQKFQGRVTMTRNTSISTAYMELSSLRS EDTAVYYCARGLNTVTNSDYWGQGTLVTV SS | ADI-50218 | Heavy chain variable region ("HC") amino acid sequence |

TABLE 3-continued

Informal Sequence Listing

| Antibody Number | SEQ ID NO: | Sequence | Clone # (ADI) | Descriptors |
|---|---|---|---|---|
| 129 | 432 | QVQLVQSGAEVKKPGASVKVSCKASGYTFT GYYMHWVRQAPGQGLEWMGWINPNSGGT NYAQKFQGWVTMTRDTSISTAYMELSRLRS DDTAVYYCASGLSPDFSVLDVWGQGTTVT VSS | ADI-42126 | Heavy chain variable region ("HC") amino acid sequence |
| 130 | 433 | QVQLQQSGPGLVKPSQTLSLTCAISGDSVST NSAAWNWIRQSPSRGLEWLGRTYYRSKWY NDYALSVKSRITIKPDTSKNQFSLQLNSVTPE DTAVYYCAREGAGYYDSSGYYPLSYDAFD IWGRGTMVTVSS | ADI-42186 | Heavy chain variable region ("HC") amino acid sequence |
| 131 | 434 | EVQLVESGGGLVQPGGSLRLSCAASGFTFSD HYMDWVRQAPGKGLEWVGRARNRANSYT TEYAASVKGRFAASRDDSKNSLYLQMNSLK TEDTAVYYCARVRGSYWDYWGQGTLVTVS S | ADI-48890 | Heavy chain variable region ("HC") amino acid sequence |
| 132 | 435 | QVQLVQSGGGLVQPGGSLRLSCAASGFTFS DHYMDWVRQAPGKGLEWVGRIRNKVNSY TTEYAASVKGRFTISRDDSKNSLYLQMNSL KTEDTAVYYCGRDRGWLDIWGQGTMVTV SS | ADI-42206 | Heavy chain variable region ("HC") amino acid sequence |
| 133 | 436 | QVQLQESGPGLVEPSGTLSLTCVVTGDSISSR SWWSWVRQPPGKGLEWIGEIYHSGTTTYSP SLKSRVIISLDKSENHFSLKMTSVTAADTAV YYCARVIRDLRDYYDGSGYGPDAFDIWGQ GTTVTVSS | ADI-46724 | Heavy chain variable region ("HC") amino acid sequence |
| 134 | 437 | EVQLVESGPGLVKPSGTLSLTCAVSGGSISSS NWWSWVRQPPGKGLEWIGEIYHSGSTNYN PSLKSRVTISVDKSKNQFSLKLSSVTAADTA VYYCARARWEDGNYYYGMDVWGQGTTV TVSS | ADI-50539 | Heavy chain variable region ("HC") amino acid sequence |
| 135 | 438 | EVQLVESGGGLVQPGGSLRLSCAASGFTFSS YAMSWVRQAPGKGLEWVSAISGSGGSTYY ADSVKGRFTISRDNSKNTLYLQMNSLRAED TAVYYCAKDQSSGWPNYYYGMDVWGQGT TVTVSS | ADI-45156 | Heavy chain variable region ("HC") amino acid sequence |
| 136 | 439 | QVQLVESGSELKKPGASVKVSCKASGYTFT SYAMNWVRQAPGQGLEWMGWINTNTGNP TYAQGFTGRFVFSLDTSVSTAYLQISSLKAE DTAVYYCVRGYCSSTSCYGGLYWFDPWG QGTLVTVSS | ADI-50536 | Heavy chain variable region ("HC") amino acid sequence |
| 137 | 440 | EVQLVESGGGVVQPGRSLRLSCADSGFTFSY SAIHWVRQAPGKGLEWVAVISYDGSNKYY ADSVKGRFTISRDNSKNTLYLQMNSLRPEDT AVYYCARHSGGYSSKDKPTEYFQHWGQG TLVTVSS | ADI-42217 | Heavy chain variable region ("HC") amino acid sequence |
| 138 | 441 | EVQLLESGPGLVKPSGTLSLTCAVSGASISSN NWWSWVRQSPGKGLEWIGEIFHSGTTNYN PSLKSRVTISVDKSKNQFSLKLNSVTAADTA VYYCARDVGVAAVITGSVRWGQGTLVTVS S | ADI-48951 | Heavy chain variable region ("HC") amino acid sequence |
| 139 | 442 | QVQLVQSGSELKKPGASVKVSCKASGYTFT SYAMNWVRQAPGQGLEWMGWINTNTGNP TYAQGFTGRFVFSLDTSVSTAYLQISSLKAE DTAVYYCARGYCSSTSCYGGLYWFDPWG QGTLVTVSS | ADI-50537 | Heavy chain variable region ("HC") amino acid sequence |
| 140 | 443 | QVQLVQSGGGVVQPGRSLRLSCAASGFTFSS YAMHWVRQAPGKGLEWVAVISYDGSNKY YADSVKGRFTISRDNSKNTLYLQMNSLRAE DTAVYYCARDGAGDYIWGSYRHKGLHYY YGMDVWGQGTTVTVSS | ADI-46737 | Heavy chain variable region ("HC") amino acid sequence |
| 141 | 444 | EVQLVESGPGLVMPSGTLSLTCTVSGISISSS NWWSWVRQSPGKGLEWIGEVYHSGSTKY NPSLKSRVTISVDKSRNQFSLKLNSVTAADT AVYYCAKDPRTFYGVVMLLDDPWGQGTL VTVSS | ADI-50538 | Heavy chain variable region ("HC") amino acid sequence |
| 142 | 445 | EVQLVESGGGVVQPGRSLRLSCAVSGFTFST SPLHWVRQAPGKGLEWVAVSSFVATDKYY ADSVKGRFTVSRDNSKNTLYLQMNSLRPED TAVYYCARGFGELPGFDIWGQGTMVTVSS | ADI-48950 | Heavy chain variable region ("HC") amino acid sequence |
| 143 | 446 | EVQLLESGGGLVKPGGSLRLSCAASGFTFSS YSMNWVRQAPGKGLEWVSSISSSSSYIYYA DSVKGRFTISRDNAKNSLYLQMNSLRAEDT AVYYCARDSWGPFDYWGQGTLVTVSS | ADI-42114 | Heavy chain variable region ("HC") amino acid sequence |
| 144 | 447 | EVQLVESGGAVVQPGRSLRLSCAASGFTFSS YGMHWVRQAPGKGLESVAVIWYDGSNKN | ADI-49194 | Heavy chain variable region |

TABLE 3-continued

Informal Sequence Listing

| Antibody Number | SEQ ID NO: | Sequence | Clone # (ADI) | Descriptors |
|---|---|---|---|---|
| | | YADSVKGRFTISRDNSKNTLFLQMNSLRAED SAMYYCAKTYDSRAYYYLDYWGQGTLVT VSS | | ("HC") amino acid sequence |
| 145 | 448 | EVQLLESGGGLVQPGGSLRLSCAASGFTFSS YAMSWVRQAPGKGLELVSAISSSGGSTYYA DSVKGRFTISRDNSKNTLYLQMNSLRAEDT ALYYCAKDLFYDFWTGITIDYWGQGTLVT VSS | ADI-42124 | Heavy chain variable region ("HC") amino acid sequence |
| 146 | 449 | EVQLLESGGGLVQPGGSLRLSCAASGFIFSN YWMSWVRQAPGKGLEWVANIKPDGSEKY YVESVRGRFTISRDNAKNSLYLQMNSLRAE DTAVFYCARDGGTVSDGLDVWGQGTTVTV SS | ADI-45123 | Heavy chain variable region ("HC") amino acid sequence |
| 147 | 450 | QVQLQESGPGLVKPSGTLSLTCAVSGGSISSS NWWSWVRQPPGKGLEWIGEIYHSGSTNYN PSLKSRVTISVDKSKNQFSLKLSSVTAADTA VYYCARVVWYSSSSHLFDYWGQGTLVTVS S | ADI-50533 | Heavy chain variable region ("HC") amino acid sequence |
| 148 | 451 | EVQLVESGGGVVQTGRSLRLSCAASGFTFSI SGMHWVRQAPGKGLEWVALIWYDGTKKY YADSVKGRFTISRDDFKNTVYLQMNSLRAD DTAVYYCARIKSDAFDLWGQGTTVTVSS | ADI-49205 | Heavy chain variable region ("HC") amino acid sequence |
| 149 | 452 | EVQLLESGGGVVQPGKSLRLSCAASGFSFGD YGMHWVRQTPDKGLEWVAVILFDGSKKF YADSVRGRFTISRDNSKNNLYLQMSSLRPED TAVYYCAKFPLRDGGSGEGFDYWGQGTLV TVSS | ADI-45151 | Heavy chain variable region ("HC") amino acid sequence |
| 150 | 453 | EVQLVESGGGVVQPGRSLRLSCAASGFTFSS YAMHWVRQAPGKGLEWVAVISYDGSNKY YADSVKGRFTISRDNSKNTLYLQMNSLRAE DTAVYYCARNTYYDRRRTFDYWGQGTLVT VSS | ADI-46728 | Heavy chain variable region ("HC") amino acid sequence |
| 151 | 454 | QVQLVQSGGGLVQPGGSLRLSCAASGFTFS DHYMDWVRQAPGKGLEWVGRTRNKANSY TTEYAASVKGRFTISRDDSKNSLYLQMNSL KTEDTAVYYCAGVGITGTTGIDYWGQGTL VTVSS | ADI-49030 | Heavy chain variable region ("HC") amino acid sequence |
| 152 | 455 | EVQLLESGGDLVQPGRSLRLSCAASGFNLID YAMHWVRQVPGKGLEWVSGISWNSRSIGY ADSVKGRFTISRDNAKNSLYLQMDSLKHED TALFYCAKGAAAGPFPYFYYAMDVWGQG TTVTVSS | ADI-50200 | Heavy chain variable region ("HC") amino acid sequence |
| 1 | 456 | QSVLTQPPSVSAAPGQKVTISCSGSSSNIGNN YVSWYQQLPGAAPKLLIYDNKKRPSGIPDRF SGSASGTSATMGITGLQTGDEADYYCGTWD SSLSAWVFGGGTKVTVL | ADI-49039 | Light chain variable region ("LC") amino acid sequence |
| 2 | 457 | DIRVTQSPATLSVSPGERATLSCRASQSVSSN LAWYQQKPGQAPRLLIYDASNRATGIPVRFS GSGSGTDFTLTISSLQSEDFAVYYCQQYDN WPLTFGGGTKVEIK | ADI-49147 | Light chain variable region ("LC") amino acid sequence |
| 3 | 458 | QSVVTQPPSVSAAPGQKVTISCSGSSSNIGNN YVSWYQQFPRTAPKLLIYDNKKRPSGIPDRF SGSASGTSATLGITGLQTGDEADYYCGTWD SSLSAWVFGGGTKVTVL | ADI-42229 | Light chain variable region ("LC") amino acid sequence |
| 4 | 459 | QPVLTQPPSASGTPGQRVTIFCSGSRSNIGTY TINWYQKLPGTAPKLLIYSNNRGPSGVPDRF SGSQSGTSASLAISGLQPEDEADYYCAAWD DSLNGWVFGGGTKVTVL | ADI-45090 | Light chain variable region ("LC") amino acid sequence |
| 5 | 460 | QSVVTQPPSVSAAPGQKVTISCSGSSSNIGNN YVAWYQQLPGRAPKLLIHDNKKRPSGIPDR FSGSASGTSATLGITGLQTGDEADYYCETW DSSLNAVVFGGGTKLTVL | ADI-45097 | Light chain variable region ("LC") amino acid sequence |
| 6 | 461 | DIQMTQSPSSLSASVGDRVTITCRASQTISVD LNWYQHKPGKAPKLLIFAASTLQSGVPSRFS GSGSGTDFTLTIRSLQPEDFATYYCQQSYSIP RITFGQGTRLEIK | ADI-49133 | Light chain variable region ("LC") amino acid sequence |
| 7 | 462 | EIVMTQSPSALSASVRDRVTITCRASQSIGSD LNWYQQRPGKAPMLLIYAATGLQSGVPSRF SGSGSGTDFTLTISNLQPEDFATYYCQQSYSP PMYTFGQGTKVDIK | ADI-49033 | Light chain variable region ("LC") amino acid sequence |
| 8 | 463 | QPVLTQPPSASGTPGQRVTISCSGSSSNIGTN TVSWYQQLPGTAPQLLVFSRTQRPSGVPDR FSGSKSGTSASLAISGLQSDDEADYYCAAWD DSRNGWVFGGGTKLTVL | ADI-49044 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 9 | 464 | QPVLTQPPSVSAAPGQKVTISCSGSNSNIGNY YVSWYQQFPGTAPKLLIYDNNKRPSGIPDRF SGSKSGTSATLAITGLQTGDEAHYYCGTWD TSSLSAGRVFGGGTKLTVL | ADI-45083 | Light chain variable region ("LC") amino acid sequence |
| 10 | 465 | QSALTQPPSVSAAPGQKVTISCSGSSSNIGNS YVSWYQQVPGTAPKLLIYDNNKRPSGIPDRF SGSKSGTSATLGITGLQAGDEADYYCGTWD TSLSAGRVFGRGTKLTVL | ADI-42225 | Light chain variable region ("LC") amino acid sequence |
| 11 | 466 | QSVLTQPPSVSAAPGQKVTISCSGSSSNIGYS HVSWYQQLPGTAPKVLIYDNDKRPSGIPDRF SGSKSGTSATLGITGLQTGDEADYYCGTWD TSLGVVFGGGTKLTVL | ADI-49139 | Light chain variable region ("LC") amino acid sequence |
| 12 | 467 | QSVLTQPRSVSGSPGQSVTISCTGTSSDVGA YNFVSWYQQYPGKAPKLMIYDVNKRPSGV PDRFSGSKSGNTASLTISGLQAEDEADYHCC SYAGTYTSNYVFGSGTKVTVL | ADI-48969 | Light chain variable region ("LC") amino acid sequence |
| 13 | 468 | QSVVTQPPSVSAAPGQKVTISCSGSSSNIGNN YVSWYQQLSETAPKLLIYDNNKRPSGIPNRF SGSKSGTSATLGITGLQTGDEADYYCGTWD NSLGAVVFGGGTKVTVL | ADI-48900 | Light chain variable region ("LC") amino acid sequence |
| 14 | N/A | N/A | ADI-42232 | Light chain variable region ("LC") amino acid sequence |
| 15 | 469 | QSVLTQPPSVSAAPGQKVTISCSGSSSNIGSN YVSWYQQFPGTAPKLLIYDNSKRPSGIPDRF SGSMSGTSATLGITGLQTGDEADYYCGTWD SSLSAVVFGGGTKVTVL | ADI-42786 | Light chain variable region ("LC") amino acid sequence |
| 16 | 470 | QSVLTQPPSVSAAPGQKVTISCSGSSSNIGNN YVSWYQQLPGTAPKLLIYDNNKRPSGIPDRF SGSKSGTSATLGITGLQTGDEADYYCGTWD TSLSAGRVFGGGTKLTVL | ADI-42210 | Light chain variable region ("LC") amino acid sequence |
| 17 | 471 | EIVLTQSPATLSVSPGERATLSCRASRSVSSN LAWYQQKPGQAPRLLIYGASTRATGIPARFT GSGSGTEFTLTISSLQSEDFAVYYCQQYNNW PPRTFGQGTKVDIK | ADI-50201 | Light chain variable region ("LC") amino acid sequence |
| 18 | 472 | DIQLTQSPSSVSASVGDRVTITCRASQGISSW LAWYQQKPGKAPKLLIHAASSLQSGVPSRFS GSGSGTDFTLTISSLQPEDFATYYCQQAKSF PPTFGQGTRLEIK | ADI-48895 | Light chain variable region ("LC") amino acid sequence |
| 19 | 473 | QPVLTQPASVSGSPGQSITISCTGTSSDVGGY NYVSWYQQHPGKAPKLLIYDVSNRPSGVSN RFSGSKSANSASLTISGLQAEDEADYYCNSY TSSSTLVFGGGTKLTVL | ADI-42228 | Light chain variable region ("LC") amino acid sequence |
| 20 | 474 | EIVMTQSPATLSVSPGERATLSCRASQSVSSN LAWYQQKPGQAPRLLIYGASTRATGIPARFS GSGSGTEFTLTISSLQSEDFALYYCQQYDDW PLFGQGTRLEIK | ADI-45113 | Light chain variable region ("LC") amino acid sequence |
| 21 | 475 | QSVLTQPPSVSAAPGQKVTISCSGSSSNIGNN YVSWYQQLPGTAPKLLIYDNNKRPSGIPDRF SGSKSGTSATLGITGLQTGDEADYICGTWDT SLSAGGVFGGGTKLTVL | ADI-42198 | Light chain variable region ("LC") amino acid sequence |
| 22 | 476 | QSVLTQPASVSGSPGQSITISCTGTSSDIGAY NYVSWYQQHPGKAPKLMIYDVTNRPSGVS NRFSGSKSGSSASLTISGLQTEDEADYYCSSY TRRSTLVFGGGTKLTVL | ADI-42190 | Light chain variable region ("LC") amino acid sequence |
| 23 | 477 | QSVLTQPPSVSAAPGQKVTISCSGSSSNIGNN YVSWYQQLPGTAPKLLIYDNNKRPSGIPDRF SGSKSGTSATLGITGLQTGDEANYYCGTWD TSLSTVFGGGTKLTVL | ADI-49154 | Light chain variable region ("LC") amino acid sequence |
| 24 | 478 | QSALTQPASVSGSPGQSITISCTGTGSDVGG YNFVSWYQQHPGKAPKLMLYDVNNRPSGV SNRFSGSKSGNTASLTISGLQAEDEADYYCSS YPGTSALVIFGGGTRLTVL | ADI-49183 | Light chain variable region ("LC") amino acid sequence |
| 25 | 479 | DIQMTQSPSSLSASVGDRVTITCRASQSISSY LNWYQQKPGEAPNLLIFAASILQSGVPSRFS GSGSGTDFTLTISSLQPEDFATYYCQQSYSTP YTFGQGTKVEIK | ADI-42201 | Light chain variable region ("LC") amino acid sequence |
| 26 | 480 | QSVLTQPPSVSGAPGQRVTISCTGSSSNIGAG YDVHWYQQLPGTAPKLLIYGNSNRPSGVPD RFSGSKSGTSASLAITGLQAEDEADYYCQSY DSSLSGHVVFGGGTKLTVL | ADI-42144 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 27 | 481 | EIVLTQSPATLSSSPGERATLSCRASQSVNSY LVWYQQKPGQAPRLLIYDASNRATGIPARFT GSGSGTDFTLTISSLEPEDFAVYYCQQRTNW PFTFGQGTKVDIK | ADI-50219 | Light chain variable region ("LC") amino acid sequence |
| 28 | 482 | EIVLTQSPATLSLSPGERATLSCRASQSVNRY LAWYQQKPGQAPRLLIYDASNRATGIPARFS GSGSGTDFTLTISSLEPEDFAVYYCHQRTNW PWTFGQGTKVEIK | ADI-48897 | Light chain variable region ("LC") amino acid sequence |
| 29 | 483 | EIVMTQSPATLSLSPGERATLSCRASQSVSNY LAWYQQKPGQAPRLLISDASSRATGIPARFR GSGSGTDFTLTISSLEPEDFAVYYCLQRTNW PFTFGPGTKVEIK | ADI-42194 | Light chain variable region ("LC") amino acid sequence |
| 30 | 484 | QSVLTQPASVSGSPGQSITISCTGTSSDIGGY NYVSWYQQHPGKVPKLVIYDVSNRPSGVSN RFSGSKSGNTASLTISGLQAEDEADYYCSSY TSGTTLGVFGTGTKLTVL | ADI-49189 | Light chain variable region ("LC") amino acid sequence |
| 31 | 485 | QSVVTQPPSVSAAPGQKVTISCSGRSSNIGNS DVSWYQQFPGRAPKLLIYDNDERPSGIPDRF SGSKSGTSATLDITGLQTGDEADYYCGTWD SSLGGVIFGGGTKVTVL | ADI-49188 | Light chain variable region ("LC") amino acid sequence |
| 32 | 486 | QSVLTQPPSVSAAPGQKVTISCSGSSSNIGNN YVSWYQQLPGTAPKLLIYDNNKRPSGIPDRF SGSKSGTSATLGITGLQTGDEADYYCETWD SSLGVVVFGGGTKLTVL | ADI-42188 | Light chain variable region ("LC") amino acid sequence |
| 33 | 487 | DIQVTQSPSSLSASVGDRVTITCQASQDISNY LNWYQHKPGRAPKLLIYDASNLERGVPSRF SGSGSGTDFTFTISSLQPEDIATYYCQQYDNL SRLTFGGGTKLEIK | ADI-50026 | Light chain variable region ("LC") amino acid sequence |
| 34 | 488 | QSVLTQPPSVSAAPGQKVTISCSGSSSNIGNN YVSWYQQLPGTAPKLLIYDNNKRPSGIPDRF SGSKSGTSATLGITGLQTGDEADYYCGTWD TSLSAGRVFGGGTKLTVL | ADI-42809 | Light chain variable region ("LC") amino acid sequence |
| 35 | 489 | QSVLTQPPSMSAAPGQKVTISCSGSSSNIGNN YVSWYRQLPGTAPKLLIYDNDKRPSGIPDRF SGSKSGTTATLGITGLQTGDEAVYYCGTWD FRLSALFGGGTKLTVL | ADI-46596 | Light chain variable region ("LC") amino acid sequence |
| 36 | 490 | QSVLIQPASVSGSPGQSITISCTGTSSDVGGD KYVSWYQQHPGKAPKLVIYEVSNRPSGVSN RFSGSKSGNTASLTISGLQAEDEADYYCSSY TSSGTPVVCGGGTKVTVL | ADI-50205 | Light chain variable region ("LC") amino acid sequence |
| 37 | 491 | QSVLTQPPSVSAAPGQKVTISCSGSSSNIGNY YVSWYQQVPGTAPKLLIYDNNKRPSGIPDRF SGSKSGTSATLGITGLHTGDEAEYYCGTWD SSPSAGRVFGGGTKLTVL | ADI-42830 | Light chain variable region ("LC") amino acid sequence |
| 38 | 492 | DIVLTQSPDSLAVSLGERATINCKSSQSVLFG SNQKSCLAWYQQKPGQSPKLLIHWASTRES GVPDRFSGSGSGTDFTLTISSLQAEDVAVYY CQQYYSTPRTFGQGTKVEIK | ADI-49186 | Light chain variable region ("LC") amino acid sequence |
| 39 | 493 | QSVLTQPPSVSAAPGQKVTISCSGSSSNIGSN FVSWYQQLPGTAPKLLIYDNNKRPSGIPDRF SGSKSGTSATLAITGLQTGDEADYYCGTWD TRLSALFGGGTKVTVL | ADI-46591 | Light chain variable region ("LC") amino acid sequence |
| 40 | 494 | QSVLTQPPSVSAAPGQKVTISCSGSSSNFGN DYVSWYQQLPGTAPKLLIYDNDKRPSGIPDR FSGSKSGTSATLGITGLQTGDEADYYCGTW DTSLSAAWVFGGGTKVTVL | ADI-48955 | Light chain variable region ("LC") amino acid sequence |
| 41 | 495 | QSVVTQPPSVSAAPGQKVTISCSGSSSNIGNN YVSWYQQLPGTAPKLLIYDNNKRPSGIPDRF SGSTSGTSATLGITGLQTGDEAVYYCGTWD TSPSAGGVFGGGTKVTVL | ADI-42818 | Light chain variable region ("LC") amino acid sequence |
| 42 | 496 | QPVLTQPASVSGSPGQSITISCTGTSSDVGGY NYVSWYQQHPGKAPKLMIYDVSNRPSGVSN RFSGSKSGNTASLTISGLQAEDEADYYCSSY TSSSTLAVFGGGTKLTVL | ADI-50531 | Light chain variable region ("LC") amino acid sequence |
| 43 | 497 | QPVLTQPPSVSAAPGQKVTISCSGSSSNIGND YVSWYQQLPGTAPKLLIYDNNKRPSGIPDRF SGSKSGTSATLGITGLQTGDEGDYYCGTWD SSLSAAWVFGGGTKVTVL | ADI-46586 | Light chain variable region ("LC") amino acid sequence |
| 44 | 498 | QPVLTQSASVSGSPGQSITISCTGTSSDVGGY KYVSWYQQHPGKAPKLMIYEVSNRPSGVSI RFSGSKSGNTASLTISGLQAADEADYYCSSY RSSGTPYVFGTGTKVTVL | ADI-49138 | Light chain variable region ("LC") amino acid sequence |

TABLE 3-continued

Informal Sequence Listing

| Antibody Number | SEQ ID NQ: | Sequence | Clone # (ADI) | Descriptors |
|---|---|---|---|---|
| 45 | 499 | EIVLTQSPSSLSASVGDRVTITCQASQDISNF LNWYQQKPGKAPKLLIYDASSLETGVPSRFS GSGSGTDFTFTISSLQPEDIATYYCQQYDNLP LTFGGGTKLEIK | ADI-45075 | Light chain variable region ("LC") amino acid sequence |
| 46 | 500 | DIRLTQSPSTLSASVGDRVTVTCRASQNINT YLAWYQQIPGKAPRLLIYRASTLESGVPSRF SGSGSGTEFTLTINSLQPDDYATYYCQHYET YSVRFGQGTKVEIK | ADI-42831 | Light chain variable region ("LC") amino acid sequence |
| 47 | 501 | DIQVTQSPSSLSASVGDRVTITCRASQGISNY LAWYQQKPGKVPKLLIFAASTLRSGVPSRFR GSGSGTDFTLTISSLQPEDVATYYCQKYNSA PLTFGGGTKVEIK | ADI-42230 | Light chain variable region ("LC") amino acid sequence |
| 48 | 502 | DIVMTQTPATLSLSPGERATLSCRASQSVSSY LAWYQQKPGQAPRLLIYGASNRATGIPARFS GSGSGTDFTLTISSLEPEDFAVYYCLQRTNW PFTFGPGTKVEIK | ADI-42847 | Light chain variable region ("LC") amino acid sequence |
| 49 | 503 | DIVLTQSPSTLSASVGDRVTVTCRASQNINT YLAWYQQIPGKAPRLLIYRASSLESGVPSRF SGSGSGTEFTLTISSLQPDDFATYYCQHYNSF SVKFGQGTKVEIK | ADI-42821 | Light chain variable region ("LC") amino acid sequence |
| 50 | 504 | SYELTQPPSVSVAPGQTARITCGGHNVGSKS VHWYQQKPGQAPVLVVYDDSDRPSGIPERF SGSNSGNTATLTISRVEAGDEADYYCQVWD SSSDHPWVFGGGTKVTVL | ADI-42849 | Light chain variable region ("LC") amino acid sequence |
| 51 | 505 | QSVVTQPPSVSAAPGQKVTISCSGSSSNIGNN YVSWYQQLPGTAPKLLIYDNNKRPSGIPDRF SGSKSGTSATLGITGLQTGDEADYYCGTWD TSLSAGRVFGGGTKLTVL | ADI-42151 | Light chain variable region ("LC") amino acid sequence |
| 52 | 506 | QPVLTQPPSVSVAPGQTARITCGGNNIGSKS VHWYQQKPGQAPMLVIYSNSDRPSGIPERFS GSNSGITATLTISRVEAGDEADYHCQVWDTS IDHHWVFGGGTKLTVL | ADI-46001 | Light chain variable region ("LC") amino acid sequence |
| 53 | 507 | QSVLIQPPSASGSPGQSVTISCTGTSSDVGGY NYVSWYQQHPGKAPKLMIYEVSKRPSGVPD RFSGSKSGNTASLTVSGLQAEDGADYYCSSY AGSNNWVVFGGGTKLTVL | ADI-45154 | Light chain variable region ("LC") amino acid sequence |
| 54 | 508 | QPVLTQPASVSGSPGQSITISCTGTSTDVGGY NYVSWYQQYPGKAPKLIIYDVTNRPSGVSH RFSGSKSGNTASLTISGLQAEDEADYYCSSY TTTSLVIFGGGTKLTVL | ADI-49161 | Light chain variable region ("LC") amino acid sequence |
| 55 | 509 | DIVMTQSPLSLPVTPGEPASISCRSSQSLLHS NGYNYLDWYLQKPGQSPQLLIYLGSNRASG VPDRFSGSGSGTDFTLKISRVEAEDVGVYYC MQALQTPPRTFGQGTRLEIK | ADI-42154 | Light chain variable region ("LC") amino acid sequence |
| 56 | 510 | DIQVTQSPSSLSASVGGRVTITCRASQGIRND LGWYQRKPGKAPKRLIYAASSLQSGVPSRFS GSGSGTEFTLTISSLQPEDFATYYCLQHNSYP LTFGGGTKVDIK | ADI-48916 | Light chain variable region ("LC") amino acid sequence |
| 57 | 511 | DIQLTQSPSTLSASVGDRVTITCRASQSISTW LAWYQQKPGKAPKLLIYRASSLESGVPSRFS ASGSGTEFTLSISSLQPDDFATYYCKQYNRN PYTFGQGTKVEIK | ADI-45085 | Light chain variable region ("LC") amino acid sequence |
| 58 | 512 | DIQMTQSPSSLSASVGDRVTITCRASQGISSY LAWFQQKPGKVPKLLIYAASTLQSGVPSRFS GSGSGTDFTLTISSLQPEDVATYYCQKYNSA PQTFGQGTKVDIK | ADI-42211 | Light chain variable region ("LC") amino acid sequence |
| 59 | 513 | EIVMTQSPATLSVSPGERATLSCRASQSVSFN LAWYQQKPGQAPRLLISRASTRAAGVPARF SGSGSGTEFTLTISSLQSEDFAVYYCQQYNN WPPLTFGGGTKLEIK | ADI-48908 | Light chain variable region ("LC") amino acid sequence |
| 60 | 514 | DIQMTQSPDSLTVSLGERATINCKSSQSVLYS SNNKNSLAWYQQKPGQPPKLLIYWASTRES GVPDRFSGSGSGTDFTLTISSLQAADVAVYY CQQYYRTPWTFGQGTKVEIK | ADI-48913 | Light chain variable region ("LC") amino acid sequence |
| 61 | 515 | QSVLTQPPSVSAAPGQKVTISCSGSSSNIGNN YVSWYQQLPGTAPKVLIYDNNKRPSGIPDRF SGSKSGTSATLGITGLQTGDEADYYCGTWD SALGAAVFGGGTKLTVL | ADI-45140 | Light chain variable region ("LC") amino acid sequence |
| 62 | 516 | DIQLTQSPSTLSASVGDRVTITCRASQSVSSW LAWYQQKPGKAPRLLIYRASSLESGVPSRFS GSGSGTEFTLTISSLQPDDFAYYCQQYNRD PYTFGQGTKVEIK | ADI-50211 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 63 | 517 | SYELTQLPSVSVSPGQTARVTCSGDAL-- QYVYWYQQKPGQAPVVVIYKDTERPSGIPE RFSGSSSGTTVTLTITGVQAEDEADYYCQSA DRSGSVIFGGGTKVTVL | ADI-42199 | Light chain variable region ("LC") amino acid sequence |
| 64 | 518 | DIVMTQSPATLSLPGERATLSCRASQSVSSY LAWYQQKPGQAPRLLIYDASNRATGIPARFS GSGSGTDFTLTISSLEPEDFAVYYCQQRSNW PSFGQGTKLEIK | ADI-42231 | Light chain variable region ("LC") amino acid sequence |
| 65 | 519 | DIRLTQSPSSLSASVGDRVTITCRASQSISSYL NWYQQKPGKAPKLLIYAASSLQSGVPSRFSG SGSGTDFTLTISSLQPEDFATYYCQQSYSTPL TFGGGTKVEIK | ADI-45164 | Light chain variable region ("LC") amino acid sequence |
| 66 | 520 | ETTLTQSPGTLSLPGERATLSCRASRSVSGN YLAWYQQKPGQAPRLLIYAASSRATGIPDRF SGGGSGTHFTLTISRLEPEDFAVYYCQQYGS SPRAFGQGTKVEIK | ADI-42233 | Light chain variable region ("LC") amino acid sequence |
| 67 | 521 | EIVMTQSPSSLSASVGDRVTITCRASQSIRSY LNWYQQKPGKAPKLLIYAASSLQSGVPLRFS GSGSGTDFTLTISSLQPEDFATYYCQQSSITP PTFGQGTKLEIK | ADI-42191 | Light chain variable region ("LC") amino acid sequence |
| 68 | 522 | DIQMTQSPSTLSASVGDRVTITCRASQSISSW LAWYQQKPGKAPKLLIYQASSLESGVPSRFS GSESGTEFTLTISSLQPDDFATYYCQQYNSFP FTFGPGTKVEIK | ADI-48899 | Light chain variable region ("LC") amino acid sequence |
| 69 | 523 | DIVLTQSPSSLSASVGDRVTITCRASQSINNY LNWYQQKPGKAPNLLIFGASTLQSGVPSRFT GSGSGTVFTLTISSLQRDDFVIYYCQQTYSAS GSFGQGTKVEIK | ADI-49145 | Light chain variable region ("LC") amino acid sequence |
| 70 | 524 | DIQLTQSPSSLSASVGDRVTITCRASQSISSYL NWYQQKPGKAPKLLIYAASSLQSGVPSRFSG SGSGTDFTLTISSLQPEDFATYYCQQSYSTP WTFGQGTKVEIK | ADI-46729 | Light chain variable region ("LC") amino acid sequence |
| 71 | 525 | QSALIQPPSVSAAPGQKVTISCSGSSSNIGNN YVSWYQQLPGTAPKLLIYDNNKRPSGIPDRF SGSKSGTSATLGITGLQTGDEADYYCGTWD NSLGVVFGGGTQLTVL | ADI-46722 | Light chain variable region ("LC") amino acid sequence |
| 72 | 526 | EIVLTQSPGTLSLPGERATLSCRASQSVSSS YLAWYQQKPGQAPRLLIYGASSRATGIPDRF SGSGSGTDFTLSINRLEPEDFAVYYCQQYGS SPGFGQGTKVEIK | ADI-45148 | Light chain variable region ("LC") amino acid sequence |
| 73 | 527 | DIVLTQSPSTLSASVGDRVTITCRASQSISDW LAWYQQKPGKAPGLLIYRASGLESGVPSRF SGSGSGTEFTLTISSLQPDDFATYYCHQYKD FPWTFGQGTKVDIK | ADI-49168 | Light chain variable region ("LC") amino acid sequence |
| 74 | 528 | DIQMTQSPSTLSASVGDRVTITCRASQSISTW LAWYQLKPGKAPKLLIYKASNLQSGVPSRF SGSGSGTEFTLTISSLQPDDFATYYCQQYNS YSPWGQGTKLEIK | ADI-49040 | Light chain variable region ("LC") amino acid sequence |
| 75 | 529 | EIVLTQSPGTLSLPGERATLSCRASQSVSSR YLAWYRQKPGQAPRLLIYGASSRATGIPDRF SGSGSGTDFTLTISRLEPEDFAVYYCQQYGS SPFFGGGTKLEIK | ADI-42187 | Light chain variable region ("LC") amino acid sequence |
| 76 | 530 | QSVLTQPASVSGSPGQSITISCTGTSSDVGGD KYVSWYQQHPGKAPKPMIYEVSNRPSGVSN RFSGSKSGNTASLTISGLQAEDEADYYCSSY TSSSTPVVFGGGTKLTVL | ADI-49561 | Light chain variable region ("LC") amino acid sequence |
| 77 | 531 | QPVLTQPRSVSGSPGQSVTISCTGTSSDVGG YNYVSWYQQHPGKAPKLMISDVSKRPSGVP DRFSGSKSGNTASLTISGLQADDEADYYCCS YATNYGVVFGGGTKVTVL | ADI-42219 | Light chain variable region ("LC") amino acid sequence |
| 78 | 532 | NFMLTQPHSVSESPGKTVTISCTRSSGSIASN YVQWYQQRPGSSPTTVIYEDNQRPSGVPDR FSGSIDSSSNSASLTISGLKTEDEADYYCQSY DSSNVVFGGGTKVTVL | ADI-50535 | Light chain variable region ("LC") amino acid sequence |
| 79 | 533 | QSVLTQPPSVSAAPGQKVTISCSGSSSNIGNN DVSWYQQLPGRAPKLLIYDNNKRPSGIPDRF SGSKSGTSATLGITGLQTGDEADYYCGAWD SSLSAHVVFGGGTKVTVL | ADI-45128 | Light chain variable region ("LC") amino acid sequence |
| 80 | 534 | DIVMTQTPSTLSASVGDRVTVTCRASQSISD WLAWYQQKAGKAPKLLIYRASSLESGVPPR FSGSGSGTEFTLTISSLRPDDFATYYCQQYNR YPYTFGQGTKVDIK | ADI-45136 | Light chain variable region ("LC") amino acid sequence |

TABLE 3-continued

Informal Sequence Listing

| Antibody Number | SEQ ID NQ: | Sequence | Clone # (ADI) | Descriptors |
|---|---|---|---|---|
| 81 | 535 | DIQVTQSPSSLSASVGDRVTITCRASQGIRND LAWYQQRPGKAPKRLIYAASSLQSGVPSRFS GSGSGTEFTLTISSLQPEDFATYYCLQHHSYP WTFGQGTKVEIK | ADI-42189 | Light chain variable region ("LC") amino acid sequence |
| 82 | 536 | DIRMTQSPSTLSASIGDRVTITCRASQSISDW LAWYLQKPGKAPSLLIYRASSLETGVPSRFS GRGSGTEFTLTISSLQPDDFGTYYCQQYNRD PYTFGQGTKVDIK | ADI-45078 | Light chain variable region ("LC") amino acid sequence |
| 83 | 537 | DIQLTQSPSTLSASVGDRVTVTCRASQNVGG WLAWYQQKPGKAPKLLIFQASRLENGVPSR FSANASGTEFTLTIGSLQPDDFATYYCQQYN TYPYTFGQGTKVDIK | ADI-49162 | Light chain variable region ("LC") amino acid sequence |
| 84 | 538 | DIQLTQSPSSLSASVGDRVTITCRASQSISQY LNWYQQKPGKAPKLLISPASSFQSGVPSRFS GSGSGTDFTLTITSLQPEDFATYYCQQSYSTP WTFGQGTKVDIK | ADI-42223 | Light chain variable region ("LC") amino acid sequence |
| 85 | 539 | QSVLTQPASVSGSPGQSITISCTGTSSDVGGY NYVSWYQQHPGKAPKLMIYDVSNRPSGVSN RFSGSKSGNTASLTISGLQAEDEADYYCSSY TSSSTLVFGGGTQLTVL | ADI-48435 | Light chain variable region ("LC") amino acid sequence |
| 86 | 540 | SYELTQPPSVSVAPGQTARIICGGNYIGGKS VHWYQQKPGQAPVLVVYNDNDRPSGIPERF SGSNSGNTATLTISRVAAGDEADYYCQVWD NSSDRRVFGGGTKLTVL | ADI-46742 | Light chain variable region ("LC") amino acid sequence |
| 87 | 541 | DIRVTQSPATLSVSPGERATLSCRASQRVNS NLAWYQQKPGQAPRLLIYGASTRATGIPVR FSGSGSGTEFTLTISSLQSEDFAVYYCQQYNT WWTFGQGTKVEIK | ADI-42787 | Light chain variable region ("LC") amino acid sequence |
| 88 | 542 | DIQMTQSPSSLSASVGDRVTITCRASQSISSY LNWYQQKPGKAPKLLIYAASSLQSGVPSRFS GSGSGTDFTLTISSLQPEDFATYYCQQSYSTP LTFGGGTKVDIK | ADI-46718 | Light chain variable region ("LC") amino acid sequence |
| 89 | 543 | DIVMTQSPATLSVSPGERATLSCRASQSVSS NLAWYQQKPGQAPRLLIYGASTRATGIPAR FSGSGSGTEFTLTISSLQSEDFAVYSCQQYNT WPKTFGQGTKVEIK | ADI-49141 | Light chain variable region ("LC") amino acid sequence |
| 90 | 544 | EIVLTQSPGTLSLSPGERATLSCRASQSVSSSF LAWYQQKPGQAPRLLIYGASSRATGIPDRFS GSGSGTDFTLTIRRLEPEDFAVYYCQQYGSS RRTFGQGTKVEIK | ADI-42213 | Light chain variable region ("LC") amino acid sequence |
| 91 | 545 | DIRVTQSPSTLSASVGDRVTITCRASQSISSW LAWYQQKPGKAPKLLIYRASSLESGVPSRFS GSGSGTEFTLTISSLQPDDFATYYCQQYNRY PYTFGQGTKVEIK | ADI-42844 | Light chain variable region ("LC") amino acid sequence |
| 92 | 546 | QSALTQPASVSGSPGQSITISCTGTSSDVGGY NYVSWYQQHPGKAPKLMIYEVSNRPSGVSN RFSGSKSGNTASLTISGLQAEDEADYYCSSY TSSSTLDVVFGGGTKLTVL | ADI-45161 | Light chain variable region ("LC") amino acid sequence |
| 93 | 547 | EIVMTQSPATLSVSPGERATLSCRASQSVSSN LAWYQQKPGQAPRLLIYGASTRATSIPARFS GSGSGTEFTLTISSLQSEDFAVYYCQQYNSW PPITFGQGTRLEIK | ADI-42192 | Light chain variable region ("LC") amino acid sequence |
| 94 | 548 | DIRLTQSPSTLSASVGDRVSITCRASQSISDW LAWYQQKPGKAPKLLIYRASGLETGVPSRF SGSGSGTEFTLTISSLQPDDFATYYCQQYNR YPYTFGQGTKVDIK | ADI-48910 | Light chain variable region ("LC") amino acid sequence |
| 95 | 549 | QPVLIQPPSASGTPGQRVTISCSGSSSNFGSN FVYWYQQLPGTAPKLLIYRVNQRPSGVPDR FSGSKSGTSASLAISGLRSEDEADYYCATWD VSLSNDVLFGGGTKLTVL | ADI-42193 | Light chain variable region ("LC") amino acid sequence |
| 96 | 550 | DIVLTQSPATLSLSPGERATLSCRASQSVSSS YLSWYQQKPGQAPRLLIYGASSRATGIPDRF SGSGSGTDFTLTISRLEPEDFAVYYCQQYGS SPPITFGGGTKVEIK | ADI-49590 | Light chain variable region ("LC") amino acid sequence |
| 97 | 551 | DIQMTQSPSSLSASVGDRVTITCRASQTITRY MNWYQQKPGEAPKLLIYATSSLQSGVPSRF SGSGSGTDFTLTITNLQPADFATYYCQQSST TRWTFGQGTKVDIK | ADI-45076 | Light chain variable region ("LC") amino acid sequence |
| 98 | 552 | DIRLTQSPSSLSASVGDRVTITCRASQDIRKF LNWYQQKLGKAPSLLIYGASSLQSGVPSRFS GSGSGTDFTLTISSLQPEDFAIYYCQHASTTP WTFGQGTKVEIK | ADI-48968 | Light chain variable region ("LC") amino acid sequence |

TABLE 3-continued

Informal Sequence Listing

| Antibody Number | SEQ ID NQ: | Sequence | Clone # (ADI) | Descriptors |
|---|---|---|---|---|
| 99 | 553 | SYELTQPPSVSVSPGQTATITCSGDKLGYTY TCWYQQKPGQSPVLVIYQDTKRPSGIPERFS GSNSGNTATLTITGTQAMDEADYYCQAWD TTAGGVFGGGTKLTVL | ADI-42212 | Light chain variable region ("LC") amino acid sequence |
| 100 | 554 | DIVLTQSPGTLSLSPGERATLSCRASQSVSSS YLAWYQQKPGQAPRLLIYGASSRATGIPDRF SGSGSGTDFTLTISRLEPEDFAVYYCQQYGS SPRAFGPGTKVEIK | ADI-48462 | Light chain variable region ("LC") amino acid sequence |
| 101 | 555 | QSVLTQPPSASGSPGQSVTISCAGTRSDVGG YNFVSWYQQHPGKAPKLLIYEVNKRPSGVP DRFSGSKSANTASLTVSGLQAEDEAEYFCSS YGGNNDLVFGGGTKVTVL | ADI-45127 | Light chain variable region ("LC") amino acid sequence |
| 102 | 556 | EIVMTQSPATLSLSPGERGTLSCRTSQSVSSF LAWYQQKPGQAPRLLMYDASNRATGIPARF SGSGSGTDFTLTISSLEPEDFAVYYCQQRSN WPYTFGQGTKVDIK | ADI-42200 | Light chain variable region ("LC") amino acid sequence |
| 103 | 557 | GIQLTQSPSTLSASVGDRVTITCRASQSVSD WLAWYQQKPGRAPNLLIYRASSLQSGVPSR FSGSGSGTEFTLTINSLQPDDFATYYCQQYK TYWTFGQGTKVEIK | ADI-50203 | Light chain variable region ("LC") amino acid sequence |
| 104 | 558 | QSVLTQPASVSGSPGQSITISCTGTSSDVGGY NYVSWYQQHPGKAPKLMIYEVSNRPSGVSN RFSGSKSGNTASLTISGLQAEDEADYYCSSY TSSGTNIFGTGTKLTVL | ADI-42149 | Light chain variable region ("LC") amino acid sequence |
| 105 | 559 | DIVMTQTPATLSVSPGERATLSCRASQSVSS NVAWYQQKPGQAPRLLIHGASTRATGIPAR FSGSGSGTEFTLTISSLQSEDFAVYYCQQYN NWPPLTFGGGTKLEIK | ADI-42181 | Light chain variable region ("LC") amino acid sequence |
| 106 | 560 | SYELTQPPSVSVSPGQTARITCSGDALPKKY VYWFQQKSGQAPVLVIYEDRRGPSGIPERFS GSTSGTMATLTIRGAQVEDEADYFCYSTDSS GLLGVFGGGTKLTVL | ADI-45126 | Light chain variable region ("LC") amino acid sequence |
| 107 | 561 | DIQMTQSPDSLAVSLGERATINCKSSQSVFY SSNSQNYLAWYQQKPGQPPKLLIYWASTRES GVPDRFSGSGSATDFSLTISSLQAEDVAVYY CQQFHSPPWTFGQGTKLEIK | ADI-45074 | Light chain variable region ("LC") amino acid sequence |
| 108 | 562 | DIVMTQSPSTLSASVGDRVVITCRASQSISN WLAWYQQKSGKAPKLLIYKASRLESGVPST FSGSGSGTEFTLTISSLQADDFASYYCQQYN DYPWTFGQGTKVEIK | ADI-49041 | Light chain variable region ("LC") amino acid sequence |
| 109 | 563 | EIVMTQSPSSLSASVGDRVTITCRASQGIRND LGWYQQKPGKAPKRLIYAASSLQSGVPSRF SGSGSGREFTLTISSLQPEDFATYYCLQHNT YPWTFGQGTKVEIK | ADI-42227 | Light chain variable region ("LC") amino acid sequence |
| 110 | 564 | DIQVTQSPSTLSASVGDRVSITCRASQTISSW LAWYQQKPGKAPKLLMYKASNLQSGVPSR FTGSGSGTEFTLTISSLQPDDFATYYCQQYYS YPYTFGPGTKVDIK | ADI-50220 | Light chain variable region ("LC") amino acid sequence |
| 111 | 565 | SYVLTQPPSVSVSPGQTARITCSGDALPKQY GYWYQQKPGQAPVLVIYKDSERPSGIPERFS GSSSGTTVTLTISGVQAEDEADYYCQSADRS GTVVFGGGTKLTVL | ADI-42141 | Light chain variable region ("LC") amino acid sequence |
| 112 | 566 | QAVVTQPPSASGSPGQSVTISCTGTSSDVGG YNYVSWYQQHPGKAPKLMVYEVTKRPSGV PDRFSGSKSGNAASLTVSGLQAEDEAEYYCS SYAGSNALVFSGGTKLTVL | ADI-42216 | Light chain variable region ("LC") amino acid sequence |
| 113 | 567 | NFMLTQPHSVSESPGKTVTISCTRSSGSIASN YVQWYQQRPGSAPTTVIYEDNQRPSGVPDR FSGSIDSSSNSASLTISGLKTEDEADYYCQSY DSSNWVFGGGTKLTVL | ADI-50534 | Light chain variable region ("LC") amino acid sequence |
| 114 | 568 | QPELTQPPSVSVSPGQTARITCSGDALSKQY AYWYQQKPGQAPVVVIYKDSERPSGIPERFS GSRSGTTVTLTISGVQAEDEADYYCHSPDSH VVFGGGTKLTVL | ADI-49140 | Light chain variable region ("LC") amino acid sequence |
| 115 | 569 | SYELIQLPSASVAPGKTARITCGGNNIGSKSV HWYQQKPGQAPVLVVYDDSDRPSGIPERFS GSNSGNTATLTISRVEAGDEADYYCQVWDS SSDHEVFGGGTKLTVL | ADI-46741 | Light chain variable region ("LC") amino acid sequence |
| 116 | 570 | DIQMTQSPSSLSASVGDRVTITCQASQDISNY LNWYQQKPGKAPKLLIYDVSKLKTGVPPRF SGSGSGTDFTFTISSLQPEDIATYYCQQWGT FGQGTKVDIK | ADI-42195 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 117 | 571 | EIVLTQSPSTLSASVGDRVTITCRASQSISDW LAWYQQKPGKAPNLLIYRASSLESGVPSRFS GSGSGTEFTLTISSLQPDDFATYYCQQYNRY PYTFGQGTKVEIK | ADI-42172 | Light chain variable region ("LC") amino acid sequence |
| 118 | 572 | DIQLTQSPSTLSASVGDRVTITCRASQSISDW LAWFQQKPGKAPKLLIYRASGLETGVPSRFS GSGSGTEFTLTISSLQPDDFATYYCQQYNRY SYTFGQGTKVEIK | ADI-42178 | Light chain variable region ("LC") amino acid sequence |
| 119 | 573 | DIRLTQSPSTLSASVGDRVTITCRASQSISGW LAWYQQKPGKAPKLLIYKASILESGVPSRFS GSQSGTEFTLTISSLQPDDFATYYCQQYNNF WTFGQGTKLEIK | ADI-49032 | Light chain variable region ("LC") amino acid sequence |
| 120 | 574 | QSVLTQPPSVSGAPGQRVTISCTGNSSNIGA GYEVHWYQQLPGTAPKLLIYGNNNRPSGVP DRFSGSKSGASGSLAVTGLRAEDEADYYCH SYDSNMSGSVFGGGTKVTVL | ADI-50197 | Light chain variable region ("LC") amino acid sequence |
| 121 | 575 | EIVLTQSPSSLSASVGDRVTITCRASQGISNY LAWYQQKPGKAPKLLIYAASTLQSGVPSRF SGSGSGTDFILTISSLQPEDVATYYCQKYYSA PLITFGPGTKVEIK | ADI-48894 | Light chain variable region ("LC") amino acid sequence |
| 122 | 576 | SYELTQPPSVSVSPGQTARITCSGDALPKQY AYWYQQKPGQAPVLVIYKDTERPSGIPERFS GSSSGTTVTLTISGVQAEDEADYYCQSADSS VADSSVVFGGGTKLTVL | ADI-42226 | Light chain variable region ("LC") amino acid sequence |
| 123 | 577 | EIVLTQSPATLSLSPGERATLSCRASQSVSNY FAWYQQKPGQAPRLLIYGASNRATGVPARF SGSGSGTDFTLTISSLEPEDFAVYYCQQRSN WPYTFGQGTKVEIK | ADI-49037 | Light chain variable region ("LC") amino acid sequence |
| 124 | 578 | NFMLTQPPSVSAAPGQKVTISCSGSNSNIGN NFVSWYQQLPGTAPKLLIYDNNERPSGIPDR FSGSKSVTSATLGITGLQTGDEADYYCGTW DNSLGMVVFGGGTKLTVL | ADI-46739 | Light chain variable region ("LC") amino acid sequence |
| 125 | 579 | QSALTQPASVSGSPGQSITISCTGTSSDVGGY NYVSWYQQHPGKAPKLMIYEVSNRPSGVSN RFSGSKSGNTASLTISGLQAEDEADYYCSSY TSSSTYVFGTGTKVTVL | ADI-42810 | Light chain variable region ("LC") amino acid sequence |
| 126 | 580 | EIVLTQSPGTLALSPGERATLSCRASQSVSSY LAWYQQKPGQAPRLLIYDSSNRATGIPARFS GSGSGTDFTLTISSLEPEDFAVYYCQQPGNW PPAFTFGGGTKLEIK | ADI-49137 | Light chain variable region ("LC") amino acid sequence |
| 127 | 581 | DIVMTQSPATLSVSPGERATLSCRASQSVTS KLAWYQQKPGQAPRLLIYGASTRATGIPAR FSGSGSGTEFTLTISSLQSEDFAVYYCQQYN NWITFGQGTRLEIK | ADI-42817 | Light chain variable region ("LC") amino acid sequence |
| 128 | 582 | DIQLTQSPSSVSASVGDRVTITCRASQGISSW LAWYQQKPGKAPKLLIYAASSLQSGVPSRFS GSGSGTDFTLTISSLQPEDFATYYCQQANSFP WTFGQGTKVDIK | ADI-50218 | Light chain variable region ("LC") amino acid sequence |
| 129 | 583 | DIVMTQSPLSLPVTPGEPASISCRSSQSLLHS NGYNSLDWYLQKPGQSPQLLIYLGSNRASG VPDRFSGSGSGTDFTLKISRVEAEDVGVYYC MQALQTPYTFGQGTKLEIK | ADI-42126 | Light chain variable region ("LC") amino acid sequence |
| 130 | 584 | QPVLTQPPSASGTPGQRVTISCSGSSSNIGSN TVHWYQQLPGTAPKLLIYSNNQRPSGVPDR LSGSRSGTSASLAISGLQSEDEAEYYCAAWD DNLIGVVFGGGTKLTVL | ADI-42186 | Light chain variable region ("LC") amino acid sequence |
| 131 | 585 | QSALTQPPSASGSPGQSVTISCTGTSSDVGG YNYVSWYQQHPGKAPKLMIYEVSKRPSGVP DRFSGSKSGNTASLTVSGLQAEDEADYYCSS FAGSNNLYVFGTGTKVTVL | ADI-48890 | Light chain variable region ("LC") amino acid sequence |
| 132 | 586 | QSVLTQPASVSGSPGQSITISCTGTSSDVGGY NYVSWYQQHPGKAPKLMIYDVTNRPSGVS NRFSGSRSGNTASLTISGLQAEDEADYYCSS YTRSSTRVFGGGTKLTVL | ADI-42206 | Light chain variable region ("LC") amino acid sequence |
| 133 | 587 | QPVLTQPPSVSAAPGQKVTISCSGSSSNIGSN FVSWYQQFPGTAPKLLIYDDNKRPSGIPDRF SGSKSGTSATLGITGLQTGDEADYYCETWD SRLSVVFGGGTKLTVL | ADI-46724 | Light chain variable region ("LC") amino acid sequence |
| 134 | 588 | QPVLTQPPSVSAAPGQKVTISCSGSSSNIGNN YVSWYQQLPGTAPKLLIYDNNKRPSGIPDRF SGSKSGTSATLGITGLQTGDEADYYCGTWD SSLSAVVFGGGTKLTVL | ADI-50539 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 135 | 589 | DIQLTQSPSSLSASVGDRVTITCRASQSISSYL NWYQQKPGKAPKLLIYAASSLQSGVPSRFSG SGSGTDFTLTISSLQPEDFATYYCQQSYSTP WTFGQGTKVDIK | ADI-45156 | Light chain variable region ("LC") amino acid sequence |
| 136 | 590 | DIRVTQSPSSLSASVGDRVTITSRASQSISSYL NWYQQKPGKAPKLLIYAASSLQSGVPSRFSG SGSGTDFTLTISSLQPEDFATYYCQQSYSTPR TFGGGTKVDIK | ADI-50536 | Light chain variable region ("LC") amino acid sequence |
| 137 | 591 | QSVLTQPPSVSGAPGQRVTISCTGSSSDIGAG YDVHWYQQLPGTAPKLLIYGNTNRPSGVPD RFSGSKSGTSASLAITGLQAEDEADYYCQSY DSSLSGVVFGGGTKLTVL | ADI-42217 | Light chain variable region ("LC") amino acid sequence |
| 138 | 592 | DIVLTQSPDSLAVSLGERAAINCKSSQSVFFS SDNKNYLAWYQQKPGQPPKLLIYWASTRES GVPDRFSGSGSGTDFTLTISSLQAEDVAVYY CQQFYTTPSTFGQGTKVEIK | ADI-48951 | Light chain variable region ("LC") amino acid sequence |
| 139 | 593 | DIQLTQSPSSLSASVGDRVTITCRASQSISSYL NWYQQKPGKAPKLLIYAASSLQSGVPSRFSG SGSGTDFTLTISSLQPEDFATYYCQQSYSTPR TFGGGTKVEIK | ADI-50537 | Light chain variable region ("LC") amino acid sequence |
| 140 | 594 | DIQLTQSPSSLSASVGDRVTITCRASQGIRND LGWYQQKPGKAPKRLIYAASSLQSGVPSRF SGSGSGTEFTLTISSLQPEDFATYYCLQHNSY PLTFGGGTKVEIK | ADI-46737 | Light chain variable region ("LC") amino acid sequence |
| 141 | 595 | NFMLTQPHSVSESPGNTVTISCTRSSGSIAST YVQWYQQRPGSAPSTVIYEDNQRPPGVPAR FSGSIDSSSNSASLTISGLETEDEADYYCQSY DSTTVVFGGGTKVTVL | ADI-50538 | Light chain variable region ("LC") amino acid sequence |
| 142 | 596 | SYVLTQPPSASGSPGQSVTISCTGTSSDFGGY NYVSWYQQHPGKAPKLMVYEVAKRPSGVP DRFSGSKSGNTASLTVSGLQAEDEADYYCSS YAGSNNFVVFGGGTKLTVL | ADI-48950 | Light chain variable region ("LC") amino acid sequence |
| 143 | 597 | QSVLTQPPSVSAAPGQKVTISCSGSSSNIGNN YVSWYQQLPGTAPKLLIYDNNKRPSGIPDRF SGSKSGTSATLGITGLQTGDEADYYCGTWD SSLSAKVFGGGTKLTVL | ADI-42114 | Light chain variable region ("LC") amino acid sequence |
| 144 | 598 | ETTLTQSPSTLSTSVGDRVTITCRASQSISSW LAWYQQKPGKAPKLLIYRASSLETEVPSRFS GSGSGTDFTLTISRLQPDDFATYFCQQYNRY PYTFGQGTKLEIK | ADI-49194 | Light chain variable region ("LC") amino acid sequence |
| 145 | 599 | QPVLTQPRSVSGSPGQSVTISCTGTSSDVGG YNYVSWYQQHPGKAPKLMIYDVSKRPSGV PDRFSGSKSGNTASLTISGLQAEDEADYYCC SYAGSYTFVLFGGGTKLTVL | ADI-42124 | Light chain variable region ("LC") amino acid sequence |
| 146 | 600 | DIRVTQSPSSLSASVGDRVTISCRASESISIYL NWYQQKPGKAPNLLIYAASSLQRGVPSRFS GSGSGTDFTLTITSLQAEDFATYYCQQTFSI WTFGQGTKVEIK | ADI-45123 | Light chain variable region ("LC") amino acid sequence |
| 147 | 601 | QPVLTQPPSVSAAPGQKVTISCSGSSSNIGNN YVSWYQQLPGTAPKLLIYDNNKRPSGIPDRF SGSKSGTSATLGITGLQTGDEADYYCGTWD SSLSAGKVFGGGTKLTVL | ADI-50533 | Light chain variable region ("LC") amino acid sequence |
| 148 | 602 | QSALTQPPSASGSPGQSVTISCTGTSSDVGGF NYVSWYQQHPGRAPKLVIYEVNRRPSGVPD RFSGSKSGYTASLTVSGLQAEDEADYYCFSY AGSNNYVFGTGTKVTVL | ADI-49205 | Light chain variable region ("LC") amino acid sequence |
| 149 | 603 | DIVMTQTPLSSPVTLGQPASISCRSSQSLVHS DGNTYLSWLQQRPGQPPRFLIYKISNRFSGV PDRFSGGGAGTDFTLKISRVEAEDVGVYYC MQASQFPLTFGGGTKVEIK | ADI-45151 | Light chain variable region ("LC") amino acid sequence |
| 150 | 604 | EIVMTQSPSSLSASVGDRVTITCQASQDISNY LNWYQQKPGKAPKLLIYDASNLETGVPSRF SGSGSGTDFTFTISSLQPEDIATYYCQQYDNL PPVTFGQGTRLEIK | ADI-46728 | Light chain variable region ("LC") amino acid sequence |
| 151 | 605 | QPVLTQPPSVSVSPGQTASITCSGDKLGDKY ACWYQQKPGQSPVLVIYQDSKRPSGIPERFS GSNSGNTATLTISGTQAMDEADYYCQAWDS STDVVFGGGTKVTVL | ADI-49030 | Light chain variable region ("LC") amino acid sequence |
| 152 | 606 | DIQVTQSPSSLSASVGDRVTITCRASQGISNN LAWYQQKPGIFPKLLIYAASTLQSGVPSRFS GSGSGTDFILTISSLQPEDVATYYCQKYQSA PPTFGGGTKLEIK | ADI-50200 | Light chain variable region ("LC") amino acid sequence |

Materials and Methods

Study Design

Study subjects aged 30 and 31 years of age were vaccinated with the YFV-17D Stamaril vaccine. Heparinized blood (50-100 cc) was obtained from subjects before vaccination and on days 10, 14, 28, 90, 180, 270, and 360 following vaccination. Samples were processed in the Immune Monitoring and Flow Cytometry core laboratory at the Geisel School of Medicine at Dartmouth to obtain plasma and to isolate peripheral blood-derived B cells. Isolated cells and plasma were stored frozen in aliquots at −80° C.

Cells: Huh 7.5.1 cells (received from Dr. Jan Carette; originally from Dr. Frank Chisari) were passaged every 3 to 4 days using 0.05% Trypsin/EDTA solution (Gibco) and maintained in Dulbecco's Modified Eagle Medium (DMEM high glucose, Gibco) supplemented with 10% heat-inactivated fetal bovine serum (FBS, Atlanta Biologicals), 1% Penicillin/Streptomycin (P/S, Gibco), 1% Gluta-MAX (Gibco) and 25 mM HEPES (Gibco). Vero African grivet monkey kidney cells (obtained from ATCC) were passaged every 3 to 4 days using 0.05% Trypsin/EDTA solution (Gibco) and maintained in Dulbecco's Modified Eagle Medium (DMEM high glucose, Gibco) supplemented with 2% heat-inactivated fetal bovine serum (FBS, Atlanta Biologicals), 1% Penicillin/Streptomycin (P/S, Gibco), 1% Gluta-MAX (Gibco) and 25 mM HEPES (Gibco).

Yellow Fever virus 17D generation: YFV-17D was obtained from BEI Resources (cat #NR-115). 15 cm plates with Huh 7.5.1 in a confluency of 80% were infected with 90 μL of passage 2 stock of YFV-17D supernatant in 3 mL of infection media (DMEM low glucose (Gibco), 7% FBS, 1% Pen-Strep, 1% Gluta-MAX (Gibco), 25 mM HEPES (Gibco)) for 1 hour at 37C and 5% CO2. After 3 days the supernatant was harvested and centrifuged twice at 4,000 rpm for 15 min at 4° C. to remove cell debris. The YFV-17D viral stock for neutralization assays was generated by ultracentrifugation of the pre-cleared supernatant at 28,000 rpm using a SW28 rotor (Beckman Coulter) in a Beckman Coulter Optima LE-80K ultracentrifuge for 4 hours through a 2 mL 30% (v/v) D-sucrose/PBS cushion. The pellet was allowed to resuspend overnight on ice in 300 ul PBS and afterwards aliquoted and frozen at −80C.

Zika virus generation: The Zika virus strain MR 766 was obtained from ATCC (ATCC® VR-84™). For neutralization assay 15 cm plates with Vero cells in a confluency of 80% were infected with 90 μL of passage 1 stock of Zika supernatant in 3 mL of infection media (DMEM low glucose (Gibco), 2% FBS, 1% Pen-Strep, 1% Gluta-MAX (Gibco), 25 mM HEPES (Gibco)) for 1 hour at 37C and 5% CO2. After 3 days the supernatant was harvested and centrifuged twice at 4,000 rpm for 15 min at 4° C. to remove cell debris.

Antigens and Antibodies

Production of recombinant YFV antigens: The coding region for the entire prM and soluble E (sE) region of the YFV Asibi Strain (Uniprot ID: Q6DV88, residues 122-678 of the genome polyprotein) was cloned into pMT-puro, an insect expression vector encoding a C-terminal double strep tag. Expression construct design was based on previously published structures of flavivirus antigens61, 62, 63. The YFV prM/E construct was used to generate an inducible, stable Drosophila S2 line. Protein expression was induced with addition of copper sulfate and allowed to proceed for 5-7 days. Recombinant protein was affinity-purified from the culture supernatant with a StrepTrap HP column (GE Healthcare). An additional purification step was carried out using size-exclusion chromatography step using an S200Increase column (GE Healthcare). The final protein preparations were stored in phosphate-buffered saline pH 7.4 supplemented with an additional 150 mM NaCl. Small aliquots were stored at −70° C. until use. The additional flavivirus antigens used in this study—DENV-2 E, DENV-4 E, WNV E and ZIKV E were expressed and purified essentially as described for YFV sE.

Flavivirus NS1 protein antigens: The NS1 proteins from dengue virus (serotypes 1-4), JEV, TBEV, WNV, YFV were purchased from Native Antigen Company (Cat #FLAVX4-NS1-100 and DENVX4-NS1-100) and the ZIKV NS1 was purchased from Meridian Life Science (Cat #R01636). The positive control antibodies reactive to the above NS1 proteins were obtained from Native Antigen Company: anti-DENV NS1 (Cat #AbDENVNS1-DA034), anti-ZIKV NS1 antibody (Cat #AbZIKVNS1-B4-100). The anti-YFV NS1 protein antibody was purchased from Meridain Life Sciences (Cat #C01906M). The anti-WNV NS1 antibody (Cat #HM484-X0632) and anti-TBEV NS1 antibody (Cat #HM477-X1462) were purchased from East Coast Bio. Flavivirus cross-reactive serum was used to detect the JEV NS1 protein.

YFV-17D DIII protein: The DIII region (aa 293-397) of YFV-17D E protein (Uniprot ID: P03314) was produced in Drosophila S2 cells using a modified pT350 vector (Felix Rey, Institut Pasteur, France). Protein expression was induced by CdCl2 and the supernatant was harvested 5-7 days post-induction. Recombinant protein was purified using a Strep-Tactin column (IBA) and size-exclusion chromatography using a S200Increase column (GE Healthcare) and 10 mMTris pH8/150 mM NaCl buffer.

Single B-Cell Sorting

For plasmablast sorting, PBMCs were stained using anti-human CD38 (PE), CD27 (BV421), CD20 (PE-Cy7), CD3 (PerCP-Cy5.5), CD8 (PerCP-Cy5.5), CD14 (PerCP-Cy5.5) and CD16 (PerCP-Cy5.5). Plasmablasts were defined as CD19+CD3−CD20−/loCD27highCD38high cells. For MBC sorting, B cells were purified using a MACS B cell isolation kit (Miltenyi Biotec; cat #130-091-151) and subsequently stained using anti-human CD19 (PE-Cy7), CD20 (PE-Cy7), CD3 (PerCP-Cy5.5), CD8 (PerCP-Cy5.5), CD14 (PerCP-Cy5.5), CD16 (PerCP-Cy5.5), IgD (BV421), IgM (AF-488), CD27 (BV510), CD21 (BV605), CD71 (APC-Cy7 and a mixture of dual-labeled (APC and PE) YFV E tetramers (25 nM each). Tetramers were prepared fresh for each experiment, and B cells that showed reactivity to the YFV E tetramers were single cell sorted. Single cells were sorted using a BD FACS Aria II (BD Biosciences) into 96-well PCR plates (BioRAD) containing 20 μL/well of lysis buffer [5 μL of 5X first strand cDNA buffer (Invitrogen), 0.625 μL of NP-40 (New England Biolabs), 0.25 μL RNaseOUT (Invitrogen), 1.25 μL dithiothreitol (Invitrogen), and 12.6 μL dH2O]. Plates were immediately stored at −80° C. Flow cytometry data were analyzed using FlowJo software.

Amplification and Cloning of Antibody Variable Genes

Antibody variable genes (IgH, IgK, and IgL) were amplified by reverse transcription PCR and nested PCRs using cocktails of IgG- and IgM-specific primers, as described previously (Tiller et al, J Immunol 2008). The primers used in the second round of PCR contained 40 base pairs of 5' and 3' homology to the digested expression vectors, which allowed for cloning by homologous recombination into S. cerevisiae. The lithium acetate method for chemical transformation was used to clone the PCR products into S. cerevisiae (Gietz and Schiestl, Nat Protoc 2007). 10 μL of unpurified heavy chain and light chain PCR product and 200 ng of the digested expression vectors were used per transformation reaction. Following transformation, individual yeast colonies were picked for sequencing and characterization.

Expression and Purification of IgGs and Fab Fragments

IgGs were expressed in S. cerevisiae cultures grown in 24-well plates, as described previously (Bornholdt et al, Science 2016b). After 6 days, the cultures were harvested by centrifugation and IgGs were purified by protein A-affinity chromatography. The bound antibodies were eluted with 200 mM acetic acid/50 mM NaCl (pH 3.5) into ⅛th volume 2 M Hepes (pH 8.0), and buffer-exchanged into PBS (pH 7.0).

The two YFV E-reactive control mAbs, 5A and 4G2, were produced in the human IgG1 constant region. The publicly available variable region sequences of the two control antibodies, 4G2 and 5A, were synthesized as gBlock fragments (IDT) with homologous overhangs for recombinational cloning into S. cerevisiae. Subsequent production was carried out as described above.

Fab fragments were generated by digesting the IgGs with papain for 2 h at 30° C. The digestion was terminated by the addition of iodoacetamide, and the Fab and Fc mixtures were passed over Protein A agarose to remove Fc fragments and undigested IgG. The flowthrough of the Protein A resin was then passed over CaptureSelect™ IgG-$C_H1$ affinity resin (ThermoFischer Scientific), and eluted with 200 mM acetic acid/50 mM NaCl pH 3.5 into ⅛th volume 2M Hepes pH 8.0. Fab fragments then were buffer-exchanged into PBS pH 7.0.

Kinetics of Binding Measurements

Surface Plasmon Resonance Kinetic Measurements (SPR) of IgG binding: A Biacore 8K system, docked with a CAP sensor chip, sample compartment was set to 10° C., flow cell temperature to 25° C., and the data collection rate to 10 Hz. HBS-EP+(10 mM HEPES pH 7.3, 150 mM NaCl, 3 mM EDTA, 0.05% Surfactant P20) was used as the running buffer. In each cycle, biotin CAPture reagent (GE Healthcare) diluted 1:20 in running buffer was injected over flow cells 1 and 2 for 600 s, at a flow rate of 5 µL/min, followed by a 900 s capture (1 µL/min) of biotinylated YFV E antigen (25 nM in HBS-EP+) over flow cell 2 to reach a minimum capture level of 400 RU. The antibodies (36-288 nM in HBS-EP+) were then injected over flow cells 1 and 2 for 300 s (30 µL/min), the dissociation monitored for 300 s (30 µL/min), and the surface regenerated at the oligonucleotide level with 6M Guanidine-HCl in 0.25 M NaOH for 120 s (10 µL/min). A minimum of two blank (HBS-EP+) injections also were run under identical conditions as described above and used to assess and subtract system artifacts. The data were aligned, double referenced, and fit to bivalent analyte binding model using Biacore 8K Evaluation Software, version 1.0.

Surface Plasmon Resonance Kinetic Measurements (SPR) of Fab binding: A Biacore 8K system, docked with a CAP sensor chip, sample compartment was set to 10° C., flow cell temperature to 25° C., and the data collection rate to 10 Hz. HBS-EP+(10 mM HEPES pH 7.3, 150 mM NaCl, 3 mM EDTA, 0.05% Surfactant P20) was used as the running buffer. In each cycle, biotin CAPture reagent (GE Healthcare) diluted 1:20 in running buffer was injected over flow cells 1 and 2 for 600 s, at a flow rate of 1 µL/min, followed by a 900 s capture (1 µL/min) of biotinylated YFV E protein (15 nM in HBS-EP+) over flow cell 2 to reach a minimum capture level of 275 RU. The Fabs (A5: 27-1 nM in HBS-EP+; 4G2: 4-0.125 nM in HBS-EP+) were then injected over flow cells 1 and 2 for 300 s (30 µL/min), the dissociation monitored for 1200 s (30 µL/min), and the surface regenerated at the oligonucleotide level with 6M Guanidine-HCl in 0.25 M NaOH for 185 s (10 µL/min). A minimum of two blank (HBS-EP+) injections also were run under identical conditions as described above and used to assess and subtract system artifacts. The data were aligned, double referenced, and fit to a 1:1 binding model using Biacore 8K Evaluation Software, version 1.0.

Bio-Layer Interferometry Kinetic Measurements (BLI): For monovalent apparent KD determination, IgG binding to recombinant YFV E antigen was measured by biolayer interferometry (BLI) using a FortéBio Octet HTX instrument (Molecular Devices). The IgGs were captured (1.5 nm) to anti-human IgG capture (AHC) biosensors Molecular Devices) and allowed to stand in PBSF (PBS with 0.1% w/v BSA) for a minimum of 30 min. After a short (60 s) baseline step in PBSF, the IgG-loaded biosensor tips were exposed (180 s, 1000 rpm of orbital shaking) to YFV E antigen (100 nM in PBSF) and then dipped (180 s, 1000 rpm of orbital shaking) into PBSF to measure any dissociation of the antigen from the biosensor tip surface. Data for which binding responses were >0.1 nm were aligned, inter-step corrected (to the association step) and fit to a 1:1 binding model using the FortéBio Data Analysis Software, version 11.1.

For bivalent apparent KD determination, IgG binding to recombinant biotinylated YFV E antigen was measured by biolayer interferometry (BLI) using a FortéBio Octet HTX instrument (Molecular Devices). Recombinant biotinylated YFV E was immobilized on streptavidin biosensors (Molecular Devices) and allowed to stand in PBSF (PBS with 0.1% w/v BSA) for a minimum of 30 min. After a short (60 s) baseline step in PBSF, the antigen-loaded biosensor tips were exposed (180 s, 1000 rpm of orbital shaking) to the IgGs (100 nM in PBSF) and then dipped (180 s, 1000 rpm of orbital shaking) into PBSF to measure any dissociation of the IgGs from the biosensor tip surface. Data for which binding responses were >0.1 nm were aligned, interstep corrected (to the association step) and fit to a 1:1 binding model using the ForteBio Data Analysis Software, version 11.1.

High Throughput Antibody Epitope Assignment

Bio-Layer Interferometry (BLI) Epitope Binning: For epitope binning, control antibodies A5 and 4G2 (produced as human IgG1 chimeras) were captured on anti-human IgG capture biosensors (0.9 nm) (Molecular Devices) and the biosensors were then blocked by exposing them to adalimumab (0.5 mg/mL; 20 min, 350 rpm of orbital shaking). After a short (60 s) baseline step in PBSF, a cross-interaction check was performed between the sample IgGs and the loaded biosensors (180 s, 1000 rpm of orbital shaking). No cross-interaction was observed for this panel of IgGs. The loaded biosensors were then subjected to a second short (60 s) baseline step in PBSF, followed by an association step in 100 nM recombinant YFV E monomer (180 s, 1000 rpm of orbital shaking). Finally, the binning step was performed in 100 nM sample IgGs in PBS with 0.1% BSA (PBSF) (180 s, 1000 rpm of orbital shaking). Data were analyzed using the FortéBio Data Analysis Software, version 11.1. Sample IgGs with a binning response lower than 0.1 nm were determined to compete with the control antibody. Sample IgGs with a binning response greater than 0.1 nm were determined to be non-competitors to the control antibody.

High-Throughput Epitope Binning Using Carterra LSA (SPR)

Binding kinetics and affinities. The kinetic rate and affinity constants for Yellow Fever antigen (supplied by Adimab as purified recombinant monomer, MW of 45 kDa) binding to a library of 770+ADI mAbs (supplied as purified human IgG) were determined at a temperature of 25° C. in a "Capture Kinetics" assay format using Carterra's high throughput surface plasmon resonance (SPR) biosensor platform equipped with HC-30M chip type. To prepare the surfaces for this experiment, the chip was coated as a "lawn" with a capture reagent, namely goat anti-human-IgG Fc polyclonal cross-adsorbed to serum proteins from multiple other species (Southern Biotech, cat #2014-01) using standard amine coupling in a run buffer of 10 mM Hepes pH 7.4, 150 mM NaCl, 3 mM EDTA, 0.05% Tween20 (HBSET). Briefly, this involved priming the single flow cell (SFC) with HBSET run buffer, injecting a freshly prepared activation solution of 1:1:1 v/v/v 0.1 M N-hydroxysulfosuccinimide (Sulfo-NHS, Pierce)+0.4 M 1-ethyl-3-(3-dimethylaminopropyl)carbodiimide hydrochloride) (EDC, Pierce)+0.1 M MES pH 5.5 (Carterra) for 10 min, coupling 50 µg/ml goat anti-human-IgG Fc diluted into 10 mM sodium acetate pH 4.3 for 15 min, and quenching excess reactive esters with 1 M ethanolamine pH 8.5 for 7 min. This resulted in mean final coupled levels of 6256 RU±4% variance (as judged by the 384 reaction spots). The 96-channel printhead (96PH) was then primed in run buffer and used to capture the ADI mAbs as ligands, which were diluted to 2 µg/ml in run buffer and batch-printed 96 at a time onto discrete spots. Four serial docks of the 96PH were used to address all 4 print block locations, thus generating a 384-ligand array. The 96PH was returned to water for cleaning and the SFC was docked over the printed array and primed with the assay run buffer of HBSET+0.5 g/l BSA. Analyte samples of Yellow Fever Monomer antigen were prepared as an 8membered 4fold dilution series spanning nominal concentrations of 0.02-367 nM and injected in the SFC in ascending concentration after several buffer (blank) injections. Association and dissociation times were 5 min and 20 min respectively. Data were analyzed in Carterra's Kinetic Software as follows. The binding data on the reaction spots were double referenced by subtracting the responses from local reference spots (representing naked capture reagent) and then subtracting the responses from a buffer blank analyte66. Double-referenced data were fit globally to a simple Langmuir model allowing each spot its own association rate constant (ka), dissociation rate constant (kd), and Rmax value. The equilibrium dissociation (affinity) constant (KD) was computed from the ratio of the kinetic rate constants, KD=kd/ka).

Epitope binning experiments: Carterra's LSA was used to perform epitope binning assays in a classical sandwich assay format67 using 6 benchmark mAbs (ADI-49582, ADI-44112, ADI-45107, ADI-49147, 4G2, and 5A) as analyte to probe the epitope diversity of the 770+ADI library as ligands. An HCX-30M (pre-activated) chip type was used and experiments were performed at 25° C. The SFC and 96PH were primed in run buffer of 25 mM Mes pH5.5+ 0.01% Tween20. The ADI mAbs were diluted to 2 µg/ml in 10 mM sodium acetate pH 4.5 (coupling buffer) and coupled via the 96PH using 7 min contact time at each print block location. After 4 serial docks of the 96PH to build up a 384-ligand array, the SFC was docked over the entire surface to quench excess reactive esters by injecting ethanolamine pH8.5 for 7 min. Final coupled levels of each mAb ranged from 1000-4000 RU per spot. The 96PH was returned to water for cleaning and the SFC was primed in an assay run buffer of HBSET+0.5 g/l BSA. Each binning cycle involved a co-inject style of sample delivery whereby the antigen (50 nM Yellow Fever Monomer) and antibody analyte (20 µg/ml mAb or buffer) samples were injected back-to-back, with minimal dissociation time between them over the 384-ligand array. Typical association times were 3 or 5 min and surfaces were regenerated with 75 mM phosphoric acid after each binning cycle. The binding data were analyzed in Carterra's Epitope Software.

Micro-Titer Neutralization Assays

Monoclonal antibodies were serially diluted in DMEM high glucose medium (Gibco) containing 10% heat-inactivated FBS (Gibco), 1% Gluta-MAX Gibco), 1% P/S (Gibco) and 25 mM HEPES (Gibco) and incubated at room temperature with YFV-17D or ZIKV for 1 hour. YFV-17D or ZIKV was diluted to achieve 60% endpoint infection. The antibody-virus mixture was added in triplicates to 96-well plates (Costar 3595) containing $5\times10^{-3}$ Huh 7.5.1 cell monolayers seeded the day before. Cells were incubated for 2 days at 37° C. and 5% CO2. Cells were then fixed with 4% paraformaldehyde (Sigma) for 10 minutes and were washed afterwards with a Tris buffer (50 mM Tris, 150 mM NaCl (all Fisher Scientific), pH 7.6, three times. Fixed cells were incubated with a pan-flavivirus mouse mAb 4G2 (ATCC) at 2 µg/ml in Tris buffer containing 3% nonfat dry milk powder (BioRad), 0.5% Triton X-100 (MP Biomedicals), and 0.05% Tween 20 (Fisher Scientific) for one hour at room temperature (RT). Afterwards, cells were washed three times and incubated with the secondary antibody conjugated to Alexa Fluor 488 goat anti-mouse (Invitrogen) at 1:500 dilution for one hour at RT. Cells were washed again and nuclei were stained with Hoechst-33342 (Invitrogen) in a 1:2,000 dilution in PBS. Viral infectivity was measured by automated enumeration of Alexa Fluor 488-positive cells from captured images using Cytation-5 automated fluorescence microscope (BioTek) and analyzed using the Gen5 data analysis software (BioTek). The half maximal inhibitory concentration (IC50) of the mAbs was calculated using a nonlinear regression analysis with GraphPad Prism software. Viral neutralization data were subjected to nonlinear regression analysis to extract the half maximal inhibitory concentration (IC50) values (4-parameter, variable slope sigmoidal dose-response equation; GraphPad Prism).

Neutralization of donor plasma samples was carried out exactly as described above for purified IgGs. Serial dilutions of plasma were pre-incubated with YFV-17D infectious stock for 1 hour before adding to cell monolayers.

Purified total human IgG from non-immunized donors was used as negative control in purified IgG neutralization assays against YFV-17D and ZIKV (Cat #AB_2337042, Jackson Immuno Research).

FRNT Assay

Virus-specific mAbs were screened as previously described. Briefly, all purified mAbs were serially diluted in 199 medium (Thermo Scientific) containing 5% heat-inactivated fetal bovine serum (FBS) (Gibco-Invitrogen) and incubated at 37° C. with YFV-17DD. After 1 hr incubation, the Ab-virus mixture was added in duplicate to 96-well plates containing 80% confluent monolayers of Vero E6 cells. Plates were incubated for 1.5 h at 37° C. Wells were then overlaid with 1% methylcellulose in supplemented OptiMEM GlutaMAX media (Invitrogen) with 5% heat-inactivated FBS (Gibco-Invitrogen) and 1% amphotericin B and incubated at 37° C., 5% CO2 for 72 hours. Cells were then fixed and permeabilized with Perm/Wash buffer (BD Biosciences) for 30 min. After permeabilization, cells were washed with phosphate-buffered saline (PBS) and incubated with 1:2000 dilution of anti-flavivirus antibody (MAB10216, EMD Millipore) in Perm/Wash buffer for 2 hours. After incubation, cells were washed with PBS and incubated with anti-mouse horseradish peroxidase (HRP)-conjugated secondary antibody (115035146, Jackson ImmunoResearch Laboratories) for 2 hrs. Plates were washed and developed with peroxidase substrate (KPL). The half maximal inhibitory concentration (IC$_{50}$) of the mAbs was calculated using a nonlinear regression analysis with GraphPad Prism software.

Serum and Purified IgG ELISAS

For NS1 and E binding ELISAs, 96-well plates (Corning; Cat #3690) were coated with 5 µg/ml of NS1 or E protein diluted in PBS and incubated overnight at 4° C. Wells were washed and then blocked with 5% non-fat dried milk (NFDM) in PBS for 1 hour at 37°C. Wells were washed 3 times with PBS and serial dilutions of human plasm in 5% NFDM-PBS were added and incubated for 1 hour at 37° C. Plates were then washed 3 times with PBS and secondary cross-adsorbed anti-human IgG-HRP (Thermo Fisher Scientific; cat #31413) or anti-human-IgM (Sigma Aldrich; cat #AP114P) detection antibodies were added at 1:8000 dilution in 5% NFDM-PBS for 1 hour at 37° C. After washing 3 times with PBS detection reagent was added per manufacturer recommendations (Thermo Scientific; Cat #34029) and absorbance was measures at 450 nM wavelength using a Spectramax microplate Reader (Molecular Devices).

For virus binding ELISAs, 96-well ELISA plates were coated with 5 µg/ml of 4G2 (Millipore MAB10216) diluted in PBS and incubated for 2 hours at 37° C. After washing 3 times with PBS, whole YFV-17D viral particles diluted in PBS pH 7.4 and incubated overnight at 4° C. Plates were then washed 3 times with PBS and blocked with 5% NFDM-PBS for 1 hour at 37°C. After removal of the blocking solution, test antibodies diluted in 5% NFDM-PBS were allowed to bind for 1 hour at 37° C. Plates were then washed 3 times with PBS and secondary cross-adsorbed anti-human IgG-HRP (Thermo Fisher Scientific; cat #31413) or anti-human-IgM (Sigma Aldrich; cat #AP114P) detection antibodies were added at 1:8000 dilution in 5% NFDM-PBS for 1 hour at 37° C. After washing 3 times with PBS detection reagent was added per manufacturer recommendations (Thermo Scientific; Cat #34029) and absorbance was measures at 450 nM wavelength using a Spectramax microplate Reader (Molecular Devices).

Binding of purified IgGs to viral particles was performed as described above. IgGs were diluted in 5% NFDM-PBS and tested at 100 nM concentration for single point reactivity test of plasmablast- and MBC-derived day 14 antibodies.

All references, patents, and patent publications cited herein are hereby incorporated by reference in their entireties for all that is taught therein.

---

SEQUENCE LISTING

```
Sequence total quantity: 1014
SEQ ID NO: 1            moltype = AA  length = 18
FEATURE                 Location/Qualifiers
REGION                  1..18
                        note = Synthetic polypeptide
source                  1..18
                        mol_type = protein
                        organism = synthetic construct
SEQUENCE: 1
ARNAPENYYG SGRESFDI                                                 18

SEQ ID NO: 2            moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 2
GTWDSSLSAW V                                                        11

SEQ ID NO: 3            moltype = AA  length = 15
FEATURE                 Location/Qualifiers
REGION                  1..15
                        note = Synthetic polypeptide
source                  1..15
                        mol_type = protein
                        organism = synthetic construct
SEQUENCE: 3
AKDHGGKYGW WYFDL                                                    15

SEQ ID NO: 4            moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 4
QQYDNWPLT                                                           9

SEQ ID NO: 5            moltype = AA  length = 18
FEATURE                 Location/Qualifiers
REGION                  1..18
                        note = Synthetic polypeptide
source                  1..18
                        mol_type = protein
```

```
                                  organism = synthetic construct
SEQUENCE: 5
ARNAPENYYG SGRESFDI                                                          18

SEQ ID NO: 6           moltype = AA   length = 11
FEATURE                Location/Qualifiers
REGION                 1..11
                       note = Synthetic polypeptide
source                 1..11
                       mol_type = protein
                       organism = synthetic construct
SEQUENCE: 6
GTWDSSLSAW V                                                                 11

SEQ ID NO: 7           moltype = AA   length = 19
FEATURE                Location/Qualifiers
REGION                 1..19
                       note = Synthetic polypeptide
source                 1..19
                       mol_type = protein
                       organism = synthetic construct
SEQUENCE: 7
ARDLEVGAEY LYYHYGMDV                                                         19

SEQ ID NO: 8           moltype = AA   length = 11
FEATURE                Location/Qualifiers
REGION                 1..11
                       note = Synthetic polypeptide
source                 1..11
                       mol_type = protein
                       organism = synthetic construct
SEQUENCE: 8
AAWDDSLNGW V                                                                 11

SEQ ID NO: 9           moltype = AA   length = 17
FEATURE                Location/Qualifiers
REGION                 1..17
                       note = Synthetic polypeptide
source                 1..17
                       mol_type = protein
                       organism = synthetic construct
SEQUENCE: 9
AKDSSTSWYQ VVYHIDY                                                           17

SEQ ID NO: 10          moltype = AA   length = 11
FEATURE                Location/Qualifiers
REGION                 1..11
                       note = Synthetic polypeptide
source                 1..11
                       mol_type = protein
                       organism = synthetic construct
SEQUENCE: 10
ETWDSSLNAV V                                                                 11

SEQ ID NO: 11          moltype = AA   length = 15
FEATURE                Location/Qualifiers
REGION                 1..15
                       note = Synthetic polypeptide
source                 1..15
                       mol_type = protein
                       organism = synthetic construct
SEQUENCE: 11
AKDLAVSTPR YWFDS                                                             15

SEQ ID NO: 12          moltype = AA   length = 10
FEATURE                Location/Qualifiers
REGION                 1..10
                       note = Synthetic polypeptide
source                 1..10
                       mol_type = protein
                       organism = synthetic construct
SEQUENCE: 12
QQSYSIPRIT                                                                   10

SEQ ID NO: 13          moltype = AA   length = 15
FEATURE                Location/Qualifiers
REGION                 1..15
                       note = Synthetic polypeptide
```

```
source                    1..15
                          mol_type = protein
                          organism = synthetic construct
SEQUENCE: 13
AKDMAVSVHR GWFDD                                                        15

SEQ ID NO: 14             moltype = AA   length = 10
FEATURE                   Location/Qualifiers
REGION                    1..10
                          note = Synthetic polypeptide
source                    1..10
                          mol_type = protein
                          organism = synthetic construct
SEQUENCE: 14
QQSYSPPMYT                                                              10

SEQ ID NO: 15             moltype = AA   length = 19
FEATURE                   Location/Qualifiers
REGION                    1..19
                          note = Synthetic polypeptide
source                    1..19
                          mol_type = protein
                          organism = synthetic construct
SEQUENCE: 15
ARDLEVGAEY IYYYYGMDV                                                    19

SEQ ID NO: 16             moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 16
AAWDDSRNGW V                                                            11

SEQ ID NO: 17             moltype = AA   length = 15
FEATURE                   Location/Qualifiers
REGION                    1..15
                          note = Synthetic polypeptide
source                    1..15
                          mol_type = protein
                          organism = synthetic construct
SEQUENCE: 17
ARSHWRSPQS VTFDL                                                        15

SEQ ID NO: 18             moltype = AA   length = 13
FEATURE                   Location/Qualifiers
REGION                    1..13
                          note = Synthetic polypeptide
source                    1..13
                          mol_type = protein
                          organism = synthetic construct
SEQUENCE: 18
GTWDTSSLSA GRV                                                          13

SEQ ID NO: 19             moltype = AA   length = 16
FEATURE                   Location/Qualifiers
REGION                    1..16
                          note = Synthetic polypeptide
source                    1..16
                          mol_type = protein
                          organism = synthetic construct
SEQUENCE: 19
ARIAAGYSTS WYYFDY                                                       16

SEQ ID NO: 20             moltype = AA   length = 12
FEATURE                   Location/Qualifiers
REGION                    1..12
                          note = Synthetic polypeptide
source                    1..12
                          mol_type = protein
                          organism = synthetic construct
SEQUENCE: 20
GTWDTSLSAG RV                                                           12
```

```
SEQ ID NO: 21            moltype = AA  length = 15
FEATURE                  Location/Qualifiers
REGION                   1..15
                         note = Synthetic polypeptide
source                   1..15
                         mol_type = protein
                         organism = synthetic construct
SEQUENCE: 21
AKDMWAGTTT NWFGP                                                    15

SEQ ID NO: 22            moltype = AA  length = 10
FEATURE                  Location/Qualifiers
REGION                   1..10
                         note = Synthetic polypeptide
source                   1..10
                         mol_type = protein
                         organism = synthetic construct
SEQUENCE: 22
GTWDTSLGVV                                                          10

SEQ ID NO: 23            moltype = AA  length = 11
FEATURE                  Location/Qualifiers
REGION                   1..11
                         note = Synthetic polypeptide
source                   1..11
                         mol_type = protein
                         organism = synthetic construct
SEQUENCE: 23
AREFSSRPFD L                                                        11

SEQ ID NO: 24            moltype = AA  length = 12
FEATURE                  Location/Qualifiers
REGION                   1..12
                         note = Synthetic polypeptide
source                   1..12
                         mol_type = protein
                         organism = synthetic construct
SEQUENCE: 24
CSYAGTYTSN YV                                                       12

SEQ ID NO: 25            moltype = AA  length = 16
FEATURE                  Location/Qualifiers
REGION                   1..16
                         note = Synthetic polypeptide
source                   1..16
                         mol_type = protein
                         organism = synthetic construct
SEQUENCE: 25
ARVNPPQYSS GWYSVY                                                   16

SEQ ID NO: 26            moltype = AA  length = 11
FEATURE                  Location/Qualifiers
REGION                   1..11
                         note = Synthetic polypeptide
source                   1..11
                         mol_type = protein
                         organism = synthetic construct
SEQUENCE: 26
GTWDNSLGAV V                                                        11

SEQ ID NO: 27            moltype = AA  length = 15
FEATURE                  Location/Qualifiers
REGION                   1..15
                         note = Synthetic polypeptide
source                   1..15
                         mol_type = protein
                         organism = synthetic construct
SEQUENCE: 27
ARVAWTSSSS CYYDY                                                    15

SEQ ID NO: 28            moltype = AA  length = 18
FEATURE                  Location/Qualifiers
REGION                   1..18
                         note = Synthetic polypeptide
source                   1..18
                         mol_type = protein
                         organism = synthetic construct
```

```
SEQUENCE: 28
ARDGEGHYYR SGDNWFDR                                                       18

SEQ ID NO: 29           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 29
GTWDSSLSAV V                                                              11

SEQ ID NO: 30           moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 30
ARAELSAWYY FDH                                                            13

SEQ ID NO: 31           moltype = AA  length = 12
FEATURE                 Location/Qualifiers
REGION                  1..12
                        note = Synthetic polypeptide
source                  1..12
                        mol_type = protein
                        organism = synthetic construct
SEQUENCE: 31
GTWDTSLSAG RV                                                             12

SEQ ID NO: 32           moltype = AA  length = 19
FEATURE                 Location/Qualifiers
REGION                  1..19
                        note = Synthetic polypeptide
source                  1..19
                        mol_type = protein
                        organism = synthetic construct
SEQUENCE: 32
ARVSPLDDGY GYTYYGMDV                                                      19

SEQ ID NO: 33           moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 33
QQYNNWPPRT                                                                10

SEQ ID NO: 34           moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 34
ARDWAELTTI TNYFYP                                                         16

SEQ ID NO: 35           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 35
QQAKSFPPT                                                                  9

SEQ ID NO: 36           moltype = AA  length = 22
FEATURE                 Location/Qualifiers
REGION                  1..22
                        note = Synthetic polypeptide
```

```
source                  1..22
                        mol_type = protein
                        organism = synthetic construct
SEQUENCE: 36
AKAENRIGYC SAGSCYLTYF DY                                              22

SEQ ID NO: 37           moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 37
NSYTSSSTLV                                                            10

SEQ ID NO: 38           moltype = AA  length = 15
FEATURE                 Location/Qualifiers
REGION                  1..15
                        note = Synthetic polypeptide
source                  1..15
                        mol_type = protein
                        organism = synthetic construct
SEQUENCE: 38
AKDPKYSSGW WAFDY                                                      15

SEQ ID NO: 39           moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 39
QQYDDWPL                                                               8

SEQ ID NO: 40           moltype = AA  length = 15
FEATURE                 Location/Qualifiers
REGION                  1..15
                        note = Synthetic polypeptide
source                  1..15
                        mol_type = protein
                        organism = synthetic construct
SEQUENCE: 40
ARVEWAYSSS WWLDY                                                      15

SEQ ID NO: 41           moltype = AA  length = 12
FEATURE                 Location/Qualifiers
REGION                  1..12
                        note = Synthetic polypeptide
source                  1..12
                        mol_type = protein
                        organism = synthetic construct
SEQUENCE: 41
GTWDTSLSAG GV                                                         12

SEQ ID NO: 42           moltype = AA  length = 20
FEATURE                 Location/Qualifiers
REGION                  1..20
                        note = Synthetic polypeptide
source                  1..20
                        mol_type = protein
                        organism = synthetic construct
SEQUENCE: 42
AKHTGDKPLV WAPSVYGLDV                                                 20

SEQ ID NO: 43           moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 43
SSYTRRSTLV                                                            10
```

```
SEQ ID NO: 44           moltype = AA   length = 14
FEATURE                 Location/Qualifiers
REGION                  1..14
                        note = Synthetic polypeptide
source                  1..14
                        mol_type = protein
                        organism = synthetic construct
SEQUENCE: 44
ARVSVSTSAW YADY                                                           14

SEQ ID NO: 45           moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 45
GTWDTSLSTV                                                                10

SEQ ID NO: 46           moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 46
ARELSSRIDY                                                                10

SEQ ID NO: 47           moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 47
SSYPGTSALV I                                                              11

SEQ ID NO: 48           moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 48
ARAQDGQQLV NYYGMDV                                                        17

SEQ ID NO: 49           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 49
QQSYSTPYT                                                                  9

SEQ ID NO: 50           moltype = AA   length = 20
FEATURE                 Location/Qualifiers
REGION                  1..20
                        note = Synthetic polypeptide
source                  1..20
                        mol_type = protein
                        organism = synthetic construct
SEQUENCE: 50
ARGGDYGDYE SNNPAEYFQH                                                     20

SEQ ID NO: 51           moltype = AA   length = 12
FEATURE                 Location/Qualifiers
REGION                  1..12
                        note = Synthetic polypeptide
source                  1..12
                        mol_type = protein
                        organism = synthetic construct
```

```
SEQUENCE: 51
QSYDSSLSGH VV                                                                    12

SEQ ID NO: 52           moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 52
AGHREDPYGA YGAS                                                                  14

SEQ ID NO: 53           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 53
QQRTNWPFT                                                                         9

SEQ ID NO: 54           moltype = AA  length = 15
FEATURE                 Location/Qualifiers
REGION                  1..15
                        note = Synthetic polypeptide
source                  1..15
                        mol_type = protein
                        organism = synthetic construct
SEQUENCE: 54
ASRKEVRGTE DYFDY                                                                 15

SEQ ID NO: 55           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 55
HQRTNWPWT                                                                         9

SEQ ID NO: 56           moltype = AA  length = 15
FEATURE                 Location/Qualifiers
REGION                  1..15
                        note = Synthetic polypeptide
source                  1..15
                        mol_type = protein
                        organism = synthetic construct
SEQUENCE: 56
AKVEEDGYTN VVRDY                                                                 15

SEQ ID NO: 57           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 57
LQRTNWPFT                                                                         9

SEQ ID NO: 58           moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 58
AREGTRGRMD                                                                       10

SEQ ID NO: 59           moltype = AA  length = 11
FEATURE                 Location/Qualifiers
REGION                  1..11
                        note = Synthetic polypeptide
```

```
source                    1..11
                          mol_type = protein
                          organism = synthetic construct
SEQUENCE: 59
SSYTSGTTLG V                                                                11

SEQ ID NO: 60             moltype = AA   length = 15
FEATURE                   Location/Qualifiers
REGION                    1..15
                          note = Synthetic polypeptide
source                    1..15
                          mol_type = protein
                          organism = synthetic construct
SEQUENCE: 60
ARDSWSGPTR NWFDP                                                            15

SEQ ID NO: 61             moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 61
GTWDSSLGGV I                                                                11

SEQ ID NO: 62             moltype = AA   length = 15
FEATURE                   Location/Qualifiers
REGION                    1..15
                          note = Synthetic polypeptide
source                    1..15
                          mol_type = protein
                          organism = synthetic construct
SEQUENCE: 62
ARVVWEYSNA WCVDF                                                            15

SEQ ID NO: 63             moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 63
ETWDSSLGVV V                                                                11

SEQ ID NO: 64             moltype = AA   length = 14
FEATURE                   Location/Qualifiers
REGION                    1..14
                          note = Synthetic polypeptide
source                    1..14
                          mol_type = protein
                          organism = synthetic construct
SEQUENCE: 64
ARNTYYDRSG LIAY                                                             14

SEQ ID NO: 65             moltype = AA   length = 10
FEATURE                   Location/Qualifiers
REGION                    1..10
                          note = Synthetic polypeptide
source                    1..10
                          mol_type = protein
                          organism = synthetic construct
SEQUENCE: 65
QQYDNLSRLT                                                                  10

SEQ ID NO: 66             moltype = AA   length = 13
FEATURE                   Location/Qualifiers
REGION                    1..13
                          note = Synthetic polypeptide
source                    1..13
                          mol_type = protein
                          organism = synthetic construct
SEQUENCE: 66
ARGPLKSYWY FDL                                                              13
```

```
SEQ ID NO: 67              moltype = AA   length = 12
FEATURE                    Location/Qualifiers
REGION                     1..12
                           note = Synthetic polypeptide
source                     1..12
                           mol_type = protein
                           organism = synthetic construct
SEQUENCE: 67
GTWDTSLSAG RV                                                              12

SEQ ID NO: 68              moltype = AA   length = 17
FEATURE                    Location/Qualifiers
REGION                     1..17
                           note = Synthetic polypeptide
source                     1..17
                           mol_type = protein
                           organism = synthetic construct
SEQUENCE: 68
ARYCSGATCY GSNGMDV                                                         17

SEQ ID NO: 69              moltype = AA   length = 10
FEATURE                    Location/Qualifiers
REGION                     1..10
                           note = Synthetic polypeptide
source                     1..10
                           mol_type = protein
                           organism = synthetic construct
SEQUENCE: 69
GTWDFRLSAL                                                                 10

SEQ ID NO: 70              moltype = AA   length = 13
FEATURE                    Location/Qualifiers
REGION                     1..13
                           note = Synthetic polypeptide
source                     1..13
                           mol_type = protein
                           organism = synthetic construct
SEQUENCE: 70
AKDQCGGDCT ADY                                                             13

SEQ ID NO: 71              moltype = AA   length = 11
FEATURE                    Location/Qualifiers
REGION                     1..11
                           note = Synthetic polypeptide
source                     1..11
                           mol_type = protein
                           organism = synthetic construct
SEQUENCE: 71
SSYTSSGTPV V                                                               11

SEQ ID NO: 72              moltype = AA   length = 15
FEATURE                    Location/Qualifiers
REGION                     1..15
                           note = Synthetic polypeptide
source                     1..15
                           mol_type = protein
                           organism = synthetic construct
SEQUENCE: 72
ASTLWGGPLS VASDY                                                           15

SEQ ID NO: 73              moltype = AA   length = 12
FEATURE                    Location/Qualifiers
REGION                     1..12
                           note = Synthetic polypeptide
source                     1..12
                           mol_type = protein
                           organism = synthetic construct
SEQUENCE: 73
GTWDSSPSAG RV                                                              12

SEQ ID NO: 74              moltype = AA   length = 14
FEATURE                    Location/Qualifiers
REGION                     1..14
                           note = Synthetic polypeptide
```

```
source                  1..14
                        mol_type = protein
                        organism = synthetic construct
SEQUENCE: 74
ARDYYASGDG YFDY                                                          14

SEQ ID NO: 75           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 75
QQYYSTPRT                                                                 9

SEQ ID NO: 76           moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 76
VRYCSSTSCY GLNGMDV                                                       17

SEQ ID NO: 77           moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 77
GTWDTRLSAL                                                               10

SEQ ID NO: 78           moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 78
ARDGSLVNAI DY                                                            12

SEQ ID NO: 79           moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 79
GTWDTSLSAA WV                                                            12

SEQ ID NO: 80           moltype = AA   length = 15
FEATURE                 Location/Qualifiers
REGION                  1..15
                        note = Synthetic polypeptide
source                  1..15
                        mol_type = protein
                        organism = synthetic construct
SEQUENCE: 80
ARVRWSGSTS WDLDY                                                         15

SEQ ID NO: 81           moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 81
GTWDTSPSAG GV                                                            12
```

```
SEQ ID NO: 82            moltype = AA   length = 23
FEATURE                  Location/Qualifiers
REGION                   1..23
                         note = Synthetic polypeptide
source                   1..23
                         mol_type = protein
                         organism = synthetic construct
SEQUENCE: 82
AHSPRRITMV RGVIITWGDG MDV                                              23

SEQ ID NO: 83            moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 83
SSYTSSSTLA V                                                           11

SEQ ID NO: 84            moltype = AA   length = 12
FEATURE                  Location/Qualifiers
REGION                   1..12
                         note = Synthetic polypeptide
source                   1..12
                         mol_type = protein
                         organism = synthetic construct
SEQUENCE: 84
ARDGSMVNAI DY                                                          12

SEQ ID NO: 85            moltype = AA   length = 12
FEATURE                  Location/Qualifiers
REGION                   1..12
                         note = Synthetic polypeptide
source                   1..12
                         mol_type = protein
                         organism = synthetic construct
SEQUENCE: 85
GTWDSSLSAA WV                                                          12

SEQ ID NO: 86            moltype = AA   length = 14
FEATURE                  Location/Qualifiers
REGION                   1..14
                         note = Synthetic polypeptide
source                   1..14
                         mol_type = protein
                         organism = synthetic construct
SEQUENCE: 86
ARDAYASGDG GIDY                                                        14

SEQ ID NO: 87            moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 87
SSYRSSGTPY V                                                           11

SEQ ID NO: 88            moltype = AA   length = 15
FEATURE                  Location/Qualifiers
REGION                   1..15
                         note = Synthetic polypeptide
source                   1..15
                         mol_type = protein
                         organism = synthetic construct
SEQUENCE: 88
AKDLRGVGGW YYFDY                                                       15

SEQ ID NO: 89            moltype = AA   length = 9
FEATURE                  Location/Qualifiers
REGION                   1..9
                         note = Synthetic polypeptide
```

```
source                   1..9
                         mol_type = protein
                         organism = synthetic construct
SEQUENCE: 89
QQYDNLPLT                                                                    9

SEQ ID NO: 90            moltype = AA  length = 14
FEATURE                  Location/Qualifiers
REGION                   1..14
                         note = Synthetic polypeptide
source                   1..14
                         mol_type = protein
                         organism = synthetic construct
SEQUENCE: 90
AKDQGVTTDW PSDY                                                             14

SEQ ID NO: 91            moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 91
QHYETYSVR                                                                    9

SEQ ID NO: 92            moltype = AA  length = 19
FEATURE                  Location/Qualifiers
REGION                   1..19
                         note = Synthetic polypeptide
source                   1..19
                         mol_type = protein
                         organism = synthetic construct
SEQUENCE: 92
PRDGLPGANQ YFFYYGMDV                                                        19

SEQ ID NO: 93            moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 93
QKYNSAPLT                                                                    9

SEQ ID NO: 94            moltype = AA  length = 15
FEATURE                  Location/Qualifiers
REGION                   1..15
                         note = Synthetic polypeptide
source                   1..15
                         mol_type = protein
                         organism = synthetic construct
SEQUENCE: 94
VRVEEYVNNE EVRDY                                                            15

SEQ ID NO: 95            moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 95
LQRTNWPFT                                                                    9

SEQ ID NO: 96            moltype = AA  length = 14
FEATURE                  Location/Qualifiers
REGION                   1..14
                         note = Synthetic polypeptide
source                   1..14
                         mol_type = protein
                         organism = synthetic construct
SEQUENCE: 96
ARDQGFTTDW PCDY                                                             14
```

```
SEQ ID NO: 97          moltype = AA   length = 9
FEATURE                Location/Qualifiers
REGION                 1..9
                       note = Synthetic polypeptide
source                 1..9
                       mol_type = protein
                       organism = synthetic construct
SEQUENCE: 97
QHYNSFSVK                                                                 9

SEQ ID NO: 98          moltype = AA   length = 12
FEATURE                Location/Qualifiers
REGION                 1..12
                       note = Synthetic polypeptide
source                 1..12
                       mol_type = protein
                       organism = synthetic construct
SEQUENCE: 98
ARDSNFNSNL DY                                                            12

SEQ ID NO: 99          moltype = AA   length = 12
FEATURE                Location/Qualifiers
REGION                 1..12
                       note = Synthetic polypeptide
source                 1..12
                       mol_type = protein
                       organism = synthetic construct
SEQUENCE: 99
QVWDSSSDHP WV                                                            12

SEQ ID NO: 100         moltype = AA   length = 13
FEATURE                Location/Qualifiers
REGION                 1..13
                       note = Synthetic polypeptide
source                 1..13
                       mol_type = protein
                       organism = synthetic construct
SEQUENCE: 100
ARGPLKTYWY FDL                                                           13

SEQ ID NO: 101         moltype = AA   length = 12
FEATURE                Location/Qualifiers
REGION                 1..12
                       note = Synthetic polypeptide
source                 1..12
                       mol_type = protein
                       organism = synthetic construct
SEQUENCE: 101
GTWDTSLSAG RV                                                            12

SEQ ID NO: 102         moltype = AA   length = 12
FEATURE                Location/Qualifiers
REGION                 1..12
                       note = Synthetic polypeptide
source                 1..12
                       mol_type = protein
                       organism = synthetic construct
SEQUENCE: 102
ARDSNYFYGL DV                                                            12

SEQ ID NO: 103         moltype = AA   length = 12
FEATURE                Location/Qualifiers
REGION                 1..12
                       note = Synthetic polypeptide
source                 1..12
                       mol_type = protein
                       organism = synthetic construct
SEQUENCE: 103
QVWDTSIDHH WV                                                            12

SEQ ID NO: 104         moltype = AA   length = 14
FEATURE                Location/Qualifiers
REGION                 1..14
                       note = Synthetic polypeptide
```

```
source                     1..14
                           mol_type = protein
                           organism = synthetic construct
SEQUENCE: 104
AKDICSGDCG GGDY                                                         14

SEQ ID NO: 105             moltype = AA   length = 11
FEATURE                    Location/Qualifiers
REGION                     1..11
                           note = Synthetic polypeptide
source                     1..11
                           mol_type = protein
                           organism = synthetic construct
SEQUENCE: 105
SSYAGSNNWV V                                                            11

SEQ ID NO: 106             moltype = AA   length = 12
FEATURE                    Location/Qualifiers
REGION                     1..12
                           note = Synthetic polypeptide
source                     1..12
                           mol_type = protein
                           organism = synthetic construct
SEQUENCE: 106
AREDDDYYSM DV                                                           12

SEQ ID NO: 107             moltype = AA   length = 10
FEATURE                    Location/Qualifiers
REGION                     1..10
                           note = Synthetic polypeptide
source                     1..10
                           mol_type = protein
                           organism = synthetic construct
SEQUENCE: 107
SSYTTTSLVI                                                              10

SEQ ID NO: 108             moltype = AA   length = 22
FEATURE                    Location/Qualifiers
REGION                     1..22
                           note = Synthetic polypeptide
source                     1..22
                           mol_type = protein
                           organism = synthetic construct
SEQUENCE: 108
ARDISCISTS CYGGYYYYGM DV                                                22

SEQ ID NO: 109             moltype = AA   length = 10
FEATURE                    Location/Qualifiers
REGION                     1..10
                           note = Synthetic polypeptide
source                     1..10
                           mol_type = protein
                           organism = synthetic construct
SEQUENCE: 109
MQALQTPPRT                                                              10

SEQ ID NO: 110             moltype = AA   length = 14
FEATURE                    Location/Qualifiers
REGION                     1..14
                           note = Synthetic polypeptide
source                     1..14
                           mol_type = protein
                           organism = synthetic construct
SEQUENCE: 110
ARDYYASGDG SIDY                                                         14

SEQ ID NO: 111             moltype = AA   length = 9
FEATURE                    Location/Qualifiers
REGION                     1..9
                           note = Synthetic polypeptide
source                     1..9
                           mol_type = protein
                           organism = synthetic construct
SEQUENCE: 111
LQHNSYPLT                                                                9
```

| | | |
|---|---|---|
| SEQ ID NO: 112 | moltype = AA   length = 14 | |
| FEATURE | Location/Qualifiers | |
| REGION | 1..14 | |
| | note = Synthetic polypeptide | |
| source | 1..14 | |
| | mol_type = protein | |
| | organism = synthetic construct | |
| SEQUENCE: 112 | | |
| AKYYDSSGYY YFDY | | 14 |
| | | |
| SEQ ID NO: 113 | moltype = AA   length = 9 | |
| FEATURE | Location/Qualifiers | |
| REGION | 1..9 | |
| | note = Synthetic polypeptide | |
| source | 1..9 | |
| | mol_type = protein | |
| | organism = synthetic construct | |
| SEQUENCE: 113 | | |
| KQYNRNPYT | | 9 |
| | | |
| SEQ ID NO: 114 | moltype = AA   length = 13 | |
| FEATURE | Location/Qualifiers | |
| REGION | 1..13 | |
| | note = Synthetic polypeptide | |
| source | 1..13 | |
| | mol_type = protein | |
| | organism = synthetic construct | |
| SEQUENCE: 114 | | |
| AKGSVSVAGA EDY | | 13 |
| | | |
| SEQ ID NO: 115 | moltype = AA   length = 9 | |
| FEATURE | Location/Qualifiers | |
| REGION | 1..9 | |
| | note = Synthetic polypeptide | |
| source | 1..9 | |
| | mol_type = protein | |
| | organism = synthetic construct | |
| SEQUENCE: 115 | | |
| QKYNSAPQT | | 9 |
| | | |
| SEQ ID NO: 116 | moltype = AA   length = 14 | |
| FEATURE | Location/Qualifiers | |
| REGION | 1..14 | |
| | note = Synthetic polypeptide | |
| source | 1..14 | |
| | mol_type = protein | |
| | organism = synthetic construct | |
| SEQUENCE: 116 | | |
| AKGYDSSGYY WADY | | 14 |
| | | |
| SEQ ID NO: 117 | moltype = AA   length = 10 | |
| FEATURE | Location/Qualifiers | |
| REGION | 1..10 | |
| | note = Synthetic polypeptide | |
| source | 1..10 | |
| | mol_type = protein | |
| | organism = synthetic construct | |
| SEQUENCE: 117 | | |
| QQYNNWPPLT | | 10 |
| | | |
| SEQ ID NO: 118 | moltype = AA   length = 14 | |
| FEATURE | Location/Qualifiers | |
| REGION | 1..14 | |
| | note = Synthetic polypeptide | |
| source | 1..14 | |
| | mol_type = protein | |
| | organism = synthetic construct | |
| SEQUENCE: 118 | | |
| ARERGGYFTE PFDI | | 14 |
| | | |
| SEQ ID NO: 119 | moltype = AA   length = 9 | |
| FEATURE | Location/Qualifiers | |
| REGION | 1..9 | |
| | note = Synthetic polypeptide | |

```
source                  1..9
                        mol_type = protein
                        organism = synthetic construct
SEQUENCE: 119
QQYYRTPWT                                                                    9

SEQ ID NO: 120          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 120
AATIFGVVSF DY                                                               12

SEQ ID NO: 121          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 121
GTWDSALGAA V                                                                11

SEQ ID NO: 122          moltype = AA   length = 14
FEATURE                 Location/Qualifiers
REGION                  1..14
                        note = Synthetic polypeptide
source                  1..14
                        mol_type = protein
                        organism = synthetic construct
SEQUENCE: 122
AKYYDSSGYY YLDY                                                             14

SEQ ID NO: 123          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 123
QQYNRDPYT                                                                    9

SEQ ID NO: 124          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 124
CRESGEGFDP                                                                  10

SEQ ID NO: 125          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 125
QSADRSGSVI                                                                  10

SEQ ID NO: 126          moltype = AA   length = 26
FEATURE                 Location/Qualifiers
REGION                  1..26
                        note = Synthetic polypeptide
source                  1..26
                        mol_type = protein
                        organism = synthetic construct
SEQUENCE: 126
ARDQSHGTFG GVIDSTTLFY YYGMDV                                                26
```

```
SEQ ID NO: 127           moltype = AA  length = 8
FEATURE                  Location/Qualifiers
REGION                   1..8
                         note = Synthetic polypeptide
source                   1..8
                         mol_type = protein
                         organism = synthetic construct
SEQUENCE: 127
QQRSNWPS                                                                  8

SEQ ID NO: 128           moltype = AA  length = 19
FEATURE                  Location/Qualifiers
REGION                   1..19
                         note = Synthetic polypeptide
source                   1..19
                         mol_type = protein
                         organism = synthetic construct
SEQUENCE: 128
ARGYCSSTSC FYYYYGMDV                                                     19

SEQ ID NO: 129           moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 129
QQSYSTPLT                                                                 9

SEQ ID NO: 130           moltype = AA  length = 22
FEATURE                  Location/Qualifiers
REGION                   1..22
                         note = Synthetic polypeptide
source                   1..22
                         mol_type = protein
                         organism = synthetic construct
SEQUENCE: 130
ARDHYFDSSG DYLSYYYNGM DV                                                 22

SEQ ID NO: 131           moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 131
QQYGSSPRA                                                                 9

SEQ ID NO: 132           moltype = AA  length = 10
FEATURE                  Location/Qualifiers
REGION                   1..10
                         note = Synthetic polypeptide
source                   1..10
                         mol_type = protein
                         organism = synthetic construct
SEQUENCE: 132
ARVYGGPDDY                                                               10

SEQ ID NO: 133           moltype = AA  length = 9
FEATURE                  Location/Qualifiers
REGION                   1..9
                         note = Synthetic polypeptide
```

```
source                  1..9
                        mol_type = protein
                        organism = synthetic construct
SEQUENCE: 133
QQSSITPPT                                                                        9

SEQ ID NO: 134          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 134
AKDGVTTING WFHFEY                                                                16

SEQ ID NO: 135          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 135
QQYNSFPFT                                                                        9

SEQ ID NO: 136          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 136
TRITGDRYWY LDL                                                                   13

SEQ ID NO: 137          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 137
QQTYSASGS                                                                        9

SEQ ID NO: 138          moltype = AA  length = 20
FEATURE                 Location/Qualifiers
REGION                  1..20
                        note = Synthetic polypeptide
source                  1..20
                        mol_type = protein
                        organism = synthetic construct
SEQUENCE: 138
ARGWFGYSNY GLYYYYGMDV                                                            20

SEQ ID NO: 139          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 139
QQSYSTPWT                                                                        9

SEQ ID NO: 140          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 140
ARDFWSGSNW FDP                                                                   13
```

```
SEQ ID NO: 141         moltype = AA   length = 10
FEATURE                Location/Qualifiers
REGION                 1..10
                       note = Synthetic polypeptide
source                 1..10
                       mol_type = protein
                       organism = synthetic construct
SEQUENCE: 141
GTWDNSLGVV                                                                10

SEQ ID NO: 142         moltype = AA   length = 25
FEATURE                Location/Qualifiers
REGION                 1..25
                       note = Synthetic polypeptide
source                 1..25
                       mol_type = protein
                       organism = synthetic construct
SEQUENCE: 142
AKDIGDSYGS GSYYLPYGAY YGMDV                                                25

SEQ ID NO: 143         moltype = AA   length = 8
FEATURE                Location/Qualifiers
REGION                 1..8
                       note = Synthetic polypeptide
source                 1..8
                       mol_type = protein
                       organism = synthetic construct
SEQUENCE: 143
QQYGSSPG                                                                   8

SEQ ID NO: 144         moltype = AA   length = 14
FEATURE                Location/Qualifiers
REGION                 1..14
                       note = Synthetic polypeptide
source                 1..14
                       mol_type = protein
                       organism = synthetic construct
SEQUENCE: 144
AKHYDSSGYY YEDY                                                           14

SEQ ID NO: 145         moltype = AA   length = 9
FEATURE                Location/Qualifiers
REGION                 1..9
                       note = Synthetic polypeptide
source                 1..9
                       mol_type = protein
                       organism = synthetic construct
SEQUENCE: 145
HQYKDFPWT                                                                  9

SEQ ID NO: 146         moltype = AA   length = 10
FEATURE                Location/Qualifiers
REGION                 1..10
                       note = Synthetic polypeptide
source                 1..10
                       mol_type = protein
                       organism = synthetic construct
SEQUENCE: 146
ARVRDGEYDY                                                                10

SEQ ID NO: 147         moltype = AA   length = 8
FEATURE                Location/Qualifiers
REGION                 1..8
                       note = Synthetic polypeptide
source                 1..8
                       mol_type = protein
                       organism = synthetic construct
SEQUENCE: 147
QQYNSYSP                                                                   8

SEQ ID NO: 148         moltype = AA   length = 23
FEATURE                Location/Qualifiers
REGION                 1..23
                       note = Synthetic polypeptide
source                 1..23
                       mol_type = protein
                       organism = synthetic construct
```

```
SEQUENCE: 148
ARDNSEVEDY GDYVLYHYYG MDV                                              23

SEQ ID NO: 149          moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 149
QQYGSSPF                                                                8

SEQ ID NO: 150          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 150
AKDQCGGDCT ADY                                                         13

SEQ ID NO: 151          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 151
SSYTSSSTPV V                                                           11

SEQ ID NO: 152          moltype = AA  length = 12
FEATURE                 Location/Qualifiers
REGION                  1..12
                        note = Synthetic polypeptide
source                  1..12
                        mol_type = protein
                        organism = synthetic construct
SEQUENCE: 152
ARGYTGYDGF DY                                                          12

SEQ ID NO: 153          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 153
CSYATNYGVV                                                             10

SEQ ID NO: 154          moltype = AA  length = 18
FEATURE                 Location/Qualifiers
REGION                  1..18
                        note = Synthetic polypeptide
source                  1..18
                        mol_type = protein
                        organism = synthetic construct
SEQUENCE: 154
ARRPYYYGSR RPAGHMDV                                                    18

SEQ ID NO: 155          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 155
QSYDSSNVV                                                               9

SEQ ID NO: 156          moltype = AA  length = 11
FEATURE                 Location/Qualifiers
REGION                  1..11
                        note = Synthetic polypeptide
```

```
source                      1..11
                            mol_type = protein
                            organism = synthetic construct
SEQUENCE: 156
GRDSDKNYFD Y                                                              11

SEQ ID NO: 157              moltype = AA  length = 12
FEATURE                     Location/Qualifiers
REGION                      1..12
                            note = Synthetic polypeptide
source                      1..12
                            mol_type = protein
                            organism = synthetic construct
SEQUENCE: 157
GAWDSSLSAH VV                                                             12

SEQ ID NO: 158              moltype = AA  length = 14
FEATURE                     Location/Qualifiers
REGION                      1..14
                            note = Synthetic polypeptide
source                      1..14
                            mol_type = protein
                            organism = synthetic construct
SEQUENCE: 158
AKTYDSNAYY YLDY                                                           14

SEQ ID NO: 159              moltype = AA  length = 9
FEATURE                     Location/Qualifiers
REGION                      1..9
                            note = Synthetic polypeptide
source                      1..9
                            mol_type = protein
                            organism = synthetic construct
SEQUENCE: 159
QQYNRYPYT                                                                  9

SEQ ID NO: 160              moltype = AA  length = 18
FEATURE                     Location/Qualifiers
REGION                      1..18
                            note = Synthetic polypeptide
source                      1..18
                            mol_type = protein
                            organism = synthetic construct
SEQUENCE: 160
ASLWFIVMTM SKNPETDY                                                       18

SEQ ID NO: 161              moltype = AA  length = 9
FEATURE                     Location/Qualifiers
REGION                      1..9
                            note = Synthetic polypeptide
source                      1..9
                            mol_type = protein
                            organism = synthetic construct
SEQUENCE: 161
LQHHSYPWT                                                                  9

SEQ ID NO: 162              moltype = AA  length = 14
FEATURE                     Location/Qualifiers
REGION                      1..14
                            note = Synthetic polypeptide
source                      1..14
                            mol_type = protein
                            organism = synthetic construct
SEQUENCE: 162
AKYYDSSGYY YFDH                                                           14

SEQ ID NO: 163              moltype = AA  length = 9
FEATURE                     Location/Qualifiers
REGION                      1..9
                            note = Synthetic polypeptide
source                      1..9
                            mol_type = protein
                            organism = synthetic construct
SEQUENCE: 163
QQYNRDPYT                                                                  9
```

```
SEQ ID NO: 164          moltype = AA   length = 14
FEATURE                 Location/Qualifiers
REGION                  1..14
                        note = Synthetic polypeptide
source                  1..14
                        mol_type = protein
                        organism = synthetic construct
SEQUENCE: 164
AKFYDSSGYY YFDY                                                          14

SEQ ID NO: 165          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 165
QQYNTYPYT                                                                 9

SEQ ID NO: 166          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 166
VRLYGDYVAY FDY                                                           13

SEQ ID NO: 167          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 167
QQSYSTPWT                                                                 9

SEQ ID NO: 168          moltype = AA   length = 21
FEATURE                 Location/Qualifiers
REGION                  1..21
                        note = Synthetic polypeptide
source                  1..21
                        mol_type = protein
                        organism = synthetic construct
SEQUENCE: 168
ARRGTTVTRF GVIQYYYGMD V                                                  21

SEQ ID NO: 169          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 169
SSYTSSSTLV                                                               10

SEQ ID NO: 170          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 170
ARETANNWFD P                                                             11

SEQ ID NO: 171          moltype = AA   length = 11
FEATURE                 Location/Qualifiers
REGION                  1..11
                        note = Synthetic polypeptide
source                  1..11
                        mol_type = protein
                        organism = synthetic construct
```

```
SEQUENCE: 171
QVWDNSSDRR V                                                              11

SEQ ID NO: 172          moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 172
ARASMMPRPP VHDY                                                           14

SEQ ID NO: 173          moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 173
QQYNTWWT                                                                  8

SEQ ID NO: 174          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 174
AKDRSQGDYG DYVADY                                                         16

SEQ ID NO: 175          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 175
QQSYSTPLT                                                                 9

SEQ ID NO: 176          moltype = AA  length = 18
FEATURE                 Location/Qualifiers
REGION                  1..18
                        note = Synthetic polypeptide
source                  1..18
                        mol_type = protein
                        organism = synthetic construct
SEQUENCE: 176
ARVQTSHSEL WFGEFGAD                                                       18

SEQ ID NO: 177          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 177
QQYNTWPKT                                                                 9

SEQ ID NO: 178          moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 178
AKDGGYSTDW YFDL                                                           14

SEQ ID NO: 179          moltype = AA  length = 9
FEATURE                 Location/Qualifiers
REGION                  1..9
                        note = Synthetic polypeptide
```

```
source                      1..9
                            mol_type = protein
                            organism = synthetic construct
SEQUENCE: 179
QQYGSSRRT                                                                9

SEQ ID NO: 180              moltype = AA  length = 14
FEATURE                     Location/Qualifiers
REGION                      1..14
                            note = Synthetic polypeptide
source                      1..14
                            mol_type = protein
                            organism = synthetic construct
SEQUENCE: 180
AKGYDSNGYY YIDY                                                         14

SEQ ID NO: 181              moltype = AA  length = 9
FEATURE                     Location/Qualifiers
REGION                      1..9
                            note = Synthetic polypeptide
source                      1..9
                            mol_type = protein
                            organism = synthetic construct
SEQUENCE: 181
QQYNRYPYT                                                                9

SEQ ID NO: 182              moltype = AA  length = 16
FEATURE                     Location/Qualifiers
REGION                      1..16
                            note = Synthetic polypeptide
source                      1..16
                            mol_type = protein
                            organism = synthetic construct
SEQUENCE: 182
ARDVGYQLLQ VYGMDV                                                       16

SEQ ID NO: 183              moltype = AA  length = 12
FEATURE                     Location/Qualifiers
REGION                      1..12
                            note = Synthetic polypeptide
source                      1..12
                            mol_type = protein
                            organism = synthetic construct
SEQUENCE: 183
SSYTSSSTLD VV                                                           12

SEQ ID NO: 184              moltype = AA  length = 21
FEATURE                     Location/Qualifiers
REGION                      1..21
                            note = Synthetic polypeptide
source                      1..21
                            mol_type = protein
                            organism = synthetic construct
SEQUENCE: 184
ARAEYDTSGY YQQRLPEYFQ H                                                 21

SEQ ID NO: 185              moltype = AA  length = 10
FEATURE                     Location/Qualifiers
REGION                      1..10
                            note = Synthetic polypeptide
source                      1..10
                            mol_type = protein
                            organism = synthetic construct
SEQUENCE: 185
QQYNSWPPIT                                                              10

SEQ ID NO: 186              moltype = AA  length = 14
FEATURE                     Location/Qualifiers
REGION                      1..14
                            note = Synthetic polypeptide
source                      1..14
                            mol_type = protein
                            organism = synthetic construct
SEQUENCE: 186
AKYYDSSGYY YFHS                                                         14
```

| | |
|---|---|
| SEQ ID NO: 187<br>FEATURE<br>REGION<br><br>source | moltype = AA   length = 9<br>Location/Qualifiers<br>1..9<br>note = Synthetic polypeptide<br>1..9<br>mol_type = protein<br>organism = synthetic construct |

SEQUENCE: 187
QQYNRYPYT                                                                        9

| | |
|---|---|
| SEQ ID NO: 188<br>FEATURE<br>REGION<br><br>source | moltype = AA   length = 11<br>Location/Qualifiers<br>1..11<br>note = Synthetic polypeptide<br>1..11<br>mol_type = protein<br>organism = synthetic construct |

SEQUENCE: 188
AREHGDYGLD Y                                                                    11

| | |
|---|---|
| SEQ ID NO: 189<br>FEATURE<br>REGION<br><br>source | moltype = AA   length = 12<br>Location/Qualifiers<br>1..12<br>note = Synthetic polypeptide<br>1..12<br>mol_type = protein<br>organism = synthetic construct |

SEQUENCE: 189
ATWDVSLSND VL                                                                   12

| | |
|---|---|
| SEQ ID NO: 190<br>FEATURE<br>REGION<br><br>source | moltype = AA   length = 17<br>Location/Qualifiers<br>1..17<br>note = Synthetic polypeptide<br>1..17<br>mol_type = protein<br>organism = synthetic construct |

SEQUENCE: 190
YVDYYYDSSG YYSPFDY                                                              17

| | |
|---|---|
| SEQ ID NO: 191<br>FEATURE<br>REGION<br><br>source | moltype = AA   length = 10<br>Location/Qualifiers<br>1..10<br>note = Synthetic polypeptide<br>1..10<br>mol_type = protein<br>organism = synthetic construct |

SEQUENCE: 191
QQYGSSPPIT                                                                      10

| | |
|---|---|
| SEQ ID NO: 192<br>FEATURE<br>REGION<br><br>source | moltype = AA   length = 12<br>Location/Qualifiers<br>1..12<br>note = Synthetic polypeptide<br>1..12<br>mol_type = protein<br>organism = synthetic construct |

SEQUENCE: 192
ARVDGEEVAL IY                                                                   12

| | |
|---|---|
| SEQ ID NO: 193<br>FEATURE<br>REGION<br><br>source | moltype = AA   length = 9<br>Location/Qualifiers<br>1..9<br>note = Synthetic polypeptide<br>1..9<br>mol_type = protein<br>organism = synthetic construct |

SEQUENCE: 193
QQSSTTRWT                                                                        9

| | |
|---|---|
| SEQ ID NO: 194<br>FEATURE<br>REGION<br><br>source | moltype = AA   length = 13<br>Location/Qualifiers<br>1..13<br>note = Synthetic polypeptide<br>1..13<br>mol_type = protein<br>organism = synthetic construct |

```
SEQUENCE: 194
VRVWGGEAAR YDY                                                              13

SEQ ID NO: 195          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 195
QHASTTPWT                                                                   9

SEQ ID NO: 196          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 196
SRHMGFGLDL                                                                  10

SEQ ID NO: 197          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 197
QAWDTTTAGG V                                                                11

SEQ ID NO: 198          moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 198
ARDYYGSGDG YFDY                                                             14

SEQ ID NO: 199          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 199
QQYGSSPRA                                                                   9

SEQ ID NO: 200          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 200
ARIPVEYGTP RGSFDT                                                           16

SEQ ID NO: 201          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 201
SSYGGNNDLV                                                                  10

SEQ ID NO: 202          moltype = AA  length = 7
FEATURE                 Location/Qualifiers
REGION                  1..7
                        note = Synthetic polypeptide
```

```
                              -continued source                  1..7
                        mol_type = protein
                        organism = synthetic construct
SEQUENCE: 202
AGGSPDY                                                              7

SEQ ID NO: 203          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 203
QQRSNWPYT                                                            9

SEQ ID NO: 204          moltype = AA   length = 14
FEATURE                 Location/Qualifiers
REGION                  1..14
                        note = Synthetic polypeptide
source                  1..14
                        mol_type = protein
                        organism = synthetic construct
SEQUENCE: 204
ARAYDSRGYY YIEH                                                     14

SEQ ID NO: 205          moltype = AA   length = 8
FEATURE                 Location/Qualifiers
REGION                  1..8
                        note = Synthetic polypeptide
source                  1..8
                        mol_type = protein
                        organism = synthetic construct
SEQUENCE: 205
QQYKTYWT                                                             8

SEQ ID NO: 206          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 206
AREIDSNYVF DY                                                       12

SEQ ID NO: 207          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 207
SSYTSSGTNI                                                          10

SEQ ID NO: 208          moltype = AA   length = 15
FEATURE                 Location/Qualifiers
REGION                  1..15
                        note = Synthetic polypeptide
source                  1..15
                        mol_type = protein
                        organism = synthetic construct
SEQUENCE: 208
ARKLSYSSGW YYFDY                                                    15

SEQ ID NO: 209          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 209
QQYNNWPPLT                                                          10
```

```
SEQ ID NO: 210              moltype = AA   length = 10
FEATURE                     Location/Qualifiers
REGION                      1..10
                            note = Synthetic polypeptide
source                      1..10
                            mol_type = protein
                            organism = synthetic construct
SEQUENCE: 210
VTTTVILFDY                                                              10

SEQ ID NO: 211              moltype = AA   length = 11
FEATURE                     Location/Qualifiers
REGION                      1..11
                            note = Synthetic polypeptide
source                      1..11
                            mol_type = protein
                            organism = synthetic construct
SEQUENCE: 211
YSTDSSGLLG V                                                            11

SEQ ID NO: 212              moltype = AA   length = 20
FEATURE                     Location/Qualifiers
REGION                      1..20
                            note = Synthetic polypeptide
source                      1..20
                            mol_type = protein
                            organism = synthetic construct
SEQUENCE: 212
ARGRLAWGLR GQKSPNFFAY                                                   20

SEQ ID NO: 213              moltype = AA   length = 9
FEATURE                     Location/Qualifiers
REGION                      1..9
                            note = Synthetic polypeptide
source                      1..9
                            mol_type = protein
                            organism = synthetic construct
SEQUENCE: 213
QQFHSPPWT                                                               9

SEQ ID NO: 214              moltype = AA   length = 16
FEATURE                     Location/Qualifiers
REGION                      1..16
                            note = Synthetic polypeptide
source                      1..16
                            mol_type = protein
                            organism = synthetic construct
SEQUENCE: 214
ATAGIFGVVI MKGFDH                                                       16

SEQ ID NO: 215              moltype = AA   length = 9
FEATURE                     Location/Qualifiers
REGION                      1..9
                            note = Synthetic polypeptide
source                      1..9
                            mol_type = protein
                            organism = synthetic construct
SEQUENCE: 215
QQYNDYPWT                                                               9

SEQ ID NO: 216              moltype = AA   length = 16
FEATURE                     Location/Qualifiers
REGION                      1..16
                            note = Synthetic polypeptide
source                      1..16
                            mol_type = protein
                            organism = synthetic construct
SEQUENCE: 216
ARETYYYGSG SVPVHD                                                       16

SEQ ID NO: 217              moltype = AA   length = 9
FEATURE                     Location/Qualifiers
REGION                      1..9
                            note = Synthetic polypeptide
source                      1..9
                            mol_type = protein
                            organism = synthetic construct
```

```
SEQUENCE: 217
LQHNTYPWT                                                                    9

SEQ ID NO: 218         moltype = AA  length = 15
FEATURE                Location/Qualifiers
REGION                 1..15
                       note = Synthetic polypeptide
source                 1..15
                       mol_type = protein
                       organism = synthetic construct
SEQUENCE: 218
ARGYDSSGYW GFGDN                                                            15

SEQ ID NO: 219         moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 219
QQYYSYPYT                                                                    9

SEQ ID NO: 220         moltype = AA  length = 13
FEATURE                Location/Qualifiers
REGION                 1..13
                       note = Synthetic polypeptide
source                 1..13
                       mol_type = protein
                       organism = synthetic construct
SEQUENCE: 220
ARVEGGAWGA FDI                                                              13

SEQ ID NO: 221         moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 221
QSADRSGTVV                                                                  10

SEQ ID NO: 222         moltype = AA  length = 14
FEATURE                Location/Qualifiers
REGION                 1..14
                       note = Synthetic polypeptide
source                 1..14
                       mol_type = protein
                       organism = synthetic construct
SEQUENCE: 222
ARLWFTEYPG AFDI                                                             14

SEQ ID NO: 223         moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 223
SSYAGSNALV                                                                  10

SEQ ID NO: 224         moltype = AA  length = 17
FEATURE                Location/Qualifiers
REGION                 1..17
                       note = Synthetic polypeptide
source                 1..17
                       mol_type = protein
                       organism = synthetic construct
SEQUENCE: 224
ARHSSGSYYL AGYYFDY                                                          17

SEQ ID NO: 225         moltype = AA  length = 9
FEATURE                Location/Qualifiers
REGION                 1..9
                       note = Synthetic polypeptide
```

```
source                    1..9
                          mol_type = protein
                          organism = synthetic construct
SEQUENCE: 225
QSYDSSNWV                                                                  9

SEQ ID NO: 226            moltype = AA   length = 10
FEATURE                   Location/Qualifiers
REGION                    1..10
                          note = Synthetic polypeptide
source                    1..10
                          mol_type = protein
                          organism = synthetic construct
SEQUENCE: 226
ARLTDSGYDD                                                                10

SEQ ID NO: 227            moltype = AA   length = 8
FEATURE                   Location/Qualifiers
REGION                    1..8
                          note = Synthetic polypeptide
source                    1..8
                          mol_type = protein
                          organism = synthetic construct
SEQUENCE: 227
HSPDSHVV                                                                   8

SEQ ID NO: 228            moltype = AA   length = 20
FEATURE                   Location/Qualifiers
REGION                    1..20
                          note = Synthetic polypeptide
source                    1..20
                          mol_type = protein
                          organism = synthetic construct
SEQUENCE: 228
ARETCSGGSC YYRVGSAFDI                                                     20

SEQ ID NO: 229            moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 229
QVWDSSSDHE V                                                              11

SEQ ID NO: 230            moltype = AA   length = 15
FEATURE                   Location/Qualifiers
REGION                    1..15
                          note = Synthetic polypeptide
source                    1..15
                          mol_type = protein
                          organism = synthetic construct
SEQUENCE: 230
VKDYCSGGRC YSFDY                                                          15

SEQ ID NO: 231            moltype = AA   length = 5
FEATURE                   Location/Qualifiers
REGION                    1..5
                          note = Synthetic polypeptide
source                    1..5
                          mol_type = protein
                          organism = synthetic construct
SEQUENCE: 231
QQWGT                                                                      5

SEQ ID NO: 232            moltype = AA   length = 14
FEATURE                   Location/Qualifiers
REGION                    1..14
                          note = Synthetic polypeptide
source                    1..14
                          mol_type = protein
                          organism = synthetic construct
SEQUENCE: 232
AKAYDSSAYY YLDY                                                           14
```

```
SEQ ID NO: 233           moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 233
QQYNRYPYT                                                                   9

SEQ ID NO: 234           moltype = AA   length = 14
FEATURE                  Location/Qualifiers
REGION                   1..14
                         note = Synthetic polypeptide
source                   1..14
                         mol_type = protein
                         organism = synthetic construct
SEQUENCE: 234
AKAYDSRGYY YLDY                                                            14

SEQ ID NO: 235           moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 235
QQYNRYSYT                                                                   9

SEQ ID NO: 236           moltype = AA   length = 22
FEATURE                  Location/Qualifiers
REGION                   1..22
                         note = Synthetic polypeptide
source                   1..22
                         mol_type = protein
                         organism = synthetic construct
SEQUENCE: 236
AKDLTHRLGS IFGKLTFDAF DI                                                   22

SEQ ID NO: 237           moltype = AA   length = 8
FEATURE                  Location/Qualifiers
REGION                   1..8
                         note = Synthetic polypeptide
source                   1..8
                         mol_type = protein
                         organism = synthetic construct
SEQUENCE: 237
QQYNNFWT                                                                    8

SEQ ID NO: 238           moltype = AA   length = 16
FEATURE                  Location/Qualifiers
REGION                   1..16
                         note = Synthetic polypeptide
source                   1..16
                         mol_type = protein
                         organism = synthetic construct
SEQUENCE: 238
AKDLTPYFYD SGAFDH                                                          16

SEQ ID NO: 239           moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 239
HSYDSNMSGS V                                                               11

SEQ ID NO: 240           moltype = AA   length = 10
FEATURE                  Location/Qualifiers
REGION                   1..10
                         note = Synthetic polypeptide
source                   1..10
                         mol_type = protein
                         organism = synthetic construct
```

```
SEQUENCE: 240
ARVFGGPTDY                                                              10

SEQ ID NO: 241          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 241
QKYYSAPLIT                                                              10

SEQ ID NO: 242          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 242
ARVVNGLDV                                                               9

SEQ ID NO: 243          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 243
QSADSSVADS SVV                                                          13

SEQ ID NO: 244          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 244
ARGQPDY                                                                 7

SEQ ID NO: 245          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 245
QQRSNWPYT                                                               9

SEQ ID NO: 246          moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 246
AGKKWELLGF RFDP                                                         14

SEQ ID NO: 247          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 247
GTWDNSLGMV V                                                            11

SEQ ID NO: 248          moltype = AA  length = 10
FEATURE                 Location/Qualifiers
REGION                  1..10
                        note = Synthetic polypeptide
```

```
source                    1..10
                          mol_type = protein
                          organism = synthetic construct
SEQUENCE: 248
ARQWLGHFDY                                                          10

SEQ ID NO: 249            moltype = AA  length = 10
FEATURE                   Location/Qualifiers
REGION                    1..10
                          note = Synthetic polypeptide
source                    1..10
                          mol_type = protein
                          organism = synthetic construct
SEQUENCE: 249
SSYTSSSTYV                                                          10

SEQ ID NO: 250            moltype = AA  length = 10
FEATURE                   Location/Qualifiers
REGION                    1..10
                          note = Synthetic polypeptide
source                    1..10
                          mol_type = protein
                          organism = synthetic construct
SEQUENCE: 250
ARVFSYYLDY                                                          10

SEQ ID NO: 251            moltype = AA  length = 11
FEATURE                   Location/Qualifiers
REGION                    1..11
                          note = Synthetic polypeptide
source                    1..11
                          mol_type = protein
                          organism = synthetic construct
SEQUENCE: 251
QQPGNWPPAF T                                                        11

SEQ ID NO: 252            moltype = AA  length = 18
FEATURE                   Location/Qualifiers
REGION                    1..18
                          note = Synthetic polypeptide
source                    1..18
                          mol_type = protein
                          organism = synthetic construct
SEQUENCE: 252
AHRHIAARLY RDDDVFDV                                                 18

SEQ ID NO: 253            moltype = AA  length = 8
FEATURE                   Location/Qualifiers
REGION                    1..8
                          note = Synthetic polypeptide
source                    1..8
                          mol_type = protein
                          organism = synthetic construct
SEQUENCE: 253
QQYNNWIT                                                             8

SEQ ID NO: 254            moltype = AA  length = 12
FEATURE                   Location/Qualifiers
REGION                    1..12
                          note = Synthetic polypeptide
source                    1..12
                          mol_type = protein
                          organism = synthetic construct
SEQUENCE: 254
ARGLNTVTNS DY                                                       12

SEQ ID NO: 255            moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 255
QQANSFPWT                                                            9
```

```
SEQ ID NO: 256          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 256
ASGLSPDFSV LDV                                                              13

SEQ ID NO: 257          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 257
MQALQTPYT                                                                    9

SEQ ID NO: 258          moltype = AA   length = 23
FEATURE                 Location/Qualifiers
REGION                  1..23
                        note = Synthetic polypeptide
source                  1..23
                        mol_type = protein
                        organism = synthetic construct
SEQUENCE: 258
AREGAGYYDS SGYYPLSYDA FDI                                                   23

SEQ ID NO: 259          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 259
AAWDDNLIGV V                                                                11

SEQ ID NO: 260          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 260
ARVRGSYWDY                                                                  10

SEQ ID NO: 261          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 261
SSFAGSNNLY V                                                                11

SEQ ID NO: 262          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 262
GRDRGWLDI                                                                    9

SEQ ID NO: 263          moltype = AA   length = 10
FEATURE                 Location/Qualifiers
REGION                  1..10
                        note = Synthetic polypeptide
source                  1..10
                        mol_type = protein
                        organism = synthetic construct
```

-continued

```
SEQUENCE: 263
SSYTRSSTRV                                                                      10

SEQ ID NO: 264          moltype = AA  length = 23
FEATURE                 Location/Qualifiers
REGION                  1..23
                        note = Synthetic polypeptide
source                  1..23
                        mol_type = protein
                        organism = synthetic construct
SEQUENCE: 264
ARVIRDLRDY YDGSGYGPDA FDI                                                       23

SEQ ID NO: 265          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 265
ETWDSRLSVV                                                                      10

SEQ ID NO: 266          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 266
ARARWEDGNY YYGMDV                                                               16

SEQ ID NO: 267          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 267
GTWDSSLSAV V                                                                    11

SEQ ID NO: 268          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 268
AKDQSSGWPN YYYGMDV                                                              17

SEQ ID NO: 269          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 269
QQSYSTPWT                                                                       9

SEQ ID NO: 270          moltype = AA  length = 19
FEATURE                 Location/Qualifiers
REGION                  1..19
                        note = Synthetic polypeptide
source                  1..19
                        mol_type = protein
                        organism = synthetic construct
SEQUENCE: 270
VRGYCSSTSC YGGLYWFDP                                                            19

SEQ ID NO: 271          moltype = AA  length = 9
FEATURE                 Location/Qualifiers
REGION                  1..9
                        note = Synthetic polypeptide
```

```
source                    1..9
                          mol_type = protein
                          organism = synthetic construct
SEQUENCE: 271
QQSYSTPRT                                                              9

SEQ ID NO: 272            moltype = AA   length = 19
FEATURE                   Location/Qualifiers
REGION                    1..19
                          note = Synthetic polypeptide
source                    1..19
                          mol_type = protein
                          organism = synthetic construct
SEQUENCE: 272
ARHSGGYSSK DKPTEYFQH                                                  19

SEQ ID NO: 273            moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 273
QSYDSSLSGV V                                                          11

SEQ ID NO: 274            moltype = AA   length = 15
FEATURE                   Location/Qualifiers
REGION                    1..15
                          note = Synthetic polypeptide
source                    1..15
                          mol_type = protein
                          organism = synthetic construct
SEQUENCE: 274
ARDVGVAAVI TGSVR                                                      15

SEQ ID NO: 275            moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 275
QQFYTTPST                                                              9

SEQ ID NO: 276            moltype = AA   length = 19
FEATURE                   Location/Qualifiers
REGION                    1..19
                          note = Synthetic polypeptide
source                    1..19
                          mol_type = protein
                          organism = synthetic construct
SEQUENCE: 276
ARGYCSSTSC YGGLYWFDP                                                  19

SEQ ID NO: 277            moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 277
QQSYSTPRT                                                              9

SEQ ID NO: 278            moltype = AA   length = 26
FEATURE                   Location/Qualifiers
REGION                    1..26
                          note = Synthetic polypeptide
source                    1..26
                          mol_type = protein
                          organism = synthetic construct
SEQUENCE: 278
ARDGAGDYIW GSYRHKGLHY YYGMDV                                          26

SEQ ID NO: 279            moltype = AA   length = 9
FEATURE                   Location/Qualifiers
REGION                    1..9
```

```
                        note = Synthetic polypeptide
source                  1..9
                        mol_type = protein
                        organism = synthetic construct
SEQUENCE: 279
LQHNSYPLT                                                                9

SEQ ID NO: 280          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 280
AKDPRTFYGV VMLLDDP                                                      17

SEQ ID NO: 281          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 281
QSYDSTTVV                                                                9

SEQ ID NO: 282          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 282
ARGFGELPGF DI                                                           12

SEQ ID NO: 283          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 283
SSYAGSNNFV V                                                            11

SEQ ID NO: 284          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 284
ARDSWGPFDY                                                              10

SEQ ID NO: 285          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 285
GTWDSSLSAK V                                                            11

SEQ ID NO: 286          moltype = AA   length = 14
FEATURE                 Location/Qualifiers
REGION                  1..14
                        note = Synthetic polypeptide
source                  1..14
                        mol_type = protein
                        organism = synthetic construct
SEQUENCE: 286
AKTYDSRAYY YLDY                                                         14
```

```
SEQ ID NO: 287         moltype = AA   length = 9
FEATURE                Location/Qualifiers
REGION                 1..9
                       note = Synthetic polypeptide
source                 1..9
                       mol_type = protein
                       organism = synthetic construct
SEQUENCE: 287
QQYNRYPYT                                                                9

SEQ ID NO: 288         moltype = AA   length = 16
FEATURE                Location/Qualifiers
REGION                 1..16
                       note = Synthetic polypeptide
source                 1..16
                       mol_type = protein
                       organism = synthetic construct
SEQUENCE: 288
AKDLFYDFWT GITIDY                                                       16

SEQ ID NO: 289         moltype = AA   length = 11
FEATURE                Location/Qualifiers
REGION                 1..11
                       note = Synthetic polypeptide
source                 1..11
                       mol_type = protein
                       organism = synthetic construct
SEQUENCE: 289
CSYAGSYTFV L                                                            11

SEQ ID NO: 290         moltype = AA   length = 13
FEATURE                Location/Qualifiers
REGION                 1..13
                       note = Synthetic polypeptide
source                 1..13
                       mol_type = protein
                       organism = synthetic construct
SEQUENCE: 290
ARDGGTVSDG LDV                                                          13

SEQ ID NO: 291         moltype = AA   length = 8
FEATURE                Location/Qualifiers
REGION                 1..8
                       note = Synthetic polypeptide
source                 1..8
                       mol_type = protein
                       organism = synthetic construct
SEQUENCE: 291
QQTFSIWT                                                                 8

SEQ ID NO: 292         moltype = AA   length = 15
FEATURE                Location/Qualifiers
REGION                 1..15
                       note = Synthetic polypeptide
source                 1..15
                       mol_type = protein
                       organism = synthetic construct
SEQUENCE: 292
ARVVWYSSSS HLFDY                                                        15

SEQ ID NO: 293         moltype = AA   length = 12
FEATURE                Location/Qualifiers
REGION                 1..12
                       note = Synthetic polypeptide
source                 1..12
                       mol_type = protein
                       organism = synthetic construct
SEQUENCE: 293
GTWDSSLSAG KV                                                           12

SEQ ID NO: 294         moltype = AA   length = 10
FEATURE                Location/Qualifiers
REGION                 1..10
                       note = Synthetic polypeptide
source                 1..10
                       mol_type = protein
                       organism = synthetic construct
```

```
SEQUENCE: 294
ARIKSDAFDL                                                                   10

SEQ ID NO: 295         moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 295
FSYAGSNNYV                                                                   10

SEQ ID NO: 296         moltype = AA  length = 16
FEATURE                Location/Qualifiers
REGION                 1..16
                       note = Synthetic polypeptide
source                 1..16
                       mol_type = protein
                       organism = synthetic construct
SEQUENCE: 296
AKFPLRDGGS GEGFDY                                                            16

SEQ ID NO: 297         moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 297
MQASQFPLT                                                                     9

SEQ ID NO: 298         moltype = AA  length = 14
FEATURE                Location/Qualifiers
REGION                 1..14
                       note = Synthetic polypeptide
source                 1..14
                       mol_type = protein
                       organism = synthetic construct
SEQUENCE: 298
ARNTYYDRRR TFDY                                                              14

SEQ ID NO: 299         moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 299
QQYDNLPPVT                                                                   10

SEQ ID NO: 300         moltype = AA  length = 13
FEATURE                Location/Qualifiers
REGION                 1..13
                       note = Synthetic polypeptide
source                 1..13
                       mol_type = protein
                       organism = synthetic construct
SEQUENCE: 300
AGVGITGTTG IDY                                                               13

SEQ ID NO: 301         moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 301
QAWDSSTDVV                                                                   10

SEQ ID NO: 302         moltype = AA  length = 18
FEATURE                Location/Qualifiers
REGION                 1..18
                       note = Synthetic polypeptide
```

```
source                  1..18
                        mol_type = protein
                        organism = synthetic construct
SEQUENCE: 302
AKGAAAGPFP YFYYAMDV                                                     18

SEQ ID NO: 303          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 303
QKYQSAPPT                                                                9

SEQ ID NO: 304          moltype = AA   length = 125
FEATURE                 Location/Qualifiers
REGION                  1..125
                        note = Synthetic polypeptide
source                  1..125
                        mol_type = protein
                        organism = synthetic construct
SEQUENCE: 304
QVQLQESGPG LVKPSETLSL TCAVSGYSIS SGFYWGWIRQ PPGKGLEWIG SMYQSGITYY        60
NPSLKSRVTI SVDTSKSQFS LKLTSVTAAD TAMYYCARNA PENYYGSGRE SFDIWGQGTM       120
VTVSS                                                                  125

SEQ ID NO: 305          moltype = AA   length = 122
FEATURE                 Location/Qualifiers
REGION                  1..122
                        note = Synthetic polypeptide
source                  1..122
                        mol_type = protein
                        organism = synthetic construct
SEQUENCE: 305
QVQLQESGGD LVQPGGSLRL SCAASGFTFS NYAMNWVRQA PGKGLEWVSA INRGGDSTYY        60
ADSVKGRFTI SRDNSKNTLY LQMNSLRAED TAVYYCAKDH GGKYGWWYFD LWGRGTLVTV       120
SS                                                                     122

SEQ ID NO: 306          moltype = AA   length = 125
FEATURE                 Location/Qualifiers
REGION                  1..125
                        note = Synthetic polypeptide
source                  1..125
                        mol_type = protein
                        organism = synthetic construct
SEQUENCE: 306
QVQLQESGPG LVKPSETLSL TCAVSGYSIS SGFYWGWIRQ PPGKGLEWIG SMYHSGITYY        60
NPSLKSRVTI SVDTSKNQFS LKLTSVTAAD TAMYYCARNA PENYYGSGRE SFDIWGQGTT       120
VTVSS                                                                  125

SEQ ID NO: 307          moltype = AA   length = 126
FEATURE                 Location/Qualifiers
REGION                  1..126
                        note = Synthetic polypeptide
source                  1..126
                        mol_type = protein
                        organism = synthetic construct
SEQUENCE: 307
EVQLVESGGG LVQPGRPLRL SCAASGFAFS SYGMHWVRQA PGKGLEWVAL IRFDGTIKYY        60
ADSVKGRFTI SRDNAKNTLY LQMSSLRAED TAVYYCARDL EVGAEYLYYH YGMDVWGQGT       120
TVTVSS                                                                 126

SEQ ID NO: 308          moltype = AA   length = 124
FEATURE                 Location/Qualifiers
REGION                  1..124
                        note = Synthetic polypeptide
source                  1..124
                        mol_type = protein
                        organism = synthetic construct
SEQUENCE: 308
EVQLVESGGG VVQPGRSLRL SCAASGFTFN SHGMHWVRQA PGKGLEWVAV ISYDGTKKYF        60
ADSVKGRFTI SRDNSKNTLY LQMSSLRADD TAVYYCAKDS STSWYQVVYH IDYWGQGTLV       120
TVSS                                                                   124
```

```
SEQ ID NO: 309            moltype = AA   length = 122
FEATURE                   Location/Qualifiers
REGION                    1..122
                          note = Synthetic polypeptide
source                    1..122
                          mol_type = protein
                          organism = synthetic construct
SEQUENCE: 309
EVQLLESGGG LVQPGGSLRL SCAASGFTFR NYAMNWVRQT PGKGLEWVSG ISGGGDSTNY   60
ADSVKGRFTI SRDNSRNTLY LQLNSLRAED TAVYYCAKDL AVSTPRYWFD SWGQGTLVTV  120
SS                                                                 122

SEQ ID NO: 310            moltype = AA   length = 122
FEATURE                   Location/Qualifiers
REGION                    1..122
                          note = Synthetic polypeptide
source                    1..122
                          mol_type = protein
                          organism = synthetic construct
SEQUENCE: 310
EVQLVESGGG LVQPGGSLRL SCAASGLIFR NYAMSWVRQA PGKGLEWVSS FSGSGGSAYY   60
ADSVKGRFTI SRDNSKSTVY LQMNRLRVED TAVYYCAKDM AVSVHRGWFD DWGQGTLVTV  120
SS                                                                 122

SEQ ID NO: 311            moltype = AA   length = 126
FEATURE                   Location/Qualifiers
REGION                    1..126
                          note = Synthetic polypeptide
source                    1..126
                          mol_type = protein
                          organism = synthetic construct
SEQUENCE: 311
QVQLVESGGG VVQPGRSLRL SCAASGFAFS SYGMHWVRQA PGKGLEWVAG MRFDGTKIYY   60
ADSVKGRFTI SRDNSKNTLY LQMNSLRAED TAVYFCARDL EVGAEYIYYY YGMDVWGQGT  120
TVTVSS                                                             126

SEQ ID NO: 312            moltype = AA   length = 122
FEATURE                   Location/Qualifiers
REGION                    1..122
                          note = Synthetic polypeptide
source                    1..122
                          mol_type = protein
                          organism = synthetic construct
SEQUENCE: 312
QVQLVESGPG LVKPSGTLSL TCAVSGGSIS SDYWWSWVRQ PPGKGLEYIG EIYHTGSTNY   60
NPSLKSRVTV SLDRSKNVFS LTLRSVTAAD TAVYYCARSH WRSPQSVTFD LWGQGTTVTV  120
SS                                                                 122

SEQ ID NO: 313            moltype = AA   length = 123
FEATURE                   Location/Qualifiers
REGION                    1..123
                          note = Synthetic polypeptide
source                    1..123
                          mol_type = protein
                          organism = synthetic construct
SEQUENCE: 313
QVQLQESGPG LVKPSGTLSL TCAVSGGSIT SSNWWSWVRQ PPGKGLEWIG DIYHSGSTSY   60
NPSLKSRVTI SVDKSKNHFS LKLTSVTAAD TAVYYCARIA AGYSTSWYYF DYWGQGTLVT  120
VSS                                                                123

SEQ ID NO: 314            moltype = AA   length = 122
FEATURE                   Location/Qualifiers
REGION                    1..122
                          note = Synthetic polypeptide
source                    1..122
                          mol_type = protein
                          organism = synthetic construct
SEQUENCE: 314
EVQLVETGSG LVRPSGTLSL TCAVSGDSIS SNNWWSWVRQ PPGKGLEWIG EIYHSGSTSY   60
NPSLKSRVTI SIDKSNNHFS LKLTSVTAAD TAVYYCAKDM WAGTTTNWFG PWGQGTLVTV  120
SS                                                                 122

SEQ ID NO: 315            moltype = AA   length = 118
FEATURE                   Location/Qualifiers
REGION                    1..118
                          note = Synthetic polypeptide
```

```
source                        1..118
                              mol_type = protein
                              organism = synthetic construct
SEQUENCE: 315
QVTLKESGGA LVKPAGSLTL SCAASGFTFG DYYMSWIRQA PGKGLEWISY ISSSGSSIYY    60
TDSVRGRFTI SRDNARNSLY LQMNSLRVED TAVYYCAREF SSRPFDLWGQ GTLVTVSS    118

SEQ ID NO: 316                moltype = AA   length = 123
FEATURE                       Location/Qualifiers
REGION                        1..123
                              note = Synthetic polypeptide
source                        1..123
                              mol_type = protein
                              organism = synthetic construct
SEQUENCE: 316
EVQLQESGPG LVKPSGTLSL TCAVSGGSIS SSDWWSWVRQ PPGKGLEWIG EIYHSGSTSY    60
NPSVKSRVSI SVDKSKNQFS LQLSSVTAAD TAIYYCARVN PPQYSSGWYS VYWGQGTLVT   120
VSS                                                                123

SEQ ID NO: 317                moltype = AA   length = 122
FEATURE                       Location/Qualifiers
REGION                        1..122
                              note = Synthetic polypeptide
source                        1..122
                              mol_type = protein
                              organism = synthetic construct
SEQUENCE: 317
QVQLQQSGPG LVKPSGTLSL TCAVSGDSIS SSHWWCWVRQ PPGKGLEWIG EIYHSGSTSY    60
NPSLKSRVTI SVDKSKNQFS LKLSSVTAAD TAVYFCARVA WTSSSSCYYD YWGQGTLVTV   120
SS                                                                 122

SEQ ID NO: 318                moltype = AA   length = 125
FEATURE                       Location/Qualifiers
REGION                        1..125
                              note = Synthetic polypeptide
source                        1..125
                              mol_type = protein
                              organism = synthetic construct
SEQUENCE: 318
EVQLVESGPG LVKPSGTLSL TCAVSGGSIS SSYWWSWVRQ SPGKGLEWIG EVYHSGSTHY    60
NPSLKSRVTI SVDKSKNQFS LKLTSVTAAD TAVYYCARDG EGHYYRSGDN WFDRWGQGTL   120
VTVSS                                                              125

SEQ ID NO: 319                moltype = AA   length = 120
FEATURE                       Location/Qualifiers
REGION                        1..120
                              note = Synthetic polypeptide
source                        1..120
                              mol_type = protein
                              organism = synthetic construct
SEQUENCE: 319
EVQLLESGPG LVQPSGTLSL TCTASGGSIS SSNWWSWVRQ PPGKGLEWIG DIYHTGSTSY    60
NPSLKSRVTI SVDKSKNQFS LKLSSVTAAD TAVYYCARAE LSAWYYFDHW GQGTLVTVSS   120

SEQ ID NO: 320                moltype = AA   length = 126
FEATURE                       Location/Qualifiers
REGION                        1..126
                              note = Synthetic polypeptide
source                        1..126
                              mol_type = protein
                              organism = synthetic construct
SEQUENCE: 320
QVQLVESGGG LVKPGGSLRL SCAASGFIFS DYYMNWIRQA PGKGLDWVST ISGSGKSIYY    60
ADSVKGRFTI SRDNAKNSLY LQMNSLSAED TAVYYCARVS PLDDGYGYTY YGMDVWGQGT   120
TVTVSS                                                             126

SEQ ID NO: 321                moltype = AA   length = 123
FEATURE                       Location/Qualifiers
REGION                        1..123
                              note = Synthetic polypeptide
source                        1..123
                              mol_type = protein
                              organism = synthetic construct
SEQUENCE: 321
EVQLLESGGG LVKPGGSLRL SCAASGFTFS DYYMSWIRQA PGKGLEWVSY ITSSGNTKYY    60
ADSVKGRFTI SRDNAKNSLY LQISSLRAED TAVYYCARDW AELTTITNYF YPWGQGTTVT   120
VSS                                                                123
```

```
SEQ ID NO: 322          moltype = AA   length = 129
FEATURE                 Location/Qualifiers
REGION                  1..129
                        note = Synthetic polypeptide
source                  1..129
                        mol_type = protein
                        organism = synthetic construct
SEQUENCE: 322
EVQLLESGGG LVQPGRSLRL SCAASGFTFD DYAMHWVRQP PGKGLEWVSG ISWNGGGIGY    60
ADSVKGRFTI SRDNAKNSLY LQMNSLRADD TALYYCAKAE NRIGYCSAGS CYLTYFDYWG   120
QGTLVTVSS                                                           129

SEQ ID NO: 323          moltype = AA   length = 122
FEATURE                 Location/Qualifiers
REGION                  1..122
                        note = Synthetic polypeptide
source                  1..122
                        mol_type = protein
                        organism = synthetic construct
SEQUENCE: 323
QVQLVQSGGG LVQPGGSLRL SCAASGFTFS SYAMSWVRQA PGKGLEWVSA ISGSGGSTYY    60
ADSVKGRFTI SRDNSKNTLH LQMSSLRAED TAVYYCAKDP KYSSGWWAFD YWGQGTLVTV   120
SS                                                                  122

SEQ ID NO: 324          moltype = AA   length = 122
FEATURE                 Location/Qualifiers
REGION                  1..122
                        note = Synthetic polypeptide
source                  1..122
                        mol_type = protein
                        organism = synthetic construct
SEQUENCE: 324
EVQLVESGPG LVKPSGTLSL TCAVSGGSIS SNKWWSWVRQ PPGKGLEWIG EIYHSGSTSY    60
NPSLKSRVSI SVDKSKNQFS LKLSSVTAAD TAVYYCARVE WAYSSSWWLD YWGQGTLVTV   120
SS                                                                  122

SEQ ID NO: 325          moltype = AA   length = 127
FEATURE                 Location/Qualifiers
REGION                  1..127
                        note = Synthetic polypeptide
source                  1..127
                        mol_type = protein
                        organism = synthetic construct
SEQUENCE: 325
QVQLVESGGG LVKPGGSLRL SCAASGFTFS DDYMSWIRQA PGKGLEWVSY ISGSGRAMYY    60
ADSVQGRFTV SRDNAKNSLF LQMNNLRAED TAVYYCAKHT GDKPLVWAPS VYGLDVWGQG   120
TTVTVSS                                                             127

SEQ ID NO: 326          moltype = AA   length = 121
FEATURE                 Location/Qualifiers
REGION                  1..121
                        note = Synthetic polypeptide
source                  1..121
                        mol_type = protein
                        organism = synthetic construct
SEQUENCE: 326
QVQLQESGPG LVKPSGTLSL TCAVSGSSIT SSHWWSWVRQ PPGKGLAWIG DIYHSGGTTY    60
NPSLKSRVTI SVDKSKNQFS LKLSSVTAAD TAVYYCARVS VSTSAWYADY WGQGTLVTVS   120
S                                                                   121

SEQ ID NO: 327          moltype = AA   length = 117
FEATURE                 Location/Qualifiers
REGION                  1..117
                        note = Synthetic polypeptide
source                  1..117
                        mol_type = protein
                        organism = synthetic construct
SEQUENCE: 327
QVQLVESGGG LVKPGGSLRL SCVASGFTFN NYYMRWMRQA PGKGLEWVSQ ISSSGSIKDY    60
ADSVKGRFTV SRDNAKNSLY LQLNSLRADD TAVYFCAREL SSRIDYWGQG TLVTVSS      117

SEQ ID NO: 328          moltype = AA   length = 124
FEATURE                 Location/Qualifiers
REGION                  1..124
                        note = Synthetic polypeptide
source                  1..124
                        mol_type = protein
                        organism = synthetic construct
```

```
SEQUENCE: 328
EVQLVESGGG VVQPGRSLRL SCVASGFTLR SYGMHWVRQV PGKGLEWVAV SWYDGSNKHY    60
ADSVKGRFSI SRDNSKNTLY LQMNSLRAED TAVYYCARAQ DGQQLVNYYG MDVWGQGTTV   120
TVSS                                                                124

SEQ ID NO: 329          moltype = AA  length = 127
FEATURE                 Location/Qualifiers
REGION                  1..127
                        note = Synthetic polypeptide
source                  1..127
                        mol_type = protein
                        organism = synthetic construct
SEQUENCE: 329
QVQLVESGGG VVQPGRSLRL SCAASGFTFS SYTMHWVRQA PGKGLEWVAV ISYDGSNKYY    60
ADSVKGRFTI SRDNSKNTLY LQMNSLRAED TAVYYCARGG DYGDYESNNP AEYFQHWGQG   120
TLVTVSS                                                             127

SEQ ID NO: 330          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 330
QVQLQESGPG LVKPSETLSL TCTVSGDSIS VSYWSWIRQF PGKGLEWIGY IYNSGNANYN    60
PSLESRVTIS IDTSKNRFSL RLSSVTAADT AVYYCAGHRE DPYGAYGASW GQGTLVTVSS   120

SEQ ID NO: 331          moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 331
EVQLLESGPG LVKPSETLSL TCTVSGGSLS SDSHFWGWIR QPPGKGLEWI GYIYYSGNAN    60
YNPSLQSRVT ISLDKSKNQF SLRLTSVTAA DTAVYYCASR KEVRGTEDYF DYWGQGTLVT   120
VSS                                                                 123

SEQ ID NO: 332          moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 332
EVQLQESGPG LVKPSETLSL TCTVSGGSVS SGSYYWSWIR QPPGKGLEWI GYIYDSGNTN    60
YNPSLKSRVT ISVDTSKRQF SLRLTSVTAA DTAVYYCAKV EEDGYTNVVR DYWGQGTLVT   120
VSS                                                                 123

SEQ ID NO: 333          moltype = AA  length = 117
FEATURE                 Location/Qualifiers
REGION                  1..117
                        note = Synthetic polypeptide
source                  1..117
                        mol_type = protein
                        organism = synthetic construct
SEQUENCE: 333
EVQLVESGGG LVKPGGSLRL SCAASGFTFS DYYMSWIRQA PGKGLECIAC ISSSGSMIYY    60
ADSVKGRFTI SRDNAKNSLY LQLNSLRVED TAVYYCAREG TRGRMDWGQG TLVTVSS      117

SEQ ID NO: 334          moltype = AA  length = 122
FEATURE                 Location/Qualifiers
REGION                  1..122
                        note = Synthetic polypeptide
source                  1..122
                        mol_type = protein
                        organism = synthetic construct
SEQUENCE: 334
EVQLLESGPG LVRPSGTLSL TCAVSGGSIS TTDWWSWVRQ PPGKGLEWIG EINQSGSTSY    60
SPSFKSRVSI SVDKSKRQFS LKLTSVTAAD TAVYYCARDS WSGPTRNWFD PWGRGTLVTV   120
SS                                                                  122

SEQ ID NO: 335          moltype = AA  length = 122
FEATURE                 Location/Qualifiers
REGION                  1..122
                        note = Synthetic polypeptide
```

```
                        source          1..122
                                        mol_type = protein
                                        organism = synthetic construct
SEQUENCE: 335
EVQLLESGPG LVKPSGTLSL TCAVSGGSIS SGNWWSWVRQ PPGKGLEWIG EIYHSGSANY      60
NPSLKSRVTI SVDKSKNQFS LKLTSVTAAD TAVYYCARVV WEYSNAWCVD FWGQGTTVTV     120
SS                                                                   122

SEQ ID NO: 336          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 336
EVQLLESGGG VVQPGRSLRL SCAASGFTFT TYAMHWVRQA PGKGLEWVAA VSYDGNNKYY      60
ADSVKGRFTI SRDNSRNTLY LQMNSLRAED TAVYFCARNT YYDRSGLIAY WGQGALVTVS     120
S                                                                    121

SEQ ID NO: 337          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 337
QVQLVESGPG LVKPSGTLSL TCAVSGDSIS STNWWSWVRQ PPGKGLEYIG EIFHSGSTNY      60
NPFLKSRVTI SVDKSKNHFS LKLSSVTAAD TAVYYCARGP LKSYWYFDLW GRGTLVTVSS     120

SEQ ID NO: 338          moltype = AA  length = 124
FEATURE                 Location/Qualifiers
REGION                  1..124
                        note = Synthetic polypeptide
source                  1..124
                        mol_type = protein
                        organism = synthetic construct
SEQUENCE: 338
QVQLQESGPG LVKPSGTLSL TCAVSGGSIS SNNWWSWVRQ PPGKGLEWIG DTYHSGSPSY      60
NPSLKSRVTI SVDKSKNEFS LKLSSVTAAD TAVYFCARYC SGATCYGSNG MDVWGQGTTV     120
TVSS                                                                 124

SEQ ID NO: 339          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 339
QVQLQESGGG VVQPGRSLRL SCAASGFTFS NFGMHWVRQA PGKGLEWVAI ISYDRSNKDY      60
ADSVKGRFTI SRDNSKNTLY LQMNSLRAED TAVYYCAKDQ CGGDCTADYW GQGTLVTVSS     120

SEQ ID NO: 340          moltype = AA  length = 122
FEATURE                 Location/Qualifiers
REGION                  1..122
                        note = Synthetic polypeptide
source                  1..122
                        mol_type = protein
                        organism = synthetic construct
SEQUENCE: 340
EVQLLESGPG LVRPSGTLSL TCAVSGASIS SNHWWTWVRQ PPGKGLEWIG EIYHSGSPTY      60
NPSLKSRVTI SVDKSKNQFS LKLNSVTAAD TAVYYCASTL WGGPLSVASD YWGQGTLVTV     120
SS                                                                   122

SEQ ID NO: 341          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 341
QVQLVESGGG VVQPGRSLRL SCAASGFTFS NSGMHWVRQA PGQGLEWVAL ISYTGETKYY      60
SDSLKARFTI SRDNSKNTLY LQMSSLSNED TAVYYCARDY YASGDGYFDY WGQGTLVTVS     120
S                                                                    121
```

```
SEQ ID NO: 342          moltype = AA  length = 124
FEATURE                 Location/Qualifiers
REGION                  1..124
                        note = Synthetic polypeptide
source                  1..124
                        mol_type = protein
                        organism = synthetic construct
SEQUENCE: 342
QVQLQQWGPE LVKPSGTLSL TCTVSGGSIS SISWWSWVRQ SPGKGLEWIG EINHSGSTVY   60
NPSLKSRVTI SVDKSKKQFS LKLRSVTAAD TAVYYCVRYC SSTSCYGLNG MDVWGQGTTV  120
TVSS                                                              124

SEQ ID NO: 343          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 343
QVQLVQSGGG LVNPGGSLRL SCAASGFTFT DYYMSWIRQA PGKGLEWVSY ISSSGNTRYY   60
ADSVKGRFTI SRDNAKNSLS LQMNSLRPED TAIYYCARDG SLVNAIDYWG QGTLVTVSS   119

SEQ ID NO: 344          moltype = AA  length = 122
FEATURE                 Location/Qualifiers
REGION                  1..122
                        note = Synthetic polypeptide
source                  1..122
                        mol_type = protein
                        organism = synthetic construct
SEQUENCE: 344
EVQLVESGPG LVKPSGTLSL TCAVSGGSIT GSNWWSWVRQ PPGKGLEWIG EIYHTGSTSY   60
NPSLKSRVTI SVDNSKNHFS LRLTSVTAAD TAVYYCARVR WSGSTSWDLD YWGQGTLVTV  120
SS                                                                122

SEQ ID NO: 345          moltype = AA  length = 131
FEATURE                 Location/Qualifiers
REGION                  1..131
                        note = Synthetic polypeptide
source                  1..131
                        mol_type = protein
                        organism = synthetic construct
SEQUENCE: 345
EVTLKESGPT LVKPTQTLTL TCTFSGFSLS TSGVGVGWIR QPPGKALEWL ALIYWDDDKR   60
YSPSLKSRLT ITKDTSKNQV VLTMTNMDPV DTATYYCAHS PRRITMVRGV IITWGDGMDV  120
WGQGTTVTVS S                                                      131

SEQ ID NO: 346          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 346
EVQLVESGGG LVKPGGSLRL SCAASGFTFT DYYMSWIRQA PGKGLEWVSY ITSSGNTKYY   60
ADSVKGRFTI SRDNAKNSLF LQMNSLRAED TAVYFCARDG SMVNAIDYWG QGTLVTVSS   119

SEQ ID NO: 347          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 347
QVQLVESGGG VVQPGRSLRL SCAASGFTFS NSGMHWVRQA PGKGLEWVSV IWYDESNKYY   60
ADSVKGRFTI SRDNSKNTVY LQMNTLRAED TAVYYCARDA YASGDGGIDY WGQGALVTVS  120
S                                                                 121

SEQ ID NO: 348          moltype = AA  length = 122
FEATURE                 Location/Qualifiers
REGION                  1..122
                        note = Synthetic polypeptide
source                  1..122
                        mol_type = protein
                        organism = synthetic construct
```

```
SEQUENCE: 348
EVQLLESGGG LVQPGGSLRL SCAASGFTFS SYAMSWVRQA PGKGLEWVSV ISDSGGSTYY    60
ADSVKGRFTI SRDNSKNTLY LQMNSLRAED TAVYYCAKDL RGVGGWYYFD YWGQGTLVTV   120
SS                                                                 122

SEQ ID NO: 349          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 349
EVQLVESGGG LVQPGGSLRL SCAASGFTFI NYAMTWVRQA PGKGLEWVSA ISGNGDGTYY    60
ADSVKGRFTL SRDNAKNTIY LHMSALRDED TALYYCAKDQ GVTTDWPSDY WGQGTLVTVS   120
S                                                                  121

SEQ ID NO: 350          moltype = AA  length = 126
FEATURE                 Location/Qualifiers
REGION                  1..126
                        note = Synthetic polypeptide
source                  1..126
                        mol_type = protein
                        organism = synthetic construct
SEQUENCE: 350
QVQLVESGGG VVQPGRSLRL SCAASGFTFS SYAMHWVRQA PGKGLEWVAV ISHDGSNKYY    60
ADSVKGRFTI SRDNSKNTLY LQINSLRAED TAVYYCPRDG LPGANQYFFY YGMDVWGQGT   120
TVTVSS                                                             126

SEQ ID NO: 351          moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 351
EVQLLESGPR LVKPSETLSL TCTVSGGSVR GGSHYWSWIR QPPGKGLEWI GYVYDSGSTN    60
YNPSLKSRVS ISVDMSKKQF SLKLRSVTAA DTAVYHCVRV EEYVNNEEVR DYWGQGTMVT   120
VSS                                                                123

SEQ ID NO: 352          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 352
EVQLLESGGG LVPPGGSLRL SCAASGFTFS NYAMSWVRQA PGKGLEWVSA ISGSGDSTYY    60
ADSVKGRFTL SRDTSKKMVY LHMSNLRDDD TAVYYCARDQ GFTTDWPCDY WGQGTLVTVS   120
S                                                                  121

SEQ ID NO: 353          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 353
QVQLVESGGG LVKPGGSLRL SCAASGFTFS DYYMSWIRQA PGKGLEWVSY ITSSGNTMYY    60
ADSVKGRFTI SRDNAKNSLY LQMNSLRAED TAVYYCARDS NFNSNLDYWG QGTLVTVSS    119

SEQ ID NO: 354          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 354
QVQLQESGPG LVKPSGTLSL TCAVSGGSIS SSNWWSWVRQ PPGKGLEWIG EIYHSGSTTY    60
NPSLKSRVTI SVDKSKNQFS LKLSSVTAAD TAVYYCARGP LKTYWYFDLW GRGTLVTVSS   120

SEQ ID NO: 355          moltype = AA  length = 119
FEATURE                 Location/Qualifiers
REGION                  1..119
                        note = Synthetic polypeptide
```

```
source                      1..119
                            mol_type = protein
                            organism = synthetic construct
SEQUENCE: 355
EVQLVESGGG LVKPGGSLRL SCAASGFTFS DYYMSWIRQA PGKGLEWVSY ISSSGNTIYY    60
ADSVKGRFTI SRDNAKNSLY LQLNSLRAGD TAVYYCARDS NYFYGLDVWG QGTTVTVSS    119

SEQ ID NO: 356              moltype = AA  length = 121
FEATURE                     Location/Qualifiers
REGION                      1..121
                            note = Synthetic polypeptide
source                      1..121
                            mol_type = protein
                            organism = synthetic construct
SEQUENCE: 356
EVQLVESGGG VVQPGRSLRL SCAASGFTFS NYGMHWVRQA PGKGLEWVAV ISYDGSNKYY    60
ADSVKGRFTI SRDDSKNTLY LQVNSLRAED TAVYYCAKDI CSGDCGGGDY WGQGTLVTVS   120
S                                                                   121

SEQ ID NO: 357              moltype = AA  length = 119
FEATURE                     Location/Qualifiers
REGION                      1..119
                            note = Synthetic polypeptide
source                      1..119
                            mol_type = protein
                            organism = synthetic construct
SEQUENCE: 357
QVQLVQSGAE VKKPGASVKV SCKASGYTFN TYAMTWVRQA PGQGLEWMGW ISTYNGNTVF    60
GQKFQGRVTL STDTSTSTAY MELRSLTSDD TAVYYCARED DDYYSMDVWG QGTTVTVSS    119

SEQ ID NO: 358              moltype = AA  length = 129
FEATURE                     Location/Qualifiers
REGION                      1..129
                            note = Synthetic polypeptide
source                      1..129
                            mol_type = protein
                            organism = synthetic construct
SEQUENCE: 358
EVQLVQSGGG LVQPGGSLRL SCAASGFTFS TYWMSWVRQA PGKGLEWVAN IKQDGSEKYY    60
VDSVKGRFTI SRDNAKNSLY LQMNSLRAED TAVYYCARDI SCISTSCYGG YYYYGMDVWG   120
QGTTVTVSS                                                           129

SEQ ID NO: 359              moltype = AA  length = 121
FEATURE                     Location/Qualifiers
REGION                      1..121
                            note = Synthetic polypeptide
source                      1..121
                            mol_type = protein
                            organism = synthetic construct
SEQUENCE: 359
EVQLVESGGG VVQPGRSLRL SCAASGFTFS NSGMHWVRQA PGKGLEWVAV IWYDSRNQNY    60
ADSVKGRFTI SRDNSKNTLF LQMNSLRAED TAVYYCARDY YASGDGSIDY WGQGTLVTVS   120
S                                                                   121

SEQ ID NO: 360              moltype = AA  length = 121
FEATURE                     Location/Qualifiers
REGION                      1..121
                            note = Synthetic polypeptide
source                      1..121
                            mol_type = protein
                            organism = synthetic construct
SEQUENCE: 360
EVQLVESGGG LVQPGGSLRL SCAASGFTFS SYAMSWVRQA PGKGLEWVST FSGRGGSTYY    60
ADFVKGRFTI SRDNSKNTLY LQMNSLRAED TAVYYCAKYY DSSGYYYFDY WGQGTLVTVS   120
S                                                                   121

SEQ ID NO: 361              moltype = AA  length = 120
FEATURE                     Location/Qualifiers
REGION                      1..120
                            note = Synthetic polypeptide
source                      1..120
                            mol_type = protein
                            organism = synthetic construct
SEQUENCE: 361
QVQLVESGGG VVQPGRSLRL SCGGSGFTFS SYGMHWVRQA PGKGLEWVAV ISYDGSKKYS    60
ADSVKGRFTI SRDNSKNTLY LQMNSLRAED TAVYYCAKGS VSVAGAEDYW GQGTLVTVSS   120

SEQ ID NO: 362              moltype = AA  length = 121
FEATURE                     Location/Qualifiers
```

```
REGION                  1..121
                        note = Synthetic polypeptide
source                  1..121
                        mol_type = protein
                        organism = synthetic construct
SEQUENCE: 362
EVQLLESGGG LVQPGRSLRL SCAVSGFTFA EYAMHWVRQA PGKGLEWVSS ISWNSGRIGY      60
VDSVRGRFTI SRDNAKNSLY LQMNSLRVED TAFYYCAKGY DSSGYYWADY WGQGTLVTVS     120
S                                                                    121

SEQ ID NO: 363          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 363
EVQLLESGPG LVKPSETLSL TCTVSGGSIS SYYWSWIRQP AGKGLELIGR IYTSGSGNYN      60
PSLKRRVTMS VDTSKNQISL RLNSVTAADT AVYYCARERG GYFTEPFDIW GQGTMVTVSS    120

SEQ ID NO: 364          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 364
EVQLLESGGG LVHPGGSLRL SCAASGFTFS DYEMNWVRQA PGKGLEWVSH ISSSGNIIYY      60
ADSVKGRFTI SRDNAKDSLY LQMNSLRAED TAVYYCAATI FGVVSFDYWG QGTLVTVSS     119

SEQ ID NO: 365          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 365
EVQLVESGGG LVQPGGSLRL SCAASGFTFS AYAMSWVRQA PGRGLEWVSA ISGSDRRIYY      60
ADSVKGRFSI SRDNSKNTLY LQMSSLRAED TAVYYCAKYY DSSGYYYLDY WGQGTLVTVS    120
S                                                                    121

SEQ ID NO: 366          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 366
EVQLVESGGG LVQPGGSLRL SCAASGFTFS DHYMAWVRQA PGKGLEWVGR IRNKPNSYTT      60
EYAASVKGRF TISRHDSENS LYLQMNSLKT EDTAVYYCCR ESGEGFDPWG QGTLVTVSS     119

SEQ ID NO: 367          moltype = AA  length = 133
FEATURE                 Location/Qualifiers
REGION                  1..133
                        note = Synthetic polypeptide
source                  1..133
                        mol_type = protein
                        organism = synthetic construct
SEQUENCE: 367
QVQLVQSGAE VKKPGASVKV SCKASGYSFT TYGISWVRQA PGQGLEWMGW ISGYSGDTNY      60
AQKVQGRVTM TTDTSTSTAY MELRSLRSDD TAVYYCARDQ SHGTFGGVID STTLFYYYGM    120
DVWGQGTTVT VSS                                                       133

SEQ ID NO: 368          moltype = AA  length = 127
FEATURE                 Location/Qualifiers
REGION                  1..127
                        note = Synthetic polypeptide
source                  1..127
                        mol_type = protein
                        organism = synthetic construct
SEQUENCE: 368
EVQLQESGPG LVKPSETLSL TCTVSGGSIS SSSYYWGWIR QPPGKGLEWI GSIYYSGSTY      60
YNPSLKSRVT ISVDTSKNQF SLKLSSVTAA DTAVYYCARG YCSSTSCFYY YYGMDVWGQG    120
TTVTVSS                                                              127
```

```
SEQ ID NO: 369          moltype = AA   length = 129
FEATURE                 Location/Qualifiers
REGION                  1..129
                        note = Synthetic polypeptide
source                  1..129
                        mol_type = protein
                        organism = synthetic construct
SEQUENCE: 369
EVQLVESGGG LVKPGGSLRL SCVASGFTFS RYSMNWVRQA PGKGLEWVSS ISHSGRYIYY  60
ADSEKGRFTI SRDNAKNSLY LQMNSLRAED TAVYYCARDH YFDSSGDYLS YYYNGMDVWG 120
QGTTVTVSS                                                        129

SEQ ID NO: 370          moltype = AA   length = 119
FEATURE                 Location/Qualifiers
REGION                  1..119
                        note = Synthetic polypeptide
source                  1..119
                        mol_type = protein
                        organism = synthetic construct
SEQUENCE: 370
EVQLVESGGG LVQPGGSLRL SCAASGFTFS DHYMDWVRQA PGKGLEWVGR TRNKPNSHTT  60
EYAASVKGRF TISRDDSKNS LYLQMNSLQT EDTAVYYCAR VYGGPDDYWG QGTLVTVSS  119

SEQ ID NO: 371          moltype = AA   length = 123
FEATURE                 Location/Qualifiers
REGION                  1..123
                        note = Synthetic polypeptide
source                  1..123
                        mol_type = protein
                        organism = synthetic construct
SEQUENCE: 371
EVQLVESGGG LVQPGGSLRL SCAASGFIYT NYAMYWVRQA PGKGLEWVSA ISGSGGITYY  60
ADSVKGRFTI SRDNSKNTLY LQMNSLRAED KAVYYCAKDG VTTINGWFHF EYWGQGTLVT 120
VSS                                                              123

SEQ ID NO: 372          moltype = AA   length = 122
FEATURE                 Location/Qualifiers
REGION                  1..122
                        note = Synthetic polypeptide
source                  1..122
                        mol_type = protein
                        organism = synthetic construct
SEQUENCE: 372
EVQLLESGGG LVQPGGSLRL SCAASGFIFS DYYMDWVRQT PGKGPEWVGR ITNRPNSYTT  60
EYAASVKGRF TISRDDSTNS LFLHMNSLKT EDTAVYYCTR ITGDRYWYLD LWGRGTLVTV 120
SS                                                               122

SEQ ID NO: 373          moltype = AA   length = 128
FEATURE                 Location/Qualifiers
REGION                  1..128
                        note = Synthetic polypeptide
source                  1..128
                        mol_type = protein
                        organism = synthetic construct
SEQUENCE: 373
EVQLVESGPG LVKPSQTLSL TCTVSGGSIS SGSYYWSWIR QPAGKGLEWI GRIYTSGSTN  60
YNPSLKSRVT MSVDTSKNQF SLKLSSVTAA DTAVYYCARG WFGYSNYGLY YYYGMDVWGQ 120
GTTVTVSS                                                         128

SEQ ID NO: 374          moltype = AA   length = 120
FEATURE                 Location/Qualifiers
REGION                  1..120
                        note = Synthetic polypeptide
source                  1..120
                        mol_type = protein
                        organism = synthetic construct
SEQUENCE: 374
EVQLVESGPG LVKPSGTLSL TCAVSGGSIS SSNWWSWVRQ PPGKGLEWIG EIYHSESTNY  60
NPSLKSRVTI SVDKSKNQFS LKLSSVTAAD TAVYYCARDF WSGSNWFDPW GQGTLVTVSS 120

SEQ ID NO: 375          moltype = AA   length = 132
FEATURE                 Location/Qualifiers
REGION                  1..132
                        note = Synthetic polypeptide
source                  1..132
                        mol_type = protein
                        organism = synthetic construct
```

```
SEQUENCE: 375
EVQLLESGGG LVQPGRSLRL SCAASGFTFD DYAMHWVRQA PGKGLEWVSG ISWNSGSIGY    60
ADSVKGRFTI SRDNAKNSLY LQMNSLRAED TALYYCAKDI GDSYGSGSYY LPYGAYYGMD   120
VWGQGTTVTV SS                                                      132

SEQ ID NO: 376          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 376
EVQLLESGGG LVQPGGSLRL SCAASGFTFS SYAMSWVRQA TGRGLEWVSS IRSSGGRTEY    60
ADSVKGRFTI SRDNSKNTLY LQMDSLRAED TALYYCAKHY DSSGYYYEDY WGQGTLVTVS   120
S                                                                  121

SEQ ID NO: 377          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 377
EVQLVESGGA LVHPGGSLGL SCAASGFTFS DHYMDWVRQA PGKGLEWVGR IRNKPNSYAT    60
QYAASVKGRF TISRDDSKKS LYLQMNSLNT EDTAVYYCAR VRDGEYDYWG QGTLVTVSS   119

SEQ ID NO: 378          moltype = AA  length = 130
FEATURE                 Location/Qualifiers
REGION                  1..130
                        note = Synthetic polypeptide
source                  1..130
                        mol_type = protein
                        organism = synthetic construct
SEQUENCE: 378
EVQLLESGGG LVKPGGSLRL SCAASGFTFS SYSMNWVRQA PGKGLEWVSS ISSRSSFMYY    60
ADSVKGRFTI SRDNAKNSLY LQMNSLRVED TAVYYCARDN SEVEDYGDYV LYHYYGMDVW   120
GQGTTVTVSS                                                         130

SEQ ID NO: 379          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 379
EVQLLESGGG VVQPGRSLRL SCVASGFTFS SYGMHWVRQA PGKGLEWVAL ISYDGSNKYY    60
ADSVKGRFTI SRDNSKNTLY LQMNSLRAED TAVYYCAKDQ CGGDCTADYW GQGTLVTVSS   120

SEQ ID NO: 380          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 380
QVQLVESGGG VVQPGRSLRL SCAASGFTFS SLAMHWVRQA PGKGLEWVAT ISYDVSNKYY    60
ADSVKGRFTI SRDNSKNTLF LQMNSLRPED TAVYYCARGY TGYDGFDYWG QGTLVTVSS   119

SEQ ID NO: 381          moltype = AA  length = 125
FEATURE                 Location/Qualifiers
REGION                  1..125
                        note = Synthetic polypeptide
source                  1..125
                        mol_type = protein
                        organism = synthetic construct
SEQUENCE: 381
QVQLVQSGAE VKKPGASVKV SCKASGYTFT SYGISWVRQA PGQGLEWMGW ISAYNGNTNY    60
AQKLQGRVTM TTDTSTSTAY MELRSLRSDD TAVYYCARRP YYYGSRRPAG HMDVWGQGTT   120
VTVSS                                                              125

SEQ ID NO: 382          moltype = AA  length = 119
FEATURE                 Location/Qualifiers
REGION                  1..119
                        note = Synthetic polypeptide
```

```
source                  1..119
                        mol_type = protein
                        organism = synthetic construct
SEQUENCE: 382
QVQLQESGPG LVRPSQTLSL TCTVSGGAIS SGDYYWSWVR QPPGKGLEWI GYIHYSGTTY    60
NNPSLKSRVT IAVDTSKNQF SLKLSSVTAA DTAVYFCGRD SDKNYFDYWG QGTLVTVSS    119

SEQ ID NO: 383          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 383
EVQLVESGGG VVRPGRSLRL SCAASGFTFS SYGMHWVRQA PGKGLEWVAV IRFDGSNTVY    60
ADSVKGRFTI SRDNSKNTLY LQMNSLRAED TAVYYCAKTY DSNAYYYLDY WGQGTLVTVS   120
S                                                                  121

SEQ ID NO: 384          moltype = AA  length = 125
FEATURE                 Location/Qualifiers
REGION                  1..125
                        note = Synthetic polypeptide
source                  1..125
                        mol_type = protein
                        organism = synthetic construct
SEQUENCE: 384
EVQLVESGGG VVQPGWSLRL SCAVSGFTFS SYAMHWVRQA PGKGLEWVAV ISYDGSYKWY    60
ADSVKGRFTI SRDNSKNTVY LQMNSLRAED TAVYYCASLW FIVMTMSKNP ETDYWGQGTL   120
VTVSS                                                              125

SEQ ID NO: 385          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 385
EVQLVESGGG LIQPGGSLRL SCAASGFSFS SHAMTWVRQA PGKGLQWVSS IRGSDRTTNY    60
ADSVKGRFTV SRDNSKNTLY LQMNSLRAED TAIYYCAKYY DSSGYYYFDH WGQGTLVTVS   120
S                                                                  121

SEQ ID NO: 386          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 386
EVQLVESGGT FLQPGGSLRL SCVASGFTFG THAMSWVRQA PGKGLEWVST FSGSGGRTYY    60
ADSVKGRFTI SRDNSKSTLY LEMSALRAED TAVYYCAKFY DSSGYYYFDY WGQGTLVTVS   120
S                                                                  121

SEQ ID NO: 387          moltype = AA  length = 122
FEATURE                 Location/Qualifiers
REGION                  1..122
                        note = Synthetic polypeptide
source                  1..122
                        mol_type = protein
                        organism = synthetic construct
SEQUENCE: 387
EVQLVESGGG LVQPGGSLRL SCAASGFTFS DYYMDWVRQA PGKGLEWVGG IRNKPNSYTT    60
EYAASVKGRF TISRDDSKNS LFLQMNSLKT EDTAVYYCVR LYGDYVAYFD YWGQGTLVTV   120
SS                                                                 122

SEQ ID NO: 388          moltype = AA  length = 128
FEATURE                 Location/Qualifiers
REGION                  1..128
                        note = Synthetic polypeptide
source                  1..128
                        mol_type = protein
                        organism = synthetic construct
SEQUENCE: 388
QVQLVQSGAE VKKPGASVKV SCKASGYTFT SYGISWVRQA PGQGLEWMGW ISAYNGNTNY    60
AQKLQGRVTM TTDTSTSTAY MELRSLRSDD TAVYYCARRG TTVTRFGVIQ YYYGMDVWGQ   120
GTTVTVSS                                                           128
```

```
SEQ ID NO: 389            moltype = AA  length = 117
FEATURE                   Location/Qualifiers
REGION                    1..117
                          note = Synthetic polypeptide
source                    1..117
                          mol_type = protein
                          organism = synthetic construct
SEQUENCE: 389
QVQLQESGPG LVKPSETLSL TCTVSGASIR SYLWSWIRQP PGKELEWLGS IYHSGSTKYN    60
PSLKSRVTIS ADTSKNQFSL KLNSVTAADT AVFYCARETA NNWFDPWGQG TLVTVSS      117

SEQ ID NO: 390            moltype = AA  length = 121
FEATURE                   Location/Qualifiers
REGION                    1..121
                          note = Synthetic polypeptide
source                    1..121
                          mol_type = protein
                          organism = synthetic construct
SEQUENCE: 390
EVQLVESGGG VVQSGRSLRL SCAASGFTFS GNAMHWVRQA PGKGLEWVAV ILYDGSNQYY    60
ADSVKGRFTI SRDNSKNTLY LQMNSLRPAD TAVYYCARAS MMPRPPVHDY WGQGTLVTVS  120
S                                                                  121

SEQ ID NO: 391            moltype = AA  length = 123
FEATURE                   Location/Qualifiers
REGION                    1..123
                          note = Synthetic polypeptide
source                    1..123
                          mol_type = protein
                          organism = synthetic construct
SEQUENCE: 391
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAKDR SQGDYGDYVA DYWSQGTLVT  120
VSS                                                                123

SEQ ID NO: 392            moltype = AA  length = 125
FEATURE                   Location/Qualifiers
REGION                    1..125
                          note = Synthetic polypeptide
source                    1..125
                          mol_type = protein
                          organism = synthetic construct
SEQUENCE: 392
EVQLQESGPG LVKPSGTLSL TCAVSGGSIS SSNWWTWVRQ PPGKGLEWIG EIYHSGSTNY    60
NPSLESRVTM SVDKSKNQFS LKLSSVTAAD TAVYYCARVQ TSHSELWFGE FGADWGQGTL  120
VTVSS                                                              125

SEQ ID NO: 393            moltype = AA  length = 121
FEATURE                   Location/Qualifiers
REGION                    1..121
                          note = Synthetic polypeptide
source                    1..121
                          mol_type = protein
                          organism = synthetic construct
SEQUENCE: 393
EVQLLESGGG LVQPGGSLRL SCAASGFTFT YYAMSWVRQA PGKGLEWVSG ISGSGDSTYN    60
ADSVKGRVTI SRDNSKNTLY LQMNSLRAED TAVYYCAKDG GYSTDWYFDL WGRGTLVTVS  120
S                                                                  121

SEQ ID NO: 394            moltype = AA  length = 121
FEATURE                   Location/Qualifiers
REGION                    1..121
                          note = Synthetic polypeptide
source                    1..121
                          mol_type = protein
                          organism = synthetic construct
SEQUENCE: 394
QVQLVESGGG VVQPGRSLRL SCTASGFTFS SYGMHWVRQA PGKGPEWVAV ISYDGSKKYF    60
ADSVKGRFTI SRDNSKNTLY LQMNSLRAED TAVYSCAKGY DSNGYYYIDY WGQGTPVTVS  120
S                                                                  121

SEQ ID NO: 395            moltype = AA  length = 123
FEATURE                   Location/Qualifiers
REGION                    1..123
                          note = Synthetic polypeptide
source                    1..123
                          mol_type = protein
                          organism = synthetic construct
```

```
SEQUENCE: 395
QVQLQESGGG VVQPGRSLRL SCAASGFTFS SYGMHWVRQA PGKGLEWVAV IWYDGSNKYY     60
ADSVKGRFTI SRDNSKNTLY LQMNSLRAED TAVYYCARDV GYQLLQVYGM DVWGQGTTVT    120
VSS                                                                 123

SEQ ID NO: 396              moltype = AA   length = 129
FEATURE                     Location/Qualifiers
REGION                      1..129
                            note = Synthetic polypeptide
source                      1..129
                            mol_type = protein
                            organism = synthetic construct
SEQUENCE: 396
EVQLLESGPG LVKPSQTLSL TCSVSGGSIS SGGYYWTWIR QPPGKGLEWI GYIYYTGSTY     60
YNPSLKSRVT ISVDTSKNQF SLKLSSVTAA DTAVYFCARA EYDTSGYYQQ RLPEYFQHWG    120
QGTLVTVSS                                                           129

SEQ ID NO: 397              moltype = AA   length = 121
FEATURE                     Location/Qualifiers
REGION                      1..121
                            note = Synthetic polypeptide
source                      1..121
                            mol_type = protein
                            organism = synthetic construct
SEQUENCE: 397
EVQLVQSGGG LVQRGGSLRL SCAASGFTFS SYAMTWVRQA PGKGLEWVSD MNHSGDRTNY     60
ADSVRGRFTI SRDNSKNTLY LQMNSLRAED TAVYYCAKYY DSSGYYYFHS WGQGTLVTVS    120
S                                                                   121

SEQ ID NO: 398              moltype = AA   length = 120
FEATURE                     Location/Qualifiers
REGION                      1..120
                            note = Synthetic polypeptide
source                      1..120
                            mol_type = protein
                            organism = synthetic construct
SEQUENCE: 398
EVQLLESGGG LVQPGGSLRL SCAASGFIFS DHYMAWVRQA PGKGLEWVGR SRNRPNSYTT     60
EYAASAKGRF TISRDDSKTS LYLQMNSLKT EDTAVYYCAR EHGDYGLDYW GQGTLVTVSS    120

SEQ ID NO: 399              moltype = AA   length = 124
FEATURE                     Location/Qualifiers
REGION                      1..124
                            note = Synthetic polypeptide
source                      1..124
                            mol_type = protein
                            organism = synthetic construct
SEQUENCE: 399
QVQLVQSGAE VKKPGASVKV SCKASGYTFT GYYMHWVRQA PGQGLEWMGR INPNSGGTNY     60
AQKFQGRVTM TRDTSISTAY MELSRLRSDD TAVYYCVDY YYDSSGYYSP FDYWGQGTLV    120
TVSS                                                                124

SEQ ID NO: 400              moltype = AA   length = 121
FEATURE                     Location/Qualifiers
REGION                      1..121
                            note = Synthetic polypeptide
source                      1..121
                            mol_type = protein
                            organism = synthetic construct
SEQUENCE: 400
EVQLVESGGG FVQPGGSLRL SCAASGFIFS DYYMDWVRQA PGKGLEWVGR IRNKPNSYTT     60
EYAASVKGRF SISRDDLKNS LYLQMNSLKT EDTAEYYCAR VDGEEVALIY WGQGALVTVS    120
S                                                                   121

SEQ ID NO: 401              moltype = AA   length = 122
FEATURE                     Location/Qualifiers
REGION                      1..122
                            note = Synthetic polypeptide
source                      1..122
                            mol_type = protein
                            organism = synthetic construct
SEQUENCE: 401
EVQLLESGGG LGQPGGSLRL SCVASKFTFS DHYMDWVRQA PGKGLEWVGR IRNKPNGYTT     60
EYAASVKGRF IISRDDSKNS LYLQMKSLKI EDTAIYYCVR VWGGEAARYD YWGQGALVTV    120
SS                                                                  122

SEQ ID NO: 402              moltype = AA   length = 119
FEATURE                     Location/Qualifiers
REGION                      1..119
```

```
                        note = Synthetic polypeptide
source                  1..119
                        mol_type = protein
                        organism = synthetic construct
SEQUENCE: 402
EVQLVESGGG LVQPGGSLRL SCAASGFTFS DHYMDWVRQA PGKGLEWVGR SRNKPNSYIT    60
EYAASVKGRF TISRDDSKNS LYLQMNSLKT EDTAVYYCSR HMGFGLDLWG QGTLVTVSS    119

SEQ ID NO: 403          moltype = AA   length = 121
FEATURE                 Location/Qualifiers
REGION                  1..121
                        note = Synthetic polypeptide
source                  1..121
                        mol_type = protein
                        organism = synthetic construct
SEQUENCE: 403
QVQLVQSGGG VVQPGRSLRL SCAASGFTFS SYGMHWVRQA PGKGLEWVAV IWYDGSNKYY    60
ADSVKGRFTI SRDNSKNTLY LQMNSLRAED TAVYYCARDY YGSGDGYFDY WGQGTTVTVS   120
S                                                                  121

SEQ ID NO: 404          moltype = AA   length = 124
FEATURE                 Location/Qualifiers
REGION                  1..124
                        note = Synthetic polypeptide
source                  1..124
                        mol_type = protein
                        organism = synthetic construct
SEQUENCE: 404
EVQLVESGPV LVKPTETLRL TCTVSGFSLS NTKLGVSWIR QPPGKALEWL AHIFSNAEKS    60
SSKSLKSRLS ISQDTSKSLV VLTMTNMDPV DTATYFCARI PVEYGTPRGS FDTWGQGTTV   120
TVSS                                                               124

SEQ ID NO: 405          moltype = AA   length = 114
FEATURE                 Location/Qualifiers
REGION                  1..114
                        note = Synthetic polypeptide
source                  1..114
                        mol_type = protein
                        organism = synthetic construct
SEQUENCE: 405
EVQLVESGGG VVQPGRSLRL SCAASGLTFS TYTLHWVRQA PGKGLEWVAV ISSDGGNKYY    60
ADSVKGRFTI SRDSSKNTLY LQMNSLRTED TAVYYCAGGS PDYWGQGALV TVSS         114

SEQ ID NO: 406          moltype = AA   length = 121
FEATURE                 Location/Qualifiers
REGION                  1..121
                        note = Synthetic polypeptide
source                  1..121
                        mol_type = protein
                        organism = synthetic construct
SEQUENCE: 406
EVQLVESGGG VVQPGRSLRL SCVPSGFTFS SYAMHWVRQA PGKGLEWVAM MSYDGGDKNY    60
ADSVKGRFTI SRDNSKNTLY LQMRSLRAED TAIYYCARAY DSRGYYYIEH WGQGTLVTVS   120
S                                                                  121

SEQ ID NO: 407          moltype = AA   length = 119
FEATURE                 Location/Qualifiers
REGION                  1..119
                        note = Synthetic polypeptide
source                  1..119
                        mol_type = protein
                        organism = synthetic construct
SEQUENCE: 407
QVQLVQSGAE VRKPGASVKV SCKASGYTFT SYGISWVRQA PGQGLEWMGW ISTYNGNTNY    60
AQKLQGRVTM TTDTSTSTAY MELRSLRSDD TAVYYCAREI DSNYVFDYWG QGTLVTVSS    119

SEQ ID NO: 408          moltype = AA   length = 122
FEATURE                 Location/Qualifiers
REGION                  1..122
                        note = Synthetic polypeptide
source                  1..122
                        mol_type = protein
                        organism = synthetic construct
SEQUENCE: 408
EVQLVESGGG LVQPGGSLRL SCAASGFTFS NYWMNWVRQA PGKGLEWVAN IKQDGSEKYY    60
VDSVKGRFTI SRDNAKNSLY LQMNSLRAED TAVYYCARKL SYSSGWYYFD YWGQGTLVTV   120
SS                                                                 122
```

```
SEQ ID NO: 409         moltype = AA  length = 119
FEATURE                Location/Qualifiers
REGION                 1..119
                       note = Synthetic polypeptide
source                 1..119
                       mol_type = protein
                       organism = synthetic construct
SEQUENCE: 409
EVQLVESGGG LVQPGGSLRL SCAASGFTFS DHYMDWVRQA PGKGLEWVGR STNKPNSYTT   60
TYAASVRGRF TISRDESKNS LYLQMNSLKS DDTAVYYCVT TTVILFDYWG QGTLVTVSS   119

SEQ ID NO: 410         moltype = AA  length = 126
FEATURE                Location/Qualifiers
REGION                 1..126
                       note = Synthetic polypeptide
source                 1..126
                       mol_type = protein
                       organism = synthetic construct
SEQUENCE: 410
QVQLQQWGAG LLKPSETLSL TCAVYGGSFS GYYWSWIRQP PGKGLEWIGE INHRGSTDYN   60
PSLKSRVTMS VDTSKNQFSL RLSSVTAADT ALYYCARGRL AWGLRGQKSP NFFAYWGQGA   120
TVTVSS                                                             126

SEQ ID NO: 411         moltype = AA  length = 125
FEATURE                Location/Qualifiers
REGION                 1..125
                       note = Synthetic polypeptide
source                 1..125
                       mol_type = protein
                       organism = synthetic construct
SEQUENCE: 411
EVQLVESGGG LVKPGGSLRL SCAASGFTFS HAWMTWVRQA PGKGLEWVGR IKSETDGGTA   60
NYAAPVKGRF TISRDDSKNT VYLQMVSLKT EDTAVYYCAT AGIFGVVIMK GFDHWGQGTT   120
VTVSS                                                              125

SEQ ID NO: 412         moltype = AA  length = 123
FEATURE                Location/Qualifiers
REGION                 1..123
                       note = Synthetic polypeptide
source                 1..123
                       mol_type = protein
                       organism = synthetic construct
SEQUENCE: 412
EVQLLESGAE VKEPGSSVKV SCKPSGGTFS SYVISWVRQA PGQGLEWMGG IIPIFGTPNY   60
AQKFQGRVTI TADDSTSTAH MELSSLTSDD TAVYYCARET YYYGSGSVPV HDWGQGTLVT   120
VSS                                                                123

SEQ ID NO: 413         moltype = AA  length = 122
FEATURE                Location/Qualifiers
REGION                 1..122
                       note = Synthetic polypeptide
source                 1..122
                       mol_type = protein
                       organism = synthetic construct
SEQUENCE: 413
EVQLVESGGG VVQPGRSLRL SCAASGFIFS SNSMHWVRQA PGKGLKWVAI ISNDGRNKFY   60
ADAVKGRFTV SRDNSKNTLY LQMNSLRPED TAVYYCARGY DSSGYWGFGD NWGQGTLVTV   120
SS                                                                 122

SEQ ID NO: 414         moltype = AA  length = 122
FEATURE                Location/Qualifiers
REGION                 1..122
                       note = Synthetic polypeptide
source                 1..122
                       mol_type = protein
                       organism = synthetic construct
SEQUENCE: 414
QVQLVQSGGG LVQPGGSLRL SCAASGFTFS DHYMDWVRQA PGKGLEWVGR TRNKANSYTT   60
KYAASVKGRF TISRDDSKNS LYLQMNSLKT EDTAVYYCAR VEGGAWGAFD IWGQGTTVTV   120
SS                                                                 122

SEQ ID NO: 415         moltype = AA  length = 122
FEATURE                Location/Qualifiers
REGION                 1..122
                       note = Synthetic polypeptide
source                 1..122
                       mol_type = protein
                       organism = synthetic construct
```

-continued

```
SEQUENCE: 415
QVTLKESGPV LVKPTETLTL TCTVSGFSLS NTKMGVTWIR QPPGKALEWL AHIFSNDEKS    60
CNTSLKSRLT ISKDTSKSQV VLTMTNMDPV DTATYYCARL WFTEYPGAFD IWGQGTMVTV   120
SS                                                                 122

SEQ ID NO: 416          moltype = AA  length = 125
FEATURE                 Location/Qualifiers
REGION                  1..125
                        note = Synthetic polypeptide
source                  1..125
                        mol_type = protein
                        organism = synthetic construct
SEQUENCE: 416
EVQLQESGPG LVKPSETLSL TCTVSGGSIS SSSYYWGWIR QPPGKGLEWI GSIYYSGSTY    60
YNPSLKSRVT ISVDTSKNQF SLKLSSVTAA DTAVYYCARH SSGSYYLAGY YFDYWGQGTL   120
VTVSS                                                              125

SEQ ID NO: 417          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 417
EVQLVESGGG LVQPGGSLRL SCAASGFTFS DHYMDWVRQA PGRGLEWVGR SRNKVNSYTT    60
DYAASVKGRF TISRDDSKNS LFLRMNSLKT EDTAVYYCAR LTDSGYDDWG LGTLVTVSS   119

SEQ ID NO: 418          moltype = AA  length = 126
FEATURE                 Location/Qualifiers
REGION                  1..126
                        note = Synthetic polypeptide
source                  1..126
                        mol_type = protein
                        organism = synthetic construct
SEQUENCE: 418
EVQLVESGPG LVKPSETLSL TCTVSGGSIS SYYWSWIRQP PGKGLEWIGY IYYSGSTNYN    60
PSLKSRVTIS VDTSKNQFSL KLSSVTAADT AVYYCARETC SGGSCYYRVG SAFDIWGQGT   120
TVTVSS                                                             126

SEQ ID NO: 419          moltype = AA  length = 122
FEATURE                 Location/Qualifiers
REGION                  1..122
                        note = Synthetic polypeptide
source                  1..122
                        mol_type = protein
                        organism = synthetic construct
SEQUENCE: 419
EVQLLESGGG MVQPGRSLRL SCAASGFTFD DYDMHWVRQG PGKGLEWVSG ISWNSGGRGY    60
ADSVKGRFTI SRDNAKNSLY LQMNSLRVED TALYYCVKDY CSGGRCYSFD YWGQGTLVTV   120
SS                                                                 122

SEQ ID NO: 420          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 420
QVQLVESGGG VVQPGRSLRL SCAASGFTFS SYGMHWVRQA PGKGLEWVAV MSYDGSNKYY    60
ADSLKGRFTI SRDNSKNTLY LQMNSLRAED TAVYFCAKAY DSSAYYYLDY WGQGTLVTVS   120
S                                                                  121

SEQ ID NO: 421          moltype = AA  length = 121
FEATURE                 Location/Qualifiers
REGION                  1..121
                        note = Synthetic polypeptide
source                  1..121
                        mol_type = protein
                        organism = synthetic construct
SEQUENCE: 421
EVQLVESGGG VIQPGRSLRL SCAASGFNFS SYGMHWVRQA PGKGLEWVAV ISYDGSNKYY    60
ADSVKGRFTI SRDNSKNTLY LQMNSLRAED TAVHYCAKAY DSRGYYYLDY WGQGTLVTVS   120
S                                                                  121
```

```
SEQ ID NO: 422          moltype = AA   length = 129
FEATURE                 Location/Qualifiers
REGION                  1..129
                        note = Synthetic polypeptide
source                  1..129
                        mol_type = protein
                        organism = synthetic construct
SEQUENCE: 422
EVQLVQSGGG LVQPGGSLRL SCVGSGLTLS SSAMSWVRQA PGKGLECVSG ITGSGSDSSY    60
AASVKGRFTI SRDNSKNTVY LQMNSLRAED TAVYYCAKDL THRLGSIFGK LTFDAFDIWG   120
PGTMVTVSS                                                          129

SEQ ID NO: 423          moltype = AA   length = 123
FEATURE                 Location/Qualifiers
REGION                  1..123
                        note = Synthetic polypeptide
source                  1..123
                        mol_type = protein
                        organism = synthetic construct
SEQUENCE: 423
EVQLVESGGG VVQPGRSLRL SCAASGFTFS SYGMHWVRQA PGKGPEWVAV ISEDGNKDHY    60
VDSVKGRFSI YRDNSKSTVF LRMTSLRAED TAVYYCAKDL TPYFYDSGAF DHWGQGTLVT   120
VSS                                                                123

SEQ ID NO: 424          moltype = AA   length = 119
FEATURE                 Location/Qualifiers
REGION                  1..119
                        note = Synthetic polypeptide
source                  1..119
                        mol_type = protein
                        organism = synthetic construct
SEQUENCE: 424
EVQLVESGGG LVQPGGSLRL SCAVSGFTFS DHYMDWVRQA PGKGLEWVGR SRNKVNSYIT    60
EYAASVKGRF SISRDDSKNS LYLQMNSLKI EDTAVYYCAR VFGGPTDYWG QGTLVTVSS    119

SEQ ID NO: 425          moltype = AA   length = 118
FEATURE                 Location/Qualifiers
REGION                  1..118
                        note = Synthetic polypeptide
source                  1..118
                        mol_type = protein
                        organism = synthetic construct
SEQUENCE: 425
EVQLLESGGG LVQPGGSLRL SCAASGFIFS DHYMDWVRQA PGKGLEWVGR IRNKPNSYTT    60
DYAAYVKGRF SISRDDSKNS LFLQMNSLKT EDTAVYYCAR VVNGLDVWGQ GTTVTVSS     118

SEQ ID NO: 426          moltype = AA   length = 114
FEATURE                 Location/Qualifiers
REGION                  1..114
                        note = Synthetic polypeptide
source                  1..114
                        mol_type = protein
                        organism = synthetic construct
SEQUENCE: 426
EVQLVESGGG VVQPGRSLRL SCAASGFTLS SYVMHWVRQA PGKGLEWVAV ISSDGTNKYY    60
ADSVKGRFTI SRDSSKNTLY LQMNSLRPED SAVYYCARGQ PDYWGQGTLV TVSS         114

SEQ ID NO: 427          moltype = AA   length = 121
FEATURE                 Location/Qualifiers
REGION                  1..121
                        note = Synthetic polypeptide
source                  1..121
                        mol_type = protein
                        organism = synthetic construct
SEQUENCE: 427
EVQLVESGPG LVKPSGTLSL TCAVSGGSIS SDNWWSWVRQ APGKGLEWIG EIYHTGSTSY    60
NPSLKSRVTI SLDKSKNHFS LKLNSLTAAD TAVYYCAGKK WELLGFRFDP WGQGTLVTVS   120
S                                                                  121

SEQ ID NO: 428          moltype = AA   length = 117
FEATURE                 Location/Qualifiers
REGION                  1..117
                        note = Synthetic polypeptide
source                  1..117
                        mol_type = protein
                        organism = synthetic construct
```

```
SEQUENCE: 428
QVQLVESGAE EKKPGASVKV SCKASGYTFT SYAMHWVRQA PGQRLEWMGW INAGNGNTKY    60
SQKFQGRVTI TRDTSASTAY MELSSLRSED TAVYYCARQW LGHFDYWGQG TLVTVSS     117

SEQ ID NO: 429            moltype = AA   length = 119
FEATURE                   Location/Qualifiers
REGION                    1..119
                          note = Synthetic polypeptide
source                    1..119
                          mol_type = protein
                          organism = synthetic construct
SEQUENCE: 429
EVQLVESGGG LVQPGGSLRL SCAASGFIFS DHYMAWVRQA PGKGLEWVGH VGNKANTYTT    60
EYAASVKGRF TISRDDSKKS LYLQMNRLKS EDTAVYYCAR VFSYYLDYWG QGTPVTVSS   119

SEQ ID NO: 430            moltype = AA   length = 126
FEATURE                   Location/Qualifiers
REGION                    1..126
                          note = Synthetic polypeptide
source                    1..126
                          mol_type = protein
                          organism = synthetic construct
SEQUENCE: 430
QVTLKESGPT LVKPTQTLTL TCTFSGFSLS TSGVGVGWTR QPPGKALEWL ALIYWDDDKR    60
YSPSLKSRLT ITKDTSKNQV VLTMTKMDPV DTATYYCAHR HIAARLYRDD DVFDVWGQGT   120
MVTVSS                                                              126

SEQ ID NO: 431            moltype = AA   length = 119
FEATURE                   Location/Qualifiers
REGION                    1..119
                          note = Synthetic polypeptide
source                    1..119
                          mol_type = protein
                          organism = synthetic construct
SEQUENCE: 431
QVQLVQSGAE VKKPGASVKV SCKASGYTFT SYDINWVRQA TGQGLEWMGW MNPNSGNTGY    60
AQKFQGRVTM TRNTSISTAY MELSSLRSED TAVYYCARGL NTVTNSDYWG QGTLVTVSS   119

SEQ ID NO: 432            moltype = AA   length = 120
FEATURE                   Location/Qualifiers
REGION                    1..120
                          note = Synthetic polypeptide
source                    1..120
                          mol_type = protein
                          organism = synthetic construct
SEQUENCE: 432
QVQLVQSGAE VKKPGASVKV SCKASGYTFT GYYMHWVRQA PGQGLEWMGW INPNSGGTNY    60
AQKFQGWVTM TRDTSISTAY MELSRLRSDD TAVYYCASGL SPDFSVLDVW GQGTTVTVSS   120

SEQ ID NO: 433            moltype = AA   length = 133
FEATURE                   Location/Qualifiers
REGION                    1..133
                          note = Synthetic polypeptide
source                    1..133
                          mol_type = protein
                          organism = synthetic construct
SEQUENCE: 433
QVQLQQSGPG LVKPSQTLSL TCAISGDSVS TNSAAWNWIR QSPSRGLEWL GRTYYRSKWY    60
NDYALSVKSR ITIKPDTSKN QFSLQLNSVT PEDTAVYYCA REGAGYYDSS GYYPLSYDAF   120
DIWGRGTMVT VSS                                                      133

SEQ ID NO: 434            moltype = AA   length = 119
FEATURE                   Location/Qualifiers
REGION                    1..119
                          note = Synthetic polypeptide
source                    1..119
                          mol_type = protein
                          organism = synthetic construct
SEQUENCE: 434
EVQLVESGGG LVQPGGSLRL SCAASGFTFS DHYMDWVRQA PGKGLEWVGR ARNRANSYTT    60
EYAASVKGRF AASRDDSKNS LYLQMNSLKT EDTAVYYCAR VRGSYWDYWG QGTLVTVSS   119

SEQ ID NO: 435            moltype = AA   length = 118
FEATURE                   Location/Qualifiers
REGION                    1..118
                          note = Synthetic polypeptide
source                    1..118
                          mol_type = protein
                          organism = synthetic construct
```

```
SEQUENCE: 435
QVQLVQSGGG LVQPGGSLRL SCAASGFTFS DHYMDWVRQA PGKGLEWVGR IRNKVNSYTT    60
EYAASVKGRF TISRDDSKNS LYLQMNSLKT EDTAVYYCGR DRGWLDIWGQ GTMVTVSS     118

SEQ ID NO: 436          moltype = AA  length = 130
FEATURE                 Location/Qualifiers
REGION                  1..130
                        note = Synthetic polypeptide
source                  1..130
                        mol_type = protein
                        organism = synthetic construct
SEQUENCE: 436
QVQLQESGPG LVEPSGTLSL TCVVTGDSIS SRSWWSWVRQ PPGKGLEWIG EIYHSGTTTY    60
SPSLKSRVII SLDKSENHFS LKMTSVTAAD TAVYYCARVI RDLRDYYDGS GYGPDAFDIW   120
GQGTTVTVSS                                                          130

SEQ ID NO: 437          moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 437
EVQLVESGPG LVKPSGTLSL TCAVSGGSIS SSNWWSWVRQ PPGKGLEWIG EIYHSGSTNY    60
NPSLKSRVTI SVDKSKNQFS LKLSSVTAAD TAVYYCARAR WEDGNYYYGM DVWGQGTTVT   120
VSS                                                                 123

SEQ ID NO: 438          moltype = AA  length = 124
FEATURE                 Location/Qualifiers
REGION                  1..124
                        note = Synthetic polypeptide
source                  1..124
                        mol_type = protein
                        organism = synthetic construct
SEQUENCE: 438
EVQLVESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAKDQ SSGWPNYYYG MDVWGQGTTV   120
TVSS                                                                124

SEQ ID NO: 439          moltype = AA  length = 126
FEATURE                 Location/Qualifiers
REGION                  1..126
                        note = Synthetic polypeptide
source                  1..126
                        mol_type = protein
                        organism = synthetic construct
SEQUENCE: 439
QVQLVESGSE LKKPGASVKV SCKASGYTFT SYAMNWVRQA PGQGLEWMGW INTNTGNPTY    60
AQGFTGRFVF SLDTSVSTAY LQISSLKAED TAVYYCVRGY CSSTSCYGGL YWFDPWGQGT   120
LVTVSS                                                              126

SEQ ID NO: 440          moltype = AA  length = 126
FEATURE                 Location/Qualifiers
REGION                  1..126
                        note = Synthetic polypeptide
source                  1..126
                        mol_type = protein
                        organism = synthetic construct
SEQUENCE: 440
EVQLVESGGG VVQPGRSLRL SCADSGFTFS YSAIHWVRQA PGKGLEWVAV ISYDGSNKYY    60
ADSVKGRFTI SRDNSKNTLY LQMNSLRPED TAVYYCARHS GGYSSKDKPT EYFQHWGQGT   120
LVTVSS                                                              126

SEQ ID NO: 441          moltype = AA  length = 122
FEATURE                 Location/Qualifiers
REGION                  1..122
                        note = Synthetic polypeptide
source                  1..122
                        mol_type = protein
                        organism = synthetic construct
SEQUENCE: 441
EVQLLESGPG LVKPSGTLSL TCAVSGASIS SNNWWSWVRQ SPGKGLEWIG EIFHSGTTNY    60
NPSLKSRVTI SVDKSKNQFS LKLNSVTAAD TAVYYCARDV GVAAVITGSV RWGQGTLVTV   120
SS                                                                  122
```

```
SEQ ID NO: 442          moltype = AA   length = 126
FEATURE                 Location/Qualifiers
REGION                  1..126
                        note = Synthetic polypeptide
source                  1..126
                        mol_type = protein
                        organism = synthetic construct
SEQUENCE: 442
QVQLVQSGSE LKKPGASVKV SCKASGYTFT SYAMNWVRQA PGQGLEWMGW INTNTGNPTY    60
AQGFTGRFVF SLDTSVSTAY LQISSLKAED TAVYYCARGY CSSTSCYGGL YWFDPWGQGT   120
LVTVSS                                                              126

SEQ ID NO: 443          moltype = AA   length = 133
FEATURE                 Location/Qualifiers
REGION                  1..133
                        note = Synthetic polypeptide
source                  1..133
                        mol_type = protein
                        organism = synthetic construct
SEQUENCE: 443
QVQLVQSGGG VVQPGRSLRL SCAASGFTFS SYAMHWVRQA PGKGLEWVAV ISYDGSNKYY    60
ADSVKGRFTI SRDNSKNTLY LQMNSLRAED TAVYYCARDG AGDYIWGSYR HKGLHYYYGM   120
DVWGQGTTVT VSS                                                      133

SEQ ID NO: 444          moltype = AA   length = 124
FEATURE                 Location/Qualifiers
REGION                  1..124
                        note = Synthetic polypeptide
source                  1..124
                        mol_type = protein
                        organism = synthetic construct
SEQUENCE: 444
EVQLVESGPG LVMPSGTLSL TCTVSGISIS SSNWWSWVRQ SPGKGLEWIG EVYHSGSTKY    60
NPSLKSRVTI SVDKSRNQFS LKLNSVTAAD TAVYYCAKDP RTFYGVVMLL DDPWGQGTLV   120
TVSS                                                                124

SEQ ID NO: 445          moltype = AA   length = 119
FEATURE                 Location/Qualifiers
REGION                  1..119
                        note = Synthetic polypeptide
source                  1..119
                        mol_type = protein
                        organism = synthetic construct
SEQUENCE: 445
EVQLVESGGG VVQPGRSLRL SCAVSGFTFS TSPLHWVRQA PGKGLEWVAV SSFVATDKYY    60
ADSVKGRFTV SRDNSKNTLY LQMNSLRPED TAVYYCARGF GELPGFDIWG QGTMVTVSS    119

SEQ ID NO: 446          moltype = AA   length = 117
FEATURE                 Location/Qualifiers
REGION                  1..117
                        note = Synthetic polypeptide
source                  1..117
                        mol_type = protein
                        organism = synthetic construct
SEQUENCE: 446
EVQLLESGGG LVKPGGSLRL SCAASGFTFS SYSMNWVRQA PGKGLEWVSS ISSSSSYIYY    60
ADSVKGRFTI SRDNAKNSLY LQMNSLRAED TAVYYCARDS WGPFDYWGQG TLVTVSS      117

SEQ ID NO: 447          moltype = AA   length = 121
FEATURE                 Location/Qualifiers
REGION                  1..121
                        note = Synthetic polypeptide
source                  1..121
                        mol_type = protein
                        organism = synthetic construct
SEQUENCE: 447
EVQLVESGGA VVQPGRSLRL SCAASGFTFS SYGMHWVRQA PGKGLESVAV IWYDGSNKNY    60
ADSVKGRFTI SRDNSKNTLF LQMNSLRAED SAMYYCAKTY DSRAYYYLDY WGQGTLVTVS   120
S                                                                   121

SEQ ID NO: 448          moltype = AA   length = 123
FEATURE                 Location/Qualifiers
REGION                  1..123
                        note = Synthetic polypeptide
source                  1..123
                        mol_type = protein
                        organism = synthetic construct
```

```
SEQUENCE: 448
EVQLLESGGG LVQPGGSLRL SCAASGFTFS SYAMSWVRQA PGKGLELVSA ISSSGGSTYY    60
ADSVKGRFTI SRDNSKNTLY LQMNSLRAED TALYYCAKDL FYDFWTGITI DYWGQGTLVT   120
VSS                                                                123

SEQ ID NO: 449          moltype = AA   length = 120
FEATURE                 Location/Qualifiers
REGION                  1..120
                        note = Synthetic polypeptide
source                  1..120
                        mol_type = protein
                        organism = synthetic construct
SEQUENCE: 449
EVQLLESGGG LVQPGGSLRL SCAASGFIFS NYWMSWVRQA PGKGLEWVAN IKPDGSEKYY    60
VESVRGRFTI SRDNAKNSLY LQMNSLRAED TAVFYCARDG GTVSDGLDVW GQGTTVTVSS   120

SEQ ID NO: 450          moltype = AA   length = 122
FEATURE                 Location/Qualifiers
REGION                  1..122
                        note = Synthetic polypeptide
source                  1..122
                        mol_type = protein
                        organism = synthetic construct
SEQUENCE: 450
QVQLQESGPG LVKPSGTLSL TCAVSGGSIS SSNWWSWVRQ PPGKGLEWIG EIYHSGSTNY    60
NPSLKSRVTI SVDKSKNQFS LKLSSVTAAD TAVYYCARVV WYSSSSHLFD YWGQGTLVTV   120
SS                                                                 122

SEQ ID NO: 451          moltype = AA   length = 117
FEATURE                 Location/Qualifiers
REGION                  1..117
                        note = Synthetic polypeptide
source                  1..117
                        mol_type = protein
                        organism = synthetic construct
SEQUENCE: 451
EVQLVESGGG VVQTGRSLRL SCAASGFTFS ISGMHWVRQA PGKGLEWVAL IWYDGTKKYY    60
ADSVKGRFTI SRDDFKNTVY LQMNSLRADD TAVYYCARIK SDAFDLWGQG TTVTVSS      117

SEQ ID NO: 452          moltype = AA   length = 123
FEATURE                 Location/Qualifiers
REGION                  1..123
                        note = Synthetic polypeptide
source                  1..123
                        mol_type = protein
                        organism = synthetic construct
SEQUENCE: 452
EVQLLESGGG VVQPGKSLRL SCAASGFSFG DYGMHWVRQT PDKGLEWVAV ILFDGSKKFY    60
ADSVRGRFTI SRDNSKNNLY LQMSSLRPED TAVYYCAKFP LRDGGSGEGF DYWGQGTLVT   120
VSS                                                                123

SEQ ID NO: 453          moltype = AA   length = 121
FEATURE                 Location/Qualifiers
REGION                  1..121
                        note = Synthetic polypeptide
source                  1..121
                        mol_type = protein
                        organism = synthetic construct
SEQUENCE: 453
EVQLVESGGG VVQPGRSLRL SCAASGFTFS SYAMHWVRQA PGKGLEWVAV ISYDGSNKYY    60
ADSVKGRFTI SRDNSKNTLY LQMNSLRAED TAVYYCARNT YDRRRTFDY WGQGTLVTVS   120
S                                                                  121

SEQ ID NO: 454          moltype = AA   length = 122
FEATURE                 Location/Qualifiers
REGION                  1..122
                        note = Synthetic polypeptide
source                  1..122
                        mol_type = protein
                        organism = synthetic construct
SEQUENCE: 454
QVQLVQSGGG LVQPGGSLRL SCAASGFTFS DHYMDWVRQA PGKGLEWVGR TRNKANSYTT    60
EYAASVKGRF TISRDDSKNS LYLQMNSLKT EDTAVYYCAG VGITGTTGID YWGQGTLVTV   120
SS                                                                 122

SEQ ID NO: 455          moltype = AA   length = 125
FEATURE                 Location/Qualifiers
REGION                  1..125
                        note = Synthetic polypeptide
```

```
                       source           1..125
                                        mol_type = protein
                                        organism = synthetic construct
SEQUENCE: 455
EVQLLESGGD LVQPGRSLRL SCAASGFNLI DYAMHWVRQV PGKGLEWVSG ISWNSRSIGY    60
ADSVKGRFTI SRDNAKNSLY LQMDSLKHED TALFYCAKGA AAGPFPYFYY AMDVWGQGTT   120
VTVSS                                                              125

SEQ ID NO: 456          moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 456
QSVLTQPPSV SAAPGQKVTI SCSGSSSNIG NNYVSWYQQL PGAAPKLLIY DNKKRPSGIP    60
DRFSGSASGT SATMGITGLQ TGDEADYYCG TWDSSLSAWV FGGGTKVTVL              110

SEQ ID NO: 457          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 457
DIRVTQSPAT LSVSPGERAT LSCRASQSVS SNLAWYQQKP GQAPRLLIYD ASNRATGIPV    60
RFSGSGSGTD FTLTISSLQS EDFAVYYCQQ YDNWPLTFGG GTKVEIK                 107

SEQ ID NO: 458          moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 458
QSVVTQPPSV SAAPGQKVTI SCSGSSSNIG NNYVSWYQQF PRTAPKLLIY DNKKRPSGIP    60
DRFSGSASGT SATLGITGLQ TGDEADYYCG TWDSSLSAWV FGGGTKVTVL              110

SEQ ID NO: 459          moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 459
QPVLTQPPSA SGTPGQRVTI FCSGSRSNIG TYTINWYQKL PGTAPKLLIY SNNRGPSGVP    60
DRFSGSQSGT SASLAISGLQ PEDEADYYCA AWDDSLNGWV FGGGTKVTVL              110

SEQ ID NO: 460          moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 460
QSVVTQPPSV SAAPGQKVTI SCSGSSSNIG NNYVAWYQQL PGRAPKLLIH DNKKRPSGIP    60
DRFSGSASGT SATLGITGLQ TGDEADYYCE TWDSSLNAVV FGGGTKLTVL              110

SEQ ID NO: 461          moltype = AA   length = 108
FEATURE                 Location/Qualifiers
REGION                  1..108
                        note = Synthetic polypeptide
source                  1..108
                        mol_type = protein
                        organism = synthetic construct
SEQUENCE: 461
DIQMTQSPSS LSASVGDRVT ITCRASQTIS VDLNWYQHKP GKAPKLLIFA ASTLQSGVPS    60
RFSGSGSGTD FTLTIRSLQP EDFATYYCQQ SYSIPRITFG QGTRLEIK                108

SEQ ID NO: 462          moltype = AA   length = 108
FEATURE                 Location/Qualifiers
REGION                  1..108
                        note = Synthetic polypeptide
```

```
                        -continued source                  1..108
                        mol_type = protein
                        organism = synthetic construct
SEQUENCE: 462
EIVMTQSPSA LSASVRDRVT ITCRASQSIG SDLNWYQQRP GKAPMLLIYA ATGLQSGVPS    60
RFSGSGSGTD FTLTISNLQP EDFATYYCQQ SYSPPMYTFG QGTKVDIK                108

SEQ ID NO: 463          moltype = AA  length = 110
FEATURE                 Location/Qualifiers
REGION                  1..110
                        note = Synthetic polypeptide
source                  1..110
                        mol_type = protein
                        organism = synthetic construct
SEQUENCE: 463
QPVLTQPPSA SGTPGQRVTI SCSGSSSNIG TNTVSWYQQL PGTAPQLLVF SRTQRPSGVP    60
DRFSGSKSGT SASLAISGLQ SDDEADYYCA AWDDSRNGWV FGGGTKLTVL              110

SEQ ID NO: 464          moltype = AA  length = 112
FEATURE                 Location/Qualifiers
REGION                  1..112
                        note = Synthetic polypeptide
source                  1..112
                        mol_type = protein
                        organism = synthetic construct
SEQUENCE: 464
QPVLTQPPSV SAAPGQKVTI SCSGSNSNIG NYYVSWYQQF PGTAPKLLIY DNNKRPSGIP    60
DRFSGSKSGT SATLAITGLQ TGDEAHYYCG TWDTSSLSAG RVFGGGTKLT VL           112

SEQ ID NO: 465          moltype = AA  length = 111
FEATURE                 Location/Qualifiers
REGION                  1..111
                        note = Synthetic polypeptide
source                  1..111
                        mol_type = protein
                        organism = synthetic construct
SEQUENCE: 465
QSALTQPPSV SAAPGQKVTI SCSGSSSNIG NSYVSWYQQV PGTAPKLLIY DNNKRPSGIP    60
DRFSGSKSGT SATLGITGLQ AGDEADYYCG TWDTSLSAGR VFGRGTKLTV L            111

SEQ ID NO: 466          moltype = AA  length = 109
FEATURE                 Location/Qualifiers
REGION                  1..109
                        note = Synthetic polypeptide
source                  1..109
                        mol_type = protein
                        organism = synthetic construct
SEQUENCE: 466
QSVLTQPPSV SAAPGQKVTI SCSGSSSNIG YSHVSWYQQL PGTAPKVLIY DNDKRPSGIP    60
DRFSGSKSGT SATLGITGLQ TGDEADYYCG TWDTSLGVVF GGGTKLTVL               109

SEQ ID NO: 467          moltype = AA  length = 112
FEATURE                 Location/Qualifiers
REGION                  1..112
                        note = Synthetic polypeptide
source                  1..112
                        mol_type = protein
                        organism = synthetic construct
SEQUENCE: 467
QSVLTQPRSV SGSPGQSVTI SCTGTSSDVG AYNFVSWYQQ YPGKAPKLMI YDVNKRPSGV    60
PDRFSGSKSG NTASLTISGL QAEDEADYHC CSYAGTYTSN YVFGSGTKVT VL           112

SEQ ID NO: 468          moltype = AA  length = 110
FEATURE                 Location/Qualifiers
REGION                  1..110
                        note = Synthetic polypeptide
source                  1..110
                        mol_type = protein
                        organism = synthetic construct
SEQUENCE: 468
QSVVTQPPSV SAAPGQKVTI SCSGSSSNIG NNYVSWYQQL SETAPKLLIY DNNKRPSGIP    60
NRFSGSKSGT SATLGITGLQ TGDEADYYCG TWDNSLGAVV FGGGTKVTVL              110

SEQ ID NO: 469          moltype = AA  length = 110
FEATURE                 Location/Qualifiers
REGION                  1..110
                        note = Synthetic polypeptide
```

```
                        source          1..110
                                        mol_type = protein
                                        organism = synthetic construct
SEQUENCE: 469
QSVLTQPPSV SAAPGQKVTI SCSGSSSNIG SNYVSWYQQF PGTAPKLLIY DNSKRPSGIP    60
DRFSGSMSGT SATLGITGLQ TGDEADYYCG TWDSSLSAVV FGGGTKVTVL              110

SEQ ID NO: 470          moltype = AA   length = 111
FEATURE                 Location/Qualifiers
REGION                  1..111
                        note = Synthetic polypeptide
source                  1..111
                        mol_type = protein
                        organism = synthetic construct
SEQUENCE: 470
QSVLTQPPSV SAAPGQKVTI SCSGSSSNIG NNYVSWYQQL PGTAPKLLIY DNNKRPSGIP    60
DRFSGSKSGT SATLGITGLQ TGDEADYYCG TWDTSLSAGR VFGGGTKLTV L            111

SEQ ID NO: 471          moltype = AA   length = 108
FEATURE                 Location/Qualifiers
REGION                  1..108
                        note = Synthetic polypeptide
source                  1..108
                        mol_type = protein
                        organism = synthetic construct
SEQUENCE: 471
EIVLTQSPAT LSVSPGERAT LSCRASRSVS SNLAWYQQKP GQAPRLLIYG ASTRATGIPA    60
RFTGSGSGTE FTLTISSLQS EDFAVYYCQQ YNNWPPRTFG QGTKVDIK                108

SEQ ID NO: 472          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 472
DIQLTQSPSS VSASVGDRVT ITCRASQGIS SWLAWYQQKP GKAPKLLIHA ASSLQSGVPS    60
RFSGSGSGTD FTLTISSLQP EDFATYYCQQ AKSFPPTFGQ GTRLEIK                 107

SEQ ID NO: 473          moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 473
QPVLTQPASV SGSPGQSITI SCTGTSSDVG GYNYVSWYQQ HPGKAPKLLI YDVSNRPSGV    60
SNRFSGSKSA NSASLTISGL QAEDEADYYC NSYTSSSTLV FGGGTKLTVL              110

SEQ ID NO: 474          moltype = AA   length = 106
FEATURE                 Location/Qualifiers
REGION                  1..106
                        note = Synthetic polypeptide
source                  1..106
                        mol_type = protein
                        organism = synthetic construct
SEQUENCE: 474
EIVMTQSPAT LSVSPGERAT LSCRASQSVS SNLAWYQQKP GQAPRLLIYG ASTRATGIPA    60
RFSGSGSGTE FTLTISSLQS EDFALYYCQQ YDDWPLFGQG TRLEIK                  106

SEQ ID NO: 475          moltype = AA   length = 111
FEATURE                 Location/Qualifiers
REGION                  1..111
                        note = Synthetic polypeptide
source                  1..111
                        mol_type = protein
                        organism = synthetic construct
SEQUENCE: 475
QSVLTQPPSV SAAPGQKVTI SCSGSSSNIG NNYVSWYQQL PGTAPKLLIY DNNKRPSGIP    60
DRFSGSKSGT SATLGITGLQ TGDEADYICG TWDTSLSAGG VFGGGTKLTV L            111

SEQ ID NO: 476          moltype = AA   length = 110
FEATURE                 Location/Qualifiers
REGION                  1..110
                        note = Synthetic polypeptide
```

```
source                    1..110
                          mol_type = protein
                          organism = synthetic construct
SEQUENCE: 476
QSVLTQPASV SGSPGQSITI SCTGTSSDIG AYNYVSWYQQ HPGKAPKLMI YDVTNRPSGV    60
SNRFSGSKSG SSASLTISGL QTEDEADYYC SSYTRRSTLV FGGGTKLTVL               110

SEQ ID NO: 477            moltype = AA  length = 109
FEATURE                   Location/Qualifiers
REGION                    1..109
                          note = Synthetic polypeptide
source                    1..109
                          mol_type = protein
                          organism = synthetic construct
SEQUENCE: 477
QSVLTQPPSV SAAPGQKVTI SCSGSSSNIG NNYVSWYQQL PGTAPKLLIY DNNKRPSGIP    60
DRFSGSKSGT SATLGITGLQ TGDEANYYCG TWDTSLSTVF GGGTKLTVL                109

SEQ ID NO: 478            moltype = AA  length = 111
FEATURE                   Location/Qualifiers
REGION                    1..111
                          note = Synthetic polypeptide
source                    1..111
                          mol_type = protein
                          organism = synthetic construct
SEQUENCE: 478
QSALTQPASV SGSPGQSITI SCTGTGSDVG GYNFVSWYQQ HPGKAPKLML YDVNNRPSGV    60
SNRFSGSKSG NTASLTISGL QAEDEADYYC SSYPGTSALV IFGGGTRLTV L             111

SEQ ID NO: 479            moltype = AA  length = 107
FEATURE                   Location/Qualifiers
REGION                    1..107
                          note = Synthetic polypeptide
source                    1..107
                          mol_type = protein
                          organism = synthetic construct
SEQUENCE: 479
DIQMTQSPSS LSASVGDRVT ITCRASQSIS SYLNWYQQKP GEAPNLLIFA ASILQSGVPS    60
RFSGSGSGTD FTLTISSLQP EDFATYYCQQ SYSTPYTFGQ GTKVEIK                  107

SEQ ID NO: 480            moltype = AA  length = 112
FEATURE                   Location/Qualifiers
REGION                    1..112
                          note = Synthetic polypeptide
source                    1..112
                          mol_type = protein
                          organism = synthetic construct
SEQUENCE: 480
QSVLTQPPSV SGAPGQRVTI SCTGSSSNIG AGYDVHWYQQ LPGTAPKLLI YGNSNRPSGV    60
PDRFSGSKSG TSASLAITGL QAEDEADYYC QSYDSSLSGH VVFGGGTKLT VL            112

SEQ ID NO: 481            moltype = AA  length = 107
FEATURE                   Location/Qualifiers
REGION                    1..107
                          note = Synthetic polypeptide
source                    1..107
                          mol_type = protein
                          organism = synthetic construct
SEQUENCE: 481
EIVLTQSPAT LSSSPGERAT LSCRASQSVN SYLVWYQQKP GQAPRLLIYD ASNRATGIPA    60
RFTGSGSGTD FTLTISSLEP EDFAVYYCQQ RTNWPFTFGQ GTKVDIK                  107

SEQ ID NO: 482            moltype = AA  length = 107
FEATURE                   Location/Qualifiers
REGION                    1..107
                          note = Synthetic polypeptide
source                    1..107
                          mol_type = protein
                          organism = synthetic construct
SEQUENCE: 482
EIVLTQSPAT LSLSPGERAT LSCRASQSVN RYLAWYQQKP GQAPRLLIYD ASNRATGIPA    60
RFSGSGSGTD FTLTISSLEP EDFAVYYCHQ RTNWPWTFGQ GTKVEIK                  107

SEQ ID NO: 483            moltype = AA  length = 107
FEATURE                   Location/Qualifiers
REGION                    1..107
                          note = Synthetic polypeptide
```

```
source                  1..107
                        mol_type = protein
                        organism = synthetic construct
SEQUENCE: 483
EIVMTQSPAT LSLSPGERAT LSCRASQSVS NYLAWYQQKP GQAPRLLISD ASSRATGIPA    60
RFRGSGSGTD FTLTISSLEP EDFAVYYCLQ RTNWPFTFGP GTKVEIK                107

SEQ ID NO: 484          moltype = AA  length = 111
FEATURE                 Location/Qualifiers
REGION                  1..111
                        note = Synthetic polypeptide
source                  1..111
                        mol_type = protein
                        organism = synthetic construct
SEQUENCE: 484
QSVLTQPASV SGSPGQSITI SCTGTSSDIG GYNYVSWYQQ HPGKVPKLVI YDVSNRPSGV    60
SNRFSGSKSG NTASLTISGL QAEDEADYYC SSYTSGTTLG VFGTGTKLTV L            111

SEQ ID NO: 485          moltype = AA  length = 110
FEATURE                 Location/Qualifiers
REGION                  1..110
                        note = Synthetic polypeptide
source                  1..110
                        mol_type = protein
                        organism = synthetic construct
SEQUENCE: 485
QSVVTQPPSV SAAPGQKVTI SCSGRSSNIG NSDVSWYQQF PGRAPKLLIY DNDERPSGIP    60
DRFSGSKSGT SATLDITGLQ TGDEADYYCG TWDSSLGGVI FGGGTKVTVL              110

SEQ ID NO: 486          moltype = AA  length = 110
FEATURE                 Location/Qualifiers
REGION                  1..110
                        note = Synthetic polypeptide
source                  1..110
                        mol_type = protein
                        organism = synthetic construct
SEQUENCE: 486
QSVLTQPPSV SAAPGQKVTI SCSGSSSNIG NNYVSWYQQL PGTAPKLLIY DNNKRPSGIP    60
DRFSGSKSGT SATLGITGLQ TGDEADYYCE TWDSSLGVVV FGGGTKLTVL              110

SEQ ID NO: 487          moltype = AA  length = 108
FEATURE                 Location/Qualifiers
REGION                  1..108
                        note = Synthetic polypeptide
source                  1..108
                        mol_type = protein
                        organism = synthetic construct
SEQUENCE: 487
DIQVTQSPSS LSASVGDRVT ITCQASQDIS NYLNWYQHKP GRAPKLLIYD ASNLERGVPS    60
RFSGSGSGTD FTFTISSLQP EDIATYYCQQ YDNLSRLTFG GGTKLEIK                108

SEQ ID NO: 488          moltype = AA  length = 111
FEATURE                 Location/Qualifiers
REGION                  1..111
                        note = Synthetic polypeptide
source                  1..111
                        mol_type = protein
                        organism = synthetic construct
SEQUENCE: 488
QSVLTQPPSV SAAPGQKVTI SCSGSSSNIG NNYVSWYQQL PGTAPKLLIY DNNKRPSGIP    60
DRFSGSKSGT SATLGITGLQ TGDEADYYCG TWDTSLSAGR VFGGGTKLTV L            111

SEQ ID NO: 489          moltype = AA  length = 109
FEATURE                 Location/Qualifiers
REGION                  1..109
                        note = Synthetic polypeptide
source                  1..109
                        mol_type = protein
                        organism = synthetic construct
SEQUENCE: 489
QSVLTQPPSM SAAPGQKVTI SCSGSSSNIG NNYVSWYRQL PGTAPKLLIY DNDKRPSGIP    60
DRFSGSKSGT TATLGITGLQ TGDEAVYYCG TWDFRLSALF GGGTKLTVL               109

SEQ ID NO: 490          moltype = AA  length = 111
FEATURE                 Location/Qualifiers
REGION                  1..111
                        note = Synthetic polypeptide
```

```
                        source                  1..111
                                                mol_type = protein
                                                organism = synthetic construct
SEQUENCE: 490
QSVLIQPASV SGSPGQSITI SCTGTSSDVG GDKYVSWYQQ HPGKAPKLVI YEVSNRPSGV    60
SNRFSGSKSG NTASLTISGL QAEDEADYYC SSYTSSGTPV VCGGGTKVTV L             111

SEQ ID NO: 491          moltype = AA  length = 111
FEATURE                 Location/Qualifiers
REGION                  1..111
                        note = Synthetic polypeptide
source                  1..111
                        mol_type = protein
                        organism = synthetic construct
SEQUENCE: 491
QSVLTQPPSV SAAPGQKVTI SCSGSSSNIG NYYVSWYQQV PGTAPKLLIY DNNKRPSGIP    60
DRFSGSKSGT SATLGITGLH TGDEAEYYCG TWDSSPSAGR VFGGGTKLTV L             111

SEQ ID NO: 492          moltype = AA  length = 113
FEATURE                 Location/Qualifiers
REGION                  1..113
                        note = Synthetic polypeptide
source                  1..113
                        mol_type = protein
                        organism = synthetic construct
SEQUENCE: 492
DIVLTQSPDS LAVSLGERAT INCKSSQSVL FGSNQKSCLA WYQQKPGQSP KLLIHWASTR    60
ESGVPDRFSG SGSGTDFTLT ISSLQAEDVA VYYCQQYYST PRTFGQGTKV EIK           113

SEQ ID NO: 493          moltype = AA  length = 109
FEATURE                 Location/Qualifiers
REGION                  1..109
                        note = Synthetic polypeptide
source                  1..109
                        mol_type = protein
                        organism = synthetic construct
SEQUENCE: 493
QSVLTQPPSV SAAPGQKVTI SCSGSSSNIG SNFVSWYQQL PGTAPKLLIY DNNKRPSGIP    60
DRFSGSKSGT SATLAITGLQ TGDEADYYCG TWDTRLSALF GGGTKVTVL                109

SEQ ID NO: 494          moltype = AA  length = 111
FEATURE                 Location/Qualifiers
REGION                  1..111
                        note = Synthetic polypeptide
source                  1..111
                        mol_type = protein
                        organism = synthetic construct
SEQUENCE: 494
QSVLTQPPSV SAAPGQKVTI SCSGSSSNFG NDYVSWYQQL PGTAPKLLIY DNDKRPSGIP    60
DRFSGSKSGT SATLGITGLQ TGDEADYYCG TWDTSLSAAW VFGGGTKVTV L             111

SEQ ID NO: 495          moltype = AA  length = 111
FEATURE                 Location/Qualifiers
REGION                  1..111
                        note = Synthetic polypeptide
source                  1..111
                        mol_type = protein
                        organism = synthetic construct
SEQUENCE: 495
QSVVTQPPSV SAAPGQKVTI SCSGSSSNIG NNYVSWYQQL PGTAPKLLIY DNNKRPSGIP    60
DRFSGSTSGT SATLGITGLQ TGDEAVYYCG TWDTSPSAGG VFGGGTKVTV L             111

SEQ ID NO: 496          moltype = AA  length = 111
FEATURE                 Location/Qualifiers
REGION                  1..111
                        note = Synthetic polypeptide
source                  1..111
                        mol_type = protein
                        organism = synthetic construct
SEQUENCE: 496
QPVLTQPASV SGSPGQSITI SCTGTSSDVG GYNYVSWYQQ HPGKAPKLMI YDVSNRPSGV    60
SNRFSGSKSG NTASLTISGL QAEDEADYYC SSYTSSSTLA VFGGGTKLTV L             111

SEQ ID NO: 497          moltype = AA  length = 111
FEATURE                 Location/Qualifiers
REGION                  1..111
                        note = Synthetic polypeptide
```

```
                          source         1..111
                                         mol_type = protein
                                         organism = synthetic construct
SEQUENCE: 497
QPVLTQPPSV SAAPGQKVTI SCSGSSSNIG NDYVSWYQQL PGTAPKLLIY DNNKRPSGIP     60
DRFSGSKSGT SATLGITGLQ TGDEGDYYCG TWDSSLSAAW VFGGGTKVTV L             111

SEQ ID NO: 498           moltype = AA   length = 111
FEATURE                  Location/Qualifiers
REGION                   1..111
                         note = Synthetic polypeptide
source                   1..111
                         mol_type = protein
                         organism = synthetic construct
SEQUENCE: 498
QPVLTQSASV SGSPGQSITI SCTGTSSDVG GYKYVSWYQQ HPGKAPKLMI YEVSNRPSGV     60
SIRFSGSKSG NTASLTISGL QAADEADYYC SSYRSSGTPY VFGTGTKVTV L             111

SEQ ID NO: 499           moltype = AA   length = 107
FEATURE                  Location/Qualifiers
REGION                   1..107
                         note = Synthetic polypeptide
source                   1..107
                         mol_type = protein
                         organism = synthetic construct
SEQUENCE: 499
EIVLTQSPSS LSASVGDRVT ITCQASQDIS NFLNWYQQKP GKAPKLLIYD ASSLETGVPS     60
RFSGSGSGTD FTFTISSLQP EDIATYYCQQ YDNLPLTFGG GTKLEIK                  107

SEQ ID NO: 500           moltype = AA   length = 107
FEATURE                  Location/Qualifiers
REGION                   1..107
                         note = Synthetic polypeptide
source                   1..107
                         mol_type = protein
                         organism = synthetic construct
SEQUENCE: 500
DIRLTQSPST LSASVGDRVT VTCRASQNIN TYLAWYQQIP GKAPRLLIYR ASTLESGVPS     60
RFSGSGSGTE FTLTINSLQP DDYATYYCQH YETYSVRFGQ GTKVEIK                  107

SEQ ID NO: 501           moltype = AA   length = 107
FEATURE                  Location/Qualifiers
REGION                   1..107
                         note = Synthetic polypeptide
source                   1..107
                         mol_type = protein
                         organism = synthetic construct
SEQUENCE: 501
DIQVTQSPSS LSASVGDRVT ITCRASQGIS NYLAWYQQKP GKVPKLLIFA ASTLRSGVPS     60
RFRGSGSGTD FTLTISSLQP EDVATYYCQK YNSAPLTFGG GTKVEIK                  107

SEQ ID NO: 502           moltype = AA   length = 107
FEATURE                  Location/Qualifiers
REGION                   1..107
                         note = Synthetic polypeptide
source                   1..107
                         mol_type = protein
                         organism = synthetic construct
SEQUENCE: 502
DIVMTQTPAT LSLSPGERAT LSCRASQSVS SYLAWYQQKP GQAPRLLIYG ASNRATGIPA     60
RFSGSGSGTD FTLTISSLEP EDFAVYYCLQ RTNWPFTFGP GTKVEIK                  107

SEQ ID NO: 503           moltype = AA   length = 107
FEATURE                  Location/Qualifiers
REGION                   1..107
                         note = Synthetic polypeptide
source                   1..107
                         mol_type = protein
                         organism = synthetic construct
SEQUENCE: 503
DIVLTQSPST LSASVGDRVT VTCRASQNIN TYLAWYQQIP GKAPRLLIYR ASSLESGVPS     60
RFSGSGSGTE FTLTISSLQP DDFATYYCQH YNSFSVKFGQ GTKVEIK                  107

SEQ ID NO: 504           moltype = AA   length = 109
FEATURE                  Location/Qualifiers
REGION                   1..109
                         note = Synthetic polypeptide
```

```
source                    1..109
                          mol_type = protein
                          organism = synthetic construct
SEQUENCE: 504
SYELTQPPSV SVAPGQTARI TCGGHNVGSK SVHWYQQKPG QAPVLVVYDD SDRPSGIPER    60
FSGSNSGNTA TLTISRVEAG DEADYYCQVW DSSSDHPWVF GGGTKVTVL              109

SEQ ID NO: 505            moltype = AA   length = 111
FEATURE                   Location/Qualifiers
REGION                    1..111
                          note = Synthetic polypeptide
source                    1..111
                          mol_type = protein
                          organism = synthetic construct
SEQUENCE: 505
QSVVTQPPSV SAAPGQKVTI SCSGSSSNIG NNYVSWYQQL PGTAPKLLIY DNNKRPSGIP    60
DRFSGSKSGT SATLGITGLQ TGDEADYYCG TWDTSLSAGR VFGGGTKLTV L            111

SEQ ID NO: 506            moltype = AA   length = 109
FEATURE                   Location/Qualifiers
REGION                    1..109
                          note = Synthetic polypeptide
source                    1..109
                          mol_type = protein
                          organism = synthetic construct
SEQUENCE: 506
QPVLTQPPSV SVAPGQTARI TCGGNNIGSK SVHWYQQKPG QAPMLVIYSN SDRPSGIPER    60
FSGSNSGITA TLTISRVEAG DEADYHCQVW DTSIDHHWVF GGGTKLTVL              109

SEQ ID NO: 507            moltype = AA   length = 111
FEATURE                   Location/Qualifiers
REGION                    1..111
                          note = Synthetic polypeptide
source                    1..111
                          mol_type = protein
                          organism = synthetic construct
SEQUENCE: 507
QSVLIQPPSA SGSPGQSVTI SCTGTSSDVG GYNYVSWYQQ HPGKAPKLMI YEVSKRPSGV    60
PDRFSGSKSG NTASLTVSGL QAEDGADYYC SSYAGSNNWV VFGGGTKLTV L            111

SEQ ID NO: 508            moltype = AA   length = 110
FEATURE                   Location/Qualifiers
REGION                    1..110
                          note = Synthetic polypeptide
source                    1..110
                          mol_type = protein
                          organism = synthetic construct
SEQUENCE: 508
QPVLTQPASV SGSPGQSITI SCTGTSTDVG GYNYVSWYQQ YPGKAPKLII YDVTNRPSGV    60
SHRFSGSKSG NTASLTISGL QAEDEADYYC SSYTTTSLVI FGGGTKLTVL             110

SEQ ID NO: 509            moltype = AA   length = 113
FEATURE                   Location/Qualifiers
REGION                    1..113
                          note = Synthetic polypeptide
source                    1..113
                          mol_type = protein
                          organism = synthetic construct
SEQUENCE: 509
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQALQTP PRTFGQGTRL EIK         113

SEQ ID NO: 510            moltype = AA   length = 107
FEATURE                   Location/Qualifiers
REGION                    1..107
                          note = Synthetic polypeptide
source                    1..107
                          mol_type = protein
                          organism = synthetic construct
SEQUENCE: 510
DIQVTQSPSS LSASVGGRVT ITCRASQGIR NDLGWYQRKP GKAPKRLIYA ASSLQSGVPS    60
RFSGSGSGTE FTLTISSLQP EDFATYYCLQ HNSYPLTFGG GTKVDIK                107

SEQ ID NO: 511            moltype = AA   length = 107
FEATURE                   Location/Qualifiers
REGION                    1..107
                          note = Synthetic polypeptide
```

```
source                  1..107
                        mol_type = protein
                        organism = synthetic construct
SEQUENCE: 511
DIQLTQSPST LSASVGDRVT ITCRASQSIS TWLAWYQQKP GKAPKLLIYR ASSLESGVPS   60
RFSASGSGTE FTLSISSLQP DDFATYYCKQ YNRNPYTFGQ GTKVEIK                107

SEQ ID NO: 512          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 512
DIQMTQSPSS LSASVGDRVT ITCRASQGIS SYLAWFQQKP GKVPKLLIYA ASTLQSGVPS   60
RFSGSGSGTD FTLTISSLQP EDVATYYCQK YNSAPQTFGQ GTKVDIK                107

SEQ ID NO: 513          moltype = AA   length = 108
FEATURE                 Location/Qualifiers
REGION                  1..108
                        note = Synthetic polypeptide
source                  1..108
                        mol_type = protein
                        organism = synthetic construct
SEQUENCE: 513
EIVMTQSPAT LSVSPGERAT LSCRASQSVS FNLAWYQQKP GQAPRLLISR ASTRAAGVPA   60
RFSGSGSGTE FTLTISSLQS EDFAVYYCQQ YNNWPPLTFG GGTKLEIK                108

SEQ ID NO: 514          moltype = AA   length = 113
FEATURE                 Location/Qualifiers
REGION                  1..113
                        note = Synthetic polypeptide
source                  1..113
                        mol_type = protein
                        organism = synthetic construct
SEQUENCE: 514
DIQMTQSPDS LTVSLGERAT INCKSSQSVL YSSNNKNSLA WYQQKPGQPP KLLIYWASTR   60
ESGVPDRFSG SGSGTDFTLT ISSLQAADVA VYYCQQYYRT PWTFGQGTKV EIK         113

SEQ ID NO: 515          moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 515
QSVLTQPPSV SAAPGQKVTI SCSGSSSNIG NNYVSWYQQL PGTAPKVLIY DNNKRPSGIP   60
DRFSGSKSGT SATLGITGLQ TGDEADYYCG TWDSALGAAV FGGGTKLTVL             110

SEQ ID NO: 516          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 516
DIQLTQSPST LSASVGDRVT ITCRASQSVS SWLAWYQQKP GKAPRLLIYR ASSLESGVPS   60
RFSGSGSGTE FTLTISSLQP DDFAAYYCQQ YNRDPYTFGQ GTKVEIK                107

SEQ ID NO: 517          moltype = AA   length = 105
FEATURE                 Location/Qualifiers
REGION                  1..105
                        note = Synthetic polypeptide
source                  1..105
                        mol_type = protein
                        organism = synthetic construct
SEQUENCE: 517
SYELTQLPSV SVSPGQTARV TCSGDALQYV YWYQQKPGQA PVVVIYKDTE RPSGIPERFS   60
GSSSGTTVTL TITGVQAEDE ADYYCQSADR SGSVIFGGGT KVTVL                  105

SEQ ID NO: 518          moltype = AA   length = 106
FEATURE                 Location/Qualifiers
REGION                  1..106
                        note = Synthetic polypeptide
```

```
                        source          1..106
                                        mol_type = protein
                                        organism = synthetic construct
SEQUENCE: 518
DIVMTQSPAT LSLSPGERAT LSCRASQSVS SYLAWYQQKP GQAPRLLIYD ASNRATGIPA          60
RFSGSGSGTD FTLTISSLEP EDFAVYYCQQ RSNWPSFGQG TKLEIK                        106

SEQ ID NO: 519          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 519
DIRLTQSPSS LSASVGDRVT ITCRASQSIS SYLNWYQQKP GKAPKLLIYA ASSLQSGVPS          60
RFSGSGSGTD FTLTISSLQP EDFATYYCQQ SYSTPLTFGG GTKVEIK                       107

SEQ ID NO: 520          moltype = AA  length = 108
FEATURE                 Location/Qualifiers
REGION                  1..108
                        note = Synthetic polypeptide
source                  1..108
                        mol_type = protein
                        organism = synthetic construct
SEQUENCE: 520
ETTLTQSPGT LSLSPGERAT LSCRASRSVS GNYLAWYQQK PGQAPRLLIY AASSRATGIP          60
DRFSGGGSGT HFTLTISRLE PEDFAVYYCQ QYGSSPRAFG QGTKVEIK                      108

SEQ ID NO: 521          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 521
EIVMTQSPSS LSASVGDRVT ITCRASQSIR SYLNWYQQKP GKAPKLLIYA ASSLQSGVPL          60
RFSGSGSGTD FTLTISSLQP EDFATYYCQQ SSITPPTFGQ GTKLEIK                       107

SEQ ID NO: 522          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 522
DIQMTQSPST LSASVGDRVT ITCRASQSIS SWLAWYQQKP GKAPKLLIYQ ASSLESGVPS          60
RFSGSESGTE FTLTISSLQP DDFATYYCQQ YNSFPFTFGP GTKVEIK                       107

SEQ ID NO: 523          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 523
DIVLTQSPSS LSASVGDRVT ITCRASQSIN NYLNWYQQKP GKAPNLLIFG ASTLQSGVPS          60
RFTGSGSGTV FTLTISSLQR DDFVIYYCQQ TYSASGSFGQ GTKVEIK                       107

SEQ ID NO: 524          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 524
DIQLTQSPSS LSASVGDRVT ITCRASQSIS SYLNWYQQKP GKAPKLLIYA ASSLQSGVPS          60
RFSGSGSGTD FTLTISSLQP EDFATYYCQQ SYSTPWTFGQ GTKVEIK                       107

SEQ ID NO: 525          moltype = AA  length = 109
FEATURE                 Location/Qualifiers
REGION                  1..109
                        note = Synthetic polypeptide
```

```
source                  1..109
                        mol_type = protein
                        organism = synthetic construct
SEQUENCE: 525
QSALIQPPSV SAAPGQKVTI SCSGSSSNIG NNYVSWYQQL PGTAPKLLIY DNNKRPSGIP    60
DRFSGSKSGT SATLGITGLQ TGDEADYYCG TWDNSLGVVF GGGTQLTVL               109

SEQ ID NO: 526          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 526
EIVLTQSPGT LSLSPGERAT LSCRASQSVS SSYLAWYQQK PGQAPRLLIY GASSRATGIP    60
DRFSGSGSGT DFTLSINRLE PEDFAVYYCQ QYGSSPGFGQ GTKVEIK                 107

SEQ ID NO: 527          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 527
DIVLTQSPST LSASVGDRVT ITCRASQSIS DWLAWYQQKP GKAPGLLIYR ASGLESGVPS    60
RFSGSGSGTE FTLTISSLQP DDFATYYCHQ YKDFPWTFGQ GTKVDIK                 107

SEQ ID NO: 528          moltype = AA  length = 106
FEATURE                 Location/Qualifiers
REGION                  1..106
                        note = Synthetic polypeptide
source                  1..106
                        mol_type = protein
                        organism = synthetic construct
SEQUENCE: 528
DIQMTQSPST LSASVGDRVT ITCRASQSIS TWLAWYQLKP GKAPKLLIYK ASNLQSGVPS    60
RFSGSGSGTE FTLTISSLQP DDFATYYCQQ YNSYSPWGQG TKLEIK                  106

SEQ ID NO: 529          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 529
EIVLTQSPGT LSLSPGERAT LSCRASQSVS SRYLAWYRQK PGQAPRLLIY GASSRATGIP    60
DRFSGSGSGT DFTLTISRLE PEDFAVYYCQ QYGSSPFFGG GTKLEIK                 107

SEQ ID NO: 530          moltype = AA  length = 111
FEATURE                 Location/Qualifiers
REGION                  1..111
                        note = Synthetic polypeptide
source                  1..111
                        mol_type = protein
                        organism = synthetic construct
SEQUENCE: 530
QSVLTQPASV SGSPGQSITI SCTGTSSDVG GDKYVSWYQQ HPGKAPKPMI YEVSNRPSGV    60
SNRFSGSKSG NTASLTISGL QAEDEADYYC SSYTSSSTPV VFGGGTKLTV L            111

SEQ ID NO: 531          moltype = AA  length = 110
FEATURE                 Location/Qualifiers
REGION                  1..110
                        note = Synthetic polypeptide
source                  1..110
                        mol_type = protein
                        organism = synthetic construct
SEQUENCE: 531
QPVLTQPRSV SGSPGQSVTI SCTGTSSDVG GYNYVSWYQQ HPGKAPKLMI SDVSKRPSGV    60
PDRFSGSKSG NTASLTISGL QADDEADYYC CSYATNYGVV FGGGTKVTVL              110

SEQ ID NO: 532          moltype = AA  length = 110
FEATURE                 Location/Qualifiers
REGION                  1..110
                        note = Synthetic polypeptide
```

```
source                  1..110
                        mol_type = protein
                        organism = synthetic construct
SEQUENCE: 532
NPMLTQPHSV SESPGKTVTI SCTRSSGSIA SNYVQWYQQR PGSSPTTVIY EDNQRPSGVP    60
DRFSGSIDSS SNSASLTISG LKTEDEADYY CQSYDSSNVV FGGGTKVTVL              110

SEQ ID NO: 533          moltype = AA   length = 111
FEATURE                 Location/Qualifiers
REGION                  1..111
                        note = Synthetic polypeptide
source                  1..111
                        mol_type = protein
                        organism = synthetic construct
SEQUENCE: 533
QSVLTQPPSV SAAPGQKVTI SCSGSSSNIG NNDVSWYQQL PGRAPKLLIY DNNKRPSGIP    60
DRFSGSKSGT SATLGITGLQ TGDEADYYCG AWDSSLSAHV VFGGGTKVTV L            111

SEQ ID NO: 534          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 534
DIVMTQTPST LSASVGDRVT VTCRASQSIS DWLAWYQQKA GKAPKLLIYR ASSLESGVPP    60
RFSGSGSGTE FTLTISSLRP DDFATYYCQQ YNRYPYTFGQ GTKVDIK                 107

SEQ ID NO: 535          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 535
DIQVTQSPSS LSASVGDRVT ITCRASQGIR NDLAWYQQRP GKAPKRLIYA ASSLQSGVPS    60
RFSGSGSGTE FTLTISSLQP EDFATYYCLQ HHSYPWTFGQ GTKVEIK                 107

SEQ ID NO: 536          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 536
DIRMTQSPST LSASIGDRVT ITCRASQSIS DWLAWYLQKP GKAPSLLIYR ASSLETGVPS    60
RFSGRGSGTE FTLTISSLQP DDFGTYYCQQ YNRDPYTFGQ GTKVDIK                 107

SEQ ID NO: 537          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 537
DIQLTQSPST LSASVGDRVT VTCRASQNVG GWLAWYQQKP GKAPKLLIFQ ASRLENGVPS    60
RFSANASGTE FTLTIGSLQP DDFATYYCQQ YNTYPYTFGQ GTKVDIK                 107

SEQ ID NO: 538          moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 538
DIQLTQSPSS LSASVGDRVT ITCRASQSIS QYLNWYQQKP GKAPKLLISP ASSFQSGVPS    60
RFSGSGSGTD FTLTITSLQP EDFATYYCQQ SYSTPWTFGQ GTKVDIK                 107

SEQ ID NO: 539          moltype = AA   length = 110
FEATURE                 Location/Qualifiers
REGION                  1..110
                        note = Synthetic polypeptide
```

```
                        source                   1..110
                                                 mol_type = protein
                                                 organism = synthetic construct
SEQUENCE: 539
QSVLTQPASV SGSPGQSITI SCTGTSSDVG GYNYVSWYQQ HPGKAPKLMI YDVSNRPSGV    60
SNRFSGSKSG NTASLTISGL QAEDEADYYC SSYTSSSTLV FGGGTQLTVL              110

SEQ ID NO: 540          moltype = AA  length = 108
FEATURE                 Location/Qualifiers
REGION                  1..108
                        note = Synthetic polypeptide
source                  1..108
                        mol_type = protein
                        organism = synthetic construct
SEQUENCE: 540
SYELTQPPSV SVAPGQTARI ICGGNYIGGK SVHWYQQKPG QAPVLVVYND NDRPSGIPER    60
FSGSNSGNTA TLTISRVAAG DEADYYCQVW DNSSDRRVFG GGTKLTVL                108

SEQ ID NO: 541          moltype = AA  length = 106
FEATURE                 Location/Qualifiers
REGION                  1..106
                        note = Synthetic polypeptide
source                  1..106
                        mol_type = protein
                        organism = synthetic construct
SEQUENCE: 541
DIRVTQSPAT LSVSPGERAT LSCRASQRVN SNLAWYQQKP GQAPRLLIYG ASTRATGIPV    60
RFSGSGSGTE FTLTISSLQS EDFAVYYCQQ YNTWWTFGQG TKVEIK                  106

SEQ ID NO: 542          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 542
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPLTFGG GTKVDIK                 107

SEQ ID NO: 543          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 543
DIVMTQSPAT LSVSPGERAT LSCRASQSVS SNLAWYQQKP GQAPRLLIYG ASTRATGIPA    60
RFSGSGSGTE FTLTISSLQS EDFAVYSCQQ YNTWPKTFGQ GTKVEIK                 107

SEQ ID NO: 544          moltype = AA  length = 108
FEATURE                 Location/Qualifiers
REGION                  1..108
                        note = Synthetic polypeptide
source                  1..108
                        mol_type = protein
                        organism = synthetic construct
SEQUENCE: 544
EIVLTQSPGT LSLSPGERAT LSCRASQSVS SSFLAWYQQK PGQAPRLLIY GASSRATGIP    60
DRFSGSGSGT DFTLTIRRLE PEDFAVYYCQ QYGSSRRTFG QGTKVEIK                108

SEQ ID NO: 545          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 545
DIRVTQSPST LSASVGDRVT ITCRASQSIS SWLAWYQQKP GKAPKLLIYR ASSLESGVPS    60
RFSGSGSGTE FTLTISSLQP DDFATYYCQQ YNRYPYTFGQ GTKVEIK                 107

SEQ ID NO: 546          moltype = AA  length = 112
FEATURE                 Location/Qualifiers
REGION                  1..112
                        note = Synthetic polypeptide
```

```
source                  1..112
                        mol_type = protein
                        organism = synthetic construct
SEQUENCE: 546
QSALTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSSTLD VVFGGGTKLT VL            112

SEQ ID NO: 547          moltype = AA  length = 108
FEATURE                 Location/Qualifiers
REGION                  1..108
                        note = Synthetic polypeptide
source                  1..108
                        mol_type = protein
                        organism = synthetic construct
SEQUENCE: 547
EIVMTQSPAT LSVSPGERAT LSCRASQSVS SNLAWYQQKP GQAPRLLIYG ASTRATSIPA    60
RFSGSGSGTE FTLTISSLQS EDFAVYYCQQ YNSWPPITFG QGTRLEIK                 108

SEQ ID NO: 548          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 548
DIRLTQSPST LSASVGDRVS ITCRASQSIS DWLAWYQQKP GKAPKLLIYR ASGLETGVPS    60
RFSGSGSGTE FTLTISSLQP DDFATYYCQQ YNRYPYTFGQ GTKVDIK                  107

SEQ ID NO: 549          moltype = AA  length = 111
FEATURE                 Location/Qualifiers
REGION                  1..111
                        note = Synthetic polypeptide
source                  1..111
                        mol_type = protein
                        organism = synthetic construct
SEQUENCE: 549
QPVLIQPPSA SGTPGQRVTI SCSGSSSNFG SNFVYWYQQL PGTAPKLLIY RVNQRPSGVP    60
DRFSGSKSGT SASLAISGLR SEDEADYYCA TWDVSLSNDV LFGGGTKLTV L             111

SEQ ID NO: 550          moltype = AA  length = 109
FEATURE                 Location/Qualifiers
REGION                  1..109
                        note = Synthetic polypeptide
source                  1..109
                        mol_type = protein
                        organism = synthetic construct
SEQUENCE: 550
DIVLTQSPAT LSLSPGERAT LSCRASQSVS SSYLSWYQQK PGQAPRLLIY GASSRATGIP    60
DRFSGSGSGT DFTLTISRLE PEDFAVYYCQ QYGSSPPITF GGGTKVEIK                109

SEQ ID NO: 551          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 551
DIQMTQSPSS LSASVGDRVT ITCRASQTIT RYMNWYQQKP GEAPKLLIYA TSSLQSGVPS    60
RFSGSGSGTD FTLTITNLQP ADFATYYCQQ SSTTRWTFGQ GTKVDIK                  107

SEQ ID NO: 552          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 552
DIRLTQSPSS LSASVGDRVT ITCRASQDIR KFLNWYQQKL GKAPSLLIYG ASSLQSGVPS    60
RFSGSGSGTD FTLTISSLQP EDFAIYYCQH ASTTPWTFGQ GTKVEIK                  107

SEQ ID NO: 553          moltype = AA  length = 108
FEATURE                 Location/Qualifiers
REGION                  1..108
                        note = Synthetic polypeptide
```

```
source                  1..108
                        mol_type = protein
                        organism = synthetic construct
SEQUENCE: 553
SYELTQPPSV SVSPGQTATI TCSGDKLGYT YTCWYQQKPG QSPVLVIYQD TKRPSGIPER      60
FSGSNSGNTA TLTITGTQAM DEADYYCQAW DTTTAGGVFG GGTKLTVL                  108

SEQ ID NO: 554          moltype = AA  length = 108
FEATURE                 Location/Qualifiers
REGION                  1..108
                        note = Synthetic polypeptide
source                  1..108
                        mol_type = protein
                        organism = synthetic construct
SEQUENCE: 554
DIVLTQSPGT LSLSPGERAT LSCRASQSVS SSYLAWYQQK PGQAPRLLIY GASSRATGIP      60
DRFSGSGSGT DFTLTISRLE PEDFAVYYCQ QYGSSPRAFG PGTKVEIK                  108

SEQ ID NO: 555          moltype = AA  length = 110
FEATURE                 Location/Qualifiers
REGION                  1..110
                        note = Synthetic polypeptide
source                  1..110
                        mol_type = protein
                        organism = synthetic construct
SEQUENCE: 555
QSVLTQPPSA SGSPGQSVTI SCAGTRSDVG GYNFVSWYQQ HPGKAPKLLI YEVNKRPSGV      60
PDRFSGSKSA NTASLTVSGL QAEDEAEYFC SSYGGNNDLV FGGGTKVTVL                110

SEQ ID NO: 556          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 556
EIVMTQSPAT LSLSPGERGT LSCRTSQSVS SFLAWYQQKP GQAPRLLMYD ASNRATGIPA      60
RFSGSGSGTD FTLTISSLEP EDFAVYYCQQ RSNWPYTFGQ GTKVDIK                   107

SEQ ID NO: 557          moltype = AA  length = 106
FEATURE                 Location/Qualifiers
REGION                  1..106
                        note = Synthetic polypeptide
source                  1..106
                        mol_type = protein
                        organism = synthetic construct
SEQUENCE: 557
GIQLTQSPST LSASVGDRVT ITCRASQSVS DWLAWYQQKP GRAPNLLIYR ASSLQSGVPS      60
RFSGSGSGTE FTLTINSLQP DDFATYYCQQ YKTYWTFGQG TKVEIK                    106

SEQ ID NO: 558          moltype = AA  length = 110
FEATURE                 Location/Qualifiers
REGION                  1..110
                        note = Synthetic polypeptide
source                  1..110
                        mol_type = protein
                        organism = synthetic construct
SEQUENCE: 558
QSVLTQPASV SGSPGQSITI SCTGTSSDVG GYNYVSWYQQ HPGKAPKLMI YEVSNRPSGV      60
SNRFSGSKSG NTASLTISGL QAEDEADYYC SSYTSSGTNI FGTGTKLTVL                110

SEQ ID NO: 559          moltype = AA  length = 108
FEATURE                 Location/Qualifiers
REGION                  1..108
                        note = Synthetic polypeptide
source                  1..108
                        mol_type = protein
                        organism = synthetic construct
SEQUENCE: 559
DIVMTQTPAT LSVSPGERAT LSCRASQSVS SNVAWYQQKP GQAPRLLIHG ASTRATGIPA      60
RFSGSGSGTE FTLTISSLQS EDFAVYYCQQ YNNWPPLTFG GGTKLEIK                  108

SEQ ID NO: 560          moltype = AA  length = 108
FEATURE                 Location/Qualifiers
REGION                  1..108
                        note = Synthetic polypeptide
```

```
source                    1..108
                          mol_type = protein
                          organism = synthetic construct
SEQUENCE: 560
SYELTQPPSV SVSPGQTARI TCSGDALPKK YVYWFQQKSG QAPVLVIYED RRGPSGIPER    60
FSGSTSGTMA TLTIRGAQVE DEADYFCYST DSSGLLGVFG GGTKLTVL                108

SEQ ID NO: 561            moltype = AA  length = 113
FEATURE                   Location/Qualifiers
REGION                    1..113
                          note = Synthetic polypeptide
source                    1..113
                          mol_type = protein
                          organism = synthetic construct
SEQUENCE: 561
DIQMTQSPDS LAVSLGERAT INCKSSQSVF YSSNSQNYLA WYQQKPGQPP KLLIYWASTR    60
ESGVPDRFSG SGSATDFSLT ISSLQAEDVA VYYCQQFHSP PWTFGQGTKL EIK          113

SEQ ID NO: 562            moltype = AA  length = 107
FEATURE                   Location/Qualifiers
REGION                    1..107
                          note = Synthetic polypeptide
source                    1..107
                          mol_type = protein
                          organism = synthetic construct
SEQUENCE: 562
DIVMTQSPST LSASVGDRVV ITCRASQSIS NWLAWYQQKS GKAPKLLIYK ASRLESGVPS    60
TFSGSGSGTE FTLTISSLQA DDFASYYCQQ YNDYPWTFGQ GTKVEIK                 107

SEQ ID NO: 563            moltype = AA  length = 107
FEATURE                   Location/Qualifiers
REGION                    1..107
                          note = Synthetic polypeptide
source                    1..107
                          mol_type = protein
                          organism = synthetic construct
SEQUENCE: 563
EIVMTQSPSS LSASVGDRVT ITCRASQGIR NDLGWYQQKP GKAPKRLIYA ASSLQSGVPS    60
RFSGSGSGRE FTLTISSLQP EDFATYYCLQ HNTYPWTFGQ GTKVEIK                 107

SEQ ID NO: 564            moltype = AA  length = 107
FEATURE                   Location/Qualifiers
REGION                    1..107
                          note = Synthetic polypeptide
source                    1..107
                          mol_type = protein
                          organism = synthetic construct
SEQUENCE: 564
DIQVTQSPST LSASVGDRVS ITCRASQTIS SWLAWYQQKP GKAPKLLMYK ASNLQSGVPS    60
RFTGSGSGTE FTLTISSLQP DDFATYYCQQ YYSYPYTFGP GTKVDIK                 107

SEQ ID NO: 565            moltype = AA  length = 107
FEATURE                   Location/Qualifiers
REGION                    1..107
                          note = Synthetic polypeptide
source                    1..107
                          mol_type = protein
                          organism = synthetic construct
SEQUENCE: 565
SYVLTQPPSV SVSPGQTARI TCSGDALPKQ YGYWYQQKPG QAPVLVIYKD SERPSGIPER    60
FSGSSSGTTV TLTISGVQAE DEADYYCQSA DRSGTVVFGG GTKLTVL                 107

SEQ ID NO: 566            moltype = AA  length = 110
FEATURE                   Location/Qualifiers
REGION                    1..110
                          note = Synthetic polypeptide
source                    1..110
                          mol_type = protein
                          organism = synthetic construct
SEQUENCE: 566
QAVVTQPPSA SGSPGQSVTI SCTGTSSDVG GYNYVSWYQQ HPGKAPKLMV YEVTKRPSGV    60
PDRFSGSKSG NAASLTVSGL QAEDEAEYYC SSYAGSNALV FSGGTKLTVL              110

SEQ ID NO: 567            moltype = AA  length = 110
FEATURE                   Location/Qualifiers
REGION                    1..110
                          note = Synthetic polypeptide
```

```
source                  1..110
                        mol_type = protein
                        organism = synthetic construct
SEQUENCE: 567
NPMLTQPHSV SESPGKTVTI SCTRSSGSIA SNYVQWYQQR PGSAPTTVIY EDNQRPSGVP    60
DRFSGSIDSS SNSASLTISG LKTEDEADYY CQSYDSSNWV FGGGTKLTVL              110

SEQ ID NO: 568          moltype = AA  length = 105
FEATURE                 Location/Qualifiers
REGION                  1..105
                        note = Synthetic polypeptide
source                  1..105
                        mol_type = protein
                        organism = synthetic construct
SEQUENCE: 568
QPELTQPPSV SVSPGQTARI TCSGDALSKQ YAYWYQQKPG QAPVVVIYKD SERPSGIPER    60
FSGSRSGTTV TLTISGVQAE DEADYYCHSP DSHVVFGGGT KLTVL                   105

SEQ ID NO: 569          moltype = AA  length = 108
FEATURE                 Location/Qualifiers
REGION                  1..108
                        note = Synthetic polypeptide
source                  1..108
                        mol_type = protein
                        organism = synthetic construct
SEQUENCE: 569
SYELIQLPSA SVAPGKTARI TCGGNNIGSK SVHWYQQKPG QAPVLVVYDD SDRPSGIPER    60
FSGSNSGNTA TLTISRVEAG DEADYYCQVW DSSSDHEVFG GGTKLTVL                108

SEQ ID NO: 570          moltype = AA  length = 103
FEATURE                 Location/Qualifiers
REGION                  1..103
                        note = Synthetic polypeptide
source                  1..103
                        mol_type = protein
                        organism = synthetic construct
SEQUENCE: 570
DIQMTQSPSS LSASVGDRVT ITCQASQDIS NYLNWYQQKP GKAPKLLIYD VSKLKTGVPP    60
RFSGSGSGTD FTFTISSLQP EDIATYYCQQ WGTFGQGTKV DIK                     103

SEQ ID NO: 571          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 571
EIVLTQSPST LSASVGDRVT ITCRASQSIS DWLAWYQQKP GKAPNLLIYR ASSLESGVPS    60
RFSGSGSGTE FTLTISSLQP DDFATYYCQQ YNRYPYTFGQ GTKVEIK                 107

SEQ ID NO: 572          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 572
DIQLTQSPST LSASVGDRVT ITCRASQSIS DWLAWFQQKP GKAPKLLIYR ASGLETGVPS    60
RFSGSGSGTE FTLTISSLQP DDFATYYCQQ YNRYSYTFGQ GTKVEIK                 107

SEQ ID NO: 573          moltype = AA  length = 106
FEATURE                 Location/Qualifiers
REGION                  1..106
                        note = Synthetic polypeptide
source                  1..106
                        mol_type = protein
                        organism = synthetic construct
SEQUENCE: 573
DIRLTQSPST LSASVGDRVT ITCRASQSIS GWLAWYQQKP GKAPKLLIYK ASILESGVPS    60
RFSGSQSGTE FTLTISSLQP DDFATYYCQQ YNNFWTFGQG TKLEIK                  106

SEQ ID NO: 574          moltype = AA  length = 111
FEATURE                 Location/Qualifiers
REGION                  1..111
                        note = Synthetic polypeptide
```

```
source                   1..111
                         mol_type = protein
                         organism = synthetic construct
SEQUENCE: 574
QSVLTQPPSV SGAPGQRVTI SCTGNSSNIG AGYEVHWYQQ LPGTAPKLLI YGNNNRPSGV    60
PDRFSGSKSG ASGSLAVTGL RAEDEADYYC HSYDSNMSGS VFGGGTKVTV L            111

SEQ ID NO: 575           moltype = AA  length = 108
FEATURE                  Location/Qualifiers
REGION                   1..108
                         note = Synthetic polypeptide
source                   1..108
                         mol_type = protein
                         organism = synthetic construct
SEQUENCE: 575
EIVLTQSPSS LSASVGDRVT ITCRASQGIS NYLAWYQQKP GKAPKLLIYA ASTLQSGVPS    60
RFSGSGSGTD FILTISSLQP EDVATYYCQK YYSAPLITFG PGTKVEIK                108

SEQ ID NO: 576           moltype = AA  length = 110
FEATURE                  Location/Qualifiers
REGION                   1..110
                         note = Synthetic polypeptide
source                   1..110
                         mol_type = protein
                         organism = synthetic construct
SEQUENCE: 576
SYELTQPPSV SVSPGQTARI TCSGDALPKQ YAYWYQQKPG QAPVLVIYKD TERPSGIPER    60
FSGSSSGTTV TLTISGVQAE DEADYYCQSA DSSVADSSVV FGGGTKLTVL               110

SEQ ID NO: 577           moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 577
EIVLTQSPAT LSLSPGERAT LSCRASQSVS NYFAWYQQKP GQAPRLLIYG ASNRATGVPA    60
RFSGSGSGTD FTLTISSLEP EDFAVYYCQQ RSNWPYTFGQ GTKVEIK                  107

SEQ ID NO: 578           moltype = AA  length = 110
FEATURE                  Location/Qualifiers
REGION                   1..110
                         note = Synthetic polypeptide
source                   1..110
                         mol_type = protein
                         organism = synthetic construct
SEQUENCE: 578
NFMLTQPPSV SAAPGQKVTI SCSGSNSNIG NNFVSWYQQL PGTAPKLLIY DNNERPSGIP    60
DRFSGSKSVT SATLGITGLQ TGDEADYYCG TWDNSLGMVV FGGGTKLTVL               110

SEQ ID NO: 579           moltype = AA  length = 110
FEATURE                  Location/Qualifiers
REGION                   1..110
                         note = Synthetic polypeptide
source                   1..110
                         mol_type = protein
                         organism = synthetic construct
SEQUENCE: 579
QSALTQPASV SGSPGQSITI SCTGTSSDVG GYNYVSWYQQ HPGKAPKLMI YEVSNRPSGV    60
SNRFSGSKSN NTASLTISGL QAEDEADYYC SSYTSSSTYV FGTGTKVTVL               110

SEQ ID NO: 580           moltype = AA  length = 109
FEATURE                  Location/Qualifiers
REGION                   1..109
                         note = Synthetic polypeptide
source                   1..109
                         mol_type = protein
                         organism = synthetic construct
SEQUENCE: 580
EIVLTQSPGT LALSPGERAT LSCRASQSVS SYLAWYQQKP GQAPRLLIYD SSNRATGIPA    60
RFSGSGSGTD FTLTISSLEP EDFAVYYCQQ PGNWPPAFTF GGGTKLEIK                109

SEQ ID NO: 581           moltype = AA  length = 106
FEATURE                  Location/Qualifiers
REGION                   1..106
                         note = Synthetic polypeptide
```

```
                       source          1..106
                                       mol_type = protein
                                       organism = synthetic construct
SEQUENCE: 581
DIVMTQSPAT LSVSPGERAT LSCRASQSVT SKLAWYQQKP GQAPRLLIYG ASTRATGIPA    60
RFSGSGSGTE FTLTISSLQS EDFAVYYCQQ YNNWITFGQG TRLEIK                  106

SEQ ID NO: 582         moltype = AA  length = 107
FEATURE                Location/Qualifiers
REGION                 1..107
                       note = Synthetic polypeptide
source                 1..107
                       mol_type = protein
                       organism = synthetic construct
SEQUENCE: 582
DIQLTQSPSS VSASVGDRVT ITCRASQGIS SWLAWYQQKP GKAPKLLIYA ASSLQSGVPS    60
RFSGSGSGTD FTLTISSLQP EDFATYYCQQ ANSFPWTFGQ GTKVDIK                 107

SEQ ID NO: 583         moltype = AA  length = 112
FEATURE                Location/Qualifiers
REGION                 1..112
                       note = Synthetic polypeptide
source                 1..112
                       mol_type = protein
                       organism = synthetic construct
SEQUENCE: 583
DIVMTQSPLS LPVTPGEPAS ISCRSSQSLL HSNGYNSLDW YLQKPGQSPQ LLIYLGSNRA    60
SGVPDRFSGS GSGTDFTLKI SRVEAEDVGV YYCMQALQTP YTFGQGTKLE IK           112

SEQ ID NO: 584         moltype = AA  length = 110
FEATURE                Location/Qualifiers
REGION                 1..110
                       note = Synthetic polypeptide
source                 1..110
                       mol_type = protein
                       organism = synthetic construct
SEQUENCE: 584
QPVLTQPPSA SGTPGQRVTI SCSGSSSNIG SNTVHWYQQL PGTAPKLLIY SNNQRPSGVP    60
DRLSGSRSGT SASLAISGLQ SEDEAEYYCA AWDDNLIGVV FGGGTKLTVL              110

SEQ ID NO: 585         moltype = AA  length = 111
FEATURE                Location/Qualifiers
REGION                 1..111
                       note = Synthetic polypeptide
source                 1..111
                       mol_type = protein
                       organism = synthetic construct
SEQUENCE: 585
QSALTQPPSA SGSPGQSVTI SCTGTSSDVG GYNYVSWYQQ HPGKAPKLMI YEVSKRPSGV    60
PDRFSGSKSG NTASLTVSGL QAEDEADYYC SSFAGSNNLY VFGTGTKVTV L            111

SEQ ID NO: 586         moltype = AA  length = 110
FEATURE                Location/Qualifiers
REGION                 1..110
                       note = Synthetic polypeptide
source                 1..110
                       mol_type = protein
                       organism = synthetic construct
SEQUENCE: 586
QSVLTQPASV SGSPGQSITI SCTGTSSDVG GYNYVSWYQQ HPGKAPKLMI YDVTNRPSGV    60
SNRFSGSRSG NTASLTISGL QAEDEADYYC SSYTRSSTRV FGGGTKLTVL              110

SEQ ID NO: 587         moltype = AA  length = 109
FEATURE                Location/Qualifiers
REGION                 1..109
                       note = Synthetic polypeptide
source                 1..109
                       mol_type = protein
                       organism = synthetic construct
SEQUENCE: 587
QPVLTQPPSV SAAPGQKVTI SCSGSSSNIG SNFVSWYQQF PGTAPKLLIY DDNKRPSGIP    60
DRFSGSKSGT SATLGITGLQ TGDEADYYCE TWDSRLSVVF GGGTKLTVL               109

SEQ ID NO: 588         moltype = AA  length = 110
FEATURE                Location/Qualifiers
REGION                 1..110
                       note = Synthetic polypeptide
```

```
source                  1..110
                        mol_type = protein
                        organism = synthetic construct
SEQUENCE: 588
QPVLTQPPSV SAAPGQKVTI SCSGSSSNIG NNYVSWYQQL PGTAPKLLIY DNNKRPSGIP    60
DRFSGSKSGT SATLGITGLQ TGDEADYYCG TWDSSLSAVV FGGGTKVTVL              110

SEQ ID NO: 589          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 589
DIQLTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPWTFGQ GTKVDIK                 107

SEQ ID NO: 590          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 590
DIRVTQSPSS LSASVGDRVT ITSRASQSIS SYLNWYQQKP GKAPKLLIYA ASSLQSGVPS    60
RFSGSGSGTD FTLTISSLQP EDFATYYCQQ SYSTPRTFGG GTKVDIK                 107

SEQ ID NO: 591          moltype = AA  length = 111
FEATURE                 Location/Qualifiers
REGION                  1..111
                        note = Synthetic polypeptide
source                  1..111
                        mol_type = protein
                        organism = synthetic construct
SEQUENCE: 591
QSVLTQPPSV SGAPGQRVTI SCTGSSSDIG AGYDVHWYQQ LPGTAPKLLI YGNTNRPSGV    60
PDRFSGSKSG TSASLAITGL QAEDEADYYC QSYDSSLSGV VFGGGTKLTV L            111

SEQ ID NO: 592          moltype = AA  length = 113
FEATURE                 Location/Qualifiers
REGION                  1..113
                        note = Synthetic polypeptide
source                  1..113
                        mol_type = protein
                        organism = synthetic construct
SEQUENCE: 592
DIVLTQSPDS LAVSLGERAA INCKSSQSVF FSSDNKNYLA WYQQKPGQPP KLLIYWASTR    60
ESGVPDRFSG SGSGTDFTLT ISSLQAEDVA VYYCQQFYTT PSTFGQGTKV EIK          113

SEQ ID NO: 593          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 593
DIQLTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPRTFGG GTKVEIK                 107

SEQ ID NO: 594          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 594
DIQLTQSPSS LSASVGDRVT ITCRASQGIR NDLGWYQQKP GKAPKRLIYA ASSLQSGVPS    60
RFSGSGSGTE FTLTISSLQP EDFATYYCLQ HNSYPLTFGG GTKVEIK                 107

SEQ ID NO: 595          moltype = AA  length = 110
FEATURE                 Location/Qualifiers
REGION                  1..110
                        note = Synthetic polypeptide
```

```
source                        1..110
                              mol_type = protein
                              organism = synthetic construct
SEQUENCE: 595
NFMLTQPHSV SESPGNTVTI SCTRSSGSIA STYVQWYQQR PGSAPSTVIY EDNQRPPGVP     60
ARFSGSIDSS SNSASLTISG LETEDEADYY CQSYDSTTVV FGGGTKVTVL              110

SEQ ID NO: 596                moltype = AA   length = 111
FEATURE                       Location/Qualifiers
REGION                        1..111
                              note = Synthetic polypeptide
source                        1..111
                              mol_type = protein
                              organism = synthetic construct
SEQUENCE: 596
SYVLTQPPSA SGSPGQSVTI SCTGTSSDFG GYNYVSWYQQ HPGKAPKLMV YEVAKRPSGV     60
PDRFSGSKSG NTASLTVSGL QAEDEADYYC SSYAGSNNFV VFGGGTKLTV L             111

SEQ ID NO: 597                moltype = AA   length = 110
FEATURE                       Location/Qualifiers
REGION                        1..110
                              note = Synthetic polypeptide
source                        1..110
                              mol_type = protein
                              organism = synthetic construct
SEQUENCE: 597
QSVLTQPPSV SAAPGQKVTI SCSGSSSNIG NNYVSWYQQL PGTAPKLLIY DNNKRPSGIP     60
DRFSGSKSGT SATLGITGLQ TGDEADYYCG TWDSSLSAKV FGGGTKLTVL              110

SEQ ID NO: 598                moltype = AA   length = 107
FEATURE                       Location/Qualifiers
REGION                        1..107
                              note = Synthetic polypeptide
source                        1..107
                              mol_type = protein
                              organism = synthetic construct
SEQUENCE: 598
ETTLTQSPST LSTSVGDRVT ITCRASQSIS SWLAWYQQKP GKAPKLLIYR ASSLETEVPS     60
RFSGSGSGTD FTLTISRLQP DDFATYFCQQ YNRYPYTFGQ GTKLEIK                 107

SEQ ID NO: 599                moltype = AA   length = 111
FEATURE                       Location/Qualifiers
REGION                        1..111
                              note = Synthetic polypeptide
source                        1..111
                              mol_type = protein
                              organism = synthetic construct
SEQUENCE: 599
QPVLTQPRSV SGSPGQSVTI SCTGTSSDVG GYNYVSWYQQ HPGKAPKLMI YDVSKRPSGV     60
PDRFSGSKSG NTASLTISGL QAEDEADYYC CSYAGSYTFV LFGGGTKLTV L             111

SEQ ID NO: 600                moltype = AA   length = 106
FEATURE                       Location/Qualifiers
REGION                        1..106
                              note = Synthetic polypeptide
source                        1..106
                              mol_type = protein
                              organism = synthetic construct
SEQUENCE: 600
DIRVTQSPSS LSASVGDRVT ISCRASESIS IYLNWYQQKP GKAPNLLIYA ASSLQRGVPS     60
RFSGSGSGTD FTLTITSLQA EDFATYYCQQ TFSIWTFGQG TKVEIK                  106

SEQ ID NO: 601                moltype = AA   length = 111
FEATURE                       Location/Qualifiers
REGION                        1..111
                              note = Synthetic polypeptide
source                        1..111
                              mol_type = protein
                              organism = synthetic construct
SEQUENCE: 601
QPVLTQPPSV SAAPGQKVTI SCSGSSSNIG NNYVSWYQQL PGTAPKLLIY DNNKRPSGIP     60
DRFSGSKSGT SATLGITGLQ TGDEADYYCG TWDSSLSAGK VFGGGTKLTV L             111

SEQ ID NO: 602                moltype = AA   length = 110
FEATURE                       Location/Qualifiers
REGION                        1..110
                              note = Synthetic polypeptide
```

```
source                    1..110
                          mol_type = protein
                          organism = synthetic construct
SEQUENCE: 602
QSALTQPPSA SGSPGQSVTI SCTGTSSDVG GFNYVSWYQQ HPGRAPKLVI YEVNRRPSGV    60
PDRFSGSKSG YTASLTVSGL QAEDEADYYC FSYAGSNNYV FGTGTKVTVL              110

SEQ ID NO: 603            moltype = AA   length = 112
FEATURE                   Location/Qualifiers
REGION                    1..112
                          note = Synthetic polypeptide
source                    1..112
                          mol_type = protein
                          organism = synthetic construct
SEQUENCE: 603
DIVMTQTPLS SPVTLGQPAS ISCRSSQSLV HSDGNTYLSW LQQRPGQPPR FLIYKISNRF    60
SGVPDRFSGG GAGTDFTLKI SRVEAEDVGV YYCMQASQFP LTFGGGTKVE IK           112

SEQ ID NO: 604            moltype = AA   length = 108
FEATURE                   Location/Qualifiers
REGION                    1..108
                          note = Synthetic polypeptide
source                    1..108
                          mol_type = protein
                          organism = synthetic construct
SEQUENCE: 604
EIVMTQSPSS LSASVGDRVT ITCQASQDIS NYLNWYQQKP GKAPKLLIYD ASNLETGVPS    60
RFSGSGSGTD FTFTISSLQP EDIATYYCQQ YDNLPPVTFG QGTRLEIK                108

SEQ ID NO: 605            moltype = AA   length = 107
FEATURE                   Location/Qualifiers
REGION                    1..107
                          note = Synthetic polypeptide
source                    1..107
                          mol_type = protein
                          organism = synthetic construct
SEQUENCE: 605
QPVLTQPPSV SVSPGQTASI TCSGDKLGDK YACWYQQKPG QSPVLVIYQD SKRPSGIPER    60
FSGSNSGNTA TLTISGTQAM DEADYYCQAW DSSTDVVFGG GTKVTVL                 107

SEQ ID NO: 606            moltype = AA   length = 107
FEATURE                   Location/Qualifiers
REGION                    1..107
                          note = Synthetic polypeptide
source                    1..107
                          mol_type = protein
                          organism = synthetic construct
SEQUENCE: 606
DIQVTQSPSS LSASVGDRVT ITCRASQGIS NNLAWYQQKP GIFPKLLIYA ASTLQSGVPS    60
RFSGSGSGTD FILTISSLQP EDVATYYCQK YQSAPPTFGG GTKLEIK                 107

SEQ ID NO: 607            moltype = AA   length = 10
FEATURE                   Location/Qualifiers
REGION                    1..10
                          note = Synthetic polypeptide
source                    1..10
                          mol_type = protein
                          organism = synthetic construct
SEQUENCE: 607
YSISSGFYWG                                                           10

SEQ ID NO: 608            moltype = AA   length = 16
FEATURE                   Location/Qualifiers
REGION                    1..16
                          note = Synthetic polypeptide
source                    1..16
                          mol_type = protein
                          organism = synthetic construct
SEQUENCE: 608
SMYQSGITYY NPSLKS                                                    16

SEQ ID NO: 609            moltype = AA   length = 9
FEATURE                   Location/Qualifiers
REGION                    1..9
                          note = Synthetic polypeptide
```

```
                                 -continued source                  1..9
                        mol_type = protein
                        organism = synthetic construct
SEQUENCE: 609
FTFSNYAMN                                                             9

SEQ ID NO: 610          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 610
AINRGGDSTY YADSVKG                                                   17

SEQ ID NO: 611          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 611
SMYHSGITYY NPSLKS                                                    16

SEQ ID NO: 612          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 612
FAFSSYGMH                                                             9

SEQ ID NO: 613          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 613
LIRFDGTIKY YADSVKG                                                   17

SEQ ID NO: 614          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 614
FTFNSHGMH                                                             9

SEQ ID NO: 615          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 615
VISYDGTKKY FADSVKG                                                   17

SEQ ID NO: 616          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 616
FTFRNYAMN                                                             9
```

```
SEQ ID NO: 617         moltype = AA   length = 17
FEATURE                Location/Qualifiers
REGION                 1..17
                       note = Synthetic polypeptide
source                 1..17
                       mol_type = protein
                       organism = synthetic construct
SEQUENCE: 617
GISGGGDSTN YADSVKG                                                          17

SEQ ID NO: 618         moltype = AA   length = 9
FEATURE                Location/Qualifiers
REGION                 1..9
                       note = Synthetic polypeptide
source                 1..9
                       mol_type = protein
                       organism = synthetic construct
SEQUENCE: 618
LIFRNYAMS                                                                    9

SEQ ID NO: 619         moltype = AA   length = 17
FEATURE                Location/Qualifiers
REGION                 1..17
                       note = Synthetic polypeptide
source                 1..17
                       mol_type = protein
                       organism = synthetic construct
SEQUENCE: 619
SFSGSGGSAY YADSVKG                                                          17

SEQ ID NO: 620         moltype = AA   length = 17
FEATURE                Location/Qualifiers
REGION                 1..17
                       note = Synthetic polypeptide
source                 1..17
                       mol_type = protein
                       organism = synthetic construct
SEQUENCE: 620
GMRFDGTKIY YADSVKG                                                          17

SEQ ID NO: 621         moltype = AA   length = 10
FEATURE                Location/Qualifiers
REGION                 1..10
                       note = Synthetic polypeptide
source                 1..10
                       mol_type = protein
                       organism = synthetic construct
SEQUENCE: 621
GSISSDYWWS                                                                  10

SEQ ID NO: 622         moltype = AA   length = 16
FEATURE                Location/Qualifiers
REGION                 1..16
                       note = Synthetic polypeptide
source                 1..16
                       mol_type = protein
                       organism = synthetic construct
SEQUENCE: 622
EIYHTGSTNY NPSLKS                                                           16

SEQ ID NO: 623         moltype = AA   length = 10
FEATURE                Location/Qualifiers
REGION                 1..10
                       note = Synthetic polypeptide
source                 1..10
                       mol_type = protein
                       organism = synthetic construct
SEQUENCE: 623
GSITSSNWWS                                                                  10

SEQ ID NO: 624         moltype = AA   length = 16
FEATURE                Location/Qualifiers
REGION                 1..16
                       note = Synthetic polypeptide
source                 1..16
                       mol_type = protein
                       organism = synthetic construct
```

```
SEQUENCE: 624
DIYHSGSTSY NPSLKS                                                    16

SEQ ID NO: 625           moltype = AA   length = 10
FEATURE                  Location/Qualifiers
REGION                   1..10
                         note = Synthetic polypeptide
source                   1..10
                         mol_type = protein
                         organism = synthetic construct
SEQUENCE: 625
DSISSNNWWS                                                           10

SEQ ID NO: 626           moltype = AA   length = 16
FEATURE                  Location/Qualifiers
REGION                   1..16
                         note = Synthetic polypeptide
source                   1..16
                         mol_type = protein
                         organism = synthetic construct
SEQUENCE: 626
EIYHSGSTSY NPSLKS                                                    16

SEQ ID NO: 627           moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 627
FTFGDYYMS                                                            9

SEQ ID NO: 628           moltype = AA   length = 17
FEATURE                  Location/Qualifiers
REGION                   1..17
                         note = Synthetic polypeptide
source                   1..17
                         mol_type = protein
                         organism = synthetic construct
SEQUENCE: 628
YISSSGSSIY YTDSVRG                                                   17

SEQ ID NO: 629           moltype = AA   length = 10
FEATURE                  Location/Qualifiers
REGION                   1..10
                         note = Synthetic polypeptide
source                   1..10
                         mol_type = protein
                         organism = synthetic construct
SEQUENCE: 629
GSISSSDWWS                                                           10

SEQ ID NO: 630           moltype = AA   length = 16
FEATURE                  Location/Qualifiers
REGION                   1..16
                         note = Synthetic polypeptide
source                   1..16
                         mol_type = protein
                         organism = synthetic construct
SEQUENCE: 630
EIYHSGSTSY NPSVKS                                                    16

SEQ ID NO: 631           moltype = AA   length = 10
FEATURE                  Location/Qualifiers
REGION                   1..10
                         note = Synthetic polypeptide
source                   1..10
                         mol_type = protein
                         organism = synthetic construct
SEQUENCE: 631
DSISSSHWWC                                                           10

SEQ ID NO: 632           moltype = AA   length = 10
FEATURE                  Location/Qualifiers
REGION                   1..10
                         note = Synthetic polypeptide
```

```
source                  1..10
                        mol_type = protein
                        organism = synthetic construct
SEQUENCE: 632
GSISSSYWWS                                                              10

SEQ ID NO: 633          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 633
EVYHSGSTHY NPSLKS                                                       16

SEQ ID NO: 634          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 634
GSISSSNWWS                                                              10

SEQ ID NO: 635          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 635
DIYHTGSTSY NPSLKS                                                       16

SEQ ID NO: 636          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 636
FIFSDYYMN                                                               9

SEQ ID NO: 637          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 637
TISGSGKSIY YADSVKG                                                      17

SEQ ID NO: 638          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 638
FTFSDYYMS                                                               9

SEQ ID NO: 639          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 639
YITSSGNTKY YADSVKG                                                      17
```

```
SEQ ID NO: 640            moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 640
FTFDDYAMH                                                                 9

SEQ ID NO: 641            moltype = AA   length = 17
FEATURE                   Location/Qualifiers
REGION                    1..17
                          note = Synthetic polypeptide
source                    1..17
                          mol_type = protein
                          organism = synthetic construct
SEQUENCE: 641
GISWNGGGIG YADSVKG                                                       17

SEQ ID NO: 642            moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 642
FTFSSYAMS                                                                 9

SEQ ID NO: 643            moltype = AA   length = 17
FEATURE                   Location/Qualifiers
REGION                    1..17
                          note = Synthetic polypeptide
source                    1..17
                          mol_type = protein
                          organism = synthetic construct
SEQUENCE: 643
AISGSGGSTY YADSVKG                                                       17

SEQ ID NO: 644            moltype = AA   length = 10
FEATURE                   Location/Qualifiers
REGION                    1..10
                          note = Synthetic polypeptide
source                    1..10
                          mol_type = protein
                          organism = synthetic construct
SEQUENCE: 644
GSISSNKWWS                                                               10

SEQ ID NO: 645            moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 645
FTFSDDYMS                                                                 9

SEQ ID NO: 646            moltype = AA   length = 17
FEATURE                   Location/Qualifiers
REGION                    1..17
                          note = Synthetic polypeptide
source                    1..17
                          mol_type = protein
                          organism = synthetic construct
SEQUENCE: 646
YISGSGRAMY YADSVQG                                                       17

SEQ ID NO: 647            moltype = AA   length = 10
FEATURE                   Location/Qualifiers
REGION                    1..10
                          note = Synthetic polypeptide
source                    1..10
                          mol_type = protein
                          organism = synthetic construct
```

| | | |
|---|---|---|
| SEQUENCE: 647 SSITSSHWWS | | 10 |
| SEQ ID NO: 648 FEATURE REGION source | moltype = AA length = 16 Location/Qualifiers 1..16 note = Synthetic polypeptide 1..16 mol_type = protein organism = synthetic construct | |
| SEQUENCE: 648 DIYHSGGTTY NPSLKS | | 16 |
| SEQ ID NO: 649 FEATURE REGION source | moltype = AA length = 9 Location/Qualifiers 1..9 note = Synthetic polypeptide 1..9 mol_type = protein organism = synthetic construct | |
| SEQUENCE: 649 FTFNNYYMR | | 9 |
| SEQ ID NO: 650 FEATURE REGION source | moltype = AA length = 17 Location/Qualifiers 1..17 note = Synthetic polypeptide 1..17 mol_type = protein organism = synthetic construct | |
| SEQUENCE: 650 QISSSGSIKD YADSVKG | | 17 |
| SEQ ID NO: 651 FEATURE REGION source | moltype = AA length = 9 Location/Qualifiers 1..9 note = Synthetic polypeptide 1..9 mol_type = protein organism = synthetic construct | |
| SEQUENCE: 651 FTLRSYGMH | | 9 |
| SEQ ID NO: 652 FEATURE REGION source | moltype = AA length = 17 Location/Qualifiers 1..17 note = Synthetic polypeptide 1..17 mol_type = protein organism = synthetic construct | |
| SEQUENCE: 652 VSWYDGSNKH YADSVKG | | 17 |
| SEQ ID NO: 653 FEATURE REGION source | moltype = AA length = 9 Location/Qualifiers 1..9 note = Synthetic polypeptide 1..9 mol_type = protein organism = synthetic construct | |
| SEQUENCE: 653 FTFSSYTMH | | 9 |
| SEQ ID NO: 654 FEATURE REGION source | moltype = AA length = 17 Location/Qualifiers 1..17 note = Synthetic polypeptide 1..17 mol_type = protein organism = synthetic construct | |
| SEQUENCE: 654 VISYDGSNKY YADSVKG | | 17 |
| SEQ ID NO: 655 FEATURE REGION | moltype = AA length = 9 Location/Qualifiers 1..9 note = Synthetic polypeptide | |

```
source                          1..9
                                mol_type = protein
                                organism = synthetic construct
SEQUENCE: 655
DSISVSYWS                                                                        9

SEQ ID NO: 656                  moltype = AA   length = 16
FEATURE                         Location/Qualifiers
REGION                          1..16
                                note = Synthetic polypeptide
source                          1..16
                                mol_type = protein
                                organism = synthetic construct
SEQUENCE: 656
YIYNSGNANY NPSLES                                                               16

SEQ ID NO: 657                  moltype = AA   length = 11
FEATURE                         Location/Qualifiers
REGION                          1..11
                                note = Synthetic polypeptide
source                          1..11
                                mol_type = protein
                                organism = synthetic construct
SEQUENCE: 657
GSLSSDSHFW G                                                                    11

SEQ ID NO: 658                  moltype = AA   length = 16
FEATURE                         Location/Qualifiers
REGION                          1..16
                                note = Synthetic polypeptide
source                          1..16
                                mol_type = protein
                                organism = synthetic construct
SEQUENCE: 658
YIYYSGNANY NPSLQS                                                               16

SEQ ID NO: 659                  moltype = AA   length = 11
FEATURE                         Location/Qualifiers
REGION                          1..11
                                note = Synthetic polypeptide
source                          1..11
                                mol_type = protein
                                organism = synthetic construct
SEQUENCE: 659
GSVSSGSYYW S                                                                    11

SEQ ID NO: 660                  moltype = AA   length = 16
FEATURE                         Location/Qualifiers
REGION                          1..16
                                note = Synthetic polypeptide
source                          1..16
                                mol_type = protein
                                organism = synthetic construct
SEQUENCE: 660
YIYDSGNTNY NPSLKS                                                               16

SEQ ID NO: 661                  moltype = AA   length = 17
FEATURE                         Location/Qualifiers
REGION                          1..17
                                note = Synthetic polypeptide
source                          1..17
                                mol_type = protein
                                organism = synthetic construct
SEQUENCE: 661
CISSSGSMIY YADSVKG                                                              17

SEQ ID NO: 662                  moltype = AA   length = 10
FEATURE                         Location/Qualifiers
REGION                          1..10
                                note = Synthetic polypeptide
source                          1..10
                                mol_type = protein
                                organism = synthetic construct
SEQUENCE: 662
GSISTTDWWS                                                                      10
```

```
SEQ ID NO: 663         moltype = AA   length = 16
FEATURE                Location/Qualifiers
REGION                 1..16
                       note = Synthetic polypeptide
source                 1..16
                       mol_type = protein
                       organism = synthetic construct
SEQUENCE: 663
EINQSGSTSY SPSFKS                                                      16

SEQ ID NO: 664         moltype = AA   length = 10
FEATURE                Location/Qualifiers
REGION                 1..10
                       note = Synthetic polypeptide
source                 1..10
                       mol_type = protein
                       organism = synthetic construct
SEQUENCE: 664
GSISSGNWWS                                                             10

SEQ ID NO: 665         moltype = AA   length = 16
FEATURE                Location/Qualifiers
REGION                 1..16
                       note = Synthetic polypeptide
source                 1..16
                       mol_type = protein
                       organism = synthetic construct
SEQUENCE: 665
EIYHSGSANY NPSLKS                                                      16

SEQ ID NO: 666         moltype = AA   length = 9
FEATURE                Location/Qualifiers
REGION                 1..9
                       note = Synthetic polypeptide
source                 1..9
                       mol_type = protein
                       organism = synthetic construct
SEQUENCE: 666
FTFTTYAMH                                                               9

SEQ ID NO: 667         moltype = AA   length = 17
FEATURE                Location/Qualifiers
REGION                 1..17
                       note = Synthetic polypeptide
source                 1..17
                       mol_type = protein
                       organism = synthetic construct
SEQUENCE: 667
AVSYDGNNKY YADSVKG                                                     17

SEQ ID NO: 668         moltype = AA   length = 10
FEATURE                Location/Qualifiers
REGION                 1..10
                       note = Synthetic polypeptide
source                 1..10
                       mol_type = protein
                       organism = synthetic construct
SEQUENCE: 668
DSISSTNWWS                                                             10

SEQ ID NO: 669         moltype = AA   length = 16
FEATURE                Location/Qualifiers
REGION                 1..16
                       note = Synthetic polypeptide
source                 1..16
                       mol_type = protein
                       organism = synthetic construct
SEQUENCE: 669
EIFHSGSTNY NPFLKS                                                      16

SEQ ID NO: 670         moltype = AA   length = 10
FEATURE                Location/Qualifiers
REGION                 1..10
                       note = Synthetic polypeptide
source                 1..10
                       mol_type = protein
                       organism = synthetic construct
```

```
SEQUENCE: 670
GSISSNNWWS                                                                      10

SEQ ID NO: 671          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 671
DTYHSGSPSY NPSLKS                                                               16

SEQ ID NO: 672          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 672
FTFSNFGMH                                                                       9

SEQ ID NO: 673          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 673
IISYDRSNKD YADSVKG                                                              17

SEQ ID NO: 674          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 674
ASISSNHWWT                                                                      10

SEQ ID NO: 675          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 675
EIYHSGSPTY NPSLKS                                                               16

SEQ ID NO: 676          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 676
FTFSNSGMH                                                                       9

SEQ ID NO: 677          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 677
LISYTGETKY YSDSLKA                                                              17

SEQ ID NO: 678          moltype = AA  length = 10
FEATURE                 Location/Qualifiers
REGION                  1..10
                        note = Synthetic polypeptide
```

```
source                    1..10
                          mol_type = protein
                          organism = synthetic construct
SEQUENCE: 678
GSISSISWWS                                                              10

SEQ ID NO: 679            moltype = AA  length = 16
FEATURE                   Location/Qualifiers
REGION                    1..16
                          note = Synthetic polypeptide
source                    1..16
                          mol_type = protein
                          organism = synthetic construct
SEQUENCE: 679
EINHSGSTVY NPSLKS                                                       16

SEQ ID NO: 680            moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 680
FTFTDYYMS                                                                9

SEQ ID NO: 681            moltype = AA  length = 17
FEATURE                   Location/Qualifiers
REGION                    1..17
                          note = Synthetic polypeptide
source                    1..17
                          mol_type = protein
                          organism = synthetic construct
SEQUENCE: 681
YISSSGNTRY YADSVKG                                                      17

SEQ ID NO: 682            moltype = AA  length = 10
FEATURE                   Location/Qualifiers
REGION                    1..10
                          note = Synthetic polypeptide
source                    1..10
                          mol_type = protein
                          organism = synthetic construct
SEQUENCE: 682
GSITGSNWWS                                                              10

SEQ ID NO: 683            moltype = AA  length = 16
FEATURE                   Location/Qualifiers
REGION                    1..16
                          note = Synthetic polypeptide
source                    1..16
                          mol_type = protein
                          organism = synthetic construct
SEQUENCE: 683
EIYHTGSTSY NPSLKS                                                       16

SEQ ID NO: 684            moltype = AA  length = 11
FEATURE                   Location/Qualifiers
REGION                    1..11
                          note = Synthetic polypeptide
source                    1..11
                          mol_type = protein
                          organism = synthetic construct
SEQUENCE: 684
FSLSTSGVGV G                                                            11

SEQ ID NO: 685            moltype = AA  length = 16
FEATURE                   Location/Qualifiers
REGION                    1..16
                          note = Synthetic polypeptide
source                    1..16
                          mol_type = protein
                          organism = synthetic construct
SEQUENCE: 685
LIYWDDDKRY SPSLKS                                                       16
```

```
SEQ ID NO: 686          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 686
VIWYDESNKY YADSVKG                                                    17

SEQ ID NO: 687          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 687
VISDSGGSTY YADSVKG                                                    17

SEQ ID NO: 688          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 688
FTFINYAMT                                                              9

SEQ ID NO: 689          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 689
AISGNGDGTY YADSVKG                                                    17

SEQ ID NO: 690          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 690
FTFSSYAMH                                                              9

SEQ ID NO: 691          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 691
VISHDGSNKY YADSVKG                                                    17

SEQ ID NO: 692          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 692
GSVRGGSHYW S                                                          11

SEQ ID NO: 693          moltype = AA   length = 16
FEATURE                 Location/Qualifiers
REGION                  1..16
                        note = Synthetic polypeptide
source                  1..16
                        mol_type = protein
                        organism = synthetic construct
```

```
SEQUENCE: 693
YVYDSGSTNY NPSLKS                                                           16

SEQ ID NO: 694          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 694
FTFSNYAMS                                                                    9

SEQ ID NO: 695          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 695
AISGSGDSTY YADSVKG                                                          17

SEQ ID NO: 696          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 696
YITSSGNTMY YADSVKG                                                          17

SEQ ID NO: 697          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 697
EIYHSGSTTY NPSLKS                                                           16

SEQ ID NO: 698          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 698
YISSSGNTIY YADSVKG                                                          17

SEQ ID NO: 699          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 699
FTFSNYGMH                                                                    9

SEQ ID NO: 700          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 700
YTFNTYAMT                                                                    9

SEQ ID NO: 701          moltype = AA  length = 17
FEATURE                 Location/Qualifiers
REGION                  1..17
                        note = Synthetic polypeptide
source                  1..17
                        mol_type = protein
```

|  |  |  |
|---|---|---|
| | organism = synthetic construct | |
| SEQUENCE: 701 | | |
| WISTYNGNTV FGQKFQG | | 17 |
| | | |
| SEQ ID NO: 702 | moltype = AA  length = 9 | |
| FEATURE | Location/Qualifiers | |
| REGION | 1..9 | |
| | note = Synthetic polypeptide | |
| source | 1..9 | |
| | mol_type = protein | |
| | organism = synthetic construct | |
| SEQUENCE: 702 | | |
| FTFSTYWMS | | 9 |
| | | |
| SEQ ID NO: 703 | moltype = AA  length = 17 | |
| FEATURE | Location/Qualifiers | |
| REGION | 1..17 | |
| | note = Synthetic polypeptide | |
| source | 1..17 | |
| | mol_type = protein | |
| | organism = synthetic construct | |
| SEQUENCE: 703 | | |
| NIKQDGSEKY YVDSVKG | | 17 |
| | | |
| SEQ ID NO: 704 | moltype = AA  length = 17 | |
| FEATURE | Location/Qualifiers | |
| REGION | 1..17 | |
| | note = Synthetic polypeptide | |
| source | 1..17 | |
| | mol_type = protein | |
| | organism = synthetic construct | |
| SEQUENCE: 704 | | |
| VIWYDSRNQN YADSVKG | | 17 |
| | | |
| SEQ ID NO: 705 | moltype = AA  length = 17 | |
| FEATURE | Location/Qualifiers | |
| REGION | 1..17 | |
| | note = Synthetic polypeptide | |
| source | 1..17 | |
| | mol_type = protein | |
| | organism = synthetic construct | |
| SEQUENCE: 705 | | |
| TFSGRGGSTY YADFVKG | | 17 |
| | | |
| SEQ ID NO: 706 | moltype = AA  length = 9 | |
| FEATURE | Location/Qualifiers | |
| REGION | 1..9 | |
| | note = Synthetic polypeptide | |
| source | 1..9 | |
| | mol_type = protein | |
| | organism = synthetic construct | |
| SEQUENCE: 706 | | |
| FTFSSYGMH | | 9 |
| | | |
| SEQ ID NO: 707 | moltype = AA  length = 17 | |
| FEATURE | Location/Qualifiers | |
| REGION | 1..17 | |
| | note = Synthetic polypeptide | |
| source | 1..17 | |
| | mol_type = protein | |
| | organism = synthetic construct | |
| SEQUENCE: 707 | | |
| VISYDGSKKY SADSVKG | | 17 |
| | | |
| SEQ ID NO: 708 | moltype = AA  length = 9 | |
| FEATURE | Location/Qualifiers | |
| REGION | 1..9 | |
| | note = Synthetic polypeptide | |
| source | 1..9 | |
| | mol_type = protein | |
| | organism = synthetic construct | |
| SEQUENCE: 708 | | |
| FTFAEYAMH | | 9 |
| | | |
| SEQ ID NO: 709 | moltype = AA  length = 17 | |
| FEATURE | Location/Qualifiers | |
| REGION | 1..17 | |
| | note = Synthetic polypeptide | |

```
source                  1..17
                        mol_type = protein
                        organism = synthetic construct
SEQUENCE: 709
SISWNSGRIG YVDSVRG                                                          17

SEQ ID NO: 710          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 710
GSISSYYWS                                                                    9

SEQ ID NO: 711          moltype = AA   length = 16
FEATURE                 Location/Qualifiers
REGION                  1..16
                        note = Synthetic polypeptide
source                  1..16
                        mol_type = protein
                        organism = synthetic construct
SEQUENCE: 711
RIYTSGSGNY NPSLKR                                                           16

SEQ ID NO: 712          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 712
FTFSDYEMN                                                                    9

SEQ ID NO: 713          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 713
HISSSGNIIY YADSVKG                                                          17

SEQ ID NO: 714          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 714
FTFSAYAMS                                                                    9

SEQ ID NO: 715          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 715
AISGSDRRIY YADSVKG                                                          17

SEQ ID NO: 716          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 716
FTFSDHYMA                                                                    9
```

```
SEQ ID NO: 717         moltype = AA   length = 19
FEATURE                Location/Qualifiers
REGION                 1..19
                       note = Synthetic polypeptide
source                 1..19
                       mol_type = protein
                       organism = synthetic construct
SEQUENCE: 717
RIRNKPNSYT TEYAASVKG                                                    19

SEQ ID NO: 718         moltype = AA   length = 9
FEATURE                Location/Qualifiers
REGION                 1..9
                       note = Synthetic polypeptide
source                 1..9
                       mol_type = protein
                       organism = synthetic construct
SEQUENCE: 718
YSFTTYGIS                                                                9

SEQ ID NO: 719         moltype = AA   length = 17
FEATURE                Location/Qualifiers
REGION                 1..17
                       note = Synthetic polypeptide
source                 1..17
                       mol_type = protein
                       organism = synthetic construct
SEQUENCE: 719
WISGYSGDTN YAQKVQG                                                      17

SEQ ID NO: 720         moltype = AA   length = 11
FEATURE                Location/Qualifiers
REGION                 1..11
                       note = Synthetic polypeptide
source                 1..11
                       mol_type = protein
                       organism = synthetic construct
SEQUENCE: 720
GSISSSSYYW G                                                            11

SEQ ID NO: 721         moltype = AA   length = 16
FEATURE                Location/Qualifiers
REGION                 1..16
                       note = Synthetic polypeptide
source                 1..16
                       mol_type = protein
                       organism = synthetic construct
SEQUENCE: 721
SIYYSGSTYY NPSLKS                                                       16

SEQ ID NO: 722         moltype = AA   length = 9
FEATURE                Location/Qualifiers
REGION                 1..9
                       note = Synthetic polypeptide
source                 1..9
                       mol_type = protein
                       organism = synthetic construct
SEQUENCE: 722
FTFSRYSMN                                                                9

SEQ ID NO: 723         moltype = AA   length = 17
FEATURE                Location/Qualifiers
REGION                 1..17
                       note = Synthetic polypeptide
source                 1..17
                       mol_type = protein
                       organism = synthetic construct
SEQUENCE: 723
SISHSGRYIY YADSEKG                                                      17

SEQ ID NO: 724         moltype = AA   length = 9
FEATURE                Location/Qualifiers
REGION                 1..9
                       note = Synthetic polypeptide
source                 1..9
                       mol_type = protein
                       organism = synthetic construct
```

```
SEQUENCE: 724
FTFSDHYMD                                                                        9

SEQ ID NO: 725          moltype = AA  length = 19
FEATURE                 Location/Qualifiers
REGION                  1..19
                        note = Synthetic polypeptide
source                  1..19
                        mol_type = protein
                        organism = synthetic construct
SEQUENCE: 725
RTRNKPNSHT TEYAASVKG                                                            19

SEQ ID NO: 726          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 726
FIYTNYAMY                                                                        9

SEQ ID NO: 727          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 727
AISGSGGITY YADSVKG                                                              17

SEQ ID NO: 728          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 728
FIFSDYYMD                                                                        9

SEQ ID NO: 729          moltype = AA  length = 19
FEATURE                 Location/Qualifiers
REGION                  1..19
                        note = Synthetic polypeptide
source                  1..19
                        mol_type = protein
                        organism = synthetic construct
SEQUENCE: 729
RITNRPNSYT TEYAASVKG                                                            19

SEQ ID NO: 730          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 730
GSISSGSYYW S                                                                    11

SEQ ID NO: 731          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 731
RIYTSGSTNY NPSLKS                                                               16

SEQ ID NO: 732          moltype = AA  length = 16
FEATURE                 Location/Qualifiers
REGION                  1..16
                        note = Synthetic polypeptide
```

```
source                  1..16
                        mol_type = protein
                        organism = synthetic construct
SEQUENCE: 732
EIYHSESTNY NPSLKS                                                        16

SEQ ID NO: 733          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 733
GISWNSGSIG YADSVKG                                                       17

SEQ ID NO: 734          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 734
SIRSSGGRTE YADSVKG                                                       17

SEQ ID NO: 735          moltype = AA   length = 19
FEATURE                 Location/Qualifiers
REGION                  1..19
                        note = Synthetic polypeptide
source                  1..19
                        mol_type = protein
                        organism = synthetic construct
SEQUENCE: 735
RIRNKPNSYA TQYAASVKG                                                     19

SEQ ID NO: 736          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 736
FTFSSYSMN                                                                 9

SEQ ID NO: 737          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 737
SISSRSSFMY YADSVKG                                                       17

SEQ ID NO: 738          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 738
LISYDGSNKY YADSVKG                                                       17

SEQ ID NO: 739          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 739
FTFSSLAMH                                                                 9
```

```
SEQ ID NO: 740          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 740
TISYDVSNKY YADSVKG                                              17

SEQ ID NO: 741          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 741
YTFTSYGIS                                                        9

SEQ ID NO: 742          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 742
WISAYNGNTN YAQKLQG                                              17

SEQ ID NO: 743          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 743
GAISSGDYYW S                                                    11

SEQ ID NO: 744          moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 744
YIHYSGTTYN NPSLKS                                               16

SEQ ID NO: 745          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 745
VIRFDGSNTV YADSVKG                                              17

SEQ ID NO: 746          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 746
VISYDGSYKW YADSVKG                                              17

SEQ ID NO: 747          moltype = AA  length = 9
FEATURE                 Location/Qualifiers
REGION                  1..9
                        note = Synthetic polypeptide
source                  1..9
                        mol_type = protein
                        organism = synthetic construct
```

```
SEQUENCE: 747
FSFSSHAMT                                                                       9

SEQ ID NO: 748           moltype = AA  length = 17
FEATURE                  Location/Qualifiers
REGION                   1..17
                         note = Synthetic polypeptide
source                   1..17
                         mol_type = protein
                         organism = synthetic construct
SEQUENCE: 748
SIRGSDRTTN YADSVKG                                                             17

SEQ ID NO: 749           moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 749
FTFGTHAMS                                                                       9

SEQ ID NO: 750           moltype = AA  length = 17
FEATURE                  Location/Qualifiers
REGION                   1..17
                         note = Synthetic polypeptide
source                   1..17
                         mol_type = protein
                         organism = synthetic construct
SEQUENCE: 750
TFSGSGGRTY YADSVKG                                                             17

SEQ ID NO: 751           moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 751
FTFSDYYMD                                                                       9

SEQ ID NO: 752           moltype = AA  length = 19
FEATURE                  Location/Qualifiers
REGION                   1..19
                         note = Synthetic polypeptide
source                   1..19
                         mol_type = protein
                         organism = synthetic construct
SEQUENCE: 752
GIRNKPNSYT TEYAASVKG                                                           19

SEQ ID NO: 753           moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 753
ASIRSYLWS                                                                       9

SEQ ID NO: 754           moltype = AA  length = 16
FEATURE                  Location/Qualifiers
REGION                   1..16
                         note = Synthetic polypeptide
source                   1..16
                         mol_type = protein
                         organism = synthetic construct
SEQUENCE: 754
SIYHSGSTKY NPSLKS                                                              16

SEQ ID NO: 755           moltype = AA  length = 9
FEATURE                  Location/Qualifiers
REGION                   1..9
                         note = Synthetic polypeptide
```

```
source                    1..9
                          mol_type = protein
                          organism = synthetic construct
SEQUENCE: 755
FTFSGNAMH                                                                      9

SEQ ID NO: 756            moltype = AA  length = 17
FEATURE                   Location/Qualifiers
REGION                    1..17
                          note = Synthetic polypeptide
source                    1..17
                          mol_type = protein
                          organism = synthetic construct
SEQUENCE: 756
VILYDGSNQY YADSVKG                                                             17

SEQ ID NO: 757            moltype = AA  length = 10
FEATURE                   Location/Qualifiers
REGION                    1..10
                          note = Synthetic polypeptide
source                    1..10
                          mol_type = protein
                          organism = synthetic construct
SEQUENCE: 757
GSISSSNWWT                                                                     10

SEQ ID NO: 758            moltype = AA  length = 16
FEATURE                   Location/Qualifiers
REGION                    1..16
                          note = Synthetic polypeptide
source                    1..16
                          mol_type = protein
                          organism = synthetic construct
SEQUENCE: 758
EIYHSGSTNY NPSLES                                                              16

SEQ ID NO: 759            moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 759
FTFTYYAMS                                                                      9

SEQ ID NO: 760            moltype = AA  length = 17
FEATURE                   Location/Qualifiers
REGION                    1..17
                          note = Synthetic polypeptide
source                    1..17
                          mol_type = protein
                          organism = synthetic construct
SEQUENCE: 760
GISGSGDSTY NADSVKG                                                             17

SEQ ID NO: 761            moltype = AA  length = 17
FEATURE                   Location/Qualifiers
REGION                    1..17
                          note = Synthetic polypeptide
source                    1..17
                          mol_type = protein
                          organism = synthetic construct
SEQUENCE: 761
VISYDGSKKY FADSVKG                                                             17

SEQ ID NO: 762            moltype = AA  length = 17
FEATURE                   Location/Qualifiers
REGION                    1..17
                          note = Synthetic polypeptide
source                    1..17
                          mol_type = protein
                          organism = synthetic construct
SEQUENCE: 762
VIWYDGSNKY YADSVKG                                                             17
```

```
SEQ ID NO: 763           moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 763
GSISSGGYYW T                                                            11

SEQ ID NO: 764           moltype = AA   length = 16
FEATURE                  Location/Qualifiers
REGION                   1..16
                         note = Synthetic polypeptide
source                   1..16
                         mol_type = protein
                         organism = synthetic construct
SEQUENCE: 764
YIYYTGSTYY NPSLKS                                                       16

SEQ ID NO: 765           moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 765
FTFSSYAMT                                                                9

SEQ ID NO: 766           moltype = AA   length = 17
FEATURE                  Location/Qualifiers
REGION                   1..17
                         note = Synthetic polypeptide
source                   1..17
                         mol_type = protein
                         organism = synthetic construct
SEQUENCE: 766
DMNHSGDRTN YADSVRG                                                      17

SEQ ID NO: 767           moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 767
FIFSDHYMA                                                                9

SEQ ID NO: 768           moltype = AA   length = 19
FEATURE                  Location/Qualifiers
REGION                   1..19
                         note = Synthetic polypeptide
source                   1..19
                         mol_type = protein
                         organism = synthetic construct
SEQUENCE: 768
RSRNRPNSYT TEYAASAKG                                                    19

SEQ ID NO: 769           moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 769
YTFTGYYMH                                                                9

SEQ ID NO: 770           moltype = AA   length = 17
FEATURE                  Location/Qualifiers
REGION                   1..17
                         note = Synthetic polypeptide
```

```
source                    1..17
                          mol_type = protein
                          organism = synthetic construct
SEQUENCE: 770
RINPNSGGTN YAQKFQG                                                 17

SEQ ID NO: 771            moltype = AA   length = 19
FEATURE                   Location/Qualifiers
REGION                    1..19
                          note = Synthetic polypeptide
source                    1..19
                          mol_type = protein
                          organism = synthetic construct
SEQUENCE: 771
RIRNKPNGYT TEYAASVKG                                               19

SEQ ID NO: 772            moltype = AA   length = 19
FEATURE                   Location/Qualifiers
REGION                    1..19
                          note = Synthetic polypeptide
source                    1..19
                          mol_type = protein
                          organism = synthetic construct
SEQUENCE: 772
RSRNKPNSYI TEYAASVKG                                               19

SEQ ID NO: 773            moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 773
FSLSNTKLGV S                                                       11

SEQ ID NO: 774            moltype = AA   length = 16
FEATURE                   Location/Qualifiers
REGION                    1..16
                          note = Synthetic polypeptide
source                    1..16
                          mol_type = protein
                          organism = synthetic construct
SEQUENCE: 774
HIFSNAEKSS SKSLKS                                                  16

SEQ ID NO: 775            moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 775
LTFSTYTLH                                                          9

SEQ ID NO: 776            moltype = AA   length = 17
FEATURE                   Location/Qualifiers
REGION                    1..17
                          note = Synthetic polypeptide
source                    1..17
                          mol_type = protein
                          organism = synthetic construct
SEQUENCE: 776
VISSDGGNKY YADSVKG                                                 17

SEQ ID NO: 777            moltype = AA   length = 17
FEATURE                   Location/Qualifiers
REGION                    1..17
                          note = Synthetic polypeptide
source                    1..17
                          mol_type = protein
                          organism = synthetic construct
SEQUENCE: 777
MMSYDGGDKN YADSVKG                                                 17
```

```
SEQ ID NO: 778            moltype = AA   length = 17
FEATURE                   Location/Qualifiers
REGION                    1..17
                          note = Synthetic polypeptide
source                    1..17
                          mol_type = protein
                          organism = synthetic construct
SEQUENCE: 778
WISTYNGNTN YAQKLQG                                                    17

SEQ ID NO: 779            moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 779
FTFSNYWMN                                                              9

SEQ ID NO: 780            moltype = AA   length = 19
FEATURE                   Location/Qualifiers
REGION                    1..19
                          note = Synthetic polypeptide
source                    1..19
                          mol_type = protein
                          organism = synthetic construct
SEQUENCE: 780
RSTNKPNSYT TTYAASVRG                                                  19

SEQ ID NO: 781            moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 781
GSFSGYYWS                                                              9

SEQ ID NO: 782            moltype = AA   length = 16
FEATURE                   Location/Qualifiers
REGION                    1..16
                          note = Synthetic polypeptide
source                    1..16
                          mol_type = protein
                          organism = synthetic construct
SEQUENCE: 782
EINHRGSTDY NPSLKS                                                     16

SEQ ID NO: 783            moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 783
FTFSHAWMT                                                              9

SEQ ID NO: 784            moltype = AA   length = 19
FEATURE                   Location/Qualifiers
REGION                    1..19
                          note = Synthetic polypeptide
source                    1..19
                          mol_type = protein
                          organism = synthetic construct
SEQUENCE: 784
RIKSETDGGT ANYAAPVKG                                                  19

SEQ ID NO: 785            moltype = AA   length = 9
FEATURE                   Location/Qualifiers
REGION                    1..9
                          note = Synthetic polypeptide
```

```
source                     1..9
                           mol_type = protein
                           organism = synthetic construct
SEQUENCE: 785
GTFSSYVIS                                                              9

SEQ ID NO: 786             moltype = AA   length = 17
FEATURE                    Location/Qualifiers
REGION                     1..17
                           note = Synthetic polypeptide
source                     1..17
                           mol_type = protein
                           organism = synthetic construct
SEQUENCE: 786
GIIPIFGTPN YAQKFQG                                                     17

SEQ ID NO: 787             moltype = AA   length = 9
FEATURE                    Location/Qualifiers
REGION                     1..9
                           note = Synthetic polypeptide
source                     1..9
                           mol_type = protein
                           organism = synthetic construct
SEQUENCE: 787
FIFSSNSMH                                                              9

SEQ ID NO: 788             moltype = AA   length = 17
FEATURE                    Location/Qualifiers
REGION                     1..17
                           note = Synthetic polypeptide
source                     1..17
                           mol_type = protein
                           organism = synthetic construct
SEQUENCE: 788
IISNDGRNKF YADAVKG                                                     17

SEQ ID NO: 789             moltype = AA   length = 19
FEATURE                    Location/Qualifiers
REGION                     1..19
                           note = Synthetic polypeptide
source                     1..19
                           mol_type = protein
                           organism = synthetic construct
SEQUENCE: 789
RTRNKANSYT TKYAASVKG                                                   19

SEQ ID NO: 790             moltype = AA   length = 11
FEATURE                    Location/Qualifiers
REGION                     1..11
                           note = Synthetic polypeptide
source                     1..11
                           mol_type = protein
                           organism = synthetic construct
SEQUENCE: 790
FSLSNTKMGV T                                                           11

SEQ ID NO: 791             moltype = AA   length = 16
FEATURE                    Location/Qualifiers
REGION                     1..16
                           note = Synthetic polypeptide
source                     1..16
                           mol_type = protein
                           organism = synthetic construct
SEQUENCE: 791
HIFSNDEKSC NTSLKS                                                      16

SEQ ID NO: 792             moltype = AA   length = 19
FEATURE                    Location/Qualifiers
REGION                     1..19
                           note = Synthetic polypeptide
source                     1..19
                           mol_type = protein
                           organism = synthetic construct
SEQUENCE: 792
RSRNKVNSYT TDYAASVKG                                                   19
```

```
SEQ ID NO: 793           moltype = AA  length = 16
FEATURE                  Location/Qualifiers
REGION                   1..16
                         note = Synthetic polypeptide
source                   1..16
                         mol_type = protein
                         organism = synthetic construct
SEQUENCE: 793
YIYYSGSTNY NPSLKS                                                          16

SEQ ID NO: 794           moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 794
FTFDDYDMH                                                                   9

SEQ ID NO: 795           moltype = AA  length = 17
FEATURE                  Location/Qualifiers
REGION                   1..17
                         note = Synthetic polypeptide
source                   1..17
                         mol_type = protein
                         organism = synthetic construct
SEQUENCE: 795
GISWNSGGRG YADSVKG                                                         17

SEQ ID NO: 796           moltype = AA  length = 17
FEATURE                  Location/Qualifiers
REGION                   1..17
                         note = Synthetic polypeptide
source                   1..17
                         mol_type = protein
                         organism = synthetic construct
SEQUENCE: 796
VMSYDGSNKY YADSLKG                                                         17

SEQ ID NO: 797           moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 797
FNFSSYGMH                                                                   9

SEQ ID NO: 798           moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 798
LTLSSSAMS                                                                   9

SEQ ID NO: 799           moltype = AA  length = 17
FEATURE                  Location/Qualifiers
REGION                   1..17
                         note = Synthetic polypeptide
source                   1..17
                         mol_type = protein
                         organism = synthetic construct
SEQUENCE: 799
GITGSGSDSS YAASVKG                                                         17

SEQ ID NO: 800           moltype = AA  length = 17
FEATURE                  Location/Qualifiers
REGION                   1..17
                         note = Synthetic polypeptide
source                   1..17
                         mol_type = protein
                         organism = synthetic construct
```

```
SEQUENCE: 800
VISEDGNKDH YVDSVKG                                                                17

SEQ ID NO: 801         moltype = AA  length = 19
FEATURE                Location/Qualifiers
REGION                 1..19
                       note = Synthetic polypeptide
source                 1..19
                       mol_type = protein
                       organism = synthetic construct
SEQUENCE: 801
RSRNKVNSYI TEYAASVKG                                                              19

SEQ ID NO: 802         moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 802
FIFSDHYMD                                                                         9

SEQ ID NO: 803         moltype = AA  length = 19
FEATURE                Location/Qualifiers
REGION                 1..19
                       note = Synthetic polypeptide
source                 1..19
                       mol_type = protein
                       organism = synthetic construct
SEQUENCE: 803
RIRNKPNSYT TDYAAYVKG                                                              19

SEQ ID NO: 804         moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 804
FTLSSYVMH                                                                         9

SEQ ID NO: 805         moltype = AA  length = 17
FEATURE                Location/Qualifiers
REGION                 1..17
                       note = Synthetic polypeptide
source                 1..17
                       mol_type = protein
                       organism = synthetic construct
SEQUENCE: 805
VISSDGTNKY YADSVKG                                                                17

SEQ ID NO: 806         moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 806
GSISSDNWWS                                                                        10

SEQ ID NO: 807         moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 807
YTFTSYAMH                                                                         9

SEQ ID NO: 808         moltype = AA  length = 17
FEATURE                Location/Qualifiers
REGION                 1..17
                       note = Synthetic polypeptide
```

```
source                   1..17
                         mol_type = protein
                         organism = synthetic construct
SEQUENCE: 808
WINAGNGNTK YSQKFQG                                                17

SEQ ID NO: 809           moltype = AA   length = 19
FEATURE                  Location/Qualifiers
REGION                   1..19
                         note = Synthetic polypeptide
source                   1..19
                         mol_type = protein
                         organism = synthetic construct
SEQUENCE: 809
HVGNKANTYT TEYAASVKG                                              19

SEQ ID NO: 810           moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 810
YTFTSYDIN                                                          9

SEQ ID NO: 811           moltype = AA   length = 17
FEATURE                  Location/Qualifiers
REGION                   1..17
                         note = Synthetic polypeptide
source                   1..17
                         mol_type = protein
                         organism = synthetic construct
SEQUENCE: 811
WMNPNSGNTG YAQKFQG                                                17

SEQ ID NO: 812           moltype = AA   length = 17
FEATURE                  Location/Qualifiers
REGION                   1..17
                         note = Synthetic polypeptide
source                   1..17
                         mol_type = protein
                         organism = synthetic construct
SEQUENCE: 812
WINPNSGGTN YAQKFQG                                                17

SEQ ID NO: 813           moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 813
DSVSTNSAAW N                                                      11

SEQ ID NO: 814           moltype = AA   length = 18
FEATURE                  Location/Qualifiers
REGION                   1..18
                         note = Synthetic polypeptide
source                   1..18
                         mol_type = protein
                         organism = synthetic construct
SEQUENCE: 814
RTYYRSKWYN DYALSVKS                                               18

SEQ ID NO: 815           moltype = AA   length = 19
FEATURE                  Location/Qualifiers
REGION                   1..19
                         note = Synthetic polypeptide
source                   1..19
                         mol_type = protein
                         organism = synthetic construct
SEQUENCE: 815
RARNRANSYT TEYAASVKG                                              19
```

```
SEQ ID NO: 816          moltype = AA   length = 19
FEATURE                 Location/Qualifiers
REGION                  1..19
                        note = Synthetic polypeptide
source                  1..19
                        mol_type = protein
                        organism = synthetic construct
SEQUENCE: 816
RIRNKVNSYT TEYAASVKG                                                    19

SEQ ID NO: 817          moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 817
DSISSRSWWS                                                              10

SEQ ID NO: 818          moltype = AA   length = 16
FEATURE                 Location/Qualifiers
REGION                  1..16
                        note = Synthetic polypeptide
source                  1..16
                        mol_type = protein
                        organism = synthetic construct
SEQUENCE: 818
EIYHSGTTTY SPSLKS                                                       16

SEQ ID NO: 819          moltype = AA   length = 16
FEATURE                 Location/Qualifiers
REGION                  1..16
                        note = Synthetic polypeptide
source                  1..16
                        mol_type = protein
                        organism = synthetic construct
SEQUENCE: 819
EIYHSGSTNY NPSLKS                                                       16

SEQ ID NO: 820          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 820
YTFTSYAMN                                                               9

SEQ ID NO: 821          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 821
WINTNTGNPT YAQGFTG                                                      17

SEQ ID NO: 822          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 822
FTFSYSAIH                                                               9

SEQ ID NO: 823          moltype = AA   length = 10
FEATURE                 Location/Qualifiers
REGION                  1..10
                        note = Synthetic polypeptide
source                  1..10
                        mol_type = protein
                        organism = synthetic construct
```

```
SEQUENCE: 823
ASISSNNWWS                                                                       10

SEQ ID NO: 824         moltype = AA  length = 16
FEATURE                Location/Qualifiers
REGION                 1..16
                       note = Synthetic polypeptide
source                 1..16
                       mol_type = protein
                       organism = synthetic construct
SEQUENCE: 824
EIFHSGTTNY NPSLKS                                                                16

SEQ ID NO: 825         moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 825
ISISSSNWWS                                                                       10

SEQ ID NO: 826         moltype = AA  length = 16
FEATURE                Location/Qualifiers
REGION                 1..16
                       note = Synthetic polypeptide
source                 1..16
                       mol_type = protein
                       organism = synthetic construct
SEQUENCE: 826
EVYHSGSTKY NPSLKS                                                                16

SEQ ID NO: 827         moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 827
FTFSTSPLH                                                                         9

SEQ ID NO: 828         moltype = AA  length = 17
FEATURE                Location/Qualifiers
REGION                 1..17
                       note = Synthetic polypeptide
source                 1..17
                       mol_type = protein
                       organism = synthetic construct
SEQUENCE: 828
VSSFVATDKY YADSVKG                                                               17

SEQ ID NO: 829         moltype = AA  length = 17
FEATURE                Location/Qualifiers
REGION                 1..17
                       note = Synthetic polypeptide
source                 1..17
                       mol_type = protein
                       organism = synthetic construct
SEQUENCE: 829
SISSSSSYIY YADSVKG                                                               17

SEQ ID NO: 830         moltype = AA  length = 17
FEATURE                Location/Qualifiers
REGION                 1..17
                       note = Synthetic polypeptide
source                 1..17
                       mol_type = protein
                       organism = synthetic construct
SEQUENCE: 830
VIWYDGSNKN YADSVKG                                                               17

SEQ ID NO: 831         moltype = AA  length = 17
FEATURE                Location/Qualifiers
REGION                 1..17
                       note = Synthetic polypeptide
```

```
source                  1..17
                        mol_type = protein
                        organism = synthetic construct
SEQUENCE: 831
AISSSGGSTY YADSVKG                                                  17

SEQ ID NO: 832          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 832
FIFSNYWMS                                                            9

SEQ ID NO: 833          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 833
NIKPDGSEKY YVESVRG                                                  17

SEQ ID NO: 834          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 834
FTFSISGMH                                                            9

SEQ ID NO: 835          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 835
LIWYDGTKKY YADSVKG                                                  17

SEQ ID NO: 836          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 836
FSFGDYGMH                                                            9

SEQ ID NO: 837          moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 837
VILFDGSKKF YADSVRG                                                  17

SEQ ID NO: 838          moltype = AA   length = 19
FEATURE                 Location/Qualifiers
REGION                  1..19
                        note = Synthetic polypeptide
source                  1..19
                        mol_type = protein
                        organism = synthetic construct
SEQUENCE: 838
RTRNKANSYT TEYAASVKG                                                19
```

```
SEQ ID NO: 839         moltype = AA   length = 9
FEATURE                Location/Qualifiers
REGION                 1..9
                       note = Synthetic polypeptide
source                 1..9
                       mol_type = protein
                       organism = synthetic construct
SEQUENCE: 839
FNLIDYAMH                                                              9

SEQ ID NO: 840         moltype = AA   length = 17
FEATURE                Location/Qualifiers
REGION                 1..17
                       note = Synthetic polypeptide
source                 1..17
                       mol_type = protein
                       organism = synthetic construct
SEQUENCE: 840
GISWNSRSIG YADSVKG                                                    17

SEQ ID NO: 841         moltype = AA   length = 13
FEATURE                Location/Qualifiers
REGION                 1..13
                       note = Synthetic polypeptide
source                 1..13
                       mol_type = protein
                       organism = synthetic construct
SEQUENCE: 841
SGSSSNIGNN YVS                                                        13

SEQ ID NO: 842         moltype = AA   length = 7
FEATURE                Location/Qualifiers
REGION                 1..7
                       note = Synthetic polypeptide
source                 1..7
                       mol_type = protein
                       organism = synthetic construct
SEQUENCE: 842
DNKKRPS                                                                7

SEQ ID NO: 843         moltype = AA   length = 11
FEATURE                Location/Qualifiers
REGION                 1..11
                       note = Synthetic polypeptide
source                 1..11
                       mol_type = protein
                       organism = synthetic construct
SEQUENCE: 843
RASQSVSSNL A                                                          11

SEQ ID NO: 844         moltype = AA   length = 7
FEATURE                Location/Qualifiers
REGION                 1..7
                       note = Synthetic polypeptide
source                 1..7
                       mol_type = protein
                       organism = synthetic construct
SEQUENCE: 844
DASNRAT                                                                7

SEQ ID NO: 845         moltype = AA   length = 13
FEATURE                Location/Qualifiers
REGION                 1..13
                       note = Synthetic polypeptide
source                 1..13
                       mol_type = protein
                       organism = synthetic construct
SEQUENCE: 845
SGSRSNIGTY TIN                                                        13

SEQ ID NO: 846         moltype = AA   length = 7
FEATURE                Location/Qualifiers
REGION                 1..7
                       note = Synthetic polypeptide
source                 1..7
                       mol_type = protein
                       organism = synthetic construct
```

```
SEQUENCE: 846
SNNRGPS                                                                  7

SEQ ID NO: 847         moltype = AA  length = 13
FEATURE                Location/Qualifiers
REGION                 1..13
                       note = Synthetic polypeptide
source                 1..13
                       mol_type = protein
                       organism = synthetic construct
SEQUENCE: 847
SGSSSNIGNN YVA                                                          13

SEQ ID NO: 848         moltype = AA  length = 11
FEATURE                Location/Qualifiers
REGION                 1..11
                       note = Synthetic polypeptide
source                 1..11
                       mol_type = protein
                       organism = synthetic construct
SEQUENCE: 848
RASQTISVDL N                                                            11

SEQ ID NO: 849         moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 849
AASTLQS                                                                  7

SEQ ID NO: 850         moltype = AA  length = 11
FEATURE                Location/Qualifiers
REGION                 1..11
                       note = Synthetic polypeptide
source                 1..11
                       mol_type = protein
                       organism = synthetic construct
SEQUENCE: 850
RASQSIGSDL N                                                            11

SEQ ID NO: 851         moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 851
AATGLQS                                                                  7

SEQ ID NO: 852         moltype = AA  length = 13
FEATURE                Location/Qualifiers
REGION                 1..13
                       note = Synthetic polypeptide
source                 1..13
                       mol_type = protein
                       organism = synthetic construct
SEQUENCE: 852
SGSSSNIGTN TVS                                                          13

SEQ ID NO: 853         moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 853
SRTQRPS                                                                  7

SEQ ID NO: 854         moltype = AA  length = 13
FEATURE                Location/Qualifiers
REGION                 1..13
                       note = Synthetic polypeptide
```

```
source                  1..13
                        mol_type = protein
                        organism = synthetic construct
SEQUENCE: 854
SGSNSNIGNY YVS                                                          13

SEQ ID NO: 855          moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 855
DNNKRPS                                                                 7

SEQ ID NO: 856          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 856
SGSSSNIGNS YVS                                                          13

SEQ ID NO: 857          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 857
SGSSSNIGYS HVS                                                          13

SEQ ID NO: 858          moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 858
DNDKRPS                                                                 7

SEQ ID NO: 859          moltype = AA   length = 14
FEATURE                 Location/Qualifiers
REGION                  1..14
                        note = Synthetic polypeptide
source                  1..14
                        mol_type = protein
                        organism = synthetic construct
SEQUENCE: 859
TGTSSDVGAY NFVS                                                         14

SEQ ID NO: 860          moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 860
DVNKRPS                                                                 7

SEQ ID NO: 861          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 861
SGSSSNIGSN YVS                                                          13
```

```
SEQ ID NO: 862            moltype = AA   length = 7
FEATURE                   Location/Qualifiers
REGION                    1..7
                          note = Synthetic polypeptide
source                    1..7
                          mol_type = protein
                          organism = synthetic construct
SEQUENCE: 862
DNSKRPS                                                                    7

SEQ ID NO: 863            moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 863
RASRSVSSNL A                                                              11

SEQ ID NO: 864            moltype = AA   length = 7
FEATURE                   Location/Qualifiers
REGION                    1..7
                          note = Synthetic polypeptide
source                    1..7
                          mol_type = protein
                          organism = synthetic construct
SEQUENCE: 864
GASTRAT                                                                    7

SEQ ID NO: 865            moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 865
RASQGISSWL A                                                              11

SEQ ID NO: 866            moltype = AA   length = 7
FEATURE                   Location/Qualifiers
REGION                    1..7
                          note = Synthetic polypeptide
source                    1..7
                          mol_type = protein
                          organism = synthetic construct
SEQUENCE: 866
AASSLQS                                                                    7

SEQ ID NO: 867            moltype = AA   length = 14
FEATURE                   Location/Qualifiers
REGION                    1..14
                          note = Synthetic polypeptide
source                    1..14
                          mol_type = protein
                          organism = synthetic construct
SEQUENCE: 867
TGTSSDVGGY NYVS                                                           14

SEQ ID NO: 868            moltype = AA   length = 7
FEATURE                   Location/Qualifiers
REGION                    1..7
                          note = Synthetic polypeptide
source                    1..7
                          mol_type = protein
                          organism = synthetic construct
SEQUENCE: 868
DVSNRPS                                                                    7

SEQ ID NO: 869            moltype = AA   length = 14
FEATURE                   Location/Qualifiers
REGION                    1..14
                          note = Synthetic polypeptide
source                    1..14
                          mol_type = protein
                          organism = synthetic construct
```

```
SEQUENCE: 869
TGTSSDIGAY NYVS                                                              14

SEQ ID NO: 870       moltype = AA  length = 7
FEATURE              Location/Qualifiers
REGION               1..7
                     note = Synthetic polypeptide
source               1..7
                     mol_type = protein
                     organism = synthetic construct
SEQUENCE: 870
DVTNRPS                                                                       7

SEQ ID NO: 871       moltype = AA  length = 14
FEATURE              Location/Qualifiers
REGION               1..14
                     note = Synthetic polypeptide
source               1..14
                     mol_type = protein
                     organism = synthetic construct
SEQUENCE: 871
TGTGSDVGGY NFVS                                                              14

SEQ ID NO: 872       moltype = AA  length = 7
FEATURE              Location/Qualifiers
REGION               1..7
                     note = Synthetic polypeptide
source               1..7
                     mol_type = protein
                     organism = synthetic construct
SEQUENCE: 872
DVNNRPS                                                                       7

SEQ ID NO: 873       moltype = AA  length = 11
FEATURE              Location/Qualifiers
REGION               1..11
                     note = Synthetic polypeptide
source               1..11
                     mol_type = protein
                     organism = synthetic construct
SEQUENCE: 873
RASQSISSYL N                                                                 11

SEQ ID NO: 874       moltype = AA  length = 7
FEATURE              Location/Qualifiers
REGION               1..7
                     note = Synthetic polypeptide
source               1..7
                     mol_type = protein
                     organism = synthetic construct
SEQUENCE: 874
AASILQS                                                                       7

SEQ ID NO: 875       moltype = AA  length = 13
FEATURE              Location/Qualifiers
REGION               1..13
                     note = Synthetic polypeptide
source               1..13
                     mol_type = protein
                     organism = synthetic construct
SEQUENCE: 875
TGSSSNIGAG YDV                                                               13

SEQ ID NO: 876       moltype = AA  length = 7
FEATURE              Location/Qualifiers
REGION               1..7
                     note = Synthetic polypeptide
source               1..7
                     mol_type = protein
                     organism = synthetic construct
SEQUENCE: 876
GNSNRPS                                                                       7

SEQ ID NO: 877       moltype = AA  length = 11
FEATURE              Location/Qualifiers
REGION               1..11
                     note = Synthetic polypeptide
```

```
source                   1..11
                         mol_type = protein
                         organism = synthetic construct
SEQUENCE: 877
RASQSVNSYL V                                                                11

SEQ ID NO: 878           moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 878
RASQSVNRYL A                                                                11

SEQ ID NO: 879           moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 879
RASQSVSNYL A                                                                11

SEQ ID NO: 880           moltype = AA   length = 7
FEATURE                  Location/Qualifiers
REGION                   1..7
                         note = Synthetic polypeptide
source                   1..7
                         mol_type = protein
                         organism = synthetic construct
SEQUENCE: 880
DASSRAT                                                                      7

SEQ ID NO: 881           moltype = AA   length = 14
FEATURE                  Location/Qualifiers
REGION                   1..14
                         note = Synthetic polypeptide
source                   1..14
                         mol_type = protein
                         organism = synthetic construct
SEQUENCE: 881
TGTSSDIGGY NYVS                                                             14

SEQ ID NO: 882           moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 882
SGRSSNIGNS DVS                                                              13

SEQ ID NO: 883           moltype = AA   length = 7
FEATURE                  Location/Qualifiers
REGION                   1..7
                         note = Synthetic polypeptide
source                   1..7
                         mol_type = protein
                         organism = synthetic construct
SEQUENCE: 883
DNDERPS                                                                      7

SEQ ID NO: 884           moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 884
QASQDISNYL N                                                                11
```

```
SEQ ID NO: 885          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 885
DASNLER                                                                   7

SEQ ID NO: 886          moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 886
TGTSSDVGGD KYVS                                                          14

SEQ ID NO: 887          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 887
EVSNRPS                                                                   7

SEQ ID NO: 888          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 888
SGSSSNIGNY YVS                                                           13

SEQ ID NO: 889          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 889
KSSQSVLFGS NQKSCLA                                                       17

SEQ ID NO: 890          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 890
WASTRES                                                                   7

SEQ ID NO: 891          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 891
SGSSSNIGSN FVS                                                           13

SEQ ID NO: 892          moltype = AA  length = 13
FEATURE                 Location/Qualifiers
REGION                  1..13
                        note = Synthetic polypeptide
source                  1..13
                        mol_type = protein
                        organism = synthetic construct
```

```
SEQUENCE: 892
SGSSSNFGND YVS                                                                  13

SEQ ID NO: 893          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 893
SGSSSNIGND YVS                                                                  13

SEQ ID NO: 894          moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 894
TGTSSDVGGY KYVS                                                                 14

SEQ ID NO: 895          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 895
QASQDISNFL N                                                                    11

SEQ ID NO: 896          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 896
DASSLET                                                                          7

SEQ ID NO: 897          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 897
RASQNINTYL A                                                                    11

SEQ ID NO: 898          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 898
RASTLES                                                                          7

SEQ ID NO: 899          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 899
RASQGISNYL A                                                                    11

SEQ ID NO: 900          moltype = AA  length = 7
FEATURE                 Location/Qualifiers
REGION                  1..7
                        note = Synthetic polypeptide
```

```
source                      1..7
                            mol_type = protein
                            organism = synthetic construct
SEQUENCE: 900
AASTLRS                                                                 7

SEQ ID NO: 901              moltype = AA  length = 11
FEATURE                     Location/Qualifiers
REGION                      1..11
                            note = Synthetic polypeptide
source                      1..11
                            mol_type = protein
                            organism = synthetic construct
SEQUENCE: 901
RASQSVSSYL A                                                           11

SEQ ID NO: 902              moltype = AA  length = 7
FEATURE                     Location/Qualifiers
REGION                      1..7
                            note = Synthetic polypeptide
source                      1..7
                            mol_type = protein
                            organism = synthetic construct
SEQUENCE: 902
GASNRAT                                                                 7

SEQ ID NO: 903              moltype = AA  length = 7
FEATURE                     Location/Qualifiers
REGION                      1..7
                            note = Synthetic polypeptide
source                      1..7
                            mol_type = protein
                            organism = synthetic construct
SEQUENCE: 903
RASSLES                                                                 7

SEQ ID NO: 904              moltype = AA  length = 11
FEATURE                     Location/Qualifiers
REGION                      1..11
                            note = Synthetic polypeptide
source                      1..11
                            mol_type = protein
                            organism = synthetic construct
SEQUENCE: 904
GGHNVGSKSV H                                                           11

SEQ ID NO: 905              moltype = AA  length = 7
FEATURE                     Location/Qualifiers
REGION                      1..7
                            note = Synthetic polypeptide
source                      1..7
                            mol_type = protein
                            organism = synthetic construct
SEQUENCE: 905
DDSDRPS                                                                 7

SEQ ID NO: 906              moltype = AA  length = 11
FEATURE                     Location/Qualifiers
REGION                      1..11
                            note = Synthetic polypeptide
source                      1..11
                            mol_type = protein
                            organism = synthetic construct
SEQUENCE: 906
GGNNIGSKSV H                                                           11

SEQ ID NO: 907              moltype = AA  length = 7
FEATURE                     Location/Qualifiers
REGION                      1..7
                            note = Synthetic polypeptide
source                      1..7
                            mol_type = protein
                            organism = synthetic construct
SEQUENCE: 907
SNSDRPS                                                                 7
```

```
SEQ ID NO: 908            moltype = AA   length = 7
FEATURE                   Location/Qualifiers
REGION                    1..7
                          note = Synthetic polypeptide
source                    1..7
                          mol_type = protein
                          organism = synthetic construct
SEQUENCE: 908
EVSKRPS                                                              7

SEQ ID NO: 909            moltype = AA   length = 14
FEATURE                   Location/Qualifiers
REGION                    1..14
                          note = Synthetic polypeptide
source                    1..14
                          mol_type = protein
                          organism = synthetic construct
SEQUENCE: 909
TGTSTDVGGY NYVS                                                     14

SEQ ID NO: 910            moltype = AA   length = 16
FEATURE                   Location/Qualifiers
REGION                    1..16
                          note = Synthetic polypeptide
source                    1..16
                          mol_type = protein
                          organism = synthetic construct
SEQUENCE: 910
RSSQSLLHSN GYNYLD                                                   16

SEQ ID NO: 911            moltype = AA   length = 7
FEATURE                   Location/Qualifiers
REGION                    1..7
                          note = Synthetic polypeptide
source                    1..7
                          mol_type = protein
                          organism = synthetic construct
SEQUENCE: 911
LGSNRAS                                                              7

SEQ ID NO: 912            moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 912
RASQGIRNDL G                                                        11

SEQ ID NO: 913            moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 913
RASQSISTWL A                                                        11

SEQ ID NO: 914            moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 914
RASQGISSYL A                                                        11

SEQ ID NO: 915            moltype = AA   length = 11
FEATURE                   Location/Qualifiers
REGION                    1..11
                          note = Synthetic polypeptide
source                    1..11
                          mol_type = protein
                          organism = synthetic construct
```

```
SEQUENCE: 915
RASQSVSFNL A                                                              11

SEQ ID NO: 916          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 916
RASTRAA                                                                    7

SEQ ID NO: 917          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 917
KSSQSVLYSS NNKNSLA                                                        17

SEQ ID NO: 918          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 918
RASQSVSSWL A                                                              11

SEQ ID NO: 919          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 919
SGDALQYVY                                                                  9

SEQ ID NO: 920          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 920
KDTERPS                                                                    7

SEQ ID NO: 921          moltype = AA  length = 12
FEATURE                 Location/Qualifiers
REGION                  1..12
                        note = Synthetic polypeptide
source                  1..12
                        mol_type = protein
                        organism = synthetic construct
SEQUENCE: 921
RASRSVSGNY LA                                                             12

SEQ ID NO: 922          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 922
AASSRAT                                                                    7

SEQ ID NO: 923          moltype = AA  length = 11
FEATURE                 Location/Qualifiers
REGION                  1..11
                        note = Synthetic polypeptide
```

```
source                  1..11
                        mol_type = protein
                        organism = synthetic construct
SEQUENCE: 923
RASQSIRSYL N                                                         11

SEQ ID NO: 924          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 924
RASQSISSWL A                                                         11

SEQ ID NO: 925          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 925
QASSLES                                                               7

SEQ ID NO: 926          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 926
RASQSINNYL N                                                         11

SEQ ID NO: 927          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 927
GASTLQS                                                               7

SEQ ID NO: 928          moltype = AA  length = 12
FEATURE                 Location/Qualifiers
REGION                  1..12
                        note = Synthetic polypeptide
source                  1..12
                        mol_type = protein
                        organism = synthetic construct
SEQUENCE: 928
RASQSVSSSY LA                                                        12

SEQ ID NO: 929          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 929
GASSRAT                                                               7

SEQ ID NO: 930          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 930
RASQSISDWL A                                                         11
```

```
SEQ ID NO: 931         moltype = AA   length = 7
FEATURE                Location/Qualifiers
REGION                 1..7
                       note = Synthetic polypeptide
source                 1..7
                       mol_type = protein
                       organism = synthetic construct
SEQUENCE: 931
RASGLES                                                                      7

SEQ ID NO: 932         moltype = AA   length = 7
FEATURE                Location/Qualifiers
REGION                 1..7
                       note = Synthetic polypeptide
source                 1..7
                       mol_type = protein
                       organism = synthetic construct
SEQUENCE: 932
KASNLQS                                                                      7

SEQ ID NO: 933         moltype = AA   length = 12
FEATURE                Location/Qualifiers
REGION                 1..12
                       note = Synthetic polypeptide
source                 1..12
                       mol_type = protein
                       organism = synthetic construct
SEQUENCE: 933
RASQSVSSRY LA                                                               12

SEQ ID NO: 934         moltype = AA   length = 7
FEATURE                Location/Qualifiers
REGION                 1..7
                       note = Synthetic polypeptide
source                 1..7
                       mol_type = protein
                       organism = synthetic construct
SEQUENCE: 934
DVSKRPS                                                                      7

SEQ ID NO: 935         moltype = AA   length = 13
FEATURE                Location/Qualifiers
REGION                 1..13
                       note = Synthetic polypeptide
source                 1..13
                       mol_type = protein
                       organism = synthetic construct
SEQUENCE: 935
TRSSGSIASN YVQ                                                              13

SEQ ID NO: 936         moltype = AA   length = 7
FEATURE                Location/Qualifiers
REGION                 1..7
                       note = Synthetic polypeptide
source                 1..7
                       mol_type = protein
                       organism = synthetic construct
SEQUENCE: 936
EDNQRPS                                                                      7

SEQ ID NO: 937         moltype = AA   length = 13
FEATURE                Location/Qualifiers
REGION                 1..13
                       note = Synthetic polypeptide
source                 1..13
                       mol_type = protein
                       organism = synthetic construct
SEQUENCE: 937
SGSSSNIGNN DVS                                                              13

SEQ ID NO: 938         moltype = AA   length = 11
FEATURE                Location/Qualifiers
REGION                 1..11
                       note = Synthetic polypeptide
source                 1..11
                       mol_type = protein
                       organism = synthetic construct
```

```
SEQUENCE: 938
RASQGIRNDL A                                                                    11

SEQ ID NO: 939          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 939
RASSLET                                                                         7

SEQ ID NO: 940          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 940
RASQNVGGWL A                                                                    11

SEQ ID NO: 941          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 941
QASRLEN                                                                         7

SEQ ID NO: 942          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 942
RASQSISQYL N                                                                    11

SEQ ID NO: 943          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 943
PASSFQS                                                                         7

SEQ ID NO: 944          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 944
GGNYIGGKSV H                                                                    11

SEQ ID NO: 945          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 945
NDNDRPS                                                                         7

SEQ ID NO: 946          moltype = AA  length = 11
FEATURE                 Location/Qualifiers
REGION                  1..11
                        note = Synthetic polypeptide
```

```
source                      1..11
                            mol_type = protein
                            organism = synthetic construct
SEQUENCE: 946
RASQRVNSNL A                                                                11

SEQ ID NO: 947              moltype = AA  length = 12
FEATURE                     Location/Qualifiers
REGION                      1..12
                            note = Synthetic polypeptide
source                      1..12
                            mol_type = protein
                            organism = synthetic construct
SEQUENCE: 947
RASQSVSSSF LA                                                               12

SEQ ID NO: 948              moltype = AA  length = 7
FEATURE                     Location/Qualifiers
REGION                      1..7
                            note = Synthetic polypeptide
source                      1..7
                            mol_type = protein
                            organism = synthetic construct
SEQUENCE: 948
RASGLET                                                                     7

SEQ ID NO: 949              moltype = AA  length = 13
FEATURE                     Location/Qualifiers
REGION                      1..13
                            note = Synthetic polypeptide
source                      1..13
                            mol_type = protein
                            organism = synthetic construct
SEQUENCE: 949
SGSSSNFGSN FVY                                                              13

SEQ ID NO: 950              moltype = AA  length = 7
FEATURE                     Location/Qualifiers
REGION                      1..7
                            note = Synthetic polypeptide
source                      1..7
                            mol_type = protein
                            organism = synthetic construct
SEQUENCE: 950
RVNQRPS                                                                     7

SEQ ID NO: 951              moltype = AA  length = 12
FEATURE                     Location/Qualifiers
REGION                      1..12
                            note = Synthetic polypeptide
source                      1..12
                            mol_type = protein
                            organism = synthetic construct
SEQUENCE: 951
RASQSVSSSY LS                                                               12

SEQ ID NO: 952              moltype = AA  length = 11
FEATURE                     Location/Qualifiers
REGION                      1..11
                            note = Synthetic polypeptide
source                      1..11
                            mol_type = protein
                            organism = synthetic construct
SEQUENCE: 952
RASQTITRYM N                                                                11

SEQ ID NO: 953              moltype = AA  length = 7
FEATURE                     Location/Qualifiers
REGION                      1..7
                            note = Synthetic polypeptide
source                      1..7
                            mol_type = protein
                            organism = synthetic construct
SEQUENCE: 953
ATSSLQS                                                                     7
```

```
SEQ ID NO: 954          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 954
RASQDIRKFL N                                                                    11

SEQ ID NO: 955          moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 955
GASSLQS                                                                         7

SEQ ID NO: 956          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 956
SGDKLGYTYT C                                                                    11

SEQ ID NO: 957          moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 957
QDTKRPS                                                                         7

SEQ ID NO: 958          moltype = AA   length = 14
FEATURE                 Location/Qualifiers
REGION                  1..14
                        note = Synthetic polypeptide
source                  1..14
                        mol_type = protein
                        organism = synthetic construct
SEQUENCE: 958
AGTRSDVGGY NFVS                                                                 14

SEQ ID NO: 959          moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 959
EVNKRPS                                                                         7

SEQ ID NO: 960          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 960
RTSQSVSSFL A                                                                    11

SEQ ID NO: 961          moltype = AA   length = 11
FEATURE                 Location/Qualifiers
REGION                  1..11
                        note = Synthetic polypeptide
source                  1..11
                        mol_type = protein
                        organism = synthetic construct
```

| | | | |
|---|---|---|---|
| SEQUENCE: 961 | | | |
| RASQSVSDWL A | | | 11 |
| | | | |
| SEQ ID NO: 962 | moltype = AA  length = 7 | | |
| FEATURE | Location/Qualifiers | | |
| REGION | 1..7 | | |
| | note = Synthetic polypeptide | | |
| source | 1..7 | | |
| | mol_type = protein | | |
| | organism = synthetic construct | | |
| SEQUENCE: 962 | | | |
| RASSLQS | | | 7 |
| | | | |
| SEQ ID NO: 963 | moltype = AA  length = 11 | | |
| FEATURE | Location/Qualifiers | | |
| REGION | 1..11 | | |
| | note = Synthetic polypeptide | | |
| source | 1..11 | | |
| | mol_type = protein | | |
| | organism = synthetic construct | | |
| SEQUENCE: 963 | | | |
| RASQSVSSNV A | | | 11 |
| | | | |
| SEQ ID NO: 964 | moltype = AA  length = 11 | | |
| FEATURE | Location/Qualifiers | | |
| REGION | 1..11 | | |
| | note = Synthetic polypeptide | | |
| source | 1..11 | | |
| | mol_type = protein | | |
| | organism = synthetic construct | | |
| SEQUENCE: 964 | | | |
| SGDALPKKYV Y | | | 11 |
| | | | |
| SEQ ID NO: 965 | moltype = AA  length = 7 | | |
| FEATURE | Location/Qualifiers | | |
| REGION | 1..7 | | |
| | note = Synthetic polypeptide | | |
| source | 1..7 | | |
| | mol_type = protein | | |
| | organism = synthetic construct | | |
| SEQUENCE: 965 | | | |
| EDRRGPS | | | 7 |
| | | | |
| SEQ ID NO: 966 | moltype = AA  length = 17 | | |
| FEATURE | Location/Qualifiers | | |
| REGION | 1..17 | | |
| | note = Synthetic polypeptide | | |
| source | 1..17 | | |
| | mol_type = protein | | |
| | organism = synthetic construct | | |
| SEQUENCE: 966 | | | |
| KSSQSVFYSS NSQNYLA | | | 17 |
| | | | |
| SEQ ID NO: 967 | moltype = AA  length = 11 | | |
| FEATURE | Location/Qualifiers | | |
| REGION | 1..11 | | |
| | note = Synthetic polypeptide | | |
| source | 1..11 | | |
| | mol_type = protein | | |
| | organism = synthetic construct | | |
| SEQUENCE: 967 | | | |
| RASQSISNWL A | | | 11 |
| | | | |
| SEQ ID NO: 968 | moltype = AA  length = 7 | | |
| FEATURE | Location/Qualifiers | | |
| REGION | 1..7 | | |
| | note = Synthetic polypeptide | | |
| source | 1..7 | | |
| | mol_type = protein | | |
| | organism = synthetic construct | | |
| SEQUENCE: 968 | | | |
| KASRLES | | | 7 |
| | | | |
| SEQ ID NO: 969 | moltype = AA  length = 11 | | |
| FEATURE | Location/Qualifiers | | |
| REGION | 1..11 | | |
| | note = Synthetic polypeptide | | |

```
source                      1..11
                            mol_type = protein
                            organism = synthetic construct
SEQUENCE: 969
RASQTISSWL A                                                        11

SEQ ID NO: 970              moltype = AA   length = 11
FEATURE                     Location/Qualifiers
REGION                      1..11
                            note = Synthetic polypeptide
source                      1..11
                            mol_type = protein
                            organism = synthetic construct
SEQUENCE: 970
SGDALPKQYG Y                                                        11

SEQ ID NO: 971              moltype = AA   length = 7
FEATURE                     Location/Qualifiers
REGION                      1..7
                            note = Synthetic polypeptide
source                      1..7
                            mol_type = protein
                            organism = synthetic construct
SEQUENCE: 971
KDSERPS                                                             7

SEQ ID NO: 972              moltype = AA   length = 7
FEATURE                     Location/Qualifiers
REGION                      1..7
                            note = Synthetic polypeptide
source                      1..7
                            mol_type = protein
                            organism = synthetic construct
SEQUENCE: 972
EVTKRPS                                                             7

SEQ ID NO: 973              moltype = AA   length = 11
FEATURE                     Location/Qualifiers
REGION                      1..11
                            note = Synthetic polypeptide
source                      1..11
                            mol_type = protein
                            organism = synthetic construct
SEQUENCE: 973
SGDALSKQYA Y                                                        11

SEQ ID NO: 974              moltype = AA   length = 7
FEATURE                     Location/Qualifiers
REGION                      1..7
                            note = Synthetic polypeptide
source                      1..7
                            mol_type = protein
                            organism = synthetic construct
SEQUENCE: 974
DVSKLKT                                                             7

SEQ ID NO: 975              moltype = AA   length = 11
FEATURE                     Location/Qualifiers
REGION                      1..11
                            note = Synthetic polypeptide
source                      1..11
                            mol_type = protein
                            organism = synthetic construct
SEQUENCE: 975
RASQSISGWL A                                                        11

SEQ ID NO: 976              moltype = AA   length = 7
FEATURE                     Location/Qualifiers
REGION                      1..7
                            note = Synthetic polypeptide
source                      1..7
                            mol_type = protein
                            organism = synthetic construct
SEQUENCE: 976
KASILES                                                             7
```

```
SEQ ID NO: 977           moltype = AA   length = 14
FEATURE                  Location/Qualifiers
REGION                   1..14
                         note = Synthetic polypeptide
source                   1..14
                         mol_type = protein
                         organism = synthetic construct
SEQUENCE: 977
TGNSSNIGAG YEVH                                                              14

SEQ ID NO: 978           moltype = AA   length = 7
FEATURE                  Location/Qualifiers
REGION                   1..7
                         note = Synthetic polypeptide
source                   1..7
                         mol_type = protein
                         organism = synthetic construct
SEQUENCE: 978
GNNNRPS                                                                       7

SEQ ID NO: 979           moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 979
SGDALPKQYA Y                                                                 11

SEQ ID NO: 980           moltype = AA   length = 11
FEATURE                  Location/Qualifiers
REGION                   1..11
                         note = Synthetic polypeptide
source                   1..11
                         mol_type = protein
                         organism = synthetic construct
SEQUENCE: 980
RASQSVSNYF A                                                                 11

SEQ ID NO: 981           moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 981
SGSNSNIGNN FVS                                                               13

SEQ ID NO: 982           moltype = AA   length = 7
FEATURE                  Location/Qualifiers
REGION                   1..7
                         note = Synthetic polypeptide
source                   1..7
                         mol_type = protein
                         organism = synthetic construct
SEQUENCE: 982
DNNERPS                                                                       7

SEQ ID NO: 983           moltype = AA   length = 7
FEATURE                  Location/Qualifiers
REGION                   1..7
                         note = Synthetic polypeptide
source                   1..7
                         mol_type = protein
                         organism = synthetic construct
SEQUENCE: 983
DSSNRAT                                                                       7

SEQ ID NO: 984           moltype = AA   length = 11
FEATURE                  Location/Qualifiers
REGION                   1..11
                         note = Synthetic polypeptide
source                   1..11
                         mol_type = protein
                         organism = synthetic construct
```

```
SEQUENCE: 984
RASQSVTSKL A                                                                    11

SEQ ID NO: 985         moltype = AA  length = 16
FEATURE                Location/Qualifiers
REGION                 1..16
                       note = Synthetic polypeptide
source                 1..16
                       mol_type = protein
                       organism = synthetic construct
SEQUENCE: 985
RSSQSLLHSN GYNSLD                                                               16

SEQ ID NO: 986         moltype = AA  length = 13
FEATURE                Location/Qualifiers
REGION                 1..13
                       note = Synthetic polypeptide
source                 1..13
                       mol_type = protein
                       organism = synthetic construct
SEQUENCE: 986
SGSSSNIGSN TVH                                                                  13

SEQ ID NO: 987         moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 987
SNNQRPS                                                                          7

SEQ ID NO: 988         moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 988
DDNKRPS                                                                          7

SEQ ID NO: 989         moltype = AA  length = 14
FEATURE                Location/Qualifiers
REGION                 1..14
                       note = Synthetic polypeptide
source                 1..14
                       mol_type = protein
                       organism = synthetic construct
SEQUENCE: 989
TGSSSDIGAG YDVH                                                                 14

SEQ ID NO: 990         moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 990
GNTNRPS                                                                          7

SEQ ID NO: 991         moltype = AA  length = 17
FEATURE                Location/Qualifiers
REGION                 1..17
                       note = Synthetic polypeptide
source                 1..17
                       mol_type = protein
                       organism = synthetic construct
SEQUENCE: 991
KSSQSVFFSS DNKNYLA                                                              17

SEQ ID NO: 992         moltype = AA  length = 13
FEATURE                Location/Qualifiers
REGION                 1..13
                       note = Synthetic polypeptide
```

```
source                  1..13
                        mol_type = protein
                        organism = synthetic construct
SEQUENCE: 992
TRSSGSIAST YVQ                                                              13

SEQ ID NO: 993          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 993
EDNQRPP                                                                      7

SEQ ID NO: 994          moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 994
TGTSSDFGGY NYVS                                                             14

SEQ ID NO: 995          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 995
EVAKRPS                                                                      7

SEQ ID NO: 996          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 996
RASESISIYL N                                                                11

SEQ ID NO: 997          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 997
AASSLQR                                                                      7

SEQ ID NO: 998          moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 998
TGTSSDVGGF NYVS                                                             14

SEQ ID NO: 999          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 999
EVNRRPS                                                                      7
```

```
SEQ ID NO: 1000         moltype = AA  length = 16
FEATURE                 Location/Qualifiers
REGION                  1..16
                        note = Synthetic polypeptide
source                  1..16
                        mol_type = protein
                        organism = synthetic construct
SEQUENCE: 1000
RSSQSLVHSD GNTYLS                                                           16

SEQ ID NO: 1001         moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 1001
KISNRFS                                                                      7

SEQ ID NO: 1002         moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 1002
DASNLET                                                                      7

SEQ ID NO: 1003         moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 1003
SGDKLGDKYA C                                                                11

SEQ ID NO: 1004         moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 1004
QDSKRPS                                                                      7

SEQ ID NO: 1005         moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 1005
RASQGISNNL A                                                                11

SEQ ID NO: 1006         moltype = AA  length = 13
FEATURE                 Location/Qualifiers
REGION                  1..13
                        note = Synthetic polypeptide
VARIANT                 5
                        note = S or T
VARIANT                 7
                        note = S or no amino acid
VARIANT                 8
                        note = L or P
VARIANT                 12..13
                        note = K, G, or R
VARIANT                 12
                        note = K, G, or R
source                  1..13
                        mol_type = protein
                        organism = synthetic construct
```

```
SEQUENCE: 1006
GTWDXSXXSA GXV                                                              13

SEQ ID NO: 1007         moltype = AA  length = 14
FEATURE                 Location/Qualifiers
REGION                  1..14
                        note = Synthetic polypeptide
VARIANT                 2
                        note = K or R
VARIANT                 3
                        note = Y, F, T, A, G, or Y
VARIANT                 7
                        note = S, N, or R
VARIANT                 8
                        note = A or G
VARIANT                 11
                        note = W or Y
VARIANT                 12
                        note = F, L, I, A, or E
VARIANT                 13
                        note = D, E, or H
VARIANT                 14
                        note = Y, H, or S
source                  1..14
                        mol_type = protein
                        organism = synthetic construct
SEQUENCE: 1007
AXXYDSXXYY XXXX                                                             14

SEQ ID NO: 1008         moltype = AA  length = 7
FEATURE                 Location/Qualifiers
REGION                  1..7
                        note = Synthetic polypeptide
VARIANT                 1
                        note = D, E, or R
VARIANT                 3
                        note = S, T, N, or A
VARIANT                 4
                        note = N, K, or Q
source                  1..7
                        mol_type = protein
                        organism = synthetic construct
SEQUENCE: 1008
XVXXRPS                                                                     7

SEQ ID NO: 1009         moltype = AA  length = 7
FEATURE                 Location/Qualifiers
REGION                  1..7
                        note = Synthetic polypeptide
VARIANT                 1
                        note = R, Q, or K
VARIANT                 4
                        note = T, S, G, R, or I
VARIANT                 7
                        note = T or S
source                  1..7
                        mol_type = protein
                        organism = synthetic construct
SEQUENCE: 1009
XASXLEX                                                                     7

SEQ ID NO: 1010         moltype = AA  length = 16
FEATURE                 Location/Qualifiers
REGION                  1..16
                        note = Synthetic polypeptide
VARIANT                 1
                        note = D, E, or S
VARIANT                 2
                        note = I or V
VARIANT                 3
                        note = F or Y
VARIANT                 5
                        note = X or T
VARIANT                 6
                        note = G or E
VARIANT                 7
                        note = S, G, or T
VARIANT                 8
                        note = T or A
```

```
VARIANT                 9
                        note = N, S, H, K, or T
VARIANT                 11
                        note = N or S
VARIANT                 13
                        note = S or F
VARIANT                 14
                        note = L or V
VARIANT                 15
                        note = K or E
source                  1..16
                        mol_type = protein
                        organism = synthetic construct
SEQUENCE: 1010
XXXHXXXXXY XPXXXS                                                           16

SEQ ID NO: 1011         moltype = AA  length = 17
FEATURE                 Location/Qualifiers
REGION                  1..17
                        note = Synthetic polypeptide
VARIANT                 1
                        note = V or L
VARIANT                 2
                        note = I or M
VARIANT                 3
                        note = S, W, or L
VARIANT                 4
                        note = F or Y
VARIANT                 6
                        note = E or G
VARIANT                 7
                        note = S or T
VARIANT                 8
                        note = K, N, or Y
VARIANT                 10
                        note = F, W, or Y
VARIANT                 11
                        note = Y or F
VARIANT                 15
                        note = V or L
VARIANT                 16
                        note = K or L
source                  1..17
                        mol_type = protein
                        organism = synthetic construct
SEQUENCE: 1011
XXXXDXXXKX XADSXXG                                                          17

SEQ ID NO: 1012         moltype = AA  length = 13
FEATURE                 Location/Qualifiers
REGION                  1..13
                        note = Synthetic polypeptide
VARIANT                 4
                        note = N or S
VARIANT                 7
                        note = I or F
VARIANT                 9
                        note = S or N
VARIANT                 10
                        note = N, Y, S, or D
VARIANT                 11
                        note = Y, F, or D
VARIANT                 13
                        note = S or A
source                  1..13
                        mol_type = protein
                        organism = synthetic construct
SEQUENCE: 1012
SGSXSNXGXX XVX                                                              13

SEQ ID NO: 1013         moltype = AA  length = 14
FEATURE                 Location/Qualifiers
REGION                  1..14
                        note = Synthetic polypeptide
VARIANT                 1
                        note = A or T
VARIANT                 4
                        note = S, G, or R
```

```
VARIANT                 5
                        note = S or T
VARIANT                 7
                        note = V, F, or I
VARIANT                 9
                        note = G or A
VARIANT                 10
                        note = Y, D, or F
VARIANT                 11
                        note = K or N
VARIANT                 12
                        note = Y or F
source                  1..14
                        mol_type = protein
                        organism = synthetic construct
SEQUENCE: 1013
XGTXXDXGXX XXVS                                                      14

SEQ ID NO: 1014         moltype = AA  length = 9
FEATURE                 Location/Qualifiers
REGION                  1..9
                        note = Synthetic polypeptide
VARIANT                 2
                        note = I or T
VARIANT                 6
                        note = H or Y
VARIANT                 9
                        note = A or D
source                  1..9
                        mol_type = protein
                        organism = synthetic construct
SEQUENCE: 1014
FXFSDXYMX                                                             9
```

What is claimed is:

1. A method of treating or preventing a Yellow Fever Virus (YFV) infection or at least one symptom arising therefrom, comprising administering to a patient in need thereof or suspected of being in need thereof an isolated antibody or antigen-binding fragment thereof,
wherein the antibody or antigen-binding fragment thereof specifically binds to a YFV protein, wherein the antibody or antigen-binding fragment thereof comprises:
(i) a heavy chain variable region comprising the amino acid sequence of SEQ ID NO:307 and a light chain variable region comprising the amino acid sequence of SEQ ID NO:459;
(ii) a heavy chain variable region comprising the amino acid sequence of SEQ ID NO:308 and a light chain variable region comprising the amino acid sequence of SEQ ID NO:460;
(iii) a heavy chain variable region comprising the amino acid sequence of SEQ ID NO:311 and a light chain variable region comprising the amino acid sequence of SEQ ID NO:463;
(iv) a heavy chain variable region comprising the amino acid sequence of SEQ ID NO:320 and a light chain variable region comprising the amino acid sequence of SEQ ID NO:471; or
(v) a heavy chain variable region comprising the amino acid sequence of SEQ ID NO:341 and a light chain variable region comprising the amino acid sequence of SEQ ID NO:492.

2. The method of claim 1, wherein the antibody or antigen-binding fragment thereof comprises a heavy chain variable region comprising the amino acid sequence of SEQ ID NO:307 and a light chain variable region comprising the amino acid sequence of SEQ ID NO:459.

3. The method of claim 1, wherein the antibody or antigen-binding fragment thereof comprises a heavy chain variable region comprising the amino acid sequence of SEQ ID NO:308 and a light chain variable region comprising the amino acid sequence of SEQ ID NO:460.

4. The method of claim 1, wherein the antibody or antigen-binding fragment thereof comprises a heavy chain variable region comprising the amino acid sequence of SEQ ID NO:311 and a light chain variable region comprising the amino acid sequence of SEQ ID NO:463.

5. The method of claim 1, wherein the antibody or antigen-binding fragment thereof comprises a heavy chain variable region comprising the amino acid sequence of SEQ ID NO:320 and a light chain variable region comprising the amino acid sequence of SEQ ID NO:471.

6. The method of claim 1, wherein the antibody or antigen-binding fragment thereof comprises a heavy chain variable region comprising the amino acid sequence of SEQ ID NO:341 and a light chain variable region comprising the amino acid sequence of SEQ ID NO:492.

7. The method of claim 1, wherein the at least one symptom associated with the YFV infection is treated, alleviated, or reduced in severity.

8. The method of claim 1, wherein the at least one symptom associated with the YFV infection is fever, chills, headache, low back pain, myalgia, loss of appetite, nausea, vomiting, or fatigue.

9. The method of claim 1, wherein the isolated antibody or antigen-binding fragment thereof:
(a) displays neutralization activity toward YFV in vitro;
(b) displays an in vitro neutralization potency ($IC_{50}$) of between about 0.5 microgram/milliliter (μl/ml) to about 5 μl/ml; between about 0.05 μl/ml to about 0.5 μl/ml; or less than about 0.05 mg/ml; and/or
(c) binds to an envelope protein of YFV.

10. The method of claim 9, wherein the isolated antibody or antigen-binding fragment thereof comprises at least two of characteristics (a), (b), and/or (c).

11. The method of claim 1, wherein the isolated antibody or antigen-binding fragment thereof displays an equilibrium dissociation constant of between about $1 \times 10^6$ M to about $1 \times 10^{10}$ M.

12. A method of treating or preventing a Yellow Fever Virus (YFV) infection or at least one symptom arising therefrom, comprising administering to a patient in need thereof or suspected of being in need thereof an isolated nucleic acid encoding an antibody or antigen-binding fragment thereof,
wherein the antibody or antigen-binding fragment thereof specifically binds to a YFV protein, wherein the antibody or antigen-binding fragment thereof comprises:
(i) a heavy chain variable region comprising the amino acid sequence of SEQ ID NO:307 and a light chain variable region comprising the amino acid sequence of SEQ ID NO:459;
(ii) a heavy chain variable region comprising the amino acid sequence of SEQ ID NO:308 and a light chain variable region comprising the amino acid sequence of SEQ ID NO:460;
(iii) a heavy chain variable region comprising the amino acid sequence of SEQ ID NO:311 and a light chain variable region comprising the amino acid sequence of SEQ ID NO:463;
(iv) a heavy chain variable region comprising the amino acid sequence of SEQ ID NO:320 and a light chain variable region comprising the amino acid sequence of SEQ ID NO:471; or
(v) a heavy chain variable region comprising the amino acid sequence of SEQ ID NO:341 and a light chain variable region comprising the amino acid sequence of SEQ ID NO:492.

13. The method of claim 12, wherein the at least one symptom associated with the YFV infection is fever, chills, headache, low back pain, myalgia, loss of appetite, nausea, vomiting, or fatigue.

14. A method of treating or preventing a Yellow Fever Virus (YFV) infection or at least one symptom arising therefrom, comprising administering to a patient in need thereof or suspected of being in need thereof a pharmaceutical composition comprising a pharmaceutically acceptable excipient and an isolated antibody or antigen-binding fragment thereof
wherein the antibody or antigen-binding fragment thereof specifically binds to a YFV protein, wherein the antibody or antigen-binding fragment thereof comprises:
(i) a heavy chain variable region comprising the amino acid sequence of SEQ ID NO:307 and a light chain variable region comprising the amino acid sequence of SEQ ID NO:459;
(ii) a heavy chain variable region comprising the amino acid sequence of SEQ ID NO:308 and a light chain variable region comprising the amino acid sequence of SEQ ID NO:460;
(iii) a heavy chain variable region comprising the amino acid sequence of SEQ ID NO:311 and a light chain variable region comprising the amino acid sequence of SEQ ID NO:463;
(iv) a heavy chain variable region comprising the amino acid sequence of SEQ ID NO:320 and a light chain variable region comprising the amino acid sequence of SEQ ID NO:471; or
(v) a heavy chain variable region comprising the amino acid sequence of SEQ ID NO:341 and a light chain variable region comprising the amino acid sequence of SEQ ID NO:492.

15. The method of claim 14, wherein the at least one symptom associated with the YFV infection is fever, chills, headache, low back pain, myalgia, loss of appetite, nausea, vomiting, or fatigue.

16. A method of treating or preventing a Yellow Fever Virus (YFV) infection or at least one symptom arising therefrom, comprising administering to a patient in need thereof or suspected of being in need thereof a pharmaceutical composition comprising a pharmaceutically acceptable excipient and an isolated nucleic acid encoding an antibody or antigen-binding fragment thereof
wherein the antibody or antigen-binding fragment thereof specifically binds to a YFV protein, wherein the antibody or antigen-binding fragment thereof comprises:
(i) a heavy chain variable region comprising the amino acid sequence of SEQ ID NO:307 and a light chain variable region comprising the amino acid sequence of SEQ ID NO:459;
(ii) a heavy chain variable region comprising the amino acid sequence of SEQ ID NO:308 and a light chain variable region comprising the amino acid sequence of SEQ ID NO:460;
(iii) a heavy chain variable region comprising the amino acid sequence of SEQ ID NO:311 and a light chain variable region comprising the amino acid sequence of SEQ ID NO:463;
(iv) a heavy chain variable region comprising the amino acid sequence of SEQ ID NO:320 and a light chain variable region comprising the amino acid sequence of SEQ ID NO:471; or
(v) a heavy chain variable region comprising the amino acid sequence of SEQ ID NO:341 and a light chain variable region comprising the amino acid sequence of SEQ ID NO:492.

17. The method of claim 16, wherein the at least one symptom associated with the YFV infection is fever, chills, headache, low back pain, myalgia, loss of appetite, nausea, vomiting, or fatigue.

* * * * *